(12) United States Patent
Buyse et al.

(10) Patent No.: US 12,209,136 B2
(45) Date of Patent: Jan. 28, 2025

(54) ADAMTS BINDING IMMUNOGLOBULINS

(71) Applicants: Merck Patent GmbH, Darmstadt (DE); ABLYNX NV, Zwijnaarde Ghent (BE)

(72) Inventors: Marie-Ange Buyse, Merelbeke (BE); Guy Hermans, Merelbeke (BE); Sven Lindemann, Darmstadt (DE); Hans Guehring, Geissenheim (DE); Ralf Guenther, Griesheim (DE); Roland Kellner, Heppenheim (DE)

(73) Assignees: Merck Patent GmbH, Darmstadt (DE); ABLYNX NV, Zwijnaarde Ghent (BE)

( * ) Notice: Subject to any disclaimer, the term of this patent is extended or adjusted under 35 U.S.C. 154(b) by 295 days.

(21) Appl. No.: 17/579,345

(22) Filed: Jan. 19, 2022

(65) Prior Publication Data

US 2022/0289860 A1     Sep. 15, 2022

Related U.S. Application Data

(62) Division of application No. 16/617,885, filed as application No. PCT/EP2018/064665 on Jun. 4, 2018, now Pat. No. 11,261,260.

(30) Foreign Application Priority Data

Jun. 2, 2017   (EP) ..................... 17174403

(51) Int. Cl.
| | | |
|---|---|---|
| C07K 16/28 | (2006.01) | |
| A61K 39/00 | (2006.01) | |
| A61P 19/02 | (2006.01) | |
| C07K 16/18 | (2006.01) | |
| C07K 16/40 | (2006.01) | |

(52) U.S. Cl.
CPC .......... *C07K 16/2896* (2013.01); *C07K 16/18* (2013.01); *C07K 16/40* (2013.01); *A61K 2039/505* (2013.01); *A61P 19/02* (2018.01); *C07K 2317/33* (2013.01); *C07K 2317/569* (2013.01); *C07K 2317/76* (2013.01); *C07K 2317/92* (2013.01)

(58) Field of Classification Search
None
See application file for complete search history.

(56) References Cited

U.S. PATENT DOCUMENTS

| | | |
|---|---|---|
| 9,156,914 B2 | 10/2015 | Blanchetot et al. |
| 9,265,834 B2 | 2/2016 | Brige et al. |
| 9,320,792 B2 | 4/2016 | Bouche et al. |
| 9,464,138 B2 | 10/2016 | Schotte et al. |
| 9,534,039 B2 | 1/2017 | Brige et al. |
| 9,713,589 B2 | 7/2017 | Depla et al. |
| 9,725,522 B2 | 8/2017 | Bouche et al. |
| 2008/0311113 A1 | 12/2008 | Morris et al. |
| 2015/0368188 A1* | 12/2015 | Klein .................. C07D 213/81 |
| | | 548/200 |
| 2016/0251440 A1 | 9/2016 | Roobrouck et al. |
| 2020/0317802 A1 | 10/2020 | Buyse et al. |
| 2021/0008160 A1 | 1/2021 | Steffensen et al. |

FOREIGN PATENT DOCUMENTS

| | | |
|---|---|---|
| EP | 3049439 B1 | 12/2019 |
| WO | 2001011074 A2 | 2/2001 |
| WO | 2002033093 A2 | 4/2002 |
| WO | 2002034895 A2 | 5/2002 |
| WO | 2002042439 A2 | 5/2002 |
| WO | 2003064597 A2 | 8/2003 |
| WO | 2005060456 A2 | 7/2005 |
| WO | 2008074840 A2 | 6/2008 |
| WO | 2008074840 A3 | 6/2008 |
| WO | 2009095235 A1 | 8/2009 |
| WO | 2011002968 A2 | 1/2011 |
| WO | 2011002968 A3 | 1/2011 |
| WO | 2011026948 A1 | 3/2011 |
| WO | 2012175741 A2 | 12/2012 |
| WO | 2013153189 A1 | 10/2013 |
| WO | 2015044386 A1 | 4/2015 |

(Continued)

OTHER PUBLICATIONS

Clinical Trial NCT0322470, first posted Jul. 21, 2017, available at http://clinicaltrials.gov.
Clinical Trial NCT03583346 first posted Jul. 11, 2018, available at http://clinicaltrials.gov.
International Search Report and Written Opinion issued in Corresponding International Application No. PCT/EP2018/064665 dated Sep. 27, 2018, twenty-four (24) pages total.
Kontermann, "Strategies for Extended Serum Half-Life of Protein Therapeutics", Current Opinion in Biotechnology, 2011, pp. 868-876, vol. 22, No. 6, 2011 Elsevier ltd.

(Continued)

*Primary Examiner* — Ruixiang Li
(74) *Attorney, Agent, or Firm* — Seth E. Cockrum

(57) ABSTRACT

The present invention relates to immunoglobulins that bind ADAMTS5 and more in particular to polypeptides, that comprise or essentially consist of one or more such immunoglobulins. The invention also relates to constructs comprising such immunoglobulins, such as immunoglobulin single variable domains (ISVDs) or polypeptides as well as nucleic acids encoding such immunoglobulins or polypeptides; to methods for preparing such immunoglobulins, polypeptides and constructs; to host cells expressing or capable of expressing such immunoglobulins or polypeptides; to compositions, and in particular to pharmaceutical compositions, that comprise such immunoglobulins, polypeptides, constructs, nucleic acids and/or host cells; and to uses of immunoglobulins, polypeptides, constructs, nucleic acids, host cells and/or compositions, in particular for prophylactic and/or therapeutic purposes, such as the prophylactic and/or therapeutic purposes mentioned herein.

14 Claims, 14 Drawing Sheets

Figure 1A:
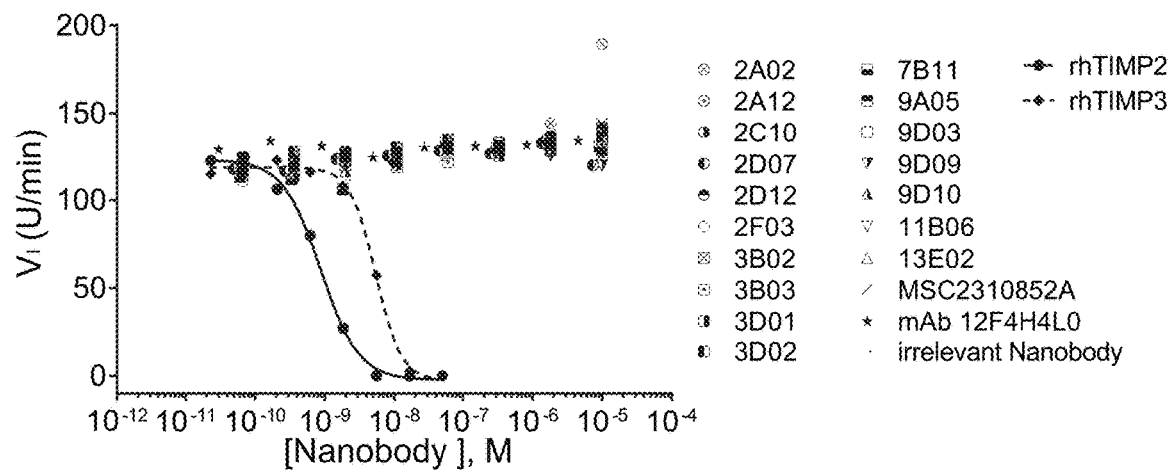

Specification includes a Sequence Listing.

(56) References Cited

FOREIGN PATENT DOCUMENTS

| WO | 2015056808 A1 | 4/2015 |
| WO | 2015173325 A2 | 11/2015 |
| WO | 2016061642 A1 | 4/2016 |
| WO | 2016124781 A1 | 8/2016 |
| WO | 2018220234 A1 | 12/2018 |
| WO | 2018220236 A1 | 12/2018 |
| WO | 2019180636 A1 | 9/2019 |

OTHER PUBLICATIONS

Santamaria et al., "Antibody-Based Exosite Inhibitors of ADAMTS-5 (aggrecanase-2)", Biochemical Journal, Nov. 1, 2015, pp. 391-401, vol. 471, 2015 Aughors; published by Portland Press Limited.

Siebuhr et al., "Purpose 363 the Anti-ADAMTS-5 Nanobody, M6495, Protects Against Cartilage Breakdown in Cartilage and Synovial Joint Tissue Explant Models", Abstracts/Osteoarthritis and Cartilage, 2018, p. S187, vol. 26, p. S187.

Caljon, et al., Affinity Is an Important Determinant of the Anti-Trypanosome Activity of Nanobodi, PLOS Neglected Tropical Diseases, 6(11), e1902, Nov. 2012.

Mitchell, et al., Comparative analysis of nanobody sequence and structure data, Proteins, 86, 697-706, 2018.

Clinical Trial NCT05462990 first posted Sep. 28, 2023, available at http://clinicaltrials.gov.

\* cited by examiner

* P<0.001. Statictics were obtained with 1way ANOVA, followed by Dunnett comparison.

* P<0.001. Statictics were obtained with 1way ANOVA, followed by Dunnett comparison.

SEQUENCE LISTING

<160> NUMBER OF SEQ ID NOS: 189

<210> SEQ ID NO 1
<211> LENGTH: 124
<212> TYPE: PRT
<213> ORGANISM: Artificial Sequence
<220> FEATURE:
<223> OTHER INFORMATION: Description of Artificial Sequence: Synthetic
      anti-ADAMTS5 Nanobody

<400> SEQUENCE: 1

Glu Val Gln Leu Val Glu Ser Gly Gly Gly Leu Val Gln Ala Gly Gly
1               5                   10                  15

Ser Leu Arg Leu Ser Cys Ala Ala Ser Gly Arg Thr Phe Ser Ser Tyr
            20                  25                  30

```
Ala Met Gly Trp Phe Arg Gln Ala Pro Gly Lys Glu Arg Asp Phe Val
            35                  40                  45

Ala Gly Ile Ser Arg Ser Ala Gly Arg Thr Tyr Tyr Val Asp Ser Val
 50                  55                  60

Lys Gly Arg Phe Thr Ile Ser Arg Asp Ser Ala Lys Asn Thr Val Tyr
 65                  70                  75                  80

Leu Gln Met Asn Arg Leu Lys Pro Glu Asp Thr Ala Val Tyr Tyr Cys
                 85                  90                  95

Ala Ala Asp Leu Asp Pro Asn Arg Ile Phe Ser Arg Asp Glu Ala Ala
                100                 105                 110

Tyr Trp Gly Gln Gly Thr Leu Val Thr Val Ser Ser
            115                 120

<210> SEQ ID NO 2
<211> LENGTH: 124
<212> TYPE: PRT
<213> ORGANISM: Artificial Sequence
<220> FEATURE:
<223> OTHER INFORMATION: Description of Artificial Sequence: Synthetic
      anti-ADAMTS5 Nanobody

<400> SEQUENCE: 2

Glu Val Gln Leu Val Glu Ser Gly Gly Gly Leu Val Gln Ala Gly Gly
 1               5                  10                  15

Ser Leu Arg Leu Ser Cys Ala Ala Ser Gly Arg Thr Val Ser Ser Tyr
             20                  25                  30

Ala Met Gly Trp Phe Arg Leu Ala Pro Gly Lys Glu Arg Glu Phe Val
            35                  40                  45

Ala Gly Ile Ser Arg Ser Ala Glu Arg Thr Tyr Tyr Val Asp Ser Leu
 50                  55                  60

Lys Gly Arg Phe Thr Ile Ser Arg Asp Ser Ala Lys Asn Thr Val Tyr
 65                  70                  75                  80

Leu His Met Asn Arg Leu Lys Pro Glu Asp Thr Ala Val Tyr Tyr Cys
                 85                  90                  95

Ala Ala Asp Leu Asp Pro Asn Arg Ile Phe Ser Arg Glu Glu Tyr Ala
                100                 105                 110

Tyr Trp Gly Gln Gly Thr Leu Val Thr Val Ser Ser
            115                 120

<210> SEQ ID NO 3
<211> LENGTH: 124
<212> TYPE: PRT
<213> ORGANISM: Artificial Sequence
<220> FEATURE:
<223> OTHER INFORMATION: Description of Artificial Sequence: Synthetic
      anti-ADAMTS5 Nanobody

<400> SEQUENCE: 3

Glu Val Gln Leu Val Glu Ser Gly Gly Gly Leu Val Gln Ser Gly Gly
 1               5                  10                  15

Ser Leu Arg Leu Ser Cys Ala Ala Ser Gly Ser Ala Val Ser Val Asn
             20                  25                  30

Ala Met Ala Trp Tyr Arg Gln Ala Pro Gly Lys Gln Arg Asp Phe Val
            35                  40                  45

Ala Gly Ile Ser Arg Ser Ala Gly Arg Thr Tyr Tyr Thr Asp Ser Val
 50                  55                  60

Lys Asp Arg Phe Thr Ile Ala Arg Asp Ser Ala Lys Asn Thr Val Tyr
 65                  70                  75                  80
```

```
Leu Gln Met Asn Arg Leu Lys Pro Glu Asp Thr Ala Val Tyr Tyr Cys
                85                  90                  95

Ala Ala Asp Leu Asp Pro Asn Arg Ile Phe Ser Arg Asp Glu Ala Ala
            100                 105                 110

Tyr Trp Gly Gln Gly Thr Leu Val Thr Val Ser Ser
        115                 120

<210> SEQ ID NO 4
<211> LENGTH: 125
<212> TYPE: PRT
<213> ORGANISM: Artificial Sequence
<220> FEATURE:
<223> OTHER INFORMATION: Description of Artificial Sequence: Synthetic
      anti-ADAMTS5 Nanobody

<400> SEQUENCE: 4

Glu Val Gln Leu Val Glu Ser Gly Gly Gly Leu Val Gln Ala Gly Asp
1               5                   10                  15

Ser Leu Arg Leu Ser Cys Ala Ala Ser Gly Arg Thr Phe Ser Thr Tyr
            20                  25                  30

Phe Val Gly Trp Phe Arg Gln Ala Pro Gly Lys Glu Arg Asp Phe Val
        35                  40                  45

Ala Ala Ile Ser Arg Asn Gly Ala Arg Thr Tyr Tyr Tyr Asp Ser Val
    50                  55                  60

Ala Gly Leu Phe Thr Ile Ser Arg Asp Asn Ala Lys Asn Thr Val Tyr
65                  70                  75                  80

Leu Gln Met Ser Ser Leu Lys Pro Glu Asp Thr Ala Val Tyr Tyr Cys
                85                  90                  95

Ala Ala Ala Arg Ile Ser Pro Ser Asp Pro Ser Asn Glu Asp Gly Tyr
            100                 105                 110

Asp Tyr Trp Gly Gln Gly Thr Leu Val Thr Val Ser Ser
        115                 120                 125

<210> SEQ ID NO 5
<211> LENGTH: 126
<212> TYPE: PRT
<213> ORGANISM: Artificial Sequence
<220> FEATURE:
<223> OTHER INFORMATION: Description of Artificial Sequence: Synthetic
      anti-ADAMTS5 Nanobody

<400> SEQUENCE: 5

Glu Val Gln Leu Val Glu Ser Gly Gly Gly Leu Val Gln Pro Gly Gly
1               5                   10                  15

Ser Leu Arg Leu Ser Cys Ala Ala Ser Arg Arg Thr Phe Ser Ser Tyr
            20                  25                  30

Val Met Ala Trp Phe Arg Gln Ala Pro Gly Lys Glu Arg Glu Phe Val
        35                  40                  45

Ala Ala Ile Ser Arg Ser Gly Asp Ser Thr Tyr Tyr Tyr Asp Ser Leu
    50                  55                  60

Glu Gly Arg Phe Thr Ile Ser Arg Asp Asn Ala Lys Asn Thr Val His
65                  70                  75                  80

Leu Gln Met Asn Ser Leu Lys Pro Glu Asp Thr Ala Val Tyr Ile Cys
                85                  90                  95

Ala Ala Ser Arg Ala Pro Ser Phe Arg Thr Ile Asp Ala Ile Asn Tyr
            100                 105                 110

Tyr Asp Tyr Trp Gly Gln Gly Thr Leu Val Thr Val Ser Ser
        115                 120                 125
```

```
<210> SEQ ID NO 6
<211> LENGTH: 126
<212> TYPE: PRT
<213> ORGANISM: Artificial Sequence
<220> FEATURE:
<223> OTHER INFORMATION: Description of Artificial Sequence: Synthetic
      anti-ADAMTS5 Nanobody

<400> SEQUENCE: 6

Glu Val Gln Leu Val Glu Ser Gly Gly Gly Leu Val Gln Ala Gly Gly
1               5                   10                  15

Ser Leu Arg Leu Ser Cys Ser Phe Ser Gly Pro Gly Arg Thr Phe Ala
            20                  25                  30

Arg Tyr Ala Met Gly Trp Phe Arg Gln Ala Pro Gly Lys Asn Arg Asp
        35                  40                  45

Phe Ile Thr Gly Ile Ser Gly Ser Gly Asp Ser Thr Tyr Tyr Val Tyr
    50                  55                  60

Pro Met Lys Asp Arg Phe Thr Ile Ser Arg Asp Asn Ala Lys Asn Met
65                  70                  75                  80

Val Tyr Leu Gln Met Asn Ala Leu Lys Pro Glu Asp Thr Ala Val Tyr
                85                  90                  95

Tyr Cys Ala Ala Asp Arg Glu Ile Asn Arg Ile Ala Asn Asp Lys Glu
            100                 105                 110

Leu Asp Phe Trp Gly Gln Gly Thr Leu Val Thr Val Ser Ser
        115                 120                 125

<210> SEQ ID NO 7
<211> LENGTH: 123
<212> TYPE: PRT
<213> ORGANISM: Artificial Sequence
<220> FEATURE:
<223> OTHER INFORMATION: Description of Artificial Sequence: Synthetic
      anti-ADAMTS5 Nanobody

<400> SEQUENCE: 7

Glu Val Gln Leu Val Glu Ser Gly Gly Gly Leu Val Gln Ala Gly Gly
1               5                   10                  15

Ser Leu Arg Leu Ser Cys Ala Ala Ser Gly Arg Thr Thr Phe Ser Ser
            20                  25                  30

Tyr Ala Met Gly Trp Phe Arg Gln Ala Pro Gly Lys Glu Arg Ala Phe
        35                  40                  45

Val Ala Thr Ile Trp Ser Gly Gly Leu Thr Val Tyr Ala Asp Ser Ala
    50                  55                  60

Lys Gly Arg Phe Thr Ile Ser Arg Asp Asn Ala Lys Asn Thr Val Tyr
65                  70                  75                  80

Leu Gln Met Asn Ser Leu Arg Pro Glu Asp Thr Ala Val Tyr Tyr Cys
                85                  90                  95

Ala Ala Glu Ala Val Gly Thr Tyr Tyr Thr Pro Asp Gly Trp Thr Tyr
            100                 105                 110

Trp Gly Gln Gly Thr Leu Val Thr Val Ser Ser
        115                 120

<210> SEQ ID NO 8
<211> LENGTH: 124
<212> TYPE: PRT
<213> ORGANISM: Artificial Sequence
<220> FEATURE:
<223> OTHER INFORMATION: Description of Artificial Sequence: Synthetic
      anti-ADAMTS5 Nanobody
```

<400> SEQUENCE: 8

Glu Val Gln Leu Val Glu Ser Gly Gly Gly Leu Val Gln Ala Gly Gly
1               5                   10                  15

Ser Leu Arg Leu Ser Cys Ala Ala Ser Gly Leu Thr Phe Arg Arg Asn
            20                  25                  30

Ala Met Gly Trp Phe Arg Gln Ala Pro Gly Lys Glu Arg Glu Leu Leu
        35                  40                  45

Ala Gly Ile Asn Trp Ser Gly Thr Thr Tyr Tyr Val Asp Ser Val
    50                  55                  60

Lys Gly Arg Phe Thr Ile Ser Arg Asp Asn Ala Lys Asn Thr Val Asp
65                  70                  75                  80

Leu Gln Met Ile Ser Pro Lys Pro Glu Asp Thr Ala Val Tyr Tyr Cys
                85                  90                  95

Ala Ala Asp Gly Asp Ile Gly Thr Leu Val Asn Asp Glu Asn Pro Arg
            100                 105                 110

Tyr Trp Gly Gln Gly Thr Leu Val Thr Val Ser Ser
        115                 120

<210> SEQ ID NO 9
<211> LENGTH: 124
<212> TYPE: PRT
<213> ORGANISM: Artificial Sequence
<220> FEATURE:
<223> OTHER INFORMATION: Description of Artificial Sequence: Synthetic
      anti-ADAMTS5 Nanobody

<400> SEQUENCE: 9

Glu Val Gln Leu Val Glu Ser Gly Gly Gly Leu Val Gln Ala Gly Gly
1               5                   10                  15

Ser Leu Arg Leu Ser Cys Ala Thr Ser Gly Phe Thr Phe Ser Pro Tyr
            20                  25                  30

Tyr Met Gly Trp Phe Arg Gln Ala Pro Gly Lys Glu Arg Asp Phe Val
        35                  40                  45

Ala Ala Ile Thr Arg Ser Arg Gly Thr Thr Tyr Tyr Leu Asp Ser Thr
    50                  55                  60

Glu Gly Arg Phe Thr Ile Ser Arg Asp Asn Ala Lys Asn Thr Met Tyr
65                  70                  75                  80

Leu Gln Met Asn Ser Leu Asn Pro Glu Asp Thr Ala Val Tyr Tyr Cys
                85                  90                  95

Ala Ala Gly Arg Ser Pro Gly Asp Pro Ser Arg Thr Tyr Leu Tyr Glu
            100                 105                 110

Tyr Trp Gly Gln Gly Thr Leu Val Thr Val Ser Ser
        115                 120

<210> SEQ ID NO 10
<211> LENGTH: 124
<212> TYPE: PRT
<213> ORGANISM: Artificial Sequence
<220> FEATURE:
<223> OTHER INFORMATION: Description of Artificial Sequence: Synthetic
      anti-ADAMTS5 Nanobody

<400> SEQUENCE: 10

Glu Val Gln Leu Val Glu Ser Gly Gly Gly Leu Val Gln Ala Gly Gly
1               5                   10                  15

Ser Leu Arg Leu Ser Cys Ala Pro Ser Gly Phe Thr Phe Ser Pro Tyr
            20                  25                  30

Tyr Met Gly Trp Phe Arg Gln Ala Pro Gly Lys Glu Arg Asp Phe Val
            35                  40                  45

Ala Ala Ile Ser Arg Ser Arg Gly Thr Thr Tyr Tyr Leu Asp Ser Thr
 50                  55                  60

Glu Gly Arg Phe Thr Ile Ser Arg Asp Asn Ala Asn Asp Thr Val Tyr
 65                  70                  75                  80

Leu Gln Met Asn Ser Leu Asn Pro Glu Asp Thr Ala Val Tyr Tyr Cys
                 85                  90                  95

Ala Ala Gly Arg Ser Pro Gly Asp Pro Ser Arg Thr Tyr Leu Tyr Asp
                100                 105                 110

Tyr Trp Gly Gln Gly Thr Leu Val Thr Val Ser Ser
            115                 120

<210> SEQ ID NO 11
<211> LENGTH: 124
<212> TYPE: PRT
<213> ORGANISM: Artificial Sequence
<220> FEATURE:
<223> OTHER INFORMATION: Description of Artificial Sequence: Synthetic
      anti-ADAMTS5 Nanobody

<400> SEQUENCE: 11

Glu Val Gln Leu Val Glu Ser Gly Gly Gly Leu Val Gln Ala Gly Ala
 1               5                  10                  15

Ser Leu Arg Leu Ser Cys Ala Thr Ser Gly Phe Thr Phe Ser Pro Tyr
             20                  25                  30

Tyr Met Gly Trp Phe Arg Gln Ala Pro Gly Lys Glu Arg Asp Phe Val
            35                  40                  45

Ala Ala Ile Ser Trp Ser Arg Gly Ile Leu Tyr Tyr Thr Asp Ser Thr
 50                  55                  60

Glu Gly Arg Phe Thr Ile Ser Arg Asp Asn Ala Lys Asn Thr Met Tyr
 65                  70                  75                  80

Leu Gln Met Asp Asn Leu Asn Pro Glu Asp Thr Ala Val Tyr Tyr Cys
                 85                  90                  95

Ala Ala Ser Arg Ser Pro Gly Asp Pro Ser Arg Thr Tyr Leu Tyr Asp
                100                 105                 110

Tyr Trp Gly Gln Gly Thr Leu Val Thr Val Ser Ser
            115                 120

<210> SEQ ID NO 12
<211> LENGTH: 127
<212> TYPE: PRT
<213> ORGANISM: Artificial Sequence
<220> FEATURE:
<223> OTHER INFORMATION: Description of Artificial Sequence: Synthetic
      anti-ADAMTS5 Nanobody

<400> SEQUENCE: 12

Glu Val Gln Leu Val Glu Ser Gly Gly Gly Leu Val Gln Ala Gly Gly
 1               5                  10                  15

Ser Leu Arg Leu Ser Cys Ala Ala Ser Gly Arg Ala Leu Ser Ser Ser
             20                  25                  30

Ile Met Gly Trp Phe Arg Gln Ala Pro Gly Lys Glu Arg Glu Phe Val
            35                  40                  45

Ala Ala Ile Thr Trp Ser Gly Gly Arg Ala Tyr Tyr Ala Asp Val Ser
 50                  55                  60

Asp Phe Glu Lys Gly Arg Phe Thr Ile Ser Arg Asp Asn Gly Lys Asn
 65                  70                  75                  80

```
Thr Val Asn Leu Gln Met Lys Gly Leu Lys Pro Glu Asp Thr Ala Val
                85                  90                  95

Tyr Tyr Cys Ala Ala Ala Leu Ala Ile Pro Val Thr Met Ser Pro His
            100                 105                 110

Glu Tyr Pro Tyr Trp Gly Gln Gly Thr Leu Val Thr Val Ser Ser
        115                 120                 125
```

<210> SEQ ID NO 13
<211> LENGTH: 121
<212> TYPE: PRT
<213> ORGANISM: Artificial Sequence
<220> FEATURE:
<223> OTHER INFORMATION: Description of Artificial Sequence: Synthetic
      anti-ADAMTS5 Nanobody

<400> SEQUENCE: 13

```
Glu Val Gln Leu Val Glu Ser Gly Gly Asp Leu Val Gln Pro Gly Gly
1               5                   10                  15

Ser Leu Arg Leu Ser Cys Ala Ala Ser Gly Ser Asp Val Val Asn
            20                  25                  30

Asp Met Gly Trp Tyr Arg Gln Ala Pro Gly Lys Gln Arg Glu Leu Val
        35                  40                  45

Ala Asp Ile Thr Thr Gly Gly Arg Thr Asn Tyr Ala Asp Ser Val Lys
    50                  55                  60

Gly Arg Phe Thr Ile Ser Arg Asp Asn Val Lys Asn Thr Val Tyr Leu
65                  70                  75                  80

Gln Met Asn Ser Leu Lys Pro Glu Asp Thr Ala Val Tyr Tyr Cys Asn
                85                  90                  95

Ala Gln Val Gly Asp Ser Asp Asp Val Trp Tyr Ala Tyr Trp Gly
            100                 105                 110

Gln Gly Thr Leu Val Thr Val Ser Ser
        115                 120
```

<210> SEQ ID NO 14
<211> LENGTH: 119
<212> TYPE: PRT
<213> ORGANISM: Artificial Sequence
<220> FEATURE:
<223> OTHER INFORMATION: Description of Artificial Sequence: Synthetic
      anti-ADAMTS5 Nanobody

<400> SEQUENCE: 14

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Ser Ile Phe Ser Ile Asn
            20                  25                  30

Val Met Gly Trp Tyr Arg Gln Ala Pro Gly Lys Gln Arg Glu Leu Val
        35                  40                  45

Ala Ala Ile Ile Ser Gly Gly Arg Thr Asn Tyr Ala Asp Ser Val Lys
    50                  55                  60

Gly Arg Phe Thr Ile Ser Arg Asp Asn Ser Lys Asn Thr Val Tyr Leu
65                  70                  75                  80

Gln Met Asn Ser Leu Arg Pro Glu Asp Thr Ala Val Tyr Tyr Cys Asn
                85                  90                  95

Ala Glu Val Asp Ala Gly Ile Tyr Ala Tyr Gly Tyr Trp Gly Gln Gly
            100                 105                 110

Thr Leu Val Thr Val Ser Ser
        115
```

<210> SEQ ID NO 15
<211> LENGTH: 124
<212> TYPE: PRT
<213> ORGANISM: Artificial Sequence
<220> FEATURE:
<223> OTHER INFORMATION: Description of Artificial Sequence: Synthetic anti-ADAMTS5 Nanobody

<400> SEQUENCE: 15

Glu Val Gln Leu Val Glu Ser Gly Gly Gly Leu Val Gln Ala Gly Gly
1               5                   10                  15

Ser Leu Arg Leu Ser Cys Ala Ala Ser Gly Leu Thr Phe Ser Ser Tyr
            20                  25                  30

Thr Met Gly Trp Phe Arg Gln Ala Pro Gly Gln Glu Arg Glu Phe Val
        35                  40                  45

Ser Ala Ile Ser Trp Asn Thr Phe Thr Thr Tyr Tyr Val Asp Ser Val
    50                  55                  60

Lys Asp Arg Phe Thr Val Ser Arg Asp Asn Ala Lys Asn Thr Leu Tyr
65                  70                  75                  80

Leu Arg Met Asn Ser Leu Lys Pro Glu Asp Thr Ala Val Tyr Tyr Cys
                85                  90                  95

Ala Ala Ala Gly Gly Ser Pro Arg Gln His Glu Pro Tyr Glu Tyr Arg
            100                 105                 110

Val Trp Gly Gln Gly Thr Leu Val Thr Val Ser Ser
        115                 120

<210> SEQ ID NO 16
<211> LENGTH: 125
<212> TYPE: PRT
<213> ORGANISM: Artificial Sequence
<220> FEATURE:
<223> OTHER INFORMATION: Description of Artificial Sequence: Synthetic anti-ADAMTS5 Nanobody

<400> SEQUENCE: 16

Glu Val Gln Leu Val Glu Ser Gly Gly Gly Phe Val Gln Ala Gly Gly
1               5                   10                  15

Ser Leu Arg Leu Ser Cys Val Ala Ser Arg Arg Thr Ile Ser Ser Gly
            20                  25                  30

Thr Met Gly Trp Phe Arg Gln Ala Pro Gly Lys Glu Arg Glu Phe Val
        35                  40                  45

Ala Ala Ile Arg Trp Ser Ser Gly Met Pro Tyr Tyr Leu Asp Ser Val
    50                  55                  60

Met Asp Arg Phe Thr Ile Ser Arg Asp Asn Ala Lys Asn Thr Val Ser
65                  70                  75                  80

Leu Gln Met Asn Ser Leu Gln Pro Glu Asp Thr Ala Val Tyr Tyr Cys
                85                  90                  95

Ala Ala Asp Arg Ser Ala Phe Arg Asp Pro Ser Phe Asp Val Asn Tyr
            100                 105                 110

Glu Tyr Trp Gly Arg Gly Thr Leu Val Thr Val Ser Ser
        115                 120                 125

<210> SEQ ID NO 17
<211> LENGTH: 125
<212> TYPE: PRT
<213> ORGANISM: Artificial Sequence
<220> FEATURE:
<223> OTHER INFORMATION: Description of Artificial Sequence: Synthetic anti-ADAMTS5 Nanobody

```
<400> SEQUENCE: 17

Glu Val Gln Leu Val Glu Ser Gly Gly Gly Phe Val Gln Ala Gly Gly
1               5                   10                  15

Ser Leu Arg Leu Ser Cys Ala Ala Ser Arg Arg Thr Ile Ser Ser Gly
            20                  25                  30

Thr Met Gly Trp Phe Arg Gln Ala Pro Gly Lys Glu Arg Glu Phe Val
        35                  40                  45

Ala Ala Ile Arg Trp Ser Ser Gly Ile Thr Tyr Pro Asp Ser Val
50                  55                  60

Glu Gly Arg Phe Thr Ile Ser Gly Asp Asn Ala Lys Asn Thr Val Ser
65                  70                  75                  80

Leu Gln Met Asn Ser Leu Lys Pro Glu Asp Thr Ala Val Tyr Tyr Cys
                85                  90                  95

Ala Ala Asp Arg Ser Ala Leu Arg Asp Pro Ser Phe Glu Val Asn Tyr
            100                 105                 110

Glu Tyr Trp Gly Arg Gly Thr Leu Val Thr Val Ser Ser
        115                 120                 125

<210> SEQ ID NO 18
<211> LENGTH: 120
<212> TYPE: PRT
<213> ORGANISM: Artificial Sequence
<220> FEATURE:
<223> OTHER INFORMATION: Description of Artificial Sequence: Synthetic
      anti-ADAMTS5 Nanobody

<400> SEQUENCE: 18

Glu Val Gln Leu Val Glu Ser Gly Gly Gly Leu Val Gln Ala Gly Gly
1               5                   10                  15

Ser Leu Arg Leu Ser Cys Val Ala Ser Gly Ser Ile Phe Ser Ile Asp
            20                  25                  30

Ala Met Gly Trp Tyr Arg Gln Ala Pro Gly Lys Glu Arg Glu Leu Val
        35                  40                  45

Ala Ser Val Thr Thr Gly Ala Ser Pro Asn Tyr Gly Asp Ser Val Thr
50                  55                  60

Gly Arg Phe Thr Ala Ser Arg Asp Arg Ala Lys Asn Ala Leu Tyr Leu
65                  70                  75                  80

Gln Met Asn Ser Leu Lys Pro Glu Asp Thr Ala Val Tyr Tyr Cys Asn
                85                  90                  95

Leu Ile Met Thr Ile Pro Gly Gly Ser Gln Ile Met Tyr Trp Gly Gln
            100                 105                 110

Gly Thr Leu Val Thr Val Ser Ser
        115                 120

<210> SEQ ID NO 19
<211> LENGTH: 120
<212> TYPE: PRT
<213> ORGANISM: Artificial Sequence
<220> FEATURE:
<223> OTHER INFORMATION: Description of Artificial Sequence: Synthetic
      anti-ADAMTS5 Nanobody

<400> SEQUENCE: 19

Glu Val Gln Leu Val Glu Ser Gly Gly Gly Ser Val Gln Ala Gly Gly
1               5                   10                  15

Ser Leu Arg Leu Ser Cys Val Ala Ser Gly Arg Tyr Pro Met Ala Trp
            20                  25                  30

Phe Arg Gln Ala Pro Gly Lys Glu Arg Glu Phe Val Ala Gly Val Ser
```

```
                        35                  40                  45
Trp Gly Gly Asp Arg Thr Tyr Tyr Ala Asp Ser Val Gln Gly Arg Phe
        50                  55                  60

Thr Val Ser Arg Asp Tyr Ala Lys Asn Thr Leu Tyr Leu Gln Met Asn
65                  70                  75                  80

Ser Leu Lys Pro Glu Asp Ala Ala Val Tyr Tyr Cys Ala Gly Asp Pro
                85                  90                  95

Trp Gly Arg Leu Phe Arg Val Lys Asp Asn Tyr Ser Asp Trp Gly Gln
            100                 105                 110

Gly Thr Leu Val Thr Val Ser Ser
        115                 120

<210> SEQ ID NO 20
<211> LENGTH: 10
<212> TYPE: PRT
<213> ORGANISM: Artificial Sequence
<220> FEATURE:
<223> OTHER INFORMATION: Description of Artificial Sequence: Synthetic
      CDR1 of anti-ADAMTS5 Nanobody

<400> SEQUENCE: 20

Gly Arg Thr Phe Ser Ser Tyr Ala Met Gly
1               5                   10

<210> SEQ ID NO 21
<211> LENGTH: 10
<212> TYPE: PRT
<213> ORGANISM: Artificial Sequence
<220> FEATURE:
<223> OTHER INFORMATION: Description of Artificial Sequence: Synthetic
      CDR1 of anti-ADAMTS5 Nanobody

<400> SEQUENCE: 21

Gly Arg Thr Val Ser Ser Tyr Ala Met Gly
1               5                   10

<210> SEQ ID NO 22
<211> LENGTH: 10
<212> TYPE: PRT
<213> ORGANISM: Artificial Sequence
<220> FEATURE:
<223> OTHER INFORMATION: Description of Artificial Sequence: Synthetic
      CDR1 of anti-ADAMTS5 Nanobody

<400> SEQUENCE: 22

Gly Ser Ala Val Ser Val Asn Ala Met Ala
1               5                   10

<210> SEQ ID NO 23
<211> LENGTH: 10
<212> TYPE: PRT
<213> ORGANISM: Artificial Sequence
<220> FEATURE:
<223> OTHER INFORMATION: Description of Artificial Sequence: Synthetic
      CDR1 of anti-ADAMTS5 Nanobody

<400> SEQUENCE: 23

Gly Arg Thr Phe Ser Thr Tyr Phe Val Gly
1               5                   10

<210> SEQ ID NO 24
<211> LENGTH: 10
<212> TYPE: PRT
<213> ORGANISM: Artificial Sequence
<220> FEATURE:
```

```
<223> OTHER INFORMATION: Description of Artificial Sequence: Synthetic
      CDR1 of anti-ADAMTS5 Nanobody

<400> SEQUENCE: 24

Arg Arg Thr Phe Ser Ser Tyr Val Met Ala
1               5                   10

<210> SEQ ID NO 25
<211> LENGTH: 12
<212> TYPE: PRT
<213> ORGANISM: Artificial Sequence
<220> FEATURE:
<223> OTHER INFORMATION: Description of Artificial Sequence: Synthetic
      CDR1 of anti-ADAMTS5 Nanobody

<400> SEQUENCE: 25

Gly Pro Gly Arg Thr Phe Ala Arg Tyr Ala Met Gly
1               5                   10

<210> SEQ ID NO 26
<211> LENGTH: 11
<212> TYPE: PRT
<213> ORGANISM: Artificial Sequence
<220> FEATURE:
<223> OTHER INFORMATION: Description of Artificial Sequence: Synthetic
      CDR1 of anti-ADAMTS5 Nanobody

<400> SEQUENCE: 26

Gly Arg Thr Thr Phe Ser Ser Tyr Ala Met Gly
1               5                   10

<210> SEQ ID NO 27
<211> LENGTH: 10
<212> TYPE: PRT
<213> ORGANISM: Artificial Sequence
<220> FEATURE:
<223> OTHER INFORMATION: Description of Artificial Sequence: Synthetic
      CDR1 of anti-ADAMTS5 Nanobody

<400> SEQUENCE: 27

Gly Leu Thr Phe Arg Arg Asn Ala Met Gly
1               5                   10

<210> SEQ ID NO 28
<211> LENGTH: 10
<212> TYPE: PRT
<213> ORGANISM: Artificial Sequence
<220> FEATURE:
<223> OTHER INFORMATION: Description of Artificial Sequence: Synthetic
      CDR1 of anti-ADAMTS5 Nanobody

<400> SEQUENCE: 28

Gly Phe Thr Phe Ser Pro Tyr Tyr Met Gly
1               5                   10

<210> SEQ ID NO 29
<211> LENGTH: 10
<212> TYPE: PRT
<213> ORGANISM: Artificial Sequence
<220> FEATURE:
<223> OTHER INFORMATION: Description of Artificial Sequence: Synthetic
      CDR1 of anti-ADAMTS5 Nanobody

<400> SEQUENCE: 29

Gly Arg Ala Leu Ser Ser Ser Ile Met Gly
1               5                   10
```

```
<210> SEQ ID NO 30
<211> LENGTH: 10
<212> TYPE: PRT
<213> ORGANISM: Artificial Sequence
<220> FEATURE:
<223> OTHER INFORMATION: Description of Artificial Sequence: Synthetic
      CDR1 of anti-ADAMTS5 Nanobody

<400> SEQUENCE: 30

Gly Ser Asp Val Val Asn Asp Met Gly
1               5                   10

<210> SEQ ID NO 31
<211> LENGTH: 10
<212> TYPE: PRT
<213> ORGANISM: Artificial Sequence
<220> FEATURE:
<223> OTHER INFORMATION: Description of Artificial Sequence: Synthetic
      CDR1 of anti-ADAMTS5 Nanobody

<400> SEQUENCE: 31

Gly Ser Ile Phe Ser Ile Asn Val Met Gly
1               5                   10

<210> SEQ ID NO 32
<211> LENGTH: 10
<212> TYPE: PRT
<213> ORGANISM: Artificial Sequence
<220> FEATURE:
<223> OTHER INFORMATION: Description of Artificial Sequence: Synthetic
      CDR1 of anti-ADAMTS5 Nanobody

<400> SEQUENCE: 32

Gly Leu Thr Phe Ser Ser Tyr Thr Met Gly
1               5                   10

<210> SEQ ID NO 33
<211> LENGTH: 10
<212> TYPE: PRT
<213> ORGANISM: Artificial Sequence
<220> FEATURE:
<223> OTHER INFORMATION: Description of Artificial Sequence: Synthetic
      CDR1 of anti-ADAMTS5 Nanobody

<400> SEQUENCE: 33

Arg Arg Thr Ile Ser Ser Gly Thr Met Gly
1               5                   10

<210> SEQ ID NO 34
<211> LENGTH: 10
<212> TYPE: PRT
<213> ORGANISM: Artificial Sequence
<220> FEATURE:
<223> OTHER INFORMATION: Description of Artificial Sequence: Synthetic
      CDR1 of anti-ADAMTS5 Nanobody

<400> SEQUENCE: 34

Gly Ser Ile Phe Ser Ile Asp Ala Met Gly
1               5                   10

<210> SEQ ID NO 35
<211> LENGTH: 6
<212> TYPE: PRT
<213> ORGANISM: Artificial Sequence
<220> FEATURE:
<223> OTHER INFORMATION: Description of Artificial Sequence: Synthetic
      CDR1 of anti-ADAMTS5 Nanobody

<400> SEQUENCE: 35
```

Gly Arg Tyr Pro Met Ala
1               5

<210> SEQ ID NO 36
<211> LENGTH: 10
<212> TYPE: PRT
<213> ORGANISM: Artificial Sequence
<220> FEATURE:
<223> OTHER INFORMATION: Description of Artificial Sequence: Synthetic
      CDR2 of anti-ADAMTS5 Nanobody

<400> SEQUENCE: 36

Gly Ile Ser Arg Ser Ala Gly Arg Thr Tyr
1               5                   10

<210> SEQ ID NO 37
<211> LENGTH: 10
<212> TYPE: PRT
<213> ORGANISM: Artificial Sequence
<220> FEATURE:
<223> OTHER INFORMATION: Description of Artificial Sequence: Synthetic
      CDR2 of anti-ADAMTS5 Nanobody

<400> SEQUENCE: 37

Gly Ile Ser Arg Ser Ala Glu Arg Thr Tyr
1               5                   10

<210> SEQ ID NO 38
<211> LENGTH: 11
<212> TYPE: PRT
<213> ORGANISM: Artificial Sequence
<220> FEATURE:
<223> OTHER INFORMATION: Description of Artificial Sequence: Synthetic
      CDR2 of anti-ADAMTS5 Nanobody

<400> SEQUENCE: 38

Ala Ile Ser Arg Asn Gly Ala Arg Thr Tyr Tyr
1               5                   10

<210> SEQ ID NO 39
<211> LENGTH: 10
<212> TYPE: PRT
<213> ORGANISM: Artificial Sequence
<220> FEATURE:
<223> OTHER INFORMATION: Description of Artificial Sequence: Synthetic
      CDR2 of anti-ADAMTS5 Nanobody

<400> SEQUENCE: 39

Ala Ile Ser Arg Ser Gly Asp Ser Thr Tyr
1               5                   10

<210> SEQ ID NO 40
<211> LENGTH: 10
<212> TYPE: PRT
<213> ORGANISM: Artificial Sequence
<220> FEATURE:
<223> OTHER INFORMATION: Description of Artificial Sequence: Synthetic
      CDR2 of anti-ADAMTS5 Nanobody

<400> SEQUENCE: 40

Gly Ile Ser Gly Ser Gly Asp Ser Thr Tyr
1               5                   10

<210> SEQ ID NO 41
<211> LENGTH: 9
<212> TYPE: PRT
<213> ORGANISM: Artificial Sequence

```
<220> FEATURE:
<223> OTHER INFORMATION: Description of Artificial Sequence: Synthetic
      CDR2 of anti-ADAMTS5 Nanobody

<400> SEQUENCE: 41

Thr Ile Trp Ser Gly Gly Leu Thr Val
1               5

<210> SEQ ID NO 42
<211> LENGTH: 10
<212> TYPE: PRT
<213> ORGANISM: Artificial Sequence
<220> FEATURE:
<223> OTHER INFORMATION: Description of Artificial Sequence: Synthetic
      CDR2 of anti-ADAMTS5 Nanobody

<400> SEQUENCE: 42

Gly Ile Asn Trp Ser Gly Gly Thr Thr Tyr
1               5                   10

<210> SEQ ID NO 43
<211> LENGTH: 10
<212> TYPE: PRT
<213> ORGANISM: Artificial Sequence
<220> FEATURE:
<223> OTHER INFORMATION: Description of Artificial Sequence: Synthetic
      CDR2 of anti-ADAMTS5 Nanobody

<400> SEQUENCE: 43

Ala Ile Thr Arg Ser Arg Gly Thr Thr Tyr
1               5                   10

<210> SEQ ID NO 44
<211> LENGTH: 10
<212> TYPE: PRT
<213> ORGANISM: Artificial Sequence
<220> FEATURE:
<223> OTHER INFORMATION: Description of Artificial Sequence: Synthetic
      CDR2 of anti-ADAMTS5 Nanobody

<400> SEQUENCE: 44

Ala Ile Ser Arg Ser Arg Gly Thr Thr Tyr
1               5                   10

<210> SEQ ID NO 45
<211> LENGTH: 10
<212> TYPE: PRT
<213> ORGANISM: Artificial Sequence
<220> FEATURE:
<223> OTHER INFORMATION: Description of Artificial Sequence: Synthetic
      CDR2 of anti-ADAMTS5 Nanobody

<400> SEQUENCE: 45

Ala Ile Ser Trp Ser Arg Gly Ile Leu Tyr
1               5                   10

<210> SEQ ID NO 46
<211> LENGTH: 13
<212> TYPE: PRT
<213> ORGANISM: Artificial Sequence
<220> FEATURE:
<223> OTHER INFORMATION: Description of Artificial Sequence: Synthetic
      CDR2 of anti-ADAMTS5 Nanobody

<400> SEQUENCE: 46

Ala Ile Thr Trp Ser Gly Gly Arg Ala Tyr Tyr Ala Asp
1               5                   10
```

```
<210> SEQ ID NO 47
<211> LENGTH: 9
<212> TYPE: PRT
<213> ORGANISM: Artificial Sequence
<220> FEATURE:
<223> OTHER INFORMATION: Description of Artificial Sequence: Synthetic
      CDR2 of anti-ADAMTS5 Nanobody

<400> SEQUENCE: 47

Asp Ile Thr Thr Gly Gly Arg Thr Asn
1               5

<210> SEQ ID NO 48
<211> LENGTH: 9
<212> TYPE: PRT
<213> ORGANISM: Artificial Sequence
<220> FEATURE:
<223> OTHER INFORMATION: Description of Artificial Sequence: Synthetic
      CDR2 of anti-ADAMTS5 Nanobody

<400> SEQUENCE: 48

Ala Ile Ile Ser Gly Gly Arg Thr Asn
1               5

<210> SEQ ID NO 49
<211> LENGTH: 10
<212> TYPE: PRT
<213> ORGANISM: Artificial Sequence
<220> FEATURE:
<223> OTHER INFORMATION: Description of Artificial Sequence: Synthetic
      CDR2 of anti-ADAMTS5 Nanobody

<400> SEQUENCE: 49

Ala Ile Ser Trp Asn Thr Phe Thr Thr Tyr
1               5                   10

<210> SEQ ID NO 50
<211> LENGTH: 10
<212> TYPE: PRT
<213> ORGANISM: Artificial Sequence
<220> FEATURE:
<223> OTHER INFORMATION: Description of Artificial Sequence: Synthetic
      CDR2 of anti-ADAMTS5 Nanobody

<400> SEQUENCE: 50

Ala Ile Arg Trp Ser Ser Gly Met Pro Tyr
1               5                   10

<210> SEQ ID NO 51
<211> LENGTH: 10
<212> TYPE: PRT
<213> ORGANISM: Artificial Sequence
<220> FEATURE:
<223> OTHER INFORMATION: Description of Artificial Sequence: Synthetic
      CDR2 of anti-ADAMTS5 Nanobody

<400> SEQUENCE: 51

Ala Ile Arg Trp Ser Ser Gly Ile Thr Phe
1               5                   10

<210> SEQ ID NO 52
<211> LENGTH: 9
<212> TYPE: PRT
<213> ORGANISM: Artificial Sequence
<220> FEATURE:
<223> OTHER INFORMATION: Description of Artificial Sequence: Synthetic
      CDR2 of anti-ADAMTS5 Nanobody
```

```
<400> SEQUENCE: 52

Ser Val Thr Thr Gly Ala Ser Pro Asn
1               5

<210> SEQ ID NO 53
<211> LENGTH: 10
<212> TYPE: PRT
<213> ORGANISM: Artificial Sequence
<220> FEATURE:
<223> OTHER INFORMATION: Description of Artificial Sequence: Synthetic
      CDR2 of anti-ADAMTS5 Nanobody

<400> SEQUENCE: 53

Gly Val Ser Trp Gly Gly Asp Arg Thr Tyr
1               5                   10

<210> SEQ ID NO 54
<211> LENGTH: 15
<212> TYPE: PRT
<213> ORGANISM: Artificial Sequence
<220> FEATURE:
<223> OTHER INFORMATION: Description of Artificial Sequence: Synthetic
      CDR3 of anti-ADAMTS5 Nanobody

<400> SEQUENCE: 54

Asp Leu Asp Pro Asn Arg Ile Phe Ser Arg Asp Glu Ala Ala Tyr
1               5                   10                  15

<210> SEQ ID NO 55
<211> LENGTH: 15
<212> TYPE: PRT
<213> ORGANISM: Artificial Sequence
<220> FEATURE:
<223> OTHER INFORMATION: Description of Artificial Sequence: Synthetic
      CDR3 of anti-ADAMTS5 Nanobody

<400> SEQUENCE: 55

Asp Leu Asp Pro Asn Arg Ile Phe Ser Arg Glu Glu Tyr Ala Tyr
1               5                   10                  15

<210> SEQ ID NO 56
<211> LENGTH: 16
<212> TYPE: PRT
<213> ORGANISM: Artificial Sequence
<220> FEATURE:
<223> OTHER INFORMATION: Description of Artificial Sequence: Synthetic
      CDR3 of anti-ADAMTS5 Nanobody

<400> SEQUENCE: 56

Ala Arg Ile Ser Pro Ser Asp Pro Ser Asn Glu Asp Gly Tyr Asp Tyr
1               5                   10                  15

<210> SEQ ID NO 57
<211> LENGTH: 17
<212> TYPE: PRT
<213> ORGANISM: Artificial Sequence
<220> FEATURE:
<223> OTHER INFORMATION: Description of Artificial Sequence: Synthetic
      CDR3 of anti-ADAMTS5 Nanobody

<400> SEQUENCE: 57

Ser Arg Ala Pro Ser Phe Arg Thr Ile Asp Ala Ile Asn Tyr Tyr Asp
1               5                   10                  15

Tyr

<210> SEQ ID NO 58
```

```
<210> SEQ ID NO 58
<211> LENGTH: 15
<212> TYPE: PRT
<213> ORGANISM: Artificial Sequence
<220> FEATURE:
<223> OTHER INFORMATION: Description of Artificial Sequence: Synthetic
      CDR3 of anti-ADAMTS5 Nanobody

<400> SEQUENCE: 58

Asp Arg Glu Ile Asn Arg Ile Ala Asn Asp Lys Glu Leu Asp Phe
1               5                   10                  15

<210> SEQ ID NO 59
<211> LENGTH: 14
<212> TYPE: PRT
<213> ORGANISM: Artificial Sequence
<220> FEATURE:
<223> OTHER INFORMATION: Description of Artificial Sequence: Synthetic
      CDR3 of anti-ADAMTS5 Nanobody

<400> SEQUENCE: 59

Glu Ala Val Gly Thr Tyr Tyr Thr Pro Asp Gly Trp Thr Tyr
1               5                   10

<210> SEQ ID NO 60
<211> LENGTH: 15
<212> TYPE: PRT
<213> ORGANISM: Artificial Sequence
<220> FEATURE:
<223> OTHER INFORMATION: Description of Artificial Sequence: Synthetic
      CDR3 of anti-ADAMTS5 Nanobody

<400> SEQUENCE: 60

Asp Gly Asp Ile Gly Thr Leu Val Asn Asp Glu Asn Pro Arg Tyr
1               5                   10                  15

<210> SEQ ID NO 61
<211> LENGTH: 15
<212> TYPE: PRT
<213> ORGANISM: Artificial Sequence
<220> FEATURE:
<223> OTHER INFORMATION: Description of Artificial Sequence: Synthetic
      CDR3 of anti-ADAMTS5 Nanobody

<400> SEQUENCE: 61

Gly Arg Ser Pro Gly Asp Pro Ser Arg Thr Tyr Leu Tyr Glu Tyr
1               5                   10                  15

<210> SEQ ID NO 62
<211> LENGTH: 15
<212> TYPE: PRT
<213> ORGANISM: Artificial Sequence
<220> FEATURE:
<223> OTHER INFORMATION: Description of Artificial Sequence: Synthetic
      CDR3 of anti-ADAMTS5 Nanobody

<400> SEQUENCE: 62

Gly Arg Ser Pro Gly Asp Pro Ser Arg Thr Tyr Leu Tyr Asp Tyr
1               5                   10                  15

<210> SEQ ID NO 63
<211> LENGTH: 15
<212> TYPE: PRT
<213> ORGANISM: Artificial Sequence
<220> FEATURE:
<223> OTHER INFORMATION: Description of Artificial Sequence: Synthetic
      CDR3 of anti-ADAMTS5 Nanobody

<400> SEQUENCE: 63
```

```
Ser Arg Ser Pro Gly Asp Pro Ser Arg Thr Tyr Leu Tyr Asp Tyr
1               5                   10                  15
```

<210> SEQ ID NO 64
<211> LENGTH: 15
<212> TYPE: PRT
<213> ORGANISM: Artificial Sequence
<220> FEATURE:
<223> OTHER INFORMATION: Description of Artificial Sequence: Synthetic
      CDR3 of anti-ADAMTS5 Nanobody

<400> SEQUENCE: 64

```
Ala Leu Ala Ile Pro Val Thr Met Ser Pro His Glu Tyr Pro Tyr
1               5                   10                  15
```

<210> SEQ ID NO 65
<211> LENGTH: 13
<212> TYPE: PRT
<213> ORGANISM: Artificial Sequence
<220> FEATURE:
<223> OTHER INFORMATION: Description of Artificial Sequence: Synthetic
      CDR3 of anti-ADAMTS5 Nanobody

<400> SEQUENCE: 65

```
Gln Val Gly Asp Ser Asp Asp Val Trp Tyr Ala Tyr
1               5                   10
```

<210> SEQ ID NO 66
<211> LENGTH: 11
<212> TYPE: PRT
<213> ORGANISM: Artificial Sequence
<220> FEATURE:
<223> OTHER INFORMATION: Description of Artificial Sequence: Synthetic
      CDR3 of anti-ADAMTS5 Nanobody

<400> SEQUENCE: 66

```
Glu Val Asp Ala Gly Ile Tyr Ala Tyr Gly Tyr
1               5                   10
```

<210> SEQ ID NO 67
<211> LENGTH: 15
<212> TYPE: PRT
<213> ORGANISM: Artificial Sequence
<220> FEATURE:
<223> OTHER INFORMATION: Description of Artificial Sequence: Synthetic
      CDR3 of anti-ADAMTS5 Nanobody

<400> SEQUENCE: 67

```
Ala Gly Gly Ser Pro Arg Gln His Glu Pro Tyr Glu Tyr Arg Val
1               5                   10                  15
```

<210> SEQ ID NO 68
<211> LENGTH: 16
<212> TYPE: PRT
<213> ORGANISM: Artificial Sequence
<220> FEATURE:
<223> OTHER INFORMATION: Description of Artificial Sequence: Synthetic
      CDR3 of anti-ADAMTS5 Nanobody

<400> SEQUENCE: 68

```
Asp Arg Ser Ala Phe Arg Asp Pro Ser Phe Asp Val Asn Tyr Glu Tyr
1               5                   10                  15
```

<210> SEQ ID NO 69
<211> LENGTH: 16
<212> TYPE: PRT
<213> ORGANISM: Artificial Sequence
<220> FEATURE:

<223> OTHER INFORMATION: Description of Artificial Sequence: Synthetic
      CDR3 of anti-ADAMTS5 Nanobody

<400> SEQUENCE: 69

Asp Arg Ser Ala Leu Arg Asp Pro Ser Phe Glu Val Asn Tyr Glu Tyr
1               5                   10                  15

<210> SEQ ID NO 70
<211> LENGTH: 12
<212> TYPE: PRT
<213> ORGANISM: Artificial Sequence
<220> FEATURE:
<223> OTHER INFORMATION: Description of Artificial Sequence: Synthetic
      CDR3 of anti-ADAMTS5 Nanobody

<400> SEQUENCE: 70

Ile Met Thr Ile Pro Gly Gly Ser Gln Ile Met Tyr
1               5                   10

<210> SEQ ID NO 71
<211> LENGTH: 15
<212> TYPE: PRT
<213> ORGANISM: Artificial Sequence
<220> FEATURE:
<223> OTHER INFORMATION: Description of Artificial Sequence: Synthetic
      CDR3 of anti-ADAMTS5 Nanobody

<400> SEQUENCE: 71

Asp Pro Trp Gly Arg Leu Phe Arg Val Lys Asp Asn Tyr Ser Asp
1               5                   10                  15

<210> SEQ ID NO 72
<211> LENGTH: 25
<212> TYPE: PRT
<213> ORGANISM: Artificial Sequence
<220> FEATURE:
<223> OTHER INFORMATION: Description of Artificial Sequence: Synthetic
      Framework FR1 of anti-ADAMTS5 Nanobody

<400> SEQUENCE: 72

Glu Val Gln Leu Val Glu Ser Gly Gly Gly Leu Val Gln Ala Gly Gly
1               5                   10                  15

Ser Leu Arg Leu Ser Cys Ala Ala Ser
            20                  25

<210> SEQ ID NO 73
<211> LENGTH: 25
<212> TYPE: PRT
<213> ORGANISM: Artificial Sequence
<220> FEATURE:
<223> OTHER INFORMATION: Description of Artificial Sequence: Synthetic
      Framework FR1 of anti-ADAMTS5 Nanobody

<400> SEQUENCE: 73

Glu Val Gln Leu Val Glu Ser Gly Gly Gly Leu Val Gln Ser Gly Gly
1               5                   10                  15

Ser Leu Arg Leu Ser Cys Ala Ala Ser
            20                  25

<210> SEQ ID NO 74
<211> LENGTH: 25
<212> TYPE: PRT
<213> ORGANISM: Artificial Sequence
<220> FEATURE:
<223> OTHER INFORMATION: Description of Artificial Sequence: Synthetic
      Framework FR1 of anti-ADAMTS5 Nanobody

```
<400> SEQUENCE: 74

Glu Val Gln Leu Val Glu Ser Gly Gly Gly Leu Val Gln Ala Gly Asp
1               5                   10                  15

Ser Leu Arg Leu Ser Cys Ala Ala Ser
            20                  25

<210> SEQ ID NO 75
<211> LENGTH: 25
<212> TYPE: PRT
<213> ORGANISM: Artificial Sequence
<220> FEATURE:
<223> OTHER INFORMATION: Description of Artificial Sequence: Synthetic
      Framework FR1 of anti-ADAMTS5 Nanobody

<400> SEQUENCE: 75

Glu Val Gln Leu Val Glu Ser Gly Gly Gly Leu Val Gln Pro Gly Gly
1               5                   10                  15

Ser Leu Arg Leu Ser Cys Ala Ala Ser
            20                  25

<210> SEQ ID NO 76
<211> LENGTH: 25
<212> TYPE: PRT
<213> ORGANISM: Artificial Sequence
<220> FEATURE:
<223> OTHER INFORMATION: Description of Artificial Sequence: Synthetic
      Framework FR1 of anti-ADAMTS5 Nanobody

<400> SEQUENCE: 76

Glu Val Gln Leu Val Glu Ser Gly Gly Gly Leu Val Gln Ala Gly Gly
1               5                   10                  15

Ser Leu Arg Leu Ser Cys Ser Phe Ser
            20                  25

<210> SEQ ID NO 77
<211> LENGTH: 25
<212> TYPE: PRT
<213> ORGANISM: Artificial Sequence
<220> FEATURE:
<223> OTHER INFORMATION: Description of Artificial Sequence: Synthetic
      Framework FR1 of anti-ADAMTS5 Nanobody

<400> SEQUENCE: 77

Glu Val Gln Leu Val Glu Ser Gly Gly Gly Leu Val Gln Ala Gly Gly
1               5                   10                  15

Ser Leu Arg Leu Ser Cys Ala Thr Ser
            20                  25

<210> SEQ ID NO 78
<211> LENGTH: 25
<212> TYPE: PRT
<213> ORGANISM: Artificial Sequence
<220> FEATURE:
<223> OTHER INFORMATION: Description of Artificial Sequence: Synthetic
      Framework FR1 of anti-ADAMTS5 Nanobody

<400> SEQUENCE: 78

Glu Val Gln Leu Val Glu Ser Gly Gly Gly Leu Val Gln Ala Gly Gly
1               5                   10                  15

Ser Leu Arg Leu Ser Cys Ala Pro Ser
            20                  25

<210> SEQ ID NO 79
<211> LENGTH: 25
```

```
<212> TYPE: PRT
<213> ORGANISM: Artificial Sequence
<220> FEATURE:
<223> OTHER INFORMATION: Description of Artificial Sequence: Synthetic
      Framework FR1 of anti-ADAMTS5 Nanobody

<400> SEQUENCE: 79

Glu Val Gln Leu Val Glu Ser Gly Gly Gly Leu Val Gln Ala Gly Ala
1               5                   10                  15

Ser Leu Arg Leu Ser Cys Ala Thr Ser
            20                  25

<210> SEQ ID NO 80
<211> LENGTH: 25
<212> TYPE: PRT
<213> ORGANISM: Artificial Sequence
<220> FEATURE:
<223> OTHER INFORMATION: Description of Artificial Sequence: Synthetic
      Framework FR1 of anti-ADAMTS5 Nanobody

<400> SEQUENCE: 80

Glu Val Gln Leu Val Glu Ser Gly Gly Asp Leu Val Gln Pro Gly Gly
1               5                   10                  15

Ser Leu Arg Leu Ser Cys Ala Ala Ser
            20                  25

<210> SEQ ID NO 81
<211> LENGTH: 25
<212> TYPE: PRT
<213> ORGANISM: Artificial Sequence
<220> FEATURE:
<223> OTHER INFORMATION: Description of Artificial Sequence: Synthetic
      Framework FR1 of anti-ADAMTS5 Nanobody

<400> SEQUENCE: 81

Glu Val Gln Leu Val Glu Ser Gly Gly Gly Phe Val Gln Ala Gly Gly
1               5                   10                  15

Ser Leu Arg Leu Ser Cys Val Ala Ser
            20                  25

<210> SEQ ID NO 82
<211> LENGTH: 25
<212> TYPE: PRT
<213> ORGANISM: Artificial Sequence
<220> FEATURE:
<223> OTHER INFORMATION: Description of Artificial Sequence: Synthetic
      Framework FR1 of anti-ADAMTS5 Nanobody

<400> SEQUENCE: 82

Glu Val Gln Leu Val Glu Ser Gly Gly Gly Phe Val Gln Ala Gly Gly
1               5                   10                  15

Ser Leu Arg Leu Ser Cys Ala Ala Ser
            20                  25

<210> SEQ ID NO 83
<211> LENGTH: 25
<212> TYPE: PRT
<213> ORGANISM: Artificial Sequence
<220> FEATURE:
<223> OTHER INFORMATION: Description of Artificial Sequence: Synthetic
      Framework FR1 of anti-ADAMTS5 Nanobody

<400> SEQUENCE: 83

Glu Val Gln Leu Val Glu Ser Gly Gly Gly Leu Val Gln Ala Gly Gly
1               5                   10                  15
```

Ser Leu Arg Leu Ser Cys Val Ala Ser
            20                  25

<210> SEQ ID NO 84
<211> LENGTH: 25
<212> TYPE: PRT
<213> ORGANISM: Artificial Sequence
<220> FEATURE:
<223> OTHER INFORMATION: Description of Artificial Sequence: Synthetic
      Framework FR1 of anti-ADAMTS5 Nanobody

<400> SEQUENCE: 84

Glu Val Gln Leu Val Glu Ser Gly Gly Gly Ser Val Gln Ala Gly Gly
1               5                   10                  15

Ser Leu Arg Leu Ser Cys Val Ala Ser
            20                  25

<210> SEQ ID NO 85
<211> LENGTH: 14
<212> TYPE: PRT
<213> ORGANISM: Artificial Sequence
<220> FEATURE:
<223> OTHER INFORMATION: Description of Artificial Sequence: Synthetic
      Framework FR2 of anti-ADAMTS5 Nanobody

<400> SEQUENCE: 85

Trp Phe Arg Gln Ala Pro Gly Lys Glu Arg Asp Phe Val Ala
1               5                   10

<210> SEQ ID NO 86
<211> LENGTH: 14
<212> TYPE: PRT
<213> ORGANISM: Artificial Sequence
<220> FEATURE:
<223> OTHER INFORMATION: Description of Artificial Sequence: Synthetic
      Framework FR2 of anti-ADAMTS5 Nanobody

<400> SEQUENCE: 86

Trp Phe Arg Leu Ala Pro Gly Lys Glu Arg Glu Phe Val Ala
1               5                   10

<210> SEQ ID NO 87
<211> LENGTH: 14
<212> TYPE: PRT
<213> ORGANISM: Artificial Sequence
<220> FEATURE:
<223> OTHER INFORMATION: Description of Artificial Sequence: Synthetic
      Framework FR2 of anti-ADAMTS5 Nanobody

<400> SEQUENCE: 87

Trp Tyr Arg Gln Ala Pro Gly Lys Gln Arg Asp Phe Val Ala
1               5                   10

<210> SEQ ID NO 88
<211> LENGTH: 14
<212> TYPE: PRT
<213> ORGANISM: Artificial Sequence
<220> FEATURE:
<223> OTHER INFORMATION: Description of Artificial Sequence: Synthetic
      Framework FR2 of anti-ADAMTS5 Nanobody

<400> SEQUENCE: 88

Trp Phe Arg Gln Ala Pro Gly Lys Glu Arg Glu Phe Val Ala
1               5                   10

<210> SEQ ID NO 89
<211> LENGTH: 14

```
<212> TYPE: PRT
<213> ORGANISM: Artificial Sequence
<220> FEATURE:
<223> OTHER INFORMATION: Description of Artificial Sequence: Synthetic
      Framework FR2 of anti-ADAMTS5 Nanobody

<400> SEQUENCE: 89

Trp Phe Arg Gln Ala Pro Gly Lys Asn Arg Asp Phe Ile Thr
1               5                   10

<210> SEQ ID NO 90
<211> LENGTH: 14
<212> TYPE: PRT
<213> ORGANISM: Artificial Sequence
<220> FEATURE:
<223> OTHER INFORMATION: Description of Artificial Sequence: Synthetic
      Framework FR2 of anti-ADAMTS5 Nanobody

<400> SEQUENCE: 90

Trp Phe Arg Gln Ala Pro Gly Lys Glu Arg Ala Phe Val Ala
1               5                   10

<210> SEQ ID NO 91
<211> LENGTH: 14
<212> TYPE: PRT
<213> ORGANISM: Artificial Sequence
<220> FEATURE:
<223> OTHER INFORMATION: Description of Artificial Sequence: Synthetic
      Framework FR2 of anti-ADAMTS5 Nanobody

<400> SEQUENCE: 91

Trp Phe Arg Gln Ala Pro Gly Lys Glu Arg Glu Leu Leu Ala
1               5                   10

<210> SEQ ID NO 92
<211> LENGTH: 14
<212> TYPE: PRT
<213> ORGANISM: Artificial Sequence
<220> FEATURE:
<223> OTHER INFORMATION: Description of Artificial Sequence: Synthetic
      Framework FR2 of anti-ADAMTS5 Nanobody

<400> SEQUENCE: 92

Trp Tyr Arg Gln Ala Pro Gly Lys Gln Arg Glu Leu Val Ala
1               5                   10

<210> SEQ ID NO 93
<211> LENGTH: 14
<212> TYPE: PRT
<213> ORGANISM: Artificial Sequence
<220> FEATURE:
<223> OTHER INFORMATION: Description of Artificial Sequence: Synthetic
      Framework FR2 of anti-ADAMTS5 Nanobody

<400> SEQUENCE: 93

Trp Phe Arg Gln Ala Pro Gly Gln Glu Arg Glu Phe Val Ser
1               5                   10

<210> SEQ ID NO 94
<211> LENGTH: 14
<212> TYPE: PRT
<213> ORGANISM: Artificial Sequence
<220> FEATURE:
<223> OTHER INFORMATION: Description of Artificial Sequence: Synthetic
      Framework FR2 of anti-ADAMTS5 Nanobody

<400> SEQUENCE: 94

Trp Tyr Arg Gln Ala Pro Gly Lys Glu Arg Glu Leu Val Ala
```

<210> SEQ ID NO 95
<211> LENGTH: 39
<212> TYPE: PRT
<213> ORGANISM: Artificial Sequence
<220> FEATURE:
<223> OTHER INFORMATION: Description of Artificial Sequence: Synthetic
      Framework FR3 of anti-ADAMTS5 Nanobody

<400> SEQUENCE: 95

Tyr Val Asp Ser Val Lys Gly Arg Phe Thr Ile Ser Arg Asp Ser Ala
1               5                   10                  15

Lys Asn Thr Val Tyr Leu Gln Met Asn Arg Leu Lys Pro Glu Asp Thr
            20                  25                  30

Ala Val Tyr Tyr Cys Ala Ala
        35

<210> SEQ ID NO 96
<211> LENGTH: 39
<212> TYPE: PRT
<213> ORGANISM: Artificial Sequence
<220> FEATURE:
<223> OTHER INFORMATION: Description of Artificial Sequence: Synthetic
      Framework FR3 of anti-ADAMTS5 Nanobody

<400> SEQUENCE: 96

Tyr Val Asp Ser Leu Lys Gly Arg Phe Thr Ile Ser Arg Asp Ser Ala
1               5                   10                  15

Lys Asn Thr Val Tyr Leu His Met Asn Arg Leu Lys Pro Glu Asp Thr
            20                  25                  30

Ala Val Tyr Tyr Cys Ala Ala
        35

<210> SEQ ID NO 97
<211> LENGTH: 39
<212> TYPE: PRT
<213> ORGANISM: Artificial Sequence
<220> FEATURE:
<223> OTHER INFORMATION: Description of Artificial Sequence: Synthetic
      Framework FR3 of anti-ADAMTS5 Nanobody

<400> SEQUENCE: 97

Tyr Thr Asp Ser Val Lys Asp Arg Phe Thr Ile Ala Arg Asp Ser Ala
1               5                   10                  15

Lys Asn Thr Val Tyr Leu Gln Met Asn Arg Leu Lys Pro Glu Asp Thr
            20                  25                  30

Ala Val Tyr Tyr Cys Ala Ala
        35

<210> SEQ ID NO 98
<211> LENGTH: 38
<212> TYPE: PRT
<213> ORGANISM: Artificial Sequence
<220> FEATURE:
<223> OTHER INFORMATION: Description of Artificial Sequence: Synthetic
      Framework FR3 of anti-ADAMTS5 Nanobody

<400> SEQUENCE: 98

Tyr Asp Ser Val Ala Gly Leu Phe Thr Ile Ser Arg Asp Asn Ala Lys
1               5                   10                  15

Asn Thr Val Tyr Leu Gln Met Ser Ser Leu Lys Pro Glu Asp Thr Ala
            20                  25                  30

Val Tyr Tyr Cys Ala Ala
        35

<210> SEQ ID NO 99
<211> LENGTH: 39
<212> TYPE: PRT
<213> ORGANISM: Artificial Sequence
<220> FEATURE:
<223> OTHER INFORMATION: Description of Artificial Sequence: Synthetic
      Framework FR3 of anti-ADAMTS5 Nanobody

<400> SEQUENCE: 99

Tyr Tyr Asp Ser Leu Glu Gly Arg Phe Thr Ile Ser Arg Asp Asn Ala
1               5                   10                  15

Lys Asn Thr Val His Leu Gln Met Asn Ser Leu Lys Pro Glu Asp Thr
            20                  25                  30

Ala Val Tyr Ile Cys Ala Ala
        35

<210> SEQ ID NO 100
<211> LENGTH: 39
<212> TYPE: PRT
<213> ORGANISM: Artificial Sequence
<220> FEATURE:
<223> OTHER INFORMATION: Description of Artificial Sequence: Synthetic
      Framework FR3 of anti-ADAMTS5 Nanobody

<400> SEQUENCE: 100

Tyr Val Tyr Pro Met Lys Asp Arg Phe Thr Ile Ser Arg Asp Asn Ala
1               5                   10                  15

Lys Asn Met Val Tyr Leu Gln Met Asn Ala Leu Lys Pro Glu Asp Thr
            20                  25                  30

Ala Val Tyr Tyr Cys Ala Ala
        35

<210> SEQ ID NO 101
<211> LENGTH: 39
<212> TYPE: PRT
<213> ORGANISM: Artificial Sequence
<220> FEATURE:
<223> OTHER INFORMATION: Description of Artificial Sequence: Synthetic
      Framework FR3 of anti-ADAMTS5 Nanobody

<400> SEQUENCE: 101

Tyr Ala Asp Ser Ala Lys Gly Arg Phe Thr Ile Ser Arg Asp Asn Ala
1               5                   10                  15

Lys Asn Thr Val Tyr Leu Gln Met Asn Ser Leu Arg Pro Glu Asp Thr
            20                  25                  30

Ala Val Tyr Tyr Cys Ala Ala
        35

<210> SEQ ID NO 102
<211> LENGTH: 39
<212> TYPE: PRT
<213> ORGANISM: Artificial Sequence
<220> FEATURE:
<223> OTHER INFORMATION: Description of Artificial Sequence: Synthetic
      Framework FR3 of anti-ADAMTS5 Nanobody

<400> SEQUENCE: 102

Tyr Val Asp Ser Val Lys Gly Arg Phe Thr Ile Ser Arg Asp Asn Ala
1               5                   10                  15

Lys Asn Thr Val Asp Leu Gln Met Ile Ser Pro Lys Pro Glu Asp Thr
            20                  25                  30

```
Ala Val Tyr Tyr Cys Ala Ala
        35

<210> SEQ ID NO 103
<211> LENGTH: 39
<212> TYPE: PRT
<213> ORGANISM: Artificial Sequence
<220> FEATURE:
<223> OTHER INFORMATION: Description of Artificial Sequence: Synthetic
      Framework FR3 of anti-ADAMTS5 Nanobody

<400> SEQUENCE: 103

Tyr Leu Asp Ser Thr Glu Gly Arg Phe Thr Ile Ser Arg Asp Asn Ala
1               5                   10                  15

Lys Asn Thr Met Tyr Leu Gln Met Asn Ser Leu Asn Pro Glu Asp Thr
            20                  25                  30

Ala Val Tyr Tyr Cys Ala Ala
        35

<210> SEQ ID NO 104
<211> LENGTH: 39
<212> TYPE: PRT
<213> ORGANISM: Artificial Sequence
<220> FEATURE:
<223> OTHER INFORMATION: Description of Artificial Sequence: Synthetic
      Framework FR3 of anti-ADAMTS5 Nanobody

<400> SEQUENCE: 104

Tyr Leu Asp Ser Thr Glu Gly Arg Phe Thr Ile Ser Arg Asp Asn Ala
1               5                   10                  15

Asn Asp Thr Val Tyr Leu Gln Met Asn Ser Leu Asn Pro Glu Asp Thr
            20                  25                  30

Ala Val Tyr Tyr Cys Ala Ala
        35

<210> SEQ ID NO 105
<211> LENGTH: 39
<212> TYPE: PRT
<213> ORGANISM: Artificial Sequence
<220> FEATURE:
<223> OTHER INFORMATION: Description of Artificial Sequence: Synthetic
      Framework FR3 of anti-ADAMTS5 Nanobody

<400> SEQUENCE: 105

Tyr Thr Asp Ser Thr Glu Gly Arg Phe Thr Ile Ser Arg Asp Asn Ala
1               5                   10                  15

Lys Asn Thr Met Tyr Leu Gln Met Asp Asn Leu Asn Pro Glu Asp Thr
            20                  25                  30

Ala Val Tyr Tyr Cys Ala Ala
        35

<210> SEQ ID NO 106
<211> LENGTH: 39
<212> TYPE: PRT
<213> ORGANISM: Artificial Sequence
<220> FEATURE:
<223> OTHER INFORMATION: Description of Artificial Sequence: Synthetic
      Framework FR3 of anti-ADAMTS5 Nanobody

<400> SEQUENCE: 106

Val Ser Asp Phe Glu Lys Gly Arg Phe Thr Ile Ser Arg Asp Asn Gly
1               5                   10                  15

Lys Asn Thr Val Asn Leu Gln Met Lys Gly Leu Lys Pro Glu Asp Thr
```

-continued

```
                20                  25                  30

Ala Val Tyr Tyr Cys Ala Ala
        35

<210> SEQ ID NO 107
<211> LENGTH: 39
<212> TYPE: PRT
<213> ORGANISM: Artificial Sequence
<220> FEATURE:
<223> OTHER INFORMATION: Description of Artificial Sequence: Synthetic
      Framework FR3 of anti-ADAMTS5 Nanobody

<400> SEQUENCE: 107

Tyr Ala Asp Ser Val Lys Gly Arg Phe Thr Ile Ser Arg Asp Asn Val
1               5                   10                  15

Lys Asn Thr Val Tyr Leu Gln Met Asn Ser Leu Lys Pro Glu Asp Thr
            20                  25                  30

Ala Val Tyr Tyr Cys Asn Ala
        35

<210> SEQ ID NO 108
<211> LENGTH: 39
<212> TYPE: PRT
<213> ORGANISM: Artificial Sequence
<220> FEATURE:
<223> OTHER INFORMATION: Description of Artificial Sequence: Synthetic
      Framework FR3 of anti-ADAMTS5 Nanobody

<400> SEQUENCE: 108

Tyr Ala Asp Ser Val Lys Gly Arg Phe Thr Ile Ser Arg Asp Asn Ser
1               5                   10                  15

Lys Asn Thr Val Tyr Leu Gln Met Asn Ser Leu Arg Pro Glu Asp Thr
            20                  25                  30

Ala Val Tyr Tyr Cys Asn Ala
        35

<210> SEQ ID NO 109
<211> LENGTH: 39
<212> TYPE: PRT
<213> ORGANISM: Artificial Sequence
<220> FEATURE:
<223> OTHER INFORMATION: Description of Artificial Sequence: Synthetic
      Framework FR3 of anti-ADAMTS5 Nanobody

<400> SEQUENCE: 109

Tyr Val Asp Ser Val Lys Asp Arg Phe Thr Val Ser Arg Asp Asn Ala
1               5                   10                  15

Lys Asn Thr Leu Tyr Leu Arg Met Asn Ser Leu Lys Pro Glu Asp Thr
            20                  25                  30

Ala Val Tyr Tyr Cys Ala Ala
        35

<210> SEQ ID NO 110
<211> LENGTH: 39
<212> TYPE: PRT
<213> ORGANISM: Artificial Sequence
<220> FEATURE:
<223> OTHER INFORMATION: Description of Artificial Sequence: Synthetic
      Framework FR3 of anti-ADAMTS5 Nanobody

<400> SEQUENCE: 110

Tyr Leu Asp Ser Val Met Asp Arg Phe Thr Ile Ser Arg Asp Asn Ala
1               5                   10                  15
```

Lys Asn Thr Val Ser Leu Gln Met Asn Ser Leu Gln Pro Glu Asp Thr
            20                  25                  30

Ala Val Tyr Tyr Cys Ala Ala
        35

<210> SEQ ID NO 111
<211> LENGTH: 39
<212> TYPE: PRT
<213> ORGANISM: Artificial Sequence
<220> FEATURE:
<223> OTHER INFORMATION: Description of Artificial Sequence: Synthetic
      Framework FR3 of anti-ADAMTS5 Nanobody

<400> SEQUENCE: 111

Tyr Pro Asp Ser Val Glu Gly Arg Phe Thr Ile Ser Gly Asp Asn Ala
1               5                   10                  15

Lys Asn Thr Val Ser Leu Gln Met Asn Ser Leu Lys Pro Glu Asp Thr
            20                  25                  30

Ala Val Tyr Tyr Cys Ala Ala
        35

<210> SEQ ID NO 112
<211> LENGTH: 39
<212> TYPE: PRT
<213> ORGANISM: Artificial Sequence
<220> FEATURE:
<223> OTHER INFORMATION: Description of Artificial Sequence: Synthetic
      Framework FR3 of anti-ADAMTS5 Nanobody

<400> SEQUENCE: 112

Tyr Gly Asp Ser Val Thr Gly Arg Phe Thr Ala Ser Arg Asp Arg Ala
1               5                   10                  15

Lys Asn Ala Leu Tyr Leu Gln Met Asn Ser Leu Lys Pro Glu Asp Thr
            20                  25                  30

Ala Val Tyr Tyr Cys Asn Leu
        35

<210> SEQ ID NO 113
<211> LENGTH: 39
<212> TYPE: PRT
<213> ORGANISM: Artificial Sequence
<220> FEATURE:
<223> OTHER INFORMATION: Description of Artificial Sequence: Synthetic
      Framework FR3 of anti-ADAMTS5 Nanobody

<400> SEQUENCE: 113

Tyr Ala Asp Ser Val Gln Gly Arg Phe Thr Val Ser Arg Asp Tyr Ala
1               5                   10                  15

Lys Asn Thr Leu Tyr Leu Gln Met Asn Ser Leu Lys Pro Glu Asp Ala
            20                  25                  30

Ala Val Tyr Tyr Cys Ala Gly
        35

<210> SEQ ID NO 114
<211> LENGTH: 11
<212> TYPE: PRT
<213> ORGANISM: Artificial Sequence
<220> FEATURE:
<223> OTHER INFORMATION: Description of Artificial Sequence: Synthetic
      Framework FR4 of anti-ADAMTS5 Nanobody

<400> SEQUENCE: 114

Trp Gly Gln Gly Thr Leu Val Thr Val Ser Ser
1               5                   10

<210> SEQ ID NO 115
<211> LENGTH: 11
<212> TYPE: PRT
<213> ORGANISM: Artificial Sequence
<220> FEATURE:
<223> OTHER INFORMATION: Description of Artificial Sequence: Synthetic
      Framework FR4 of anti-ADAMTS5 Nanobody

<400> SEQUENCE: 115

Trp Gly Arg Gly Thr Leu Val Thr Val Ser Ser
1               5                   10

<210> SEQ ID NO 116
<211> LENGTH: 120
<212> TYPE: PRT
<213> ORGANISM: Artificial Sequence
<220> FEATURE:
<223> OTHER INFORMATION: Description of Artificial Sequence: Synthetic
      anti-ADAMTS5 Nanobody

<400> SEQUENCE: 116

Glu Val Gln Leu Val Glu Ser Gly Gly Gly Ser Val Gln Ala Gly Gly
1               5                   10                  15

Ser Leu Arg Leu Ser Cys Val Ala Ser Gly Arg Tyr Pro Met Ala Trp
            20                  25                  30

Phe Arg Gln Ala Pro Gly Lys Glu Arg Glu Phe Val Ala Gly Val Ser
        35                  40                  45

Trp Gly Gly Asp Arg Thr Tyr Tyr Ala Asp Ser Val Gln Gly Arg Phe
    50                  55                  60

Thr Val Ser Arg Asp Tyr Ala Lys Asn Thr Leu Tyr Leu Gln Met Asn
65                  70                  75                  80

Ser Leu Lys Pro Glu Asp Ala Ala Val Tyr Tyr Cys Ala Gly Asp Pro
                85                  90                  95

Trp Gly Arg Leu Phe Arg Val Lys Asp Gln Tyr Ser Asp Trp Gly Gln
            100                 105                 110

Gly Thr Leu Val Thr Val Ser Ser
        115                 120

<210> SEQ ID NO 117
<211> LENGTH: 124
<212> TYPE: PRT
<213> ORGANISM: Artificial Sequence
<220> FEATURE:
<223> OTHER INFORMATION: Description of Artificial Sequence: Synthetic
      anti-ADAMTS5 Nanobody

<400> SEQUENCE: 117

Glu Val Gln Leu Val Glu Ser Gly Gly Gly Leu Val Gln Ala Gly Gly
1               5                   10                  15

Ser Leu Arg Leu Ser Cys Ala Ala Ser Gly Leu Thr Phe Arg Arg Asn
            20                  25                  30

Ala Met Gly Trp Phe Arg Gln Ala Pro Gly Lys Glu Arg Glu Leu Leu
        35                  40                  45

Ala Gly Ile Ser Trp Ser Gly Gly Thr Thr Tyr Tyr Val Asp Ser Val
    50                  55                  60

Lys Gly Arg Phe Thr Ile Ser Arg Asp Asn Ala Lys Asn Thr Val Asp
65                  70                  75                  80

Leu Gln Met Ile Ser Pro Lys Pro Glu Asp Thr Ala Val Tyr Tyr Cys
                85                  90                  95

Ala Ala Asp Gly Asp Ile Gly Thr Leu Val Asn Asp Glu Asn Pro Arg
            100                 105                 110

Tyr Trp Gly Gln Gly Thr Leu Val Thr Val Ser Ser
        115                 120

<210> SEQ ID NO 118
<211> LENGTH: 15
<212> TYPE: PRT
<213> ORGANISM: Artificial Sequence
<220> FEATURE:
<223> OTHER INFORMATION: Description of Artificial Sequence: Synthetic
      CDR3 of anti-ADAMTS5 Nanobody

<400> SEQUENCE: 118

Asp Pro Trp Gly Arg Leu Phe Arg Val Lys Asp Gln Tyr Ser Asp
1               5                   10                  15

<210> SEQ ID NO 119
<211> LENGTH: 10
<212> TYPE: PRT
<213> ORGANISM: Artificial Sequence
<220> FEATURE:
<223> OTHER INFORMATION: Description of Artificial Sequence: Synthetic
      CDR2 of anti-ADAMTS5 Nanobody

<400> SEQUENCE: 119

Gly Ile Ser Trp Ser Gly Gly Thr Thr Tyr
1               5                   10

<210> SEQ ID NO 120
<211> LENGTH: 274
<212> TYPE: PRT
<213> ORGANISM: Artificial Sequence
<220> FEATURE:
<223> OTHER INFORMATION: Description of Artificial Sequence: Synthetic
      anti-ADAMTS5 Nanobody

<400> SEQUENCE: 120

Glu Val Gln Leu Val Glu Ser Gly Gly Gly Leu Val Gln Ala Gly Gly
1               5                   10                  15

Ser Leu Arg Leu Ser Cys Ala Ala Ser Gly Arg Thr Phe Ser Ser Tyr
            20                  25                  30

Ala Met Gly Trp Phe Arg Gln Ala Pro Gly Lys Glu Arg Asp Phe Val
        35                  40                  45

Ala Gly Ile Ser Arg Ser Ala Gly Arg Thr Tyr Tyr Val Asp Ser Val
    50                  55                  60

Lys Gly Arg Phe Thr Ile Ser Arg Asp Ser Ala Lys Asn Thr Val Tyr
65                  70                  75                  80

Leu Gln Met Asn Arg Leu Lys Pro Glu Asp Thr Ala Val Tyr Tyr Cys
                85                  90                  95

Ala Ala Asp Leu Asp Pro Asn Arg Ile Phe Ser Arg Asp Glu Ala Ala
            100                 105                 110

Tyr Trp Gly Gln Gly Thr Leu Val Thr Val Ser Ser Gly Gly Gly Gly
        115                 120                 125

Ser Gly Gly Gly Gly Ser Gly Gly Gly Gly Ser Gly Gly Gly Gly Ser
    130                 135                 140

Gly Gly Gly Gly Ser Gly Gly Gly Gly Ser Gly Gly Gly Gly Ser Glu
145                 150                 155                 160

Val Gln Leu Val Glu Ser Gly Gly Gly Leu Val Gln Pro Gly Asn Ser
                165                 170                 175

Leu Arg Leu Ser Cys Ala Ala Ser Gly Phe Thr Phe Ser Ser Phe Gly

```
              180                 185                 190
Met Ser Trp Val Arg Gln Ala Pro Gly Lys Gly Leu Glu Trp Val Ser
            195                 200                 205
Ser Ile Ser Gly Ser Gly Ser Asp Thr Leu Tyr Ala Asp Ser Val Lys
            210                 215                 220
Gly Arg Phe Thr Ile Ser Arg Asp Asn Ala Lys Thr Thr Leu Tyr Leu
225                 230                 235                 240
Gln Met Asn Ser Leu Arg Pro Glu Asp Thr Ala Val Tyr Tyr Cys Thr
            245                 250                 255
Ile Gly Gly Ser Leu Ser Arg Ser Ser Gln Gly Thr Leu Val Thr Val
            260                 265                 270
Ser Ser

<210> SEQ ID NO 121
<211> LENGTH: 276
<212> TYPE: PRT
<213> ORGANISM: Artificial Sequence
<220> FEATURE:
<223> OTHER INFORMATION: Description of Artificial Sequence: Synthetic
      anti-ADAMTS5 Nanobody

<400> SEQUENCE: 121

Glu Val Gln Leu Val Glu Ser Gly Gly Gly Leu Val Gln Ala Gly Gly
1               5                   10                  15
Ser Leu Arg Leu Ser Cys Ser Phe Ser Gly Pro Gly Arg Thr Phe Ala
            20                  25                  30
Arg Tyr Ala Met Gly Trp Phe Arg Gln Ala Pro Gly Lys Asn Arg Asp
        35                  40                  45
Phe Ile Thr Gly Ile Ser Gly Ser Gly Asp Ser Thr Tyr Tyr Val Tyr
    50                  55                  60
Pro Met Lys Asp Arg Phe Thr Ile Ser Arg Asp Asn Ala Lys Asn Met
65                  70                  75                  80
Val Tyr Leu Gln Met Asn Ala Leu Lys Pro Glu Asp Thr Ala Val Tyr
                85                  90                  95
Tyr Cys Ala Ala Asp Arg Glu Ile Asn Arg Ile Ala Asn Asp Lys Glu
            100                 105                 110
Leu Asp Phe Trp Gly Gln Gly Thr Leu Val Thr Val Ser Ser Gly Gly
        115                 120                 125
Gly Gly Ser Gly Gly Gly Ser Gly Gly Gly Ser Gly Gly Gly
    130                 135                 140
Gly Ser Gly Gly Gly Ser Gly Gly Gly Ser Gly Gly Gly Gly
145                 150                 155                 160
Ser Glu Val Gln Leu Val Glu Ser Gly Gly Gly Leu Val Gln Pro Gly
                165                 170                 175
Asn Ser Leu Arg Leu Ser Cys Ala Ala Ser Gly Phe Thr Phe Ser Ser
            180                 185                 190
Phe Gly Met Ser Trp Val Arg Gln Ala Pro Gly Lys Gly Leu Glu Trp
        195                 200                 205
Val Ser Ser Ile Ser Gly Ser Gly Ser Asp Thr Leu Tyr Ala Asp Ser
    210                 215                 220
Val Lys Gly Arg Phe Thr Ile Ser Arg Asp Asn Ala Lys Thr Thr Leu
225                 230                 235                 240
Tyr Leu Gln Met Asn Ser Leu Arg Pro Glu Asp Thr Ala Val Tyr Tyr
                245                 250                 255
Cys Thr Ile Gly Gly Ser Leu Ser Arg Ser Ser Gln Gly Thr Leu Val
```

```
                    260             265             270
Thr Val Ser Ser
            275

<210> SEQ ID NO 122
<211> LENGTH: 274
<212> TYPE: PRT
<213> ORGANISM: Artificial Sequence
<220> FEATURE:
<223> OTHER INFORMATION: Description of Artificial Sequence: Synthetic
      anti-ADAMTS5 Nanobody

<400> SEQUENCE: 122

Glu Val Gln Leu Val Glu Ser Gly Gly Gly Leu Val Gln Ala Gly Gly
1               5                   10                  15

Ser Leu Arg Leu Ser Cys Ala Ala Ser Gly Arg Thr Val Ser Ser Tyr
            20                  25                  30

Ala Met Gly Trp Phe Arg Leu Ala Pro Gly Lys Glu Arg Glu Phe Val
        35                  40                  45

Ala Gly Ile Ser Arg Ser Ala Glu Arg Thr Tyr Tyr Val Asp Ser Leu
    50                  55                  60

Lys Gly Arg Phe Thr Ile Ser Arg Asp Ser Ala Lys Asn Thr Val Tyr
65                  70                  75                  80

Leu His Met Asn Arg Leu Lys Pro Glu Asp Thr Ala Val Tyr Tyr Cys
                85                  90                  95

Ala Ala Asp Leu Asp Pro Asn Arg Ile Phe Ser Arg Glu Glu Tyr Ala
            100                 105                 110

Tyr Trp Gly Gln Gly Thr Leu Val Thr Val Ser Ser Gly Gly Gly Gly
        115                 120                 125

Ser Gly Gly Gly Gly Ser Gly Gly Gly Gly Ser Gly Gly Gly Gly Ser
    130                 135                 140

Gly Gly Gly Gly Ser Gly Gly Gly Ser Gly Gly Gly Gly Ser Glu
145                 150                 155                 160

Val Gln Leu Val Glu Ser Gly Gly Leu Val Gln Pro Gly Asn Ser
                165                 170                 175

Leu Arg Leu Ser Cys Ala Ala Ser Gly Phe Thr Phe Ser Ser Phe Gly
            180                 185                 190

Met Ser Trp Val Arg Gln Ala Pro Gly Lys Gly Leu Glu Trp Val Ser
        195                 200                 205

Ser Ile Ser Gly Ser Gly Ser Asp Thr Leu Tyr Ala Asp Ser Val Lys
    210                 215                 220

Gly Arg Phe Thr Ile Ser Arg Asp Asn Ala Lys Thr Thr Leu Tyr Leu
225                 230                 235                 240

Gln Met Asn Ser Leu Arg Pro Glu Asp Thr Ala Val Tyr Tyr Cys Thr
                245                 250                 255

Ile Gly Gly Ser Leu Ser Arg Ser Ser Gln Gly Thr Leu Val Thr Val
            260                 265                 270

Ser Ser

<210> SEQ ID NO 123
<211> LENGTH: 274
<212> TYPE: PRT
<213> ORGANISM: Artificial Sequence
<220> FEATURE:
<223> OTHER INFORMATION: Description of Artificial Sequence: Synthetic
      anti-ADAMTS5 Nanobody

<400> SEQUENCE: 123
```

```
Glu Val Gln Leu Val Glu Ser Gly Gly Gly Leu Val Gln Ala Gly Gly
1               5                   10                  15

Ser Leu Arg Leu Ser Cys Ala Ala Ser Gly Leu Thr Phe Arg Arg Asn
            20                  25                  30

Ala Met Gly Trp Phe Arg Gln Ala Pro Gly Lys Glu Arg Glu Leu Leu
        35                  40                  45

Ala Gly Ile Ser Trp Ser Gly Thr Thr Tyr Tyr Val Asp Ser Val
    50                  55                  60

Lys Gly Arg Phe Thr Ile Ser Arg Asp Asn Ala Lys Asn Thr Val Asp
65                  70                  75                  80

Leu Gln Met Ile Ser Pro Lys Pro Glu Asp Thr Ala Val Tyr Tyr Cys
                85                  90                  95

Ala Ala Asp Gly Asp Ile Gly Thr Leu Val Asn Asp Glu Asn Pro Arg
            100                 105                 110

Tyr Trp Gly Gln Gly Thr Leu Val Thr Val Ser Ser Gly Gly Gly Gly
        115                 120                 125

Ser Gly Gly Gly Gly Ser Gly Gly Gly Ser Gly Gly Gly Gly Ser
    130                 135                 140

Gly Gly Gly Gly Ser Gly Gly Gly Ser Gly Gly Gly Gly Ser Glu
145                 150                 155                 160

Val Gln Leu Val Glu Ser Gly Gly Leu Val Gln Pro Gly Asn Ser
            165                 170                 175

Leu Arg Leu Ser Cys Ala Ala Ser Gly Phe Thr Phe Ser Ser Phe Gly
        180                 185                 190

Met Ser Trp Val Arg Gln Ala Pro Gly Lys Gly Leu Glu Trp Val Ser
        195                 200                 205

Ser Ile Ser Gly Ser Gly Ser Asp Thr Leu Tyr Ala Asp Ser Val Lys
    210                 215                 220

Gly Arg Phe Thr Ile Ser Arg Asp Asn Ala Lys Thr Thr Leu Tyr Leu
225                 230                 235                 240

Gln Met Asn Ser Leu Arg Pro Glu Asp Thr Ala Val Tyr Tyr Cys Thr
            245                 250                 255

Ile Gly Gly Ser Leu Ser Arg Ser Ser Gln Gly Thr Leu Val Thr Val
            260                 265                 270

Ser Ser

<210> SEQ ID NO 124
<211> LENGTH: 274
<212> TYPE: PRT
<213> ORGANISM: Artificial Sequence
<220> FEATURE:
<223> OTHER INFORMATION: Description of Artificial Sequence: Synthetic
      anti-ADAMTS5 Nanobody

<400> SEQUENCE: 124

Glu Val Gln Leu Val Glu Ser Gly Gly Gly Leu Val Gln Ser Gly Gly
1               5                   10                  15

Ser Leu Arg Leu Ser Cys Ala Ala Ser Gly Ser Ala Val Ser Val Asn
            20                  25                  30

Ala Met Ala Trp Tyr Arg Gln Ala Pro Gly Lys Gln Arg Asp Phe Val
        35                  40                  45

Ala Gly Ile Ser Arg Ser Ala Gly Arg Thr Tyr Tyr Thr Asp Ser Val
    50                  55                  60

Lys Asp Arg Phe Thr Ile Ala Arg Asp Ser Ala Lys Asn Thr Val Tyr
65                  70                  75                  80
```

Leu Gln Met Asn Arg Leu Lys Pro Glu Asp Thr Ala Val Tyr Tyr Cys
                85                  90                  95

Ala Ala Asp Leu Asp Pro Asn Arg Ile Phe Ser Arg Asp Glu Ala Ala
            100                 105                 110

Tyr Trp Gly Gln Gly Thr Leu Val Thr Val Ser Ser Gly Gly Gly Gly
        115                 120                 125

Ser Gly Gly Gly Gly Ser Gly Gly Gly Ser Gly Gly Gly Gly Ser
    130                 135                 140

Gly Gly Gly Gly Ser Gly Gly Gly Ser Gly Gly Gly Ser Glu
145                 150                 155                 160

Val Gln Leu Val Glu Ser Gly Gly Leu Val Gln Pro Gly Asn Ser
                165                 170                 175

Leu Arg Leu Ser Cys Ala Ala Ser Gly Phe Thr Phe Ser Ser Phe Gly
            180                 185                 190

Met Ser Trp Val Arg Gln Ala Pro Gly Lys Gly Leu Glu Trp Val Ser
        195                 200                 205

Ser Ile Ser Gly Ser Gly Ser Asp Thr Leu Tyr Ala Asp Ser Val Lys
    210                 215                 220

Gly Arg Phe Thr Ile Ser Arg Asp Asn Ala Lys Thr Thr Leu Tyr Leu
225                 230                 235                 240

Gln Met Asn Ser Leu Arg Pro Glu Asp Thr Ala Val Tyr Tyr Cys Thr
                245                 250                 255

Ile Gly Gly Ser Leu Ser Arg Ser Ser Gln Gly Thr Leu Val Thr Val
            260                 265                 270

Ser Ser

<210> SEQ ID NO 125
<211> LENGTH: 275
<212> TYPE: PRT
<213> ORGANISM: Artificial Sequence
<220> FEATURE:
<223> OTHER INFORMATION: Description of Artificial Sequence: Synthetic
      anti-ADAMTS5 Nanobody

<400> SEQUENCE: 125

Glu Val Gln Leu Val Glu Ser Gly Gly Gly Phe Val Gln Ala Gly Gly
1               5                   10                  15

Ser Leu Arg Leu Ser Cys Val Ala Ser Arg Arg Thr Ile Ser Ser Gly
            20                  25                  30

Thr Met Gly Trp Phe Arg Gln Ala Pro Gly Lys Glu Arg Glu Phe Val
        35                  40                  45

Ala Ala Ile Arg Trp Ser Ser Gly Met Pro Tyr Tyr Leu Asp Ser Val
    50                  55                  60

Met Asp Arg Phe Thr Ile Ser Arg Asp Asn Ala Lys Asn Thr Val Ser
65                  70                  75                  80

Leu Gln Met Asn Ser Leu Gln Pro Glu Asp Thr Ala Val Tyr Tyr Cys
                85                  90                  95

Ala Ala Asp Arg Ser Ala Phe Arg Asp Pro Ser Phe Asp Val Asn Tyr
            100                 105                 110

Glu Tyr Trp Gly Arg Gly Thr Leu Val Thr Val Ser Ser Gly Gly Gly
        115                 120                 125

Gly Ser Gly Gly Gly Gly Ser Gly Gly Gly Gly Ser Gly Gly Gly Gly
    130                 135                 140

Ser Gly Gly Gly Gly Ser Gly Gly Gly Gly Ser Gly Gly Gly Gly Ser
145                 150                 155                 160

-continued

```
Glu Val Gln Leu Val Glu Ser Gly Gly Gly Leu Val Gln Pro Gly Asn
                165                 170                 175

Ser Leu Arg Leu Ser Cys Ala Ala Ser Gly Phe Thr Phe Ser Ser Phe
            180                 185                 190

Gly Met Ser Trp Val Arg Gln Ala Pro Gly Lys Gly Leu Glu Trp Val
        195                 200                 205

Ser Ser Ile Ser Gly Ser Gly Ser Asp Thr Leu Tyr Ala Asp Ser Val
    210                 215                 220

Lys Gly Arg Phe Thr Ile Ser Arg Asp Asn Ala Lys Thr Thr Leu Tyr
225                 230                 235                 240

Leu Gln Met Asn Ser Leu Arg Pro Glu Asp Thr Ala Val Tyr Tyr Cys
                245                 250                 255

Thr Ile Gly Gly Ser Leu Ser Arg Ser Ser Gln Gly Thr Leu Val Thr
            260                 265                 270

Val Ser Ser
        275

<210> SEQ ID NO 126
<211> LENGTH: 429
<212> TYPE: PRT
<213> ORGANISM: Artificial Sequence
<220> FEATURE:
<223> OTHER INFORMATION: Description of Artificial Sequence: Synthetic
      anti-ADAMTS5 Nanobody

<400> SEQUENCE: 126

Glu Val Gln Leu Val Glu Ser Gly Gly Gly Leu Val Gln Ala Gly Gly
1               5                   10                  15

Ser Leu Arg Leu Ser Cys Ala Ala Ser Gly Arg Thr Val Ser Ser Tyr
            20                  25                  30

Ala Met Gly Trp Phe Arg Leu Ala Pro Gly Lys Glu Arg Glu Phe Val
        35                  40                  45

Ala Gly Ile Ser Arg Ser Ala Glu Arg Thr Tyr Tyr Val Asp Ser Leu
    50                  55                  60

Lys Gly Arg Phe Thr Ile Ser Arg Asp Ser Ala Lys Asn Thr Val Tyr
65                  70                  75                  80

Leu His Met Asn Arg Leu Lys Pro Glu Asp Thr Ala Val Tyr Tyr Cys
                85                  90                  95

Ala Ala Asp Leu Asp Pro Asn Arg Ile Phe Ser Arg Glu Glu Tyr Ala
            100                 105                 110

Tyr Trp Gly Gln Gly Thr Leu Val Thr Val Ser Ser Gly Gly Gly Gly
        115                 120                 125

Ser Gly Gly Gly Gly Ser Gly Gly Gly Gly Ser Gly Gly Gly Gly Ser
    130                 135                 140

Gly Gly Gly Gly Ser Gly Gly Gly Ser Gly Gly Gly Ser Glu
145                 150                 155                 160

Val Gln Leu Val Glu Ser Gly Gly Gly Ser Val Gln Ala Gly Gly Ser
                165                 170                 175

Leu Arg Leu Ser Cys Val Ala Ser Gly Arg Tyr Pro Met Ala Trp Phe
            180                 185                 190

Arg Gln Ala Pro Gly Lys Glu Arg Glu Phe Val Ala Gly Val Ser Trp
        195                 200                 205

Gly Gly Asp Arg Thr Tyr Tyr Ala Asp Ser Val Gln Gly Arg Phe Thr
    210                 215                 220

Val Ser Arg Asp Tyr Ala Lys Asn Thr Leu Tyr Leu Gln Met Asn Ser
```

```
                    225                 230                 235                 240
Leu Lys Pro Glu Asp Ala Ala Val Tyr Tyr Cys Ala Gly Asp Pro Trp
                245                 250                 255

Gly Arg Leu Phe Arg Val Lys Asp Gln Tyr Ser Asp Trp Gly Gln Gly
                260                 265                 270

Thr Leu Val Thr Val Ser Ser Gly Gly Gly Ser Gly Gly Gly Gly
                275                 280                 285

Ser Gly Gly Gly Ser Gly Gly Gly Gly Ser Gly Gly Gly Gly Ser
        290                 295                 300

Gly Gly Gly Gly Ser Gly Gly Gly Ser Glu Val Gln Leu Val Glu
305                 310                 315                 320

Ser Gly Gly Gly Leu Val Gln Pro Gly Asn Ser Leu Arg Leu Ser Cys
                325                 330                 335

Ala Ala Ser Gly Phe Thr Phe Ser Ser Phe Gly Met Ser Trp Val Arg
                340                 345                 350

Gln Ala Pro Gly Lys Gly Leu Glu Trp Val Ser Ser Ile Ser Gly Ser
                355                 360                 365

Gly Ser Asp Thr Leu Tyr Ala Asp Ser Val Lys Gly Arg Phe Thr Ile
                370                 375                 380

Ser Arg Asp Asn Ala Lys Thr Thr Leu Tyr Leu Gln Met Asn Ser Leu
385                 390                 395                 400

Arg Pro Glu Asp Thr Ala Val Tyr Tyr Cys Thr Ile Gly Gly Ser Leu
                405                 410                 415

Ser Arg Ser Ser Gln Gly Thr Leu Val Thr Val Ser Ser
                420                 425

<210> SEQ ID NO 127
<211> LENGTH: 429
<212> TYPE: PRT
<213> ORGANISM: Artificial Sequence
<220> FEATURE:
<223> OTHER INFORMATION: Description of Artificial Sequence: Synthetic
      anti-ADAMTS5 Nanobody

<400> SEQUENCE: 127

Glu Val Gln Leu Val Glu Ser Gly Gly Gly Leu Val Gln Ala Gly Gly
1               5                   10                  15

Ser Leu Arg Leu Ser Cys Ala Ala Ser Gly Leu Thr Phe Arg Arg Asn
                20                  25                  30

Ala Met Gly Trp Phe Arg Gln Ala Pro Gly Lys Glu Arg Glu Leu Leu
            35                  40                  45

Ala Gly Ile Ser Trp Ser Gly Thr Thr Tyr Tyr Val Asp Ser Val
        50                  55                  60

Lys Gly Arg Phe Thr Ile Ser Arg Asp Asn Ala Lys Asn Thr Val Asp
65                  70                  75                  80

Leu Gln Met Ile Ser Pro Lys Pro Glu Asp Thr Ala Val Tyr Tyr Cys
                85                  90                  95

Ala Ala Asp Gly Asp Ile Gly Thr Leu Val Asn Asp Glu Asn Pro Arg
                100                 105                 110

Tyr Trp Gly Gln Gly Thr Leu Val Thr Val Ser Ser Gly Gly Gly
            115                 120                 125

Ser Gly Gly Gly Gly Ser Gly Gly Gly Gly Ser Gly Gly Gly Gly Ser
        130                 135                 140

Gly Gly Gly Gly Ser Gly Gly Gly Gly Ser Gly Gly Gly Gly Ser Glu
145                 150                 155                 160
```

Val Gln Leu Val Glu Ser Gly Gly Gly Ser Val Gln Ala Gly Gly Ser
            165                 170                 175

Leu Arg Leu Ser Cys Val Ala Ser Gly Arg Tyr Pro Met Ala Trp Phe
            180                 185                 190

Arg Gln Ala Pro Gly Lys Glu Arg Glu Phe Val Ala Gly Val Ser Trp
            195                 200                 205

Gly Gly Asp Arg Thr Tyr Tyr Ala Asp Ser Val Gln Gly Arg Phe Thr
            210                 215                 220

Val Ser Arg Asp Tyr Ala Lys Asn Thr Leu Tyr Leu Gln Met Asn Ser
225                 230                 235                 240

Leu Lys Pro Glu Asp Ala Ala Val Tyr Tyr Cys Ala Gly Asp Pro Trp
            245                 250                 255

Gly Arg Leu Phe Arg Val Lys Asp Gln Tyr Ser Asp Trp Gly Gln Gly
            260                 265                 270

Thr Leu Val Thr Val Ser Ser Gly Gly Gly Ser Gly Gly Gly Gly
            275                 280                 285

Ser Gly Gly Gly Ser Gly Gly Gly Ser Gly Gly Gly Ser
            290                 295                 300

Gly Gly Gly Gly Ser Gly Gly Gly Ser Glu Val Gln Leu Val Glu
305                 310                 315                 320

Ser Gly Gly Gly Leu Val Gln Pro Gly Asn Ser Leu Arg Leu Ser Cys
            325                 330                 335

Ala Ala Ser Gly Phe Thr Phe Ser Ser Phe Gly Met Ser Trp Val Arg
            340                 345                 350

Gln Ala Pro Gly Lys Gly Leu Glu Trp Val Ser Ser Ile Ser Gly Ser
            355                 360                 365

Gly Ser Asp Thr Leu Tyr Ala Asp Ser Val Lys Gly Arg Phe Thr Ile
            370                 375                 380

Ser Arg Asp Asn Ala Lys Thr Thr Leu Tyr Leu Gln Met Asn Ser Leu
385                 390                 395                 400

Arg Pro Glu Asp Thr Ala Val Tyr Tyr Cys Thr Ile Gly Gly Ser Leu
            405                 410                 415

Ser Arg Ser Ser Gln Gly Thr Leu Val Thr Val Ser Ser
            420                 425

<210> SEQ ID NO 128
<211> LENGTH: 429
<212> TYPE: PRT
<213> ORGANISM: Artificial Sequence
<220> FEATURE:
<223> OTHER INFORMATION: Description of Artificial Sequence: Synthetic
      anti-ADAMTS5 Nanobody

<400> SEQUENCE: 128

Glu Val Gln Leu Val Glu Ser Gly Gly Gly Leu Val Gln Ser Gly Gly
1               5                   10                  15

Ser Leu Arg Leu Ser Cys Ala Ala Ser Gly Ser Ala Val Ser Val Asn
            20                  25                  30

Ala Met Ala Trp Tyr Arg Gln Ala Pro Gly Lys Gln Arg Asp Phe Val
            35                  40                  45

Ala Gly Ile Ser Arg Ser Ala Gly Arg Thr Tyr Tyr Thr Asp Ser Val
            50                  55                  60

Lys Asp Arg Phe Thr Ile Ala Arg Asp Ser Ala Lys Asn Thr Val Tyr
65                  70                  75                  80

Leu Gln Met Asn Arg Leu Lys Pro Glu Asp Thr Ala Val Tyr Tyr Cys
            85                  90                  95

Ala Ala Asp Leu Asp Pro Asn Arg Ile Phe Ser Arg Asp Glu Ala Ala
            100                 105                 110

Tyr Trp Gly Gln Gly Thr Leu Val Thr Val Ser Ser Gly Gly Gly Gly
            115                 120                 125

Ser Gly Gly Gly Gly Ser Gly Gly Gly Gly Ser Gly Gly Gly Gly Ser
            130                 135                 140

Gly Gly Gly Gly Ser Gly Gly Gly Ser Gly Gly Gly Gly Ser Glu
145                 150                 155                 160

Val Gln Leu Val Glu Ser Gly Gly Ser Val Gln Ala Gly Ser
            165                 170                 175

Leu Arg Leu Ser Cys Val Ala Ser Gly Arg Tyr Pro Met Ala Trp Phe
            180                 185                 190

Arg Gln Ala Pro Gly Lys Glu Arg Glu Phe Val Ala Gly Val Ser Trp
            195                 200                 205

Gly Gly Asp Arg Thr Tyr Tyr Ala Asp Ser Val Gln Gly Arg Phe Thr
            210                 215                 220

Val Ser Arg Asp Tyr Ala Lys Asn Thr Leu Tyr Leu Gln Met Asn Ser
225                 230                 235                 240

Leu Lys Pro Glu Asp Ala Ala Val Tyr Tyr Cys Ala Gly Asp Pro Trp
            245                 250                 255

Gly Arg Leu Phe Arg Val Lys Asp Gln Tyr Ser Asp Trp Gly Gln Gly
            260                 265                 270

Thr Leu Val Thr Val Ser Ser Gly Gly Gly Ser Gly Gly Gly Gly
            275                 280                 285

Ser Gly Gly Gly Gly Ser Gly Gly Gly Gly Ser Gly Gly Gly Gly Ser
            290                 295                 300

Gly Gly Gly Gly Ser Gly Gly Gly Ser Glu Val Gln Leu Val Glu
305                 310                 315                 320

Ser Gly Gly Gly Leu Val Gln Pro Gly Asn Ser Leu Arg Leu Ser Cys
            325                 330                 335

Ala Ala Ser Gly Phe Thr Phe Ser Ser Phe Gly Met Ser Trp Val Arg
            340                 345                 350

Gln Ala Pro Gly Lys Gly Leu Glu Trp Val Ser Ser Ile Ser Gly Ser
            355                 360                 365

Gly Ser Asp Thr Leu Tyr Ala Asp Ser Val Lys Gly Arg Phe Thr Ile
            370                 375                 380

Ser Arg Asp Asn Ala Lys Thr Thr Leu Tyr Leu Gln Met Asn Ser Leu
385                 390                 395                 400

Arg Pro Glu Asp Thr Ala Val Tyr Tyr Cys Thr Ile Gly Gly Ser Leu
            405                 410                 415

Ser Arg Ser Ser Gln Gly Thr Leu Val Thr Val Ser Ser
            420                 425

<210> SEQ ID NO 129
<211> LENGTH: 275
<212> TYPE: PRT
<213> ORGANISM: Artificial Sequence
<220> FEATURE:
<223> OTHER INFORMATION: Description of Artificial Sequence: Synthetic
      anti-ADAMTS5 Nanobody

<400> SEQUENCE: 129

Asp Val Gln Leu Val Glu Ser Gly Gly Gly Val Val Gln Pro Gly Gly
1               5                   10                  15

Ser Leu Arg Leu Ser Cys Ala Ala Ser Gly Arg Thr Val Ser Ser Tyr

```
            20                  25                  30
Ala Met Gly Trp Phe Arg Gln Ala Pro Gly Lys Glu Arg Glu Phe Val
            35                  40                  45

Ala Gly Ile Ser Arg Ser Ala Glu Arg Thr Tyr Tyr Val Asp Ser Leu
        50                  55                  60

Lys Gly Arg Phe Thr Ile Ser Arg Asp Asn Ser Lys Asn Thr Val Tyr
 65                  70                  75                  80

Leu Gln Met Asn Ser Leu Arg Pro Glu Asp Thr Ala Leu Tyr Tyr Cys
                85                  90                  95

Ala Ala Asp Leu Asp Pro Asn Arg Ile Phe Ser Arg Glu Glu Tyr Ala
            100                 105                 110

Tyr Trp Gly Gln Gly Thr Leu Val Thr Val Ser Ser Gly Gly Gly Gly
            115                 120                 125

Ser Gly Gly Gly Gly Ser Gly Gly Gly Ser Gly Gly Gly Gly Gly Ser
            130                 135                 140

Gly Gly Gly Gly Ser Gly Gly Gly Ser Gly Gly Gly Gly Ser Gly Glu
145                 150                 155                 160

Val Gln Leu Val Glu Ser Gly Gly Val Val Gln Pro Gly Asn Ser
                165                 170                 175

Leu Arg Leu Ser Cys Ala Ala Ser Gly Phe Thr Phe Ser Ser Phe Gly
                180                 185                 190

Met Ser Trp Val Arg Gln Ala Pro Gly Lys Gly Leu Glu Trp Val Ser
                195                 200                 205

Ser Ile Ser Gly Ser Gly Ser Asp Thr Leu Tyr Ala Asp Ser Val Lys
            210                 215                 220

Gly Arg Phe Thr Ile Ser Arg Asp Asn Ala Lys Thr Thr Leu Tyr Leu
225                 230                 235                 240

Gln Met Asn Ser Leu Arg Pro Glu Asp Thr Ala Leu Tyr Tyr Cys Thr
                245                 250                 255

Ile Gly Gly Ser Leu Ser Arg Ser Ser Gln Gly Thr Leu Val Thr Val
            260                 265                 270

Ser Ser Ala
        275

<210> SEQ ID NO 130
<211> LENGTH: 430
<212> TYPE: PRT
<213> ORGANISM: Artificial Sequence
<220> FEATURE:
<223> OTHER INFORMATION: Description of Artificial Sequence: Synthetic
      anti-ADAMTS5 Nanobody

<400> SEQUENCE: 130

Asp Val Gln Leu Val Glu Ser Gly Gly Val Val Gln Pro Gly Gly
1               5                   10                  15

Ser Leu Arg Leu Ser Cys Ala Ala Ser Gly Arg Thr Val Ser Ser Tyr
            20                  25                  30

Ala Met Gly Trp Phe Arg Gln Ala Pro Gly Lys Glu Arg Glu Phe Val
            35                  40                  45

Ala Gly Ile Ser Arg Ser Ala Glu Arg Thr Tyr Tyr Val Asp Ser Leu
        50                  55                  60

Lys Gly Arg Phe Thr Ile Ser Arg Asp Asn Ser Lys Asn Thr Val Tyr
 65                  70                  75                  80

Leu Gln Met Asn Ser Leu Arg Pro Glu Asp Thr Ala Leu Tyr Tyr Cys
                85                  90                  95
```

Ala Ala Asp Leu Asp Pro Asn Arg Ile Phe Ser Arg Glu Glu Tyr Ala
            100                 105                 110

Tyr Trp Gly Gln Gly Thr Leu Val Thr Val Ser Ser Gly Gly Gly Gly
        115                 120                 125

Ser Gly Gly Gly Gly Ser Gly Gly Gly Gly Ser Gly Gly Gly Gly Ser
130                 135                 140

Gly Gly Gly Gly Ser Gly Gly Gly Ser Gly Gly Gly Ser Glu
145                 150                 155                 160

Val Gln Leu Val Glu Ser Gly Gly Val Gln Pro Gly Gly Ser
                165                 170                 175

Leu Arg Leu Ser Cys Ala Ala Ser Gly Arg Tyr Pro Met Ala Trp Phe
            180                 185                 190

Arg Gln Ala Pro Gly Lys Glu Arg Glu Phe Val Ala Gly Val Ser Trp
            195                 200                 205

Gly Gly Asp Arg Thr Tyr Tyr Ala Asp Ser Val Lys Gly Arg Phe Thr
        210                 215                 220

Ile Ser Arg Asp Tyr Ser Lys Asn Thr Leu Tyr Leu Gln Met Asn Ser
225                 230                 235                 240

Leu Arg Pro Glu Asp Thr Ala Leu Tyr Tyr Cys Ala Gly Asp Pro Phe
            245                 250                 255

Gly Arg Leu Phe Arg Val Lys Asp Gln Tyr Ser Asp Trp Gly Gln Gly
            260                 265                 270

Thr Leu Val Thr Val Ser Ser Gly Gly Gly Ser Gly Gly Gly Gly
        275                 280                 285

Ser Gly Gly Gly Gly Ser Gly Gly Gly Gly Ser Gly Gly Gly Gly Ser
290                 295                 300

Gly Gly Gly Gly Ser Gly Gly Gly Ser Glu Val Gln Leu Val Glu
305                 310                 315                 320

Ser Gly Gly Val Val Gln Pro Gly Asn Ser Leu Arg Leu Ser Cys
            325                 330                 335

Ala Ala Ser Gly Phe Thr Phe Ser Ser Phe Gly Met Ser Trp Val Arg
            340                 345                 350

Gln Ala Pro Gly Lys Gly Leu Glu Trp Val Ser Ser Ile Ser Gly Ser
            355                 360                 365

Gly Ser Asp Thr Leu Tyr Ala Asp Ser Val Lys Gly Arg Phe Thr Ile
        370                 375                 380

Ser Arg Asp Asn Ala Lys Thr Thr Leu Tyr Leu Gln Met Asn Ser Leu
385                 390                 395                 400

Arg Pro Glu Asp Thr Ala Leu Tyr Tyr Cys Thr Ile Gly Gly Ser Leu
            405                 410                 415

Ser Arg Ser Ser Gln Gly Thr Leu Val Thr Val Ser Ser Ala
            420                 425                 430

<210> SEQ ID NO 131
<211> LENGTH: 115
<212> TYPE: PRT
<213> ORGANISM: Artificial Sequence
<220> FEATURE:
<223> OTHER INFORMATION: Description of Artificial Sequence: Synthetic
      Serum albumin binding ISVD sequences

<400> SEQUENCE: 131

```
Glu Val Gln Leu Val Glu Ser Gly Gly Gly Leu Val Gln Pro Gly Asn
1               5                   10                  15

Ser Leu Arg Leu Ser Cys Ala Ala Ser Gly Phe Thr Phe Ser Ser Phe
            20                  25                  30
```

```
Gly Met Ser Trp Val Arg Gln Ala Pro Gly Lys Gly Leu Glu Trp Val
            35                  40                  45

Ser Ser Ile Ser Gly Ser Gly Ser Asp Thr Leu Tyr Ala Asp Ser Val
 50                  55                  60

Lys Gly Arg Phe Thr Ile Ser Arg Asp Asn Ala Lys Thr Thr Leu Tyr
 65                  70                  75                  80

Leu Gln Met Asn Ser Leu Arg Pro Glu Asp Thr Ala Val Tyr Tyr Cys
                 85                  90                  95

Thr Ile Gly Gly Ser Leu Ser Arg Ser Ser Gln Gly Thr Leu Val Thr
            100                 105                 110

Val Ser Ser
        115

<210> SEQ ID NO 132
<211> LENGTH: 115
<212> TYPE: PRT
<213> ORGANISM: Artificial Sequence
<220> FEATURE:
<223> OTHER INFORMATION: Description of Artificial Sequence: Synthetic
      Serum albumin binding ISVD sequences

<400> SEQUENCE: 132

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Arg Ser Phe
                20                  25                  30

Gly Met Ser Trp Val Arg Gln Ala Pro Gly Lys Gly Pro Glu Trp Val
            35                  40                  45

Ser Ser Ile Ser Gly Ser Gly Ser Asp Thr Leu Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Pro Glu Asp Thr Ala Val Tyr Tyr Cys
                 85                  90                  95

Thr Ile Gly Gly Ser Leu Ser Arg Ser Ser Gln Gly Thr Leu Val Thr
            100                 105                 110

Val Ser Ser
        115

<210> SEQ ID NO 133
<211> LENGTH: 116
<212> TYPE: PRT
<213> ORGANISM: Artificial Sequence
<220> FEATURE:
<223> OTHER INFORMATION: Description of Artificial Sequence: Synthetic
      Serum albumin binding ISVD sequences

<400> SEQUENCE: 133

Glu Val Gln Leu Val Glu Ser Gly Gly Gly Val Val Gln Pro Gly Asn
 1               5                  10                  15

Ser Leu Arg Leu Ser Cys Ala Ala Ser Gly Phe Thr Phe Ser Ser Phe
                20                  25                  30

Gly Met Ser Trp Val Arg Gln Ala Pro Gly Lys Gly Leu Glu Trp Val
            35                  40                  45

Ser Ser Ile Ser Gly Ser Gly Ser Asp Thr Leu Tyr Ala Asp Ser Val
 50                  55                  60

Lys Gly Arg Phe Thr Ile Ser Arg Asp Asn Ala Lys Thr Thr Leu Tyr
 65                  70                  75                  80
```

-continued

Leu Gln Met Asn Ser Leu Arg Pro Glu Asp Thr Ala Thr Tyr Tyr Cys
                85                  90                  95

Thr Ile Gly Gly Ser Leu Ser Arg Ser Ser Gln Gly Thr Leu Val Thr
            100                 105                 110

Val Ser Ser Ala
        115

<210> SEQ ID NO 134
<211> LENGTH: 116
<212> TYPE: PRT
<213> ORGANISM: Artificial Sequence
<220> FEATURE:
<223> OTHER INFORMATION: Description of Artificial Sequence: Synthetic
      Serum albumin binding ISVD sequences

<400> SEQUENCE: 134

Glu Val Gln Leu Val Glu Ser Gly Gly Gly Val Val Gln Pro Gly Gly
1               5                   10                  15

Ser Leu Arg Leu Ser Cys Ala Ala Ser Gly Phe Thr Phe Arg Ser Phe
            20                  25                  30

Gly Met Ser Trp Val Arg Gln Ala Pro Gly Lys Gly Pro Glu Trp Val
        35                  40                  45

Ser Ser Ile Ser Gly Ser Gly Ser Asp Thr Leu Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Pro Glu Asp Thr Ala Thr Tyr Tyr Cys
                85                  90                  95

Thr Ile Gly Gly Ser Leu Ser Arg Ser Ser Gln Gly Thr Leu Val Thr
            100                 105                 110

Val Ser Ser Ala
        115

<210> SEQ ID NO 135
<211> LENGTH: 115
<212> TYPE: PRT
<213> ORGANISM: Artificial Sequence
<220> FEATURE:
<223> OTHER INFORMATION: Description of Artificial Sequence: Synthetic
      Serum albumin binding ISVD sequences

<400> SEQUENCE: 135

Glu Val Gln Leu Val Glu Ser Gly Gly Gly Leu Val Gln Pro Gly Asn
1               5                   10                  15

Ser Leu Arg Leu Ser Cys Ala Ala Ser Gly Phe Thr Phe Ser Ser Phe
            20                  25                  30

Gly Met Ser Trp Val Arg Gln Ala Pro Gly Lys Gly Leu Glu Trp Val
        35                  40                  45

Ser Ser Ile Ser Gly Ser Gly Ser Asp Thr Leu Tyr Ala Asp Ser Val
    50                  55                  60

Lys Gly Arg Phe Thr Ile Ser Arg Asp Asn Ala Lys Thr Thr Leu Tyr
65                  70                  75                  80

Leu Gln Met Asn Ser Leu Arg Pro Glu Asp Thr Ala Val Tyr Tyr Cys
                85                  90                  95

Thr Ile Gly Gly Ser Leu Ser Arg Ser Ser Gln Gly Thr Leu Val Thr
            100                 105                 110

Val Ser Ser
        115

<210> SEQ ID NO 136
<211> LENGTH: 116
<212> TYPE: PRT
<213> ORGANISM: Artificial Sequence
<220> FEATURE:
<223> OTHER INFORMATION: Description of Artificial Sequence: Synthetic
      Serum albumin binding ISVD sequences

<400> SEQUENCE: 136

Glu Val Gln Leu Val Glu Ser Gly Gly Gly Leu Val Gln Pro Gly Asn
1               5                   10                  15

Ser Leu Arg Leu Ser Cys Ala Ala Ser Gly Phe Thr Phe Ser Ser Phe
            20                  25                  30

Gly Met Ser Trp Val Arg Gln Ala Pro Gly Lys Gly Leu Glu Trp Val
        35                  40                  45

Ser Ser Ile Ser Gly Ser Gly Ser Asp Thr Leu Tyr Ala Asp Ser Val
    50                  55                  60

Lys Gly Arg Phe Thr Ile Ser Arg Asp Asn Ala Lys Thr Thr Leu Tyr
65                  70                  75                  80

Leu Gln Met Asn Ser Leu Arg Pro Glu Asp Thr Ala Val Tyr Tyr Cys
                85                  90                  95

Thr Ile Gly Gly Ser Leu Ser Arg Ser Ser Gln Gly Thr Leu Val Lys
            100                 105                 110

Val Ser Ser Ala
        115

<210> SEQ ID NO 137
<211> LENGTH: 115
<212> TYPE: PRT
<213> ORGANISM: Artificial Sequence
<220> FEATURE:
<223> OTHER INFORMATION: Description of Artificial Sequence: Synthetic
      Serum albumin binding ISVD sequences

<400> SEQUENCE: 137

Glu Val Gln Leu Val Glu Ser Gly Gly Gly Val Val Gln Pro Gly Asn
1               5                   10                  15

Ser Leu Arg Leu Ser Cys Ala Ala Ser Gly Phe Thr Phe Ser Ser Phe
            20                  25                  30

Gly Met Ser Trp Val Arg Gln Ala Pro Gly Lys Gly Leu Glu Trp Val
        35                  40                  45

Ser Ser Ile Ser Gly Ser Gly Ser Asp Thr Leu Tyr Ala Asp Ser Val
    50                  55                  60

Lys Gly Arg Phe Thr Ile Ser Arg Asp Asn Ala Lys Thr Thr Leu Tyr
65                  70                  75                  80

Leu Gln Met Asn Ser Leu Arg Pro Glu Asp Thr Ala Leu Tyr Tyr Cys
                85                  90                  95

Thr Ile Gly Gly Ser Leu Ser Arg Ser Ser Gln Gly Thr Leu Val Thr
            100                 105                 110

Val Ser Ser
        115

<210> SEQ ID NO 138
<211> LENGTH: 116
<212> TYPE: PRT
<213> ORGANISM: Artificial Sequence
<220> FEATURE:
<223> OTHER INFORMATION: Description of Artificial Sequence: Synthetic
      Serum albumin binding ISVD sequences

```
<400> SEQUENCE: 138

Glu Val Gln Leu Val Glu Ser Gly Gly Gly Val Val Gln Pro Gly Asn
1               5                   10                  15

Ser Leu Arg Leu Ser Cys Ala Ala Ser Gly Phe Thr Phe Ser Ser Phe
            20                  25                  30

Gly Met Ser Trp Val Arg Gln Ala Pro Gly Lys Gly Leu Glu Trp Val
        35                  40                  45

Ser Ser Ile Ser Gly Ser Gly Ser Asp Thr Leu Tyr Ala Asp Ser Val
    50                  55                  60

Lys Gly Arg Phe Thr Ile Ser Arg Asp Asn Ala Lys Thr Thr Leu Tyr
65                  70                  75                  80

Leu Gln Met Asn Ser Leu Arg Pro Glu Asp Thr Ala Leu Tyr Tyr Cys
                85                  90                  95

Thr Ile Gly Gly Ser Leu Ser Arg Ser Ser Gln Gly Thr Leu Val Thr
            100                 105                 110

Val Ser Ser Ala
        115

<210> SEQ ID NO 139
<211> LENGTH: 117
<212> TYPE: PRT
<213> ORGANISM: Artificial Sequence
<220> FEATURE:
<223> OTHER INFORMATION: Description of Artificial Sequence: Synthetic
      Serum albumin binding ISVD sequences

<400> SEQUENCE: 139

Glu Val Gln Leu Val Glu Ser Gly Gly Gly Val Val Gln Pro Gly Asn
1               5                   10                  15

Ser Leu Arg Leu Ser Cys Ala Ala Ser Gly Phe Thr Phe Ser Ser Phe
            20                  25                  30

Gly Met Ser Trp Val Arg Gln Ala Pro Gly Lys Gly Leu Glu Trp Val
        35                  40                  45

Ser Ser Ile Ser Gly Ser Gly Ser Asp Thr Leu Tyr Ala Asp Ser Val
    50                  55                  60

Lys Gly Arg Phe Thr Ile Ser Arg Asp Asn Ala Lys Thr Thr Leu Tyr
65                  70                  75                  80

Leu Gln Met Asn Ser Leu Arg Pro Glu Asp Thr Ala Leu Tyr Tyr Cys
                85                  90                  95

Thr Ile Gly Gly Ser Leu Ser Arg Ser Ser Gln Gly Thr Leu Val Thr
            100                 105                 110

Val Ser Ser Ala Ala
        115

<210> SEQ ID NO 140
<211> LENGTH: 118
<212> TYPE: PRT
<213> ORGANISM: Artificial Sequence
<220> FEATURE:
<223> OTHER INFORMATION: Description of Artificial Sequence: Synthetic
      Serum albumin binding ISVD sequences

<400> SEQUENCE: 140

Glu Val Gln Leu Val Glu Ser Gly Gly Gly Val Val Gln Pro Gly Asn
1               5                   10                  15

Ser Leu Arg Leu Ser Cys Ala Ala Ser Gly Phe Thr Phe Ser Ser Phe
            20                  25                  30
```

Gly Met Ser Trp Val Arg Gln Ala Pro Gly Lys Gly Leu Glu Trp Val
        35                  40                  45

Ser Ser Ile Ser Gly Ser Gly Ser Asp Thr Leu Tyr Ala Asp Ser Val
 50                  55                  60

Lys Gly Arg Phe Thr Ile Ser Arg Asp Asn Ala Lys Thr Thr Leu Tyr
 65                  70                  75                  80

Leu Gln Met Asn Ser Leu Arg Pro Glu Asp Thr Ala Leu Tyr Tyr Cys
                 85                  90                  95

Thr Ile Gly Gly Ser Leu Ser Arg Ser Ser Gln Gly Thr Leu Val Thr
            100                 105                 110

Val Ser Ser Ala Ala Ala
        115

<210> SEQ ID NO 141
<211> LENGTH: 116
<212> TYPE: PRT
<213> ORGANISM: Artificial Sequence
<220> FEATURE:
<223> OTHER INFORMATION: Description of Artificial Sequence: Synthetic
      Serum albumin binding ISVD sequences

<400> SEQUENCE: 141

Glu Val Gln Leu Val Glu Ser Gly Gly Gly Val Val Gln Pro Gly Asn
1               5                  10                  15

Ser Leu Arg Leu Ser Cys Ala Ala Ser Gly Phe Thr Phe Ser Ser Phe
            20                  25                  30

Gly Met Ser Trp Val Arg Gln Ala Pro Gly Lys Gly Leu Glu Trp Val
        35                  40                  45

Ser Ser Ile Ser Gly Ser Gly Ser Asp Thr Leu Tyr Ala Asp Ser Val
 50                  55                  60

Lys Gly Arg Phe Thr Ile Ser Arg Asp Asn Ala Lys Thr Thr Leu Tyr
 65                  70                  75                  80

Leu Gln Met Asn Ser Leu Arg Pro Glu Asp Thr Ala Leu Tyr Tyr Cys
                 85                  90                  95

Thr Ile Gly Gly Ser Leu Ser Arg Ser Ser Gln Gly Thr Leu Val Thr
            100                 105                 110

Val Ser Ser Gly
        115

<210> SEQ ID NO 142
<211> LENGTH: 117
<212> TYPE: PRT
<213> ORGANISM: Artificial Sequence
<220> FEATURE:
<223> OTHER INFORMATION: Description of Artificial Sequence: Synthetic
      Serum albumin binding ISVD sequences

<400> SEQUENCE: 142

Glu Val Gln Leu Val Glu Ser Gly Gly Gly Val Val Gln Pro Gly Asn
1               5                  10                  15

Ser Leu Arg Leu Ser Cys Ala Ala Ser Gly Phe Thr Phe Ser Ser Phe
            20                  25                  30

Gly Met Ser Trp Val Arg Gln Ala Pro Gly Lys Gly Leu Glu Trp Val
        35                  40                  45

Ser Ser Ile Ser Gly Ser Gly Ser Asp Thr Leu Tyr Ala Asp Ser Val
 50                  55                  60

Lys Gly Arg Phe Thr Ile Ser Arg Asp Asn Ala Lys Thr Thr Leu Tyr
 65                  70                  75                  80

```
Leu Gln Met Asn Ser Leu Arg Pro Glu Asp Thr Ala Leu Tyr Tyr Cys
                85                  90                  95

Thr Ile Gly Gly Ser Leu Ser Arg Ser Ser Gln Gly Thr Leu Val Thr
            100                 105                 110

Val Ser Ser Gly Gly
        115

<210> SEQ ID NO 143
<211> LENGTH: 118
<212> TYPE: PRT
<213> ORGANISM: Artificial Sequence
<220> FEATURE:
<223> OTHER INFORMATION: Description of Artificial Sequence: Synthetic
      Serum albumin binding ISVD sequences

<400> SEQUENCE: 143

Glu Val Gln Leu Val Glu Ser Gly Gly Val Val Gln Pro Gly Asn
1               5                   10                  15

Ser Leu Arg Leu Ser Cys Ala Ala Ser Gly Phe Thr Phe Ser Ser Phe
            20                  25                  30

Gly Met Ser Trp Val Arg Gln Ala Pro Gly Lys Gly Leu Glu Trp Val
        35                  40                  45

Ser Ser Ile Ser Gly Ser Gly Ser Asp Thr Leu Tyr Ala Asp Ser Val
    50                  55                  60

Lys Gly Arg Phe Thr Ile Ser Arg Asp Asn Ala Lys Thr Thr Leu Tyr
65                  70                  75                  80

Leu Gln Met Asn Ser Leu Arg Pro Glu Asp Thr Ala Leu Tyr Tyr Cys
                85                  90                  95

Thr Ile Gly Gly Ser Leu Ser Arg Ser Ser Gln Gly Thr Leu Val Thr
            100                 105                 110

Val Ser Ser Gly Gly Gly
        115

<210> SEQ ID NO 144
<211> LENGTH: 115
<212> TYPE: PRT
<213> ORGANISM: Artificial Sequence
<220> FEATURE:
<223> OTHER INFORMATION: Description of Artificial Sequence: Synthetic
      Serum albumin binding ISVD sequences

<400> SEQUENCE: 144

Glu Val Gln Leu Val Glu Ser Gly Gly Gly Val Val Gln Pro Gly Gly
1               5                   10                  15

Ser Leu Arg Leu Ser Cys Ala Ala Ser Gly Phe Thr Phe Arg Ser Phe
            20                  25                  30

Gly Met Ser Trp Val Arg Gln Ala Pro Gly Lys Gly Pro Glu Trp Val
        35                  40                  45

Ser Ser Ile Ser Gly Ser Gly Ser Asp Thr Leu Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Pro Glu Asp Thr Ala Leu Tyr Tyr Cys
                85                  90                  95

Thr Ile Gly Gly Ser Leu Ser Arg Ser Ser Gln Gly Thr Leu Val Thr
            100                 105                 110

Val Ser Ser
        115
```

-continued

```
<210> SEQ ID NO 145
<211> LENGTH: 116
<212> TYPE: PRT
<213> ORGANISM: Artificial Sequence
<220> FEATURE:
<223> OTHER INFORMATION: Description of Artificial Sequence: Synthetic
      Serum albumin binding ISVD sequences

<400> SEQUENCE: 145

Glu Val Gln Leu Val Glu Ser Gly Gly Val Val Gln Pro Gly Gly
1               5                   10                  15

Ser Leu Arg Leu Ser Cys Ala Ala Ser Gly Phe Thr Phe Arg Ser Phe
            20                  25                  30

Gly Met Ser Trp Val Arg Gln Ala Pro Gly Lys Gly Pro Glu Trp Val
        35                  40                  45

Ser Ser Ile Ser Gly Ser Gly Ser Asp Thr Leu Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Pro Glu Asp Thr Ala Leu Tyr Tyr Cys
                85                  90                  95

Thr Ile Gly Gly Ser Leu Ser Arg Ser Ser Gln Gly Thr Leu Val Thr
            100                 105                 110

Val Ser Ser Ala
        115

<210> SEQ ID NO 146
<211> LENGTH: 5
<212> TYPE: PRT
<213> ORGANISM: Artificial Sequence
<220> FEATURE:
<223> OTHER INFORMATION: Description of Artificial Sequence: Synthetic
      Serum albumin binding ISVD sequences

<400> SEQUENCE: 146

Ser Phe Gly Met Ser
1               5

<210> SEQ ID NO 147
<211> LENGTH: 17
<212> TYPE: PRT
<213> ORGANISM: Artificial Sequence
<220> FEATURE:
<223> OTHER INFORMATION: Description of Artificial Sequence: Synthetic
      Serum albumin binding ISVD sequences

<400> SEQUENCE: 147

Ser Ile Ser Gly Ser Gly Ser Asp Thr Leu Tyr Ala Asp Ser Val Lys
1               5                   10                  15

Gly

<210> SEQ ID NO 148
<211> LENGTH: 6
<212> TYPE: PRT
<213> ORGANISM: Artificial Sequence
<220> FEATURE:
<223> OTHER INFORMATION: Description of Artificial Sequence: Synthetic
      Serum albumin binding ISVD sequences

<400> SEQUENCE: 148

Gly Gly Ser Leu Ser Arg
1               5
```

```
<210> SEQ ID NO 149
<211> LENGTH: 930
<212> TYPE: PRT
<213> ORGANISM: Homo sapiens
<220> FEATURE:
<223> OTHER INFORMATION: Human ADAMTS5

<400> SEQUENCE: 149

Met Leu Leu Gly Trp Ala Ser Leu Leu Cys Ala Phe Arg Leu Pro
1               5                   10                  15

Leu Ala Ala Val Gly Pro Ala Ala Thr Pro Ala Gln Asp Lys Ala Gly
            20                  25                  30

Gln Pro Pro Thr Ala Ala Ala Ala Gln Pro Arg Arg Arg Gln Gly
        35                  40                  45

Glu Glu Val Gln Glu Arg Ala Glu Pro Pro Gly His Pro His Pro Leu
50                  55                  60

Ala Gln Arg Arg Arg Ser Lys Gly Leu Val Gln Asn Ile Asp Gln Leu
65                  70                  75                  80

Tyr Ser Gly Gly Gly Lys Val Gly Tyr Leu Val Tyr Ala Gly Gly Arg
                85                  90                  95

Arg Phe Leu Leu Asp Leu Glu Arg Asp Gly Ser Val Gly Ile Ala Gly
            100                 105                 110

Phe Val Pro Ala Gly Gly Gly Thr Ser Ala Pro Trp Arg His Arg Ser
        115                 120                 125

His Cys Phe Tyr Arg Gly Thr Val Asp Gly Ser Pro Arg Ser Leu Ala
130                 135                 140

Val Phe Asp Leu Cys Gly Gly Leu Asp Gly Phe Phe Ala Val Lys His
145                 150                 155                 160

Ala Arg Tyr Thr Leu Lys Pro Leu Leu Arg Gly Pro Trp Ala Glu Glu
                165                 170                 175

Glu Lys Gly Arg Val Tyr Gly Asp Gly Ser Ala Arg Ile Leu His Val
            180                 185                 190

Tyr Thr Arg Glu Gly Phe Ser Phe Glu Ala Leu Pro Pro Arg Ala Ser
        195                 200                 205

Cys Glu Thr Pro Ala Ser Thr Pro Glu Ala His Glu His Ala Pro Ala
210                 215                 220

His Ser Asn Pro Ser Gly Arg Ala Ala Leu Ala Ser Gln Leu Leu Asp
225                 230                 235                 240

Gln Ser Ala Leu Ser Pro Ala Gly Gly Ser Gly Pro Gln Thr Trp Trp
                245                 250                 255

Arg Arg Arg Arg Ser Ile Ser Arg Ala Arg Gln Val Glu Leu Leu
            260                 265                 270

Leu Val Ala Asp Ala Ser Met Ala Arg Leu Tyr Gly Arg Gly Leu Gln
        275                 280                 285

His Tyr Leu Leu Thr Leu Ala Ser Ile Ala Asn Arg Leu Tyr Ser His
290                 295                 300

Ala Ser Ile Glu Asn His Ile Arg Leu Ala Val Val Lys Val Val Val
305                 310                 315                 320

Leu Gly Asp Lys Asp Lys Ser Leu Glu Val Ser Lys Asn Ala Ala Thr
                325                 330                 335

Thr Leu Lys Asn Phe Cys Lys Trp Gln His Gln His Asn Gln Leu Gly
            340                 345                 350

Asp Asp His Glu Glu His Tyr Asp Ala Ala Ile Leu Phe Thr Arg Glu
        355                 360                 365
```

-continued

```
Asp Leu Cys Gly His His Cys Asp Thr Leu Gly Met Ala Asp Val
    370                 375                 380

Gly Thr Ile Cys Ser Pro Glu Arg Ser Cys Ala Val Ile Glu Asp
385                 390                 395                 400

Gly Leu His Ala Ala Phe Thr Val Ala His Glu Ile Gly His Leu Leu
                    405                 410                 415

Gly Leu Ser His Asp Asp Ser Lys Phe Cys Glu Glu Thr Phe Gly Ser
                420                 425                 430

Thr Glu Asp Lys Arg Leu Met Ser Ile Leu Thr Ser Ile Asp Ala
                435                 440                 445

Ser Lys Pro Trp Ser Lys Cys Thr Ser Ala Thr Ile Thr Glu Phe Leu
450                 455                 460

Asp Asp Gly His Gly Asn Cys Leu Leu Asp Leu Pro Arg Lys Gln Ile
465                 470                 475                 480

Leu Gly Pro Glu Glu Leu Pro Gly Gln Thr Tyr Asp Ala Thr Gln Gln
                485                 490                 495

Cys Asn Leu Thr Phe Gly Pro Glu Tyr Ser Val Cys Pro Gly Met Asp
                500                 505                 510

Val Cys Ala Arg Leu Trp Cys Ala Val Val Arg Gln Gly Gln Met Val
                515                 520                 525

Cys Leu Thr Lys Lys Leu Pro Ala Val Glu Gly Thr Pro Cys Gly Lys
                530                 535                 540

Gly Arg Ile Cys Leu Gln Gly Lys Cys Val Asp Lys Thr Lys Lys Lys
545                 550                 555                 560

Tyr Tyr Ser Thr Ser Ser His Gly Asn Trp Gly Ser Trp Gly Ser Trp
                565                 570                 575

Gly Gln Cys Ser Arg Ser Cys Gly Gly Val Gln Phe Ala Tyr Arg
                580                 585                 590

His Cys Asn Asn Pro Ala Pro Arg Asn Asn Gly Arg Tyr Cys Thr Gly
                595                 600                 605

Lys Arg Ala Ile Tyr Arg Ser Cys Ser Leu Met Pro Cys Pro Pro Asn
610                 615                 620

Gly Lys Ser Phe Arg His Glu Gln Cys Glu Ala Lys Asn Gly Tyr Gln
625                 630                 635                 640

Ser Asp Ala Lys Gly Val Lys Thr Phe Val Glu Trp Val Pro Lys Tyr
                645                 650                 655

Ala Gly Val Leu Pro Ala Asp Val Cys Lys Leu Thr Cys Arg Ala Lys
                660                 665                 670

Gly Thr Gly Tyr Tyr Val Val Phe Ser Pro Lys Val Thr Asp Gly Thr
                675                 680                 685

Glu Cys Arg Leu Tyr Ser Asn Ser Val Cys Val Arg Gly Lys Cys Val
690                 695                 700

Arg Thr Gly Cys Asp Gly Ile Ile Gly Ser Lys Leu Gln Tyr Asp Lys
705                 710                 715                 720

Cys Gly Val Cys Gly Gly Asp Asn Ser Ser Cys Thr Lys Ile Val Gly
                725                 730                 735

Thr Phe Asn Lys Lys Ser Lys Gly Tyr Thr Asp Val Val Arg Ile Pro
                740                 745                 750

Glu Gly Ala Thr His Ile Lys Val Arg Gln Phe Lys Ala Lys Asp Gln
                755                 760                 765

Thr Arg Phe Thr Ala Tyr Leu Ala Leu Lys Lys Asn Gly Glu Tyr
770                 775                 780

Leu Ile Asn Gly Lys Tyr Met Ile Ser Thr Ser Glu Thr Ile Ile Asp
```

```
                785                 790                 795                 800
        Ile Asn Gly Thr Val Met Asn Tyr Ser Gly Trp Ser His Arg Asp Asp
                        805                 810                 815

Phe Leu His Gly Met Gly Tyr Ser Ala Thr Lys Glu Ile Leu Ile Val
                        820                 825                 830

Gln Ile Leu Ala Thr Asp Pro Thr Lys Pro Leu Asp Val Arg Tyr Ser
                        835                 840                 845

Phe Phe Val Pro Lys Lys Ser Thr Pro Lys Val Asn Ser Val Thr Ser
                850                 855                 860

His Gly Ser Asn Lys Val Gly Ser His Thr Ser Gln Pro Gln Trp Val
        865                 870                 875                 880

Thr Gly Pro Trp Leu Ala Cys Ser Arg Thr Cys Asp Thr Gly Trp His
                        885                 890                 895

Thr Arg Thr Val Gln Cys Gln Asp Gly Asn Arg Lys Leu Ala Lys Gly
                        900                 905                 910

Cys Pro Leu Ser Gln Arg Pro Ser Ala Phe Lys Gln Cys Leu Leu Lys
                        915                 920                 925

Lys Cys
            930

<210> SEQ ID NO 150
<211> LENGTH: 636
<212> TYPE: PRT
<213> ORGANISM: Artificial Sequence
<220> FEATURE:
<223> OTHER INFORMATION: Description of Artificial Sequence: Synthetic
      bovine ADAMTS5

<400> SEQUENCE: 150

Met Leu Leu Gly Trp Ala Ala Leu Met Leu Cys Ala Leu Arg Leu Pro
        1               5                   10                  15

Pro Val Ala Ala Gly Pro Thr Ala Ala Pro Ala Gln Asp Lys Ala Gly
                        20                  25                  30

Gln Pro Arg Ala Ala Ala Val Ala Ala Ala Gln Pro Arg Gly Arg
                    35                  40                  45

Arg Gly Glu Glu Ala Gln Glu Pro Ala Glu Pro Gly His Pro His
            50                  55                  60

Pro Leu Ala Pro Gln Arg Gly Ser Arg Gly Leu Val Gln Asn Ile Asp
        65                  70                  75                  80

Gln Leu Tyr Ser Gly Gly Lys Val Gly Tyr Leu Val Tyr Ala Gly
                        85                  90                  95

Gly Arg Arg Phe Leu Leu Asp Leu Glu Arg Asp Ser Val Gly Ala
                    100                 105                 110

Ala Gly Leu Val Pro Ala Gly Gly Pro Asn Ala Thr Arg Arg His
                115                 120                 125

Arg Gly His Cys Phe Tyr Arg Gly Thr Val Asp Gly Ser Pro Arg Ser
                    130                 135                 140

Leu Ala Val Phe Asp Leu Cys Gly Gly Leu Asp Gly Phe Phe Ala Val
        145                 150                 155                 160

Lys Arg Ala Arg Tyr Thr Leu Gln Pro Leu Leu Arg Gly Pro Trp Ala
                        165                 170                 175

Glu Ala Glu Gly Asp Ala Arg Val Tyr Gly Asp Glu Ser Ala Arg Ile
                    180                 185                 190

Leu His Val Tyr Thr Arg Glu Gly Phe Ser Phe Glu Ala Leu Pro Pro
                    195                 200                 205
```

```
Arg Thr Ser Cys Glu Thr His Ala Ser Pro Pro Gly Ala Arg Glu Arg
    210                 215                 220

Pro Pro Ala Pro Ser Arg Pro Asp Gly Arg Trp Ala Leu Ala Pro Gln
225                 230                 235                 240

Gln Leu Pro Gly Gln Ser Ala Pro Ser Ser Asp Gly Ser Gln Gly Pro
                245                 250                 255

Arg Thr Trp Trp Arg Arg Arg Arg Ser Ile Ser Arg Ala Arg Gln
            260                 265                 270

Val Glu Leu Leu Val Ala Asp Ala Ser Met Ala Arg Met Tyr Gly
        275                 280                 285

Arg Gly Leu Gln His Tyr Leu Leu Thr Leu Ala Ser Ile Ala Asn Lys
    290                 295                 300

Leu Tyr Ser His Ala Ser Ile Glu Asn His Ile Arg Leu Val Val Val
305                 310                 315                 320

Lys Val Val Val Leu Gly Asp Lys Asp Lys Ser Leu Glu Val Ser Lys
                325                 330                 335

Asn Ala Ala Thr Thr Leu Lys Asn Phe Cys Lys Trp Gln His Gln His
            340                 345                 350

Asn Gln Leu Gly Asp Asp His Glu Glu His Tyr Asp Ala Ala Ile Leu
    355                 360                 365

Phe Thr Arg Glu Asp Leu Cys Gly His His Ser Cys Asp Thr Leu Gly
370                 375                 380

Met Ala Asp Val Gly Thr Ile Cys Ser Pro Glu Arg Ser Cys Ala Val
385                 390                 395                 400

Ile Glu Asp Asp Gly Leu His Ala Ala Phe Thr Val Ala His Glu Ile
                405                 410                 415

Gly His Leu Leu Gly Leu Ser His Asp Asp Ser Lys Phe Cys Glu Glu
            420                 425                 430

Asn Phe Gly Ser Thr Glu Asp Lys Arg Leu Met Ser Ser Ile Leu Thr
        435                 440                 445

Ser Ile Asp Ala Ser Lys Pro Trp Ser Lys Cys Thr Ser Ala Thr Ile
    450                 455                 460

Thr Glu Phe Leu Asp Asp Gly His Gly Asn Cys Leu Leu Asp Leu Pro
465                 470                 475                 480

Arg Lys Gln Ile Pro Gly Pro Glu Glu Leu Pro Gly Gln Thr Tyr Asp
                485                 490                 495

Ala Ser Gln Gln Cys Asn Leu Thr Phe Gly Pro Glu Tyr Ser Val Cys
            500                 505                 510

Pro Gly Met Asp Val Cys Ala Arg Leu Trp Cys Ala Val Val Arg Gln
        515                 520                 525

Gly Gln Met Val Cys Leu Thr Lys Lys Leu Pro Ala Val Glu Gly Thr
    530                 535                 540

Pro Cys Gly Lys Gly Arg Ile Cys Leu Gln Gly Lys Cys Val Asp Lys
545                 550                 555                 560

Thr Lys Lys Lys Tyr Tyr Ser Thr Ser Ser His Gly Asn Trp Gly Ser
                565                 570                 575

Trp Gly Ser Trp Gly Gln Cys Ser Arg Ser Cys Gly Gly Val Gln
            580                 585                 590

Phe Ala Tyr Arg His Cys Asn Asn Pro Ala Pro Arg Asn Gly Arg
    595                 600                 605

Tyr Cys Thr Gly Lys Arg Ala Ile Tyr Arg Ser Cys Ser Val Thr Pro
    610                 615                 620

Cys Pro His His His His His His His His His
```

<210> SEQ ID NO 151
<211> LENGTH: 629
<212> TYPE: PRT
<213> ORGANISM: Artificial Sequence
<220> FEATURE:
<223> OTHER INFORMATION: Description of Artificial Sequence: Synthetic rat ADAMTS5

<400> SEQUENCE: 151

| Met | Arg | Leu | Glu | Trp | Ala | Ser | Leu | Leu | Leu | Leu | Leu | Leu | Leu | Cys |
|---|---|---|---|---|---|---|---|---|---|---|---|---|---|---|
| 1 | | | | 5 | | | | | 10 | | | | | 15 |

| Ala | Ser | Cys | Leu | Ala | Leu | Ala | Ala | Asp | Asn | Pro | Ala | Ala | Pro | Ala |
|---|---|---|---|---|---|---|---|---|---|---|---|---|---|---|
| | | | 20 | | | | | 25 | | | | | 30 | |

| Gln | Asp | Lys | Thr | Arg | Gln | Pro | Arg | Ala | Ala | Ala | Ala | Ala | Gln | Pro |
|---|---|---|---|---|---|---|---|---|---|---|---|---|---|---|
| | | | | 35 | | | | | 40 | | | | | 45 |

| Asp | Gln | Arg | Gln | Trp | Glu | Glu | Thr | Gln | Glu | Arg | Gly | His | Pro | Gln | Pro |
|---|---|---|---|---|---|---|---|---|---|---|---|---|---|---|---|
| | 50 | | | | | 55 | | | | | 60 | | | | |

| Leu | Ala | Arg | Gln | Arg | Ser | Ser | Gly | Leu | Val | Gln | Asn | Ile | Asp | Gln |
|---|---|---|---|---|---|---|---|---|---|---|---|---|---|---|
| 65 | | | | | 70 | | | | | 75 | | | | 80 |

| Leu | Tyr | Ser | Gly | Gly | Lys | Val | Gly | Tyr | Leu | Val | Tyr | Ala | Gly | Gly |
|---|---|---|---|---|---|---|---|---|---|---|---|---|---|---|
| | | | | 85 | | | | | 90 | | | | | 95 |

| Arg | Arg | Phe | Leu | Leu | Asp | Leu | Glu | Arg | Asp | Asp | Thr | Val | Gly | Ala | Ala |
|---|---|---|---|---|---|---|---|---|---|---|---|---|---|---|---|
| | | | 100 | | | | | 105 | | | | | 110 | | |

| Gly | Gly | Ile | Val | Thr | Ala | Gly | Gly | Leu | Ser | Ala | Ser | Ser | Gly | His | Arg |
|---|---|---|---|---|---|---|---|---|---|---|---|---|---|---|---|
| | | 115 | | | | | 120 | | | | | 125 | | | |

| Gly | His | Cys | Phe | Tyr | Arg | Gly | Thr | Val | Asp | Gly | Ser | Pro | Arg | Ser | Leu |
|---|---|---|---|---|---|---|---|---|---|---|---|---|---|---|---|
| | 130 | | | | | 135 | | | | | 140 | | | | |

| Ala | Val | Phe | Asp | Leu | Cys | Gly | Gly | Leu | Asp | Gly | Phe | Phe | Ala | Val | Lys |
|---|---|---|---|---|---|---|---|---|---|---|---|---|---|---|---|
| 145 | | | | | 150 | | | | | 155 | | | | | 160 |

| His | Ala | Arg | Tyr | Thr | Leu | Lys | Pro | Leu | Leu | Arg | Gly | Ser | Trp | Ala | Glu |
|---|---|---|---|---|---|---|---|---|---|---|---|---|---|---|---|
| | | | | 165 | | | | | 170 | | | | | 175 | |

| Ser | Glu | Arg | Val | Tyr | Gly | Asp | Gly | Ser | Ser | Arg | Ile | Leu | His | Val | Tyr |
|---|---|---|---|---|---|---|---|---|---|---|---|---|---|---|---|
| | | | | 180 | | | | | 185 | | | | | 190 | |

| Thr | Arg | Glu | Gly | Phe | Ser | Phe | Glu | Ala | Leu | Pro | Pro | Arg | Thr | Ser | Cys |
|---|---|---|---|---|---|---|---|---|---|---|---|---|---|---|---|
| | | | 195 | | | | | 200 | | | | | 205 | | |

| Glu | Thr | Pro | Ala | Ser | Pro | Ser | Gly | Ala | Gln | Glu | Ser | Pro | Ser | Val | His |
|---|---|---|---|---|---|---|---|---|---|---|---|---|---|---|---|
| | 210 | | | | | 215 | | | | | 220 | | | | |

| Ser | Ser | Arg | Arg | Arg | Thr | Glu | Leu | Ala | Pro | Gln | Leu | Leu | Asp | His |
|---|---|---|---|---|---|---|---|---|---|---|---|---|---|---|
| 225 | | | | | 230 | | | | | 235 | | | | 240 |

| Ser | Ala | Phe | Ser | Pro | Ala | Gly | Asn | Ala | Gly | Pro | Gln | Thr | Trp | Trp | Arg |
|---|---|---|---|---|---|---|---|---|---|---|---|---|---|---|---|
| | | | | 245 | | | | | 250 | | | | | 255 | |

| Arg | Arg | Arg | Arg | Ser | Ile | Ser | Arg | Ala | Arg | Gln | Val | Glu | Leu | Leu | Leu |
|---|---|---|---|---|---|---|---|---|---|---|---|---|---|---|---|
| | | | 260 | | | | | 265 | | | | | 270 | | |

| Val | Ala | Asp | Ser | Ser | Met | Ala | Lys | Met | Tyr | Gly | Arg | Gly | Leu | Gln | His |
|---|---|---|---|---|---|---|---|---|---|---|---|---|---|---|---|
| | | 275 | | | | | 280 | | | | | 285 | | | |

| Tyr | Leu | Leu | Thr | Leu | Ala | Ser | Ile | Ala | Asn | Arg | Leu | Tyr | Ser | His | Ala |
|---|---|---|---|---|---|---|---|---|---|---|---|---|---|---|---|
| | 290 | | | | | 295 | | | | | 300 | | | | |

| Ser | Ile | Glu | Asn | His | Ile | Arg | Leu | Ala | Val | Val | Lys | Val | Val | Val | Leu |
|---|---|---|---|---|---|---|---|---|---|---|---|---|---|---|---|
| 305 | | | | | 310 | | | | | 315 | | | | | 320 |

| Thr | Asp | Lys | Ser | Leu | Glu | Val | Ser | Lys | Asn | Ala | Ala | Thr | Thr | Leu | Lys |
|---|---|---|---|---|---|---|---|---|---|---|---|---|---|---|---|
| | | | 325 | | | | | 330 | | | | | 335 | | |

| Asn | Phe | Cys | Lys | Trp | Gln | His | Gln | His | Asn | Gln | Leu | Gly | Asp | Asp | His |
|---|---|---|---|---|---|---|---|---|---|---|---|---|---|---|---|
| | | | 340 | | | | | 345 | | | | | 350 | | |

Glu Glu His Tyr Asp Ala Ala Ile Leu Phe Thr Arg Glu Asp Leu Cys
              355                 360                 365

Gly His His Ser Cys Asp Thr Leu Gly Met Ala Asp Val Gly Thr Ile
370                 375                 380

Cys Ser Pro Glu Arg Ser Cys Ala Val Ile Glu Asp Asp Gly Leu His
385                 390                 395                 400

Ala Ala Phe Thr Val Ala His Glu Ile Gly His Leu Leu Gly Leu Ser
              405                 410                 415

His Asp Asp Ser Lys Phe Cys Glu Glu Asn Phe Gly Ser Thr Glu Asp
              420                 425                 430

Lys Arg Leu Met Ser Ser Ile Leu Thr Ser Ile Asp Ala Ser Lys Pro
              435                 440                 445

Trp Ser Lys Cys Thr Ser Ala Thr Ile Thr Glu Phe Leu Asp Asp Gly
450                 455                 460

His Gly Asn Cys Leu Leu Asp Val Pro Arg Lys Gln Ile Leu Gly Pro
465                 470                 475                 480

Glu Glu Leu Pro Gly Gln Thr Tyr Asp Ala Thr Gln Gln Cys Asn Leu
              485                 490                 495

Thr Phe Gly Pro Glu Tyr Ser Val Cys Pro Gly Met Asp Val Cys Ala
              500                 505                 510

Arg Leu Trp Cys Ala Val Val Arg Gln Gly Gln Met Val Cys Leu Thr
              515                 520                 525

Lys Lys Leu Pro Ala Val Glu Gly Thr Pro Cys Gly Lys Gly Arg Ile
              530                 535                 540

Cys Leu Gln Gly Lys Cys Val Asp Lys Thr Lys Lys Lys Tyr Tyr Ser
545                 550                 555                 560

Thr Ser Ser His Gly Asn Trp Gly Ser Trp Gly Pro Trp Gly Gln Cys
              565                 570                 575

Ser Arg Ser Cys Gly Gly Val Gln Phe Ala Tyr Arg His Cys Asn
              580                 585                 590

Asn Pro Ala Pro Arg Asn Ser Gly Arg Tyr Cys Thr Gly Lys Arg Ala
              595                 600                 605

Ile Tyr Arg Ser Cys Ser Val Ile Pro Cys Pro His His His His
              610                 615                 620

His His His His His
625

<210> SEQ ID NO 152
<211> LENGTH: 632
<212> TYPE: PRT
<213> ORGANISM: Artificial Sequence
<220> FEATURE:
<223> OTHER INFORMATION: Description of Artificial Sequence: Synthetic
      guinea pig ADAMTS5

<400> SEQUENCE: 152

Met Leu Leu Gly Trp Ala Ser Leu Leu Leu Cys Ala Phe Arg Leu Pro
1               5                   10                  15

Gln Ala Ala Ala Ser Ala Ala Ala Pro Ala Gln Asp Lys Ala Gly
              20                  25                  30

Gln Pro Arg Ala Ala Ala Ala Pro Gln Pro Arg Arg Gln Gly
              35                  40                  45

Glu His Ala Pro Leu Arg Val Glu Pro Pro Gly His Pro His Ala Leu
              50                  55                  60

Ala Pro Gln Arg Arg Gly Arg Gly Leu Leu Gln Ser Ile Asp Arg Leu
65                  70                  75                  80

```
Tyr Ser Gly Gly Gly Lys Val Gly Tyr Leu Val Tyr Ala Gly Gly Arg
                85                  90                  95

Arg Phe Leu Leu Asp Leu Glu Arg Asp Gly Ser Val Gly Ala Ala Gly
            100                 105                 110

Leu Phe Pro Ala Gly Gly Leu Ser Ala Pro Arg Arg His Arg Ser
            115                 120                 125

His Cys Phe Tyr Arg Gly Thr Val Asp Gly Ser Pro Arg Ser Leu Ala
    130                 135                 140

Val Phe Asp Leu Cys Gly Gly Leu Arg Gly Phe Phe Ala Val Lys His
145                 150                 155                 160

Ala Arg Tyr Thr Val Lys Pro Leu Leu Arg Gly Pro Trp Ala Glu Ala
                165                 170                 175

Asp Thr Pro Arg Val Tyr Gly Asp Glu Ser Ala Arg Ile Pro His Val
            180                 185                 190

Tyr Thr Arg Glu Gly Phe Ser Phe Glu Ala Leu Pro Pro Arg Ala Ser
        195                 200                 205

Cys Glu Thr Pro Ala Ser Gln Pro Gly Pro His Glu Arg Pro Pro Ala
    210                 215                 220

His Asn Ser Pro Gly Arg His Ser Thr Val Asp Pro Gln Leu Pro Glu
225                 230                 235                 240

Leu Ser Ala Leu Ser Pro Ala Gly Asp Pro Gly Gln Gln Ile Trp Trp
                245                 250                 255

Arg Arg Arg Arg Arg Ser Ile Ser Arg Ala Arg Gln Val Glu Leu Leu
            260                 265                 270

Leu Val Ala Asp Gly Ser Met Ala Lys Met Tyr Gly Arg Gly Leu Gln
        275                 280                 285

His Tyr Leu Leu Thr Leu Ala Ser Ile Ala Asn Arg Leu Tyr Ser His
    290                 295                 300

Ala Ser Ile Glu Asn His Ile Arg Leu Ala Val Val Lys Val Val Val
305                 310                 315                 320

Leu Gly Asp Lys Asp Lys Ser Leu Glu Val Ser Lys Asn Ala Ala Thr
                325                 330                 335

Thr Leu Lys Asn Phe Cys Lys Trp Gln His Gln His Asn Gln Leu Gly
            340                 345                 350

Asp Asp His Glu Glu His Tyr Asp Ala Ala Ile Leu Phe Thr Arg Glu
        355                 360                 365

Asp Leu Cys Gly His His Ser Cys Asp Thr Leu Gly Met Ala Asp Val
    370                 375                 380

Gly Thr Ile Cys Ser Pro Glu Arg Ser Cys Ala Val Ile Glu Asp Asp
385                 390                 395                 400

Gly Leu His Ala Ala Phe Thr Val Ala His Glu Ile Gly His Leu Leu
                405                 410                 415

Gly Leu Ser His Asp Asp Ser Lys Phe Cys Glu Glu Asn Phe Gly Leu
            420                 425                 430

Thr Glu Asp Lys Arg Leu Met Ser Ser Ile Leu Thr Ser Ile Asp Ala
        435                 440                 445

Ser Lys Pro Trp Ser Lys Cys Thr Ser Ala Thr Met Thr Glu Phe Leu
    450                 455                 460

Asp Asp Gly His Gly Asn Cys Leu Leu Asp Val Pro Arg Lys Gln Ile
465                 470                 475                 480

Pro Ser Pro Glu Glu Leu Pro Gly Gln Thr Tyr Asp Ala Thr Gln Gln
                485                 490                 495
```

```
Cys Asn Leu Thr Phe Gly Pro Glu Tyr Ser Val Cys Pro Gly Met Asp
                500                 505                 510

Val Cys Ala Arg Leu Trp Cys Ala Val Val Arg Gln Gly Gln Met Val
                515                 520                 525

Cys Leu Thr Lys Lys Leu Pro Ala Val Glu Gly Thr Pro Cys Gly Lys
                530                 535                 540

Gly Arg Ile Cys Leu Gln Gly Lys Cys Val Asp Lys Thr Lys Lys Lys
545                 550                 555                 560

Tyr Tyr Ser Thr Ser Ser His Gly Asn Trp Gly Ser Trp Gly Pro Trp
                565                 570                 575

Gly Gln Cys Ser Arg Ser Cys Gly Gly Gly Val Gln Phe Ala Tyr Arg
                580                 585                 590

His Cys Asn Asn Pro Ala Pro Arg Asn Ser Gly Arg Tyr Cys Thr Gly
                595                 600                 605

Lys Arg Ala Ile Tyr Arg Ser Cys Ser Val Thr Pro Cys Pro His His
610                 615                 620

His His His His His His His
625                 630

<210> SEQ ID NO 153
<211> LENGTH: 632
<212> TYPE: PRT
<213> ORGANISM: Artificial Sequence
<220> FEATURE:
<223> OTHER INFORMATION: Description of Artificial Sequence: Synthetic
      mouse ADAMTS5

<400> SEQUENCE: 153

Met Arg Leu Glu Trp Ala Pro Leu Leu Leu Leu Leu Leu Leu Leu Ser
1               5                   10                  15

Ala Ser Cys Leu Ser Leu Ala Ala Asp Ser Pro Ala Ala Ala Pro Ala
                20                  25                  30

Gln Asp Lys Thr Arg Gln Pro Gln Ala Ala Ala Ala Ala Ala Glu Pro
                35                  40                  45

Asp Gln Pro Gln Gly Glu Glu Thr Arg Glu Arg Gly His Leu Gln Pro
        50                  55                  60

Leu Ala Gly Gln Arg Arg Ser Gly Gly Leu Val Gln Asn Ile Asp Gln
65                  70                  75                  80

Leu Tyr Ser Gly Gly Gly Lys Val Gly Tyr Leu Val Tyr Ala Gly Gly
                85                  90                  95

Arg Arg Phe Leu Leu Asp Leu Glu Arg Asp Asp Thr Val Gly Ala Ala
                100                 105                 110

Gly Ser Ile Val Thr Ala Gly Gly Gly Leu Ser Ala Ser Ser Gly His
                115                 120                 125

Arg Gly His Cys Phe Tyr Arg Gly Thr Val Asp Gly Ser Pro Arg Ser
                130                 135                 140

Leu Ala Val Phe Asp Leu Cys Gly Gly Leu Asp Gly Phe Phe Ala Val
145                 150                 155                 160

Lys His Ala Arg Tyr Thr Leu Lys Pro Leu Leu Arg Gly Ser Trp Ala
                165                 170                 175

Glu Tyr Glu Arg Ile Tyr Gly Asp Gly Ser Ser Arg Ile Leu His Val
                180                 185                 190

Tyr Asn Arg Glu Gly Phe Ser Phe Glu Ala Leu Pro Pro Arg Ala Ser
                195                 200                 205

Cys Glu Thr Pro Ala Ser Pro Ser Gly Pro Gln Glu Ser Pro Ser Val
                210                 215                 220
```

```
His Ser Arg Ser Arg Arg Ser Ala Leu Ala Pro Gln Leu Leu Asp
225                 230                 235                 240

His Ser Ala Phe Ser Pro Ser Gly Asn Ala Gly Pro Gln Thr Trp Trp
                245                 250                 255

Arg Arg Arg Arg Arg Ser Ile Ser Arg Ala Arg Gln Val Glu Leu Leu
            260                 265                 270

Leu Val Ala Asp Ser Ser Met Ala Arg Met Tyr Gly Arg Gly Leu Gln
                275                 280                 285

His Tyr Leu Leu Thr Leu Ala Ser Ile Ala Asn Arg Leu Tyr Ser His
        290                 295                 300

Ala Ser Ile Glu Asn His Ile Arg Leu Ala Val Val Lys Val Val Val
305                 310                 315                 320

Leu Thr Asp Lys Asp Thr Ser Leu Glu Val Ser Lys Asn Ala Ala Thr
                325                 330                 335

Thr Leu Lys Asn Phe Cys Lys Trp Gln His Gln His Asn Gln Leu Gly
                340                 345                 350

Asp Asp His Glu Glu His Tyr Asp Ala Ala Ile Leu Phe Thr Arg Glu
                355                 360                 365

Asp Leu Cys Gly His His Ser Cys Asp Thr Leu Gly Met Ala Asp Val
            370                 375                 380

Gly Thr Ile Cys Ser Pro Glu Arg Ser Cys Ala Val Ile Glu Asp Asp
385                 390                 395                 400

Gly Leu His Ala Ala Phe Thr Val Ala His Glu Ile Gly His Leu Leu
                405                 410                 415

Gly Leu Ser His Asp Asp Ser Lys Phe Cys Glu Glu Asn Phe Gly Thr
            420                 425                 430

Thr Glu Asp Lys Arg Leu Met Ser Ser Ile Leu Thr Ser Ile Asp Ala
            435                 440                 445

Ser Lys Pro Trp Ser Lys Cys Thr Ser Ala Thr Ile Thr Glu Phe Leu
450                 455                 460

Asp Asp Gly His Gly Asn Cys Leu Leu Asp Leu Pro Arg Lys Gln Ile
465                 470                 475                 480

Leu Gly Pro Glu Glu Leu Pro Gly Gln Thr Tyr Asp Ala Thr Gln Gln
                485                 490                 495

Cys Asn Leu Thr Phe Gly Pro Glu Tyr Ser Val Cys Pro Gly Met Asp
                500                 505                 510

Val Cys Ala Arg Leu Trp Cys Ala Val Val Arg Gln Gly Gln Met Val
            515                 520                 525

Cys Leu Thr Lys Lys Leu Pro Ala Val Glu Gly Thr Pro Cys Gly Lys
            530                 535                 540

Gly Arg Val Cys Leu Gln Gly Lys Cys Val Asp Lys Thr Lys Lys Lys
545                 550                 555                 560

Tyr Tyr Ser Thr Ser Ser His Gly Asn Trp Gly Ser Trp Gly Pro Trp
                565                 570                 575

Gly Gln Cys Ser Arg Ser Cys Gly Gly Gly Val Gln Phe Ala Tyr Arg
            580                 585                 590

His Cys Asn Asn Pro Ala Pro Arg Asn Ser Gly Arg Tyr Cys Thr Gly
            595                 600                 605

Lys Arg Ala Ile Tyr Arg Ser Cys Ser Val Thr Pro Cys Pro His His
            610                 615                 620

His His His His His His
625                 630
```

<210> SEQ ID NO 154
<211> LENGTH: 632
<212> TYPE: PRT
<213> ORGANISM: Artificial Sequence
<220> FEATURE:
<223> OTHER INFORMATION: Description of Artificial Sequence: Synthetic cynomolgus ADAMTS5

<400> SEQUENCE: 154

```
Met Leu Leu Gly Trp Ala Ser Leu Leu Leu Cys Ala Phe Arg Leu Pro
1               5                   10                  15

Leu Ala Ala Ala Gly Pro Ala Ala Pro Ala Gln Asp Lys Ala Gly
            20                  25                  30

Gln Pro Ala Thr Ala Ala Ala Ala Gln Pro Arg Arg Arg Gln Gly
            35                  40                  45

Glu Glu Val Gln Glu Arg Thr Glu Pro Gly His Pro His Pro Leu
50                  55                  60

Ala Gln Arg Arg Ser Ser Lys Gly Leu Val Gln Asn Ile Asp Gln Leu
65                  70                  75                  80

Tyr Ser Gly Gly Gly Lys Val Gly Tyr Leu Val Tyr Ala Gly Gly Arg
                85                  90                  95

Arg Phe Leu Leu Asp Leu Glu Arg Asp Gly Ser Val Gly Thr Ala Gly
                100                 105                 110

Phe Val Pro Thr Glu Gly Gly Thr Ser Ala Pro Trp Arg His Arg Ser
            115                 120                 125

His Cys Phe Tyr Arg Gly Thr Val Asp Gly Ser Pro Arg Ser Leu Ala
        130                 135                 140

Val Phe Asp Leu Cys Gly Gly Leu Asp Gly Phe Phe Ala Val Lys His
145                 150                 155                 160

Ala Arg Tyr Thr Leu Lys Pro Leu Leu Arg Gly Pro Trp Ala Glu Glu
                165                 170                 175

Glu Thr Arg Arg Val Tyr Gly Asp Gly Ser Ala Arg Ile Leu His Val
            180                 185                 190

Tyr Thr Arg Glu Gly Phe Ser Phe Glu Ala Leu Gln Pro Arg Ala Ser
        195                 200                 205

Cys Glu Thr Pro Ala Ser Thr Pro Glu Pro His Glu Arg Pro Pro Ala
210                 215                 220

His Ser Asn Pro Gly Gly Arg Ala Ala Leu Ala Ser Gln Leu Leu Asp
225                 230                 235                 240

Gln Ser Ala Val Ser Pro Ala Gly Gly Pro Gly Pro Gln Thr Trp Trp
                245                 250                 255

Arg Arg Arg Arg Arg Ser Ile Ser Arg Ala Arg Gln Val Glu Leu Leu
            260                 265                 270

Leu Val Ala Asp Ala Ser Met Ala Arg Leu Tyr Gly Arg Gly Leu Gln
        275                 280                 285

His Tyr Leu Leu Thr Leu Ala Ser Ile Ala Asn Arg Leu Tyr Ser His
    290                 295                 300

Ala Ser Ile Glu Asn His Ile Arg Leu Ala Val Val Lys Val Val Val
305                 310                 315                 320

Leu Gly Asp Lys Asp Lys Ser Leu Glu Val Ser Lys Asn Ala Ala Thr
                325                 330                 335

Thr Leu Lys Asn Phe Cys Lys Trp Gln His Gln His Asn Gln Leu Gly
            340                 345                 350

Asp Asp His Glu Glu His Tyr Asp Ala Ala Ile Leu Phe Thr Arg Glu
        355                 360                 365
```

```
Asp Leu Cys Gly His His Ser Cys Asp Thr Leu Gly Met Ala Asp Val
    370                 375                 380

Gly Thr Ile Cys Ser Pro Glu Arg Ser Cys Ala Val Ile Glu Asp Asp
385                 390                 395                 400

Gly Leu His Ala Ala Phe Thr Val Ala His Glu Ile Gly His Leu Leu
                405                 410                 415

Gly Leu Ser His Asp Asp Ser Lys Phe Cys Glu Glu Thr Phe Gly Ser
                420                 425                 430

Thr Glu Asp Lys Arg Leu Met Ser Ser Ile Leu Thr Ser Ile Asp Ala
            435                 440                 445

Ser Lys Pro Trp Ser Lys Cys Thr Ser Ala Thr Ile Thr Glu Phe Leu
450                 455                 460

Asp Asp Gly His Gly Asn Cys Leu Leu Asp Gln Pro Arg Lys Gln Ile
465                 470                 475                 480

Leu Gly Pro Glu Glu Leu Pro Gly Gln Thr Tyr Asp Ala Thr Gln Gln
                485                 490                 495

Cys Asn Leu Thr Phe Gly Pro Glu Tyr Ser Val Cys Pro Gly Met Asp
                500                 505                 510

Val Cys Ala Arg Leu Trp Cys Ala Val Val Arg Gln Gly Gln Met Val
            515                 520                 525

Cys Leu Thr Lys Lys Leu Pro Ala Val Glu Gly Thr Pro Cys Gly Lys
530                 535                 540

Gly Arg Ile Cys Leu Gln Gly Lys Cys Val Asp Lys Thr Lys Lys Lys
545                 550                 555                 560

Tyr Tyr Ser Thr Ser Ser His Gly Asn Trp Gly Ser Trp Gly Ser Trp
                565                 570                 575

Gly Gln Cys Ser Arg Ser Cys Gly Gly Gly Val Gln Phe Ala Tyr Arg
                580                 585                 590

His Cys Asn Asn Pro Ala Pro Arg Asn Asn Gly Arg Tyr Cys Thr Gly
            595                 600                 605

Lys Arg Ala Ile Tyr Arg Ser Cys Gly Leu Met Pro Cys Pro His His
610                 615                 620

His His His His His His His
625                 630

<210> SEQ ID NO 155
<211> LENGTH: 2415
<212> TYPE: PRT
<213> ORGANISM: Homo sapiens
<220> FEATURE:
<223> OTHER INFORMATION: human Aggrecan

<400> SEQUENCE: 155

Met Thr Thr Leu Leu Trp Val Phe Val Thr Leu Arg Val Ile Thr Ala
1               5                   10                  15

Ala Val Thr Val Glu Thr Ser Asp His Asp Asn Ser Leu Ser Val Ser
                20                  25                  30

Ile Pro Gln Pro Ser Pro Leu Arg Val Leu Leu Gly Thr Ser Leu Thr
                35                  40                  45

Ile Pro Cys Tyr Phe Ile Asp Pro Met His Pro Val Thr Thr Ala Pro
            50                  55                  60

Ser Thr Ala Pro Leu Ala Pro Arg Ile Lys Trp Ser Arg Val Ser Lys
65                  70                  75                  80

Glu Lys Glu Val Val Leu Leu Val Ala Thr Glu Gly Arg Val Arg Val
                85                  90                  95
```

```
Asn Ser Ala Tyr Gln Asp Lys Val Ser Leu Pro Asn Tyr Pro Ala Ile
                100                 105                 110

Pro Ser Asp Ala Thr Leu Glu Val Gln Ser Leu Arg Ser Asn Asp Ser
            115                 120                 125

Gly Val Tyr Arg Cys Glu Val Met His Gly Ile Glu Asp Ser Glu Ala
        130                 135                 140

Thr Leu Glu Val Val Lys Gly Ile Val Phe His Tyr Arg Ala Ile
145                 150                 155                 160

Ser Thr Arg Tyr Thr Leu Asp Phe Asp Arg Ala Gln Arg Ala Cys Leu
                165                 170                 175

Gln Asn Ser Ala Ile Ile Ala Thr Pro Glu Gln Leu Gln Ala Ala Tyr
            180                 185                 190

Glu Asp Gly Phe His Gln Cys Asp Ala Gly Trp Leu Ala Asp Gln Thr
        195                 200                 205

Val Arg Tyr Pro Ile His Thr Pro Arg Glu Gly Cys Tyr Gly Asp Lys
    210                 215                 220

Asp Glu Phe Pro Gly Val Arg Thr Tyr Gly Ile Arg Asp Thr Asn Glu
225                 230                 235                 240

Thr Tyr Asp Val Tyr Cys Phe Ala Glu Glu Met Glu Gly Glu Val Phe
                245                 250                 255

Tyr Ala Thr Ser Pro Glu Lys Phe Thr Phe Gln Glu Ala Ala Asn Glu
            260                 265                 270

Cys Arg Arg Leu Gly Ala Arg Leu Ala Thr Thr Gly His Val Tyr Leu
        275                 280                 285

Ala Trp Gln Ala Gly Met Asp Met Cys Ser Ala Gly Trp Leu Ala Asp
    290                 295                 300

Arg Ser Val Arg Tyr Pro Ile Ser Lys Ala Arg Pro Asn Cys Gly Gly
305                 310                 315                 320

Asn Leu Leu Gly Val Arg Thr Val Tyr Val His Ala Asn Gln Thr Gly
                325                 330                 335

Tyr Pro Asp Pro Ser Ser Arg Tyr Asp Ala Ile Cys Tyr Thr Gly Glu
            340                 345                 350

Asp Phe Val Asp Ile Pro Glu Asn Phe Phe Gly Val Gly Gly Glu Glu
        355                 360                 365

Asp Ile Thr Val Gln Thr Val Thr Trp Pro Asp Met Glu Leu Pro Leu
    370                 375                 380

Pro Arg Asn Ile Thr Glu Gly Glu Ala Arg Gly Ser Val Ile Leu Thr
385                 390                 395                 400

Val Lys Pro Ile Phe Glu Val Ser Pro Ser Pro Leu Glu Pro Glu Glu
                405                 410                 415

Pro Phe Thr Phe Ala Pro Glu Ile Gly Ala Thr Ala Phe Ala Glu Val
            420                 425                 430

Glu Asn Glu Thr Gly Glu Ala Thr Arg Pro Trp Gly Phe Pro Thr Pro
        435                 440                 445

Gly Leu Gly Pro Ala Thr Ala Phe Thr Ser Glu Asp Leu Val Val Gln
    450                 455                 460

Val Thr Ala Val Pro Gly Gln Pro His Leu Pro Gly Gly Val Val Phe
465                 470                 475                 480

His Tyr Arg Pro Gly Pro Thr Arg Tyr Ser Leu Thr Phe Glu Glu Ala
                485                 490                 495

Gln Gln Ala Cys Pro Gly Thr Gly Ala Val Ile Ala Ser Pro Glu Gln
            500                 505                 510
```

-continued

Leu Gln Ala Ala Tyr Glu Ala Gly Tyr Glu Gln Cys Asp Ala Gly Trp
        515                 520                 525

Leu Arg Asp Gln Thr Val Arg Tyr Pro Ile Val Ser Pro Arg Thr Pro
530                 535                 540

Cys Val Gly Asp Lys Asp Ser Ser Pro Gly Val Arg Thr Tyr Gly Val
545                 550                 555                 560

Arg Pro Ser Thr Glu Thr Tyr Asp Val Tyr Cys Phe Val Asp Arg Leu
                565                 570                 575

Glu Gly Glu Val Phe Phe Ala Thr Arg Leu Gln Phe Thr Phe Gln
            580                 585                 590

Glu Ala Leu Glu Phe Cys Glu Ser His Asn Ala Thr Ala Thr Thr Gly
        595                 600                 605

Gln Leu Tyr Ala Ala Trp Ser Arg Gly Leu Asp Lys Cys Tyr Ala Gly
    610                 615                 620

Trp Leu Ala Asp Gly Ser Leu Arg Tyr Pro Ile Val Thr Pro Arg Pro
625                 630                 635                 640

Ala Cys Gly Gly Asp Lys Pro Gly Val Arg Thr Val Tyr Leu Tyr Pro
                645                 650                 655

Asn Gln Thr Gly Leu Pro Asp Pro Leu Ser Arg His His Ala Phe Cys
            660                 665                 670

Phe Arg Gly Ile Ser Ala Val Pro Ser Pro Gly Glu Glu Glu Gly Gly
        675                 680                 685

Thr Pro Thr Ser Pro Ser Gly Val Glu Glu Trp Ile Val Thr Gln Val
    690                 695                 700

Val Pro Gly Val Ala Ala Val Pro Val Glu Glu Thr Thr Ala Val
705                 710                 715                 720

Pro Ser Gly Glu Thr Thr Ala Ile Leu Glu Phe Thr Thr Glu Pro Glu
                725                 730                 735

Asn Gln Thr Glu Trp Glu Pro Ala Tyr Thr Pro Val Gly Thr Ser Pro
            740                 745                 750

Leu Pro Gly Ile Leu Pro Thr Trp Pro Pro Thr Gly Ala Glu Thr Glu
        755                 760                 765

Glu Ser Thr Glu Gly Pro Ser Ala Thr Glu Val Pro Ser Ala Ser Glu
    770                 775                 780

Glu Pro Ser Pro Ser Glu Val Pro Phe Pro Ser Glu Glu Pro Ser Pro
785                 790                 795                 800

Ser Glu Glu Pro Phe Pro Ser Val Arg Pro Phe Pro Ser Val Glu Leu
                805                 810                 815

Phe Pro Ser Glu Glu Pro Phe Pro Ser Lys Glu Pro Ser Pro Ser Glu
            820                 825                 830

Glu Pro Ser Ala Ser Glu Glu Pro Tyr Thr Pro Ser Pro Pro Glu Pro
        835                 840                 845

Ser Trp Thr Glu Leu Pro Ser Ser Gly Glu Glu Ser Gly Ala Pro Asp
    850                 855                 860

Val Ser Gly Asp Phe Thr Gly Ser Gly Asp Val Ser Gly His Leu Asp
865                 870                 875                 880

Phe Ser Gly Gln Leu Ser Gly Asp Arg Ala Ser Gly Leu Pro Ser Gly
                885                 890                 895

Asp Leu Asp Ser Ser Gly Leu Thr Ser Thr Val Gly Ser Gly Leu Thr
            900                 905                 910

Val Glu Ser Gly Leu Pro Ser Gly Asp Glu Glu Arg Ile Glu Trp Pro
        915                 920                 925

Ser Thr Pro Thr Val Gly Glu Leu Pro Ser Gly Ala Glu Ile Leu Glu

```
                930             935             940
Gly Ser Ala Ser Gly Val Gly Asp Leu Ser Gly Leu Pro Ser Gly Glu
945                 950             955             960
Val Leu Glu Thr Ser Ala Ser Gly Val Gly Asp Leu Ser Gly Leu Pro
                965             970             975
Ser Gly Glu Val Leu Glu Thr Thr Ala Pro Gly Val Glu Asp Ile Ser
            980             985             990
Gly Leu Pro Ser Gly Glu Val Leu Glu Thr Thr Ala Pro Gly Val Glu
        995             1000            1005
Asp Ile Ser Gly Leu Pro Ser Gly Glu Val Leu Glu Thr Thr Ala
    1010            1015            1020
Pro Gly Val Glu Asp Ile Ser Gly Leu Pro Ser Gly Glu Val Leu
    1025            1030            1035
Glu Thr Thr Ala Pro Gly Val Glu Asp Ile Ser Gly Leu Pro Ser
    1040            1045            1050
Gly Glu Val Leu Glu Thr Thr Ala Pro Gly Val Glu Asp Ile Ser
    1055            1060            1065
Gly Leu Pro Ser Gly Glu Val Leu Glu Thr Ala Ala Pro Gly Val
    1070            1075            1080
Glu Asp Ile Ser Gly Leu Pro Ser Gly Glu Val Leu Glu Thr Ala
    1085            1090            1095
Ala Pro Gly Val Glu Asp Ile Ser Gly Leu Pro Ser Gly Glu Val
    1100            1105            1110
Leu Glu Thr Ala Ala Pro Gly Val Glu Asp Ile Ser Gly Leu Pro
    1115            1120            1125
Ser Gly Glu Val Leu Glu Thr Ala Ala Pro Gly Val Glu Asp Ile
    1130            1135            1140
Ser Gly Leu Pro Ser Gly Glu Val Leu Glu Thr Ala Ala Pro Gly
    1145            1150            1155
Val Glu Asp Ile Ser Gly Leu Pro Ser Gly Glu Val Leu Glu Thr
    1160            1165            1170
Ala Ala Pro Gly Val Glu Asp Ile Ser Gly Leu Pro Ser Gly Glu
    1175            1180            1185
Val Leu Glu Thr Ala Ala Pro Gly Val Glu Asp Ile Ser Gly Leu
    1190            1195            1200
Pro Ser Gly Glu Val Leu Glu Thr Ala Ala Pro Gly Val Glu Asp
    1205            1210            1215
Ile Ser Gly Leu Pro Ser Gly Glu Val Leu Glu Thr Ala Ala Pro
    1220            1225            1230
Gly Val Glu Asp Ile Ser Gly Leu Pro Ser Gly Glu Val Leu Glu
    1235            1240            1245
Thr Ala Ala Pro Gly Val Glu Asp Ile Ser Gly Leu Pro Ser Gly
    1250            1255            1260
Glu Val Leu Glu Thr Ala Ala Pro Gly Val Glu Asp Ile Ser Gly
    1265            1270            1275
Leu Pro Ser Gly Glu Val Leu Glu Thr Thr Ala Pro Gly Val Glu
    1280            1285            1290
Glu Ile Ser Gly Leu Pro Ser Gly Glu Val Leu Glu Thr Thr Ala
    1295            1300            1305
Pro Gly Val Asp Glu Ile Ser Gly Leu Pro Ser Gly Glu Val Leu
    1310            1315            1320
Glu Thr Thr Ala Pro Gly Val Glu Glu Ile Ser Gly Leu Pro Ser
    1325            1330            1335
```

```
Gly Glu Val Leu Glu Thr Ser Thr Ser Ala Val Gly Asp Leu Ser
    1340                1345                1350

Gly Leu Pro Ser Gly Gly Glu Val Leu Glu Ile Ser Val Ser Gly
    1355                1360                1365

Val Glu Asp Ile Ser Gly Leu Pro Ser Gly Glu Val Val Glu Thr
    1370                1375                1380

Ser Ala Ser Gly Ile Glu Asp Val Ser Glu Leu Pro Ser Gly Glu
    1385                1390                1395

Gly Leu Glu Thr Ser Ala Ser Gly Val Glu Asp Leu Ser Arg Leu
    1400                1405                1410

Pro Ser Gly Glu Glu Val Leu Glu Ile Ser Ala Ser Gly Phe Gly
    1415                1420                1425

Asp Leu Ser Gly Val Pro Ser Gly Gly Glu Gly Leu Glu Thr Ser
    1430                1435                1440

Ala Ser Glu Val Gly Thr Asp Leu Ser Gly Leu Pro Ser Gly Arg
    1445                1450                1455

Glu Gly Leu Glu Thr Ser Ala Ser Gly Ala Glu Asp Leu Ser Gly
    1460                1465                1470

Leu Pro Ser Gly Lys Glu Asp Leu Val Gly Ser Ala Ser Gly Asp
    1475                1480                1485

Leu Asp Leu Gly Lys Leu Pro Ser Gly Thr Leu Gly Ser Gly Gln
    1490                1495                1500

Ala Pro Glu Thr Ser Gly Leu Pro Ser Gly Phe Ser Gly Glu Tyr
    1505                1510                1515

Ser Gly Val Asp Leu Gly Ser Gly Pro Pro Ser Gly Leu Pro Asp
    1520                1525                1530

Phe Ser Gly Leu Pro Ser Gly Phe Pro Thr Val Ser Leu Val Asp
    1535                1540                1545

Ser Thr Leu Val Glu Val Val Thr Ala Ser Thr Ala Ser Glu Leu
    1550                1555                1560

Glu Gly Arg Gly Thr Ile Gly Ile Ser Gly Ala Gly Glu Ile Ser
    1565                1570                1575

Gly Leu Pro Ser Ser Glu Leu Asp Ile Ser Gly Arg Ala Ser Gly
    1580                1585                1590

Leu Pro Ser Gly Thr Glu Leu Ser Gly Gln Ala Ser Gly Ser Pro
    1595                1600                1605

Asp Val Ser Gly Glu Ile Pro Gly Leu Phe Gly Val Ser Gly Gln
    1610                1615                1620

Pro Ser Gly Phe Pro Asp Thr Ser Gly Glu Thr Ser Gly Val Thr
    1625                1630                1635

Glu Leu Ser Gly Leu Ser Ser Gly Gln Pro Gly Val Ser Gly Glu
    1640                1645                1650

Ala Ser Gly Val Leu Tyr Gly Thr Ser Gln Pro Phe Gly Ile Thr
    1655                1660                1665

Asp Leu Ser Gly Glu Thr Ser Gly Val Pro Asp Leu Ser Gly Gln
    1670                1675                1680

Pro Ser Gly Leu Pro Gly Phe Ser Gly Ala Thr Ser Gly Val Pro
    1685                1690                1695

Asp Leu Val Ser Gly Thr Thr Ser Gly Ser Gly Glu Ser Ser Gly
    1700                1705                1710

Ile Thr Phe Val Asp Thr Ser Leu Val Glu Val Ala Pro Thr Thr
    1715                1720                1725
```

-continued

```
Phe Lys Glu Glu Gly Leu Gly Ser Val Glu Leu Ser Gly Leu
    1730                1735                1740

Pro Ser Gly Glu Ala Asp Leu Ser Gly Lys Ser Gly Met Val Asp
    1745                1750                1755

Val Ser Gly Gln Phe Ser Gly Thr Val Asp Ser Ser Gly Phe Thr
    1760                1765                1770

Ser Gln Thr Pro Glu Phe Ser Gly Leu Pro Ser Gly Ile Ala Glu
    1775                1780                1785

Val Ser Gly Glu Ser Ser Arg Ala Glu Ile Gly Ser Ser Leu Pro
    1790                1795                1800

Ser Gly Ala Tyr Tyr Gly Ser Gly Thr Pro Ser Ser Phe Pro Thr
    1805                1810                1815

Val Ser Leu Val Asp Arg Thr Leu Val Glu Ser Val Thr Gln Ala
    1820                1825                1830

Pro Thr Ala Gln Glu Ala Gly Glu Gly Pro Ser Gly Ile Leu Glu
    1835                1840                1845

Leu Ser Gly Ala His Ser Gly Ala Pro Asp Met Ser Gly Glu His
    1850                1855                1860

Ser Gly Phe Leu Asp Leu Ser Gly Leu Gln Ser Gly Leu Ile Glu
    1865                1870                1875

Pro Ser Gly Glu Pro Pro Gly Thr Pro Tyr Phe Ser Gly Asp Phe
    1880                1885                1890

Ala Ser Thr Thr Asn Val Ser Gly Glu Ser Ser Val Ala Met Gly
    1895                1900                1905

Thr Ser Gly Glu Ala Ser Gly Leu Pro Glu Val Thr Leu Ile Thr
    1910                1915                1920

Ser Glu Phe Val Glu Gly Val Thr Glu Pro Thr Ile Ser Gln Glu
    1925                1930                1935

Leu Gly Gln Arg Pro Pro Val Thr His Thr Pro Gln Leu Phe Glu
    1940                1945                1950

Ser Ser Gly Lys Val Ser Thr Ala Gly Asp Ile Ser Gly Ala Thr
    1955                1960                1965

Pro Val Leu Pro Gly Ser Gly Val Glu Val Ser Ser Val Pro Glu
    1970                1975                1980

Ser Ser Ser Glu Thr Ser Ala Tyr Pro Glu Ala Gly Phe Gly Ala
    1985                1990                1995

Ser Ala Ala Pro Glu Ala Ser Arg Glu Asp Ser Gly Ser Pro Asp
    2000                2005                2010

Leu Ser Glu Thr Thr Ser Ala Phe His Glu Ala Asn Leu Glu Arg
    2015                2020                2025

Ser Ser Gly Leu Gly Val Ser Gly Ser Thr Leu Thr Phe Gln Glu
    2030                2035                2040

Gly Glu Ala Ser Ala Ala Pro Glu Val Ser Gly Glu Ser Thr Thr
    2045                2050                2055

Thr Ser Asp Val Gly Thr Glu Ala Pro Gly Leu Pro Ser Ala Thr
    2060                2065                2070

Pro Thr Ala Ser Gly Asp Arg Thr Glu Ile Ser Gly Asp Leu Ser
    2075                2080                2085

Gly His Thr Ser Gln Leu Gly Val Val Ile Ser Thr Ser Ile Pro
    2090                2095                2100

Glu Ser Glu Trp Thr Gln Gln Thr Gln Arg Pro Ala Glu Thr His
    2105                2110                2115

Leu Glu Ile Glu Ser Ser Ser Leu Leu Tyr Ser Gly Glu Glu Thr
```

```
                2120                2125                2130
His Thr Val Glu Thr Ala Thr Ser Pro Thr Asp Ala Ser Ile Pro
        2135                2140                2145

Ala Ser Pro Glu Trp Lys Arg Glu Ser Glu Ser Thr Ala Ala Ala
    2150                2155                2160

Pro Ala Arg Ser Cys Ala Glu Glu Pro Cys Gly Ala Gly Thr Cys
    2165                2170                2175

Lys Glu Thr Glu Gly His Val Ile Cys Leu Cys Pro Pro Gly Tyr
    2180                2185                2190

Thr Gly Glu His Cys Asn Ile Asp Gln Glu Val Cys Glu Glu Gly
    2195                2200                2205

Trp Asn Lys Tyr Gln Gly His Cys Tyr Arg His Phe Pro Asp Arg
    2210                2215                2220

Glu Thr Trp Val Asp Ala Glu Arg Arg Cys Arg Glu Gln Gln Ser
    2225                2230                2235

His Leu Ser Ser Ile Val Thr Pro Glu Glu Gln Glu Phe Val Asn
    2240                2245                2250

Asn Asn Ala Gln Asp Tyr Gln Trp Ile Gly Leu Asn Asp Arg Thr
    2255                2260                2265

Ile Glu Gly Asp Phe Arg Trp Ser Asp Gly His Pro Met Gln Phe
    2270                2275                2280

Glu Asn Trp Arg Pro Asn Gln Pro Asp Asn Phe Phe Ala Ala Gly
    2285                2290                2295

Glu Asp Cys Val Val Met Ile Trp His Glu Lys Gly Glu Trp Asn
    2300                2305                2310

Asp Val Pro Cys Asn Tyr His Leu Pro Phe Thr Cys Lys Lys Gly
    2315                2320                2325

Thr Val Ala Cys Gly Glu Pro Pro Val Val Glu His Ala Arg Thr
    2330                2335                2340

Phe Gly Gln Lys Lys Asp Arg Tyr Glu Ile Asn Ser Leu Val Arg
    2345                2350                2355

Tyr Gln Cys Thr Glu Gly Phe Val Gln Arg His Met Pro Thr Ile
    2360                2365                2370

Arg Cys Gln Pro Ser Gly His Trp Glu Pro Arg Ile Thr Cys
    2375                2380                2385

Thr Asp Ala Thr Thr Tyr Lys Arg Arg Leu Gln Lys Arg Ser Ser
    2390                2395                2400

Arg His Pro Arg Arg Ser Arg Pro Ser Thr Ala His
    2405                2410                2415

<210> SEQ ID NO 156
<211> LENGTH: 122
<212> TYPE: PRT
<213> ORGANISM: Artificial Sequence
<220> FEATURE:
<223> OTHER INFORMATION: Description of Artificial Sequence: Synthetic
      Aggrecan binding ISVD sequences

<400> SEQUENCE: 156

Glu Val Gln Leu Val Glu Ser Gly Gly Gly Val Val Gln Pro Gly Gly
1               5                   10                  15

Ser Leu Arg Leu Ser Cys Ala Ala Ser Gly Ser Thr Phe Ile Ile Asn
            20                  25                  30

Val Val Arg Trp Tyr Arg Arg Ala Pro Gly Lys Gln Arg Glu Leu Val
        35                  40                  45
```

Ala Thr Ile Ser Ser Gly Gly Asn Ala Asn Tyr Val Asp Ser Val Arg
 50                  55                  60

Gly Arg Phe Thr Ile Ser Arg Asp Asn Ser Lys Asn Thr Val Tyr Leu
 65                  70                  75                  80

Gln Met Asn Ser Leu Arg Pro Glu Asp Thr Ala Leu Tyr Tyr Cys Asn
                 85                  90                  95

Val Pro Thr Thr His Tyr Gly Val Tyr Tyr Gly Pro Tyr Trp Gly
            100                 105                 110

Gln Gly Thr Leu Val Thr Val Ser Ser Ala
        115                 120

<210> SEQ ID NO 157
<211> LENGTH: 125
<212> TYPE: PRT
<213> ORGANISM: Artificial Sequence
<220> FEATURE:
<223> OTHER INFORMATION: Description of Artificial Sequence: Synthetic
      Aggrecan binding ISVD sequences

<400> SEQUENCE: 157

Glu Val Gln Leu Val Glu Ser Gly Gly Gly Val Val Gln Pro Gly Gly
 1               5                   10                  15

Ser Leu Arg Leu Ser Cys Ala Ala Ser Gly Arg Thr Phe Ser Ser Tyr
                20                  25                  30

Thr Met Gly Trp Phe Arg Gln Ala Pro Gly Lys Glu Arg Glu Phe Val
            35                  40                  45

Ala Ala Ile Ser Trp Ser Gly Gly Arg Thr Tyr Tyr Ala Asp Ser Val
 50                  55                  60

Lys Gly Arg Phe Thr Ile Ser Arg Asp Asn Ser Lys Asn Thr Val Tyr
 65                  70                  75                  80

Leu Gln Met Asn Ser Leu Arg Pro Glu Asp Thr Ala Leu Tyr Tyr Cys
                 85                  90                  95

Ala Ala Tyr Arg Arg Arg Arg Ala Ser Ser Asn Arg Gly Leu Trp Asp
            100                 105                 110

Tyr Trp Gly Gln Gly Thr Leu Val Thr Val Ser Ser Ala
        115                 120                 125

<210> SEQ ID NO 158
<211> LENGTH: 3
<212> TYPE: PRT
<213> ORGANISM: Artificial Sequence
<220> FEATURE:
<223> OTHER INFORMATION: Description of Artificial Sequence: Synthetic
      Linker sequence

<400> SEQUENCE: 158

Ala Ala Ala
 1

<210> SEQ ID NO 159
<211> LENGTH: 5
<212> TYPE: PRT
<213> ORGANISM: Artificial Sequence
<220> FEATURE:
<223> OTHER INFORMATION: Description of Artificial Sequence: Synthetic
      Linker sequence

<400> SEQUENCE: 159

Gly Gly Gly Gly Ser
 1               5

```
<210> SEQ ID NO 160
<211> LENGTH: 7
<212> TYPE: PRT
<213> ORGANISM: Artificial Sequence
<220> FEATURE:
<223> OTHER INFORMATION: Description of Artificial Sequence: Synthetic
      Linker sequence

<400> SEQUENCE: 160

Ser Gly Gly Ser Gly Gly Ser
1               5

<210> SEQ ID NO 161
<211> LENGTH: 8
<212> TYPE: PRT
<213> ORGANISM: Artificial Sequence
<220> FEATURE:
<223> OTHER INFORMATION: Description of Artificial Sequence: Synthetic
      Linker sequence

<400> SEQUENCE: 161

Gly Gly Gly Gly Gly Gly Gly Ser
1               5

<210> SEQ ID NO 162
<211> LENGTH: 9
<212> TYPE: PRT
<213> ORGANISM: Artificial Sequence
<220> FEATURE:
<223> OTHER INFORMATION: Description of Artificial Sequence: Synthetic
      Linker sequence

<400> SEQUENCE: 162

Gly Gly Gly Gly Ser Gly Gly Gly Ser
1               5

<210> SEQ ID NO 163
<211> LENGTH: 10
<212> TYPE: PRT
<213> ORGANISM: Artificial Sequence
<220> FEATURE:
<223> OTHER INFORMATION: Description of Artificial Sequence: Synthetic
      Linker sequence

<400> SEQUENCE: 163

Gly Gly Gly Gly Ser Gly Gly Gly Gly Ser
1               5                   10

<210> SEQ ID NO 164
<211> LENGTH: 15
<212> TYPE: PRT
<213> ORGANISM: Artificial Sequence
<220> FEATURE:
<223> OTHER INFORMATION: Description of Artificial Sequence: Synthetic
      Linker sequence

<400> SEQUENCE: 164

Gly Gly Gly Gly Ser Gly Gly Gly Gly Ser Gly Gly Gly Gly Ser
1               5                   10                  15

<210> SEQ ID NO 165
<211> LENGTH: 18
<212> TYPE: PRT
<213> ORGANISM: Artificial Sequence
<220> FEATURE:
<223> OTHER INFORMATION: Description of Artificial Sequence: Synthetic
      Linker sequence

<400> SEQUENCE: 165
```

```
Gly Gly Gly Gly Ser Gly Gly Gly Ser Gly Gly Gly Gly Gly
1               5                   10                  15

Gly Ser

<210> SEQ ID NO 166
<211> LENGTH: 20
<212> TYPE: PRT
<213> ORGANISM: Artificial Sequence
<220> FEATURE:
<223> OTHER INFORMATION: Description of Artificial Sequence: Synthetic
      Linker sequence

<400> SEQUENCE: 166

Gly Gly Gly Gly Ser Gly Gly Gly Ser Gly Gly Gly Ser Gly
1               5                   10                  15

Gly Gly Gly Ser
            20

<210> SEQ ID NO 167
<211> LENGTH: 25
<212> TYPE: PRT
<213> ORGANISM: Artificial Sequence
<220> FEATURE:
<223> OTHER INFORMATION: Description of Artificial Sequence: Synthetic
      Linker sequence

<400> SEQUENCE: 167

Gly Gly Gly Gly Ser Gly Gly Gly Ser Gly Gly Gly Ser Gly
1               5                   10                  15

Gly Gly Gly Ser Gly Gly Gly Gly Ser
            20                  25

<210> SEQ ID NO 168
<211> LENGTH: 30
<212> TYPE: PRT
<213> ORGANISM: Artificial Sequence
<220> FEATURE:
<223> OTHER INFORMATION: Description of Artificial Sequence: Synthetic
      Linker sequence

<400> SEQUENCE: 168

Gly Gly Gly Gly Ser Gly Gly Gly Ser Gly Gly Gly Ser Gly
1               5                   10                  15

Gly Gly Gly Ser Gly Gly Gly Ser Gly Gly Gly Gly Ser
            20                  25                  30

<210> SEQ ID NO 169
<211> LENGTH: 35
<212> TYPE: PRT
<213> ORGANISM: Artificial Sequence
<220> FEATURE:
<223> OTHER INFORMATION: Description of Artificial Sequence: Synthetic
      Linker sequence

<400> SEQUENCE: 169

Gly Gly Gly Gly Ser Gly Gly Gly Ser Gly Gly Gly Ser Gly
1               5                   10                  15

Gly Gly Gly Ser Gly Gly Gly Ser Gly Gly Gly Ser Gly Gly
            20                  25                  30

Gly Gly Ser
        35

<210> SEQ ID NO 170
```

```
<211> LENGTH: 40
<212> TYPE: PRT
<213> ORGANISM: Artificial Sequence
<220> FEATURE:
<223> OTHER INFORMATION: Description of Artificial Sequence: Synthetic
      Linker sequence

<400> SEQUENCE: 170

Gly Gly Gly Gly Ser Gly Gly Gly Ser Gly Gly Gly Gly Ser Gly
1               5                   10                  15

Gly Gly Gly Ser Gly Gly Gly Ser Gly Gly Gly Ser Gly Gly
            20                  25                  30

Gly Gly Ser Gly Gly Gly Gly Ser
        35                  40

<210> SEQ ID NO 171
<211> LENGTH: 15
<212> TYPE: PRT
<213> ORGANISM: Artificial Sequence
<220> FEATURE:
<223> OTHER INFORMATION: Description of Artificial Sequence: Synthetic
      Linker sequence

<400> SEQUENCE: 171

Glu Pro Lys Ser Cys Asp Lys Thr His Thr Cys Pro Pro Cys Pro
1               5                   10                  15

<210> SEQ ID NO 172
<211> LENGTH: 24
<212> TYPE: PRT
<213> ORGANISM: Artificial Sequence
<220> FEATURE:
<223> OTHER INFORMATION: Description of Artificial Sequence: Synthetic
      Linker sequence

<400> SEQUENCE: 172

Gly Gly Gly Gly Ser Gly Gly Gly Ser Glu Pro Lys Ser Cys Asp Lys
1               5                   10                  15

Thr His Thr Cys Pro Pro Cys Pro
            20

<210> SEQ ID NO 173
<211> LENGTH: 12
<212> TYPE: PRT
<213> ORGANISM: Artificial Sequence
<220> FEATURE:
<223> OTHER INFORMATION: Description of Artificial Sequence: Synthetic
      Linker sequence

<400> SEQUENCE: 173

Glu Pro Lys Thr Pro Lys Pro Gln Pro Ala Ala Ala
1               5                   10

<210> SEQ ID NO 174
<211> LENGTH: 62
<212> TYPE: PRT
<213> ORGANISM: Artificial Sequence
<220> FEATURE:
<223> OTHER INFORMATION: Description of Artificial Sequence: Synthetic
      Linker sequence

<400> SEQUENCE: 174

Glu Leu Lys Thr Pro Leu Gly Asp Thr Thr His Thr Cys Pro Arg Cys
1               5                   10                  15

Pro Glu Pro Lys Ser Cys Asp Thr Pro Pro Cys Pro Arg Cys Pro
            20                  25                  30
```

```
Glu Pro Lys Ser Cys Asp Thr Pro Pro Cys Pro Arg Cys Pro Glu
         35                  40                  45

Pro Lys Ser Cys Asp Thr Pro Pro Cys Pro Arg Cys Pro
    50                  55                  60

<210> SEQ ID NO 175
<211> LENGTH: 8
<212> TYPE: PRT
<213> ORGANISM: Unknown
<220> FEATURE:
<223> OTHER INFORMATION: Description of Unknown:
      Aggrecan cleavage site

<400> SEQUENCE: 175

Thr Glu Gly Glu Ala Arg Gly Ser
1               5

<210> SEQ ID NO 176
<211> LENGTH: 4
<212> TYPE: PRT
<213> ORGANISM: Unknown
<220> FEATURE:
<223> OTHER INFORMATION: Description of Unknown:
      Aggrecan neo-epitope

<400> SEQUENCE: 176

Ala Arg Gly Ser
1

<210> SEQ ID NO 177
<211> LENGTH: 8
<212> TYPE: PRT
<213> ORGANISM: Bos sp.

<400> SEQUENCE: 177

Lys Glu Glu Glu Gly Leu Gly Ser
1               5

<210> SEQ ID NO 178
<211> LENGTH: 8
<212> TYPE: PRT
<213> ORGANISM: Bos sp.

<400> SEQUENCE: 178

Gly Glu Leu Glu Gly Arg Gly Thr
1               5

<210> SEQ ID NO 179
<211> LENGTH: 10
<212> TYPE: PRT
<213> ORGANISM: Bos sp.

<400> SEQUENCE: 179

Asn Ile Thr Glu Gly Glu Ala Arg Gly Ser
1               5                   10

<210> SEQ ID NO 180
<211> LENGTH: 8
<212> TYPE: PRT
<213> ORGANISM: Bos sp.

<400> SEQUENCE: 180

Thr Ala Gln Glu Ala Gly Glu Gly
1               5
```

```
<210> SEQ ID NO 181
<211> LENGTH: 8
<212> TYPE: PRT
<213> ORGANISM: Bos sp.

<400> SEQUENCE: 181

Val Ser Gln Glu Leu Gly Gln Arg
1               5

<210> SEQ ID NO 182
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 182

Ala Ala Ala Glu Gln Lys Leu Ile Ser Glu Glu Asp Leu Asn Gly Ala
1               5                   10                  15

Ala

<210> SEQ ID NO 183
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 183

Gly Gly Gly Ser Ser Gly Gly Ser Ser Gly Gly Gly Ser Ser
1               5                   10                  15

<210> SEQ ID NO 184
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (11)..(11)
<223> OTHER INFORMATION: Dap(Dnp)

<400> SEQUENCE: 184

Thr Glu Gly Glu Ala Arg Gly Ser Val Ile Xaa Lys Lys
1               5                   10

<210> SEQ ID NO 185
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 185

Ala Arg Gly Ser Val
1               5

<210> SEQ ID NO 186
<211> LENGTH: 4
<212> TYPE: PRT
<213> ORGANISM: Unknown
<220> FEATURE:
```

```
<223> OTHER INFORMATION: Description of Unknown:
      Aggrecan neo-epitope

<400> SEQUENCE: 186

Thr Glu Gly Glu
1

<210> SEQ ID NO 187
<211> LENGTH: 4
<212> TYPE: PRT
<213> ORGANISM: Macaca fascicularis

<400> SEQUENCE: 187

Ala Arg Gly Ser
1

<210> SEQ ID NO 188
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 188

Gly Ser Gly Ser
1

<210> SEQ ID NO 189
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: Dpa

<400> SEQUENCE: 189

Pro Leu Gly Leu Xaa Ala Arg
1               5
```

ADAMTS BINDING IMMUNOGLOBULINS

1 RELATED APPLICATIONS

The present application is a divisional application of U.S. application Ser. No. 16/617,885 filed on Nov. 27, 2019, which claims priority under 37 U.S.C. § 371 to International Patent Application No. PCT/EP2018/064665, filed Jun. 4, 2018, which claims priority to and the benefit of European Patent Application No. 17174403.0, filed on Jun. 2, 2017. The contents of these applications are hereby incorporated by reference in their entireties.

2 SEQUENCE LISTING

The instant application contains a Sequence Listing which has been submitted electronically in ASCII format and is hereby incorporated by reference in its entirety. Said ASCII copy, created on Jun. 23, 2020, is named PAT058985-US-CNT_SL and is 177,837 bytes in size.

3 FIELD OF THE INVENTION

The present invention relates to immunoglobulins that bind ADAMTS5 and more in particular to polypeptides, that comprise or essentially consist of one or more such immunoglobulins (also referred to herein as "immunoglobulin(s) of the invention", and "polypeptides of the invention", respectively). The invention also relates to constructs comprising such immunoglobulins, such as immunoglobulin single variable domains (ISVDs) or polypeptides as well as nucleic acids encoding such immunoglobulins or polypeptides (also referred to herein as "nucleic acid(s) of the invention"; to methods for preparing such immunoglobulins, polypeptides and constructs; to host cells expressing or capable of expressing such immunoglobulins or polypeptides; to compositions, and in particular to pharmaceutical compositions, that comprise such immunoglobulins, polypeptides, constructs, nucleic acids and/or host cells; and to uses of immunoglobulins, polypeptides, constructs, nucleic acids, host cells and/or compositions, in particular for prophylactic and/or therapeutic purposes, such as the prophylactic and/or therapeutic purposes mentioned herein. Other aspects, embodiments, advantages and applications of the invention will become clear from the further description herein.

4 BACKGROUND OF THE INVENTION

Osteoarthritis (OA) is one of the most common causes of disability worldwide. It affects 30 million Americans and is the most common joint disorder. It is projected to affect more than 20 percent of the U.S. population by 2025. The disease is non-systemic and is usually restricted to few joints. However, the disease can occur in all joints, most often the knees, hips, hands, shoulder and spine. OA is characterized by progressive erosion of articular cartilage (cartilage that covers the bones) resulting in chronic pain and disability. Eventually, the disease leads to total destruction of the articular cartilage, sclerosis of underlying bone, osteophyte formation etc., all leading to loss of movement and pain. Osteoarthritis can be defined as a diverse group of conditions characterised by a combination of joint symptoms, signs stemming from defects in the articular cartilage and changes in adjacent tissues including bone, tendons and muscle. Pain is the most prominent symptom of OA and most often the reason patients seek medical help. There is no cure for OA, i.e. current treatments do not inhibit structural deterioration of the OA joint. Disease management is limited to treatments that are palliative at best and do little to address the underlying cause of disease progression. Although disease initiation may be multi-factorial, the cartilage destruction appears to be a result of uncontrolled proteolytic destruction of the extracellular matrix (ECM). The most abundant ECM components of articular cartilage are Collagen (foremost Collagen II) and the proteoglycans, mainly Aggrecan (Kiani et al. 2002 Cell Research 12:19-32).

Aggrecan is important in the proper functioning of the articular cartilage because it provides a hydrated gel structure that endows the cartilage with load-bearing properties. Aggrecan is a large, multimodular molecule (2317 amino acids) expressed by chondrocytes. Its core protein is composed of three globular domains (G1, G2 and G3) and a large extended region between G2 and G3 for glycosaminoglycan chain attachment. This extended region comprises two domains, one substituted with keratan sulfate chains (KS domain) and one with chondroitin sulfate chains (CS domain). The CS domain has 100-150 glycosaminoglycan (GAG) chains attached to it. Aggrecan forms large complexes with Hyaluronan in which 50-100 Aggrecan molecules interact via the G1 domain and Link Protein with one Hyaluronan molecule. Upon uptake of water (due to the GAG content) these complexes form a reversibly deformable gel that resists compression. The structure, fluid retention and function of joint cartilage is linked to the matrix content of Aggrecan, and the amount of chondroitin sulfate bound to the intact core protein. Structurally, OA is characterized by degradation of Aggrecan, progressively releasing domains G3 and G2 (resulting in 'deflation' of the cartilage) and eventually release of the G1 domain and degradation of Collagen, irreversibly destroying the cartilage structure. The most significant Aggrecan cleavage site for OA pathogenesis is located at the sequence TEGE$^{373}\downarrow^{374}$ARGS (SEQ ID NO: 175). This cleavage site is positioned in the interglobular domain (IGD) of Aggrecan. Antibodies that recognize the $^{374}$ARGS neo-epitope (SEQ ID NO: 176) led to the discovery of aggrecanase-1, which proved to be ADAMTS4 and aggrecanase-2, which is ADAMTS5. Subsequently, other related ADAMTS enzymes, including ADAMTS1, -8, -9, -15 and -20, were shown to have aggrecanase activity. ADAMTS16 and 18 are also weak aggrecanases. The ADAMTSs and matrix metalloproteinases (MMPs) share a binding site to Aggrecan that is very similar both in sequence and in overall shape (El Bakali et al. 2014 Future Medicinal Chemistry (Review) 6:1399).

The ADAMTS (A Disintegrin and Metalloproteinase with Thrombospondin motifs) enzymes are secreted, multi-domain matrix-associated zinc metalloendopeptidases that have diverse roles in tissue morphogenesis and pathophysiological remodeling, in inflammation and in vascular biology (Kelwick et al. 2015 Genome Biology 16:113). The human family includes 19 members that can be sub-grouped on the basis of their known substrates. The aggrecanases or proteoglycanases include ADAMTS1, -4, -5, -8, -9, -15 and -20, which can cleave hyaluronan-binding chondroitin sulfate proteoglycan (CSPG) extracellular proteins, including Aggrecan, versican, brevican and neurocan. The two most preferred cleavage sites in bovine Aggrecan are at KEEE1667$\downarrow^{1668}$GLGS (SEQ ID NO: 177), followed by GELE$^{1480}\downarrow^{1481}$GRGT (SEQ ID NO: 178). Thereafter, cleavage occurs at NITEGE$^{373}\downarrow^{374}$ARGS (SEQ ID NO: 179) in the IGD (at which MMPs do not cut), releasing the afore-mentioned neo-epitope, and at TAQE$^{1771}\downarrow^{1772}$AGEG (SEQ ID NO: 180) and VSQE$^{1871}\downarrow^{1872}$LGQR (SEQ ID NO:

181) in the CS-2 region (Fosang et al. 2008 European Cells and Materials 15:11-26). These cleavage sites are highly conserved in humans, bovine, mice and rats.

Various lines of evidence indicate that ADAMTS5 is a principal enzyme involved in the pathogenesis of osteoarthritis. ADAMTS5 is a major aggrecanase present in cartilage. In human cartilage explants and chondrocytes, knockdown of ADAMTS5 attenuated Aggrecan breakdown, suggesting that this enzyme may be involved in human tissues. Expression of the enzyme is augmented by cytokines such as interleukin-1 and oncostatin-M, which provoke Aggrecan breakdown in tissues. ADAMTS5 generated Aggrecan fragments are detected in the synovial fluid and serum of OA patients (Germaschewski et al., 2014 Osteoarthritis Cartilage 22:690-697).

ADAMTS5 is first synthesized as an inactive protein, including a protease domain at the N-terminus and an ancillary domain at the C-terminus. The protease domain consists of a signal peptide, a prodomain with a furin recognition sequence and a catalytic domain. The prodomain is cleaved by proprotein convertases in order to produce the active enzymes. ADAMTS5 further contains ancillary domains which actively participate in substrate recognition and modulate the affinity of the proteinase for its substrate(s) ("exosites"). The disintegrin-like domain, central thrombospondin type I-like (TS) repeat, cysteine-rich domain, spacer region and additional TS motif of ADAMTS5 are ancillary domains with potential exosite functions. The cysteine-rich domain appears to be essential for the binding and docking of ADAMTS5 onto glycosaminoglycans. The greatest variability in the ADAMTS members is found in these ancillary domains (Kelwick et al., 2015 Genome Biology 16:113).

Disease modifying anti-osteoarthritic drugs (DMOADs), which can be defined as drugs that inhibit structural disease progression and ideally also improves symptoms and/or function are intensely sought after. DMOADs are likely to be prescribed for long periods in this chronic illness of an aging population, therefore demanding excellent safety data in a target population with multiple comorbidities and the potential for drug-drug interactions.

Several pharmaceutical companies have developed small molecule inhibitors of ADAMTS5. Some of these compounds are claimed to be specific for ADAMTS5, whereas others have effect also against other ADAMTS members, or even against MMPs. These cross-inhibitions are considered to be responsible for musculoskeletal syndrome, a side effect caused by broad-spectrum inhibitors and involving arthralgia, myalgia, joint stiffness and tendonitis (Santamaria et al., 2015 Biochem J 471:391-401). The Wyeth aggrecanase inhibitor AGG-523 was used in 5 phase I clinical trials in healthy subjects and patient with OA, but has not been taken further. Nor have the other small molecule ADAMTS inhibitors entered any further clinical development as potential DMOAD (Bondeson et al., 2015 Drug Discovery 10:5-14). Indeed, despite a number of recent clinical trials specifically investigating DMOADs, no such treatments have been approved so far (El Bakali et al., 2014 Future Medicinal Chemistry (Review) 6:1399).

In view of the success of targeted biologic therapy using antibodies ("Abs"), there was interest in developing similar therapeutic strategies for OA. A study of the Rottapharm monoclonal antibody (mAb) CRB0017, directed against the spacer domain of ADAMTS5, showed that in mice, intra-articular administration of this mAb significantly prevented disease progression in a dose-dependent manner (Chiusaroli et al., 2013 Osteoarthritis Cartilage 21:1807). There was no comparison with systemic administration, nor was it assessed to what degree the mAb leaked from the synovial space. Another study used systemic administration of the mAb 12F4 in mice, which demonstrated both structural disease modification and alleviation of pain-related behaviour (Miller et al., 2014 Osteoarthritis Cartilage 22iii, S35). However, a single administration of mAb 12F4 in cynomolgus monkey caused focal haemorrhage, a dose-dependent increased mean arterial pressure and cardiac conductance abnormalities (more specifically, ST elevations and ventricular arrhythmias on the ECG) indicating cardiac ischemia, which were sustained for up to 8 months after administration of the single dose (Larkin et al., 2014 Osteoarthritis Cartilage 22iii, S483). These side effects halted further clinical development of mAb 12F4.

WO2008/074840 in the name of Ablynx NV describes the generation of Nanobodies® against members of the A Disintegrin and Metalloproteinases (ADAM) family, including ADAMTS5.

Therapeutic interventions in joints have further been hindered by the difficulty of targeting drugs to articular cartilage. Because articular cartilage is an avascular and alymphatic tissue, traditional routes of drug delivery (oral, intravenous, intramuscular) ultimately rely on transsynovial transfer of drugs from the synovial capillaries to cartilage by passive diffusion. This prompted the development of intra-articular (IA) delivery of medicaments.

On the other hand, IA delivery of therapeutic proteins has been limited by their rapid clearance from the joint space and lack of retention within cartilage; and restriction to large joints. Synovial residence time of a drug in the joint is often less than 24 h (Edwards 2011 Vet J 190:15-21; Larsen et al., 2008 J Pham Sci 97:4622-4654). Due to the rapid clearance of most IA injected drugs, frequent injections would be needed to maintain an effective concentration (Owen et al., 1994 Br J Clin Pharmacol 38:349-355). Moreover, IA delivery of therapeutic proteins is not feasible practically for small joints, which hampers treatment of e.g. OA-fingers.

There remains a need for effective DMOADs.

5 SUMMARY OF THE INVENTION

The present invention aims to provide polypeptides against OA with improved prophylactic, therapeutic and/or pharmacological properties, in addition to other advantageous properties (such as, for example, improved ease of preparation, good stability, and/or reduced costs of goods), compared to the prior art amino acid sequences and antibodies. In particular, the present invention aims to provide polypeptides inhibiting ADAMTS and especially inhibiting ADAMTS5.

The ADAMs, ADAMTSs and MMPs share a binding site to Aggrecan that is very similar both in sequence and in overall shape. Since the various other ADAM (including TACE) and ADAMTS family members have diverse roles in normal physiology are strongly associated with many common pathological conditions, including asthma, arthritis, cancer, connective tissue disorders or thrombotic thrombocytopenic purpura (El Bakali et al., supra), the inventors appreciated the importance of preserving selectivity. In order to effectively silence only ADAMTS5 activity, targeting the catalytic domain appeared to be the best option. However, the catalytic domains of ADAMTS4 and ADAMTS5 share a high degree of sequence similarity (cf. El Bakali et al., supra). In addition, it turned out that the high sequence conservation of the catalytic domain between various species foregoes a robust immune response.

Surprisingly, the ISVDs of the invention met these two seemingly mutually exclusive requirements of inhibiting the (enzymatic) activity of ADAMTS5 on the one hand, while preserving selectivity on the other hand.

Various monovalent ISVDs of the present invention were equipotent to the conventional bivalent antibody mAb 12F4 H4L0 in an AlphaLISA enzymatic assay. In addition thereto, the ISVDs of the present invention were also equipotent to the conventional bivalent antibody mAb12F4 H4L0 at high or even excess Aggrecan substrate concentration, which is reminiscent of the joints. On the other hand, in an ex vivo bovine explant assay, which resembles even more closely physiological conditions, most monovalent ISVDs had a better $IC_{50}$ than the comparator mAb 12F4 H4L0 ("12F4") and mAb CRB0017 of Rottapharm. In a human ex vivo explant assay, the ISVDs of the present invention also were substantially better than the prior art conventional antibody CRB0017, as demonstrated by $IC_{50}$.

After further engineering the ISVDs in view of various diverse and favorable features, including stability, affinity and inhibitory activity as well as minimizing immunogenicity, these ISVDs were next evaluated in vivo.

Systemic administration of the ISVDs of the present invention demonstrated potent inhibition of the aggrecanase activity in vivo as evaluated in cynomolgus monkey. In addition, the ISVDs were also safe to use, in contrast to the prior art antibody 12F4. Also in an in vivo mouse medial meniscal destabilization (DMM) model, the ISVDs of the present invention showed a structural benefit up to 50% for both prophylactic as well as therapeutic treatment by systemic administration. Early treatment with the ISVDs of the present invention caused a dose-dependent, significant and meaningful symptomatic benefit during Anterior Cruciate Ligament Transection and Resection of the medial meniscus (ACLT+tMx) induced OA in rats.

The ISVDs are eventually intended for inhibiting ADAMTS5 in the joints and therefore will need to resist the conditions of synovial fluid in the joints, which contains various proteases. Next to the favourable characteristics of above, it was shown that the isolated ISVDs were extremely stable in synovial fluid. It is anticipated that this stability enables a less frequent dosage regimen.

Accordingly, the present invention relates to a polypeptide comprising at least 1 immunoglobulin single variable domain (ISVD) binding an A Disintegrin and Metalloproteinase with Thrombospondin motifs (ADAMTS), preferably wherein said ADAMTS is chosen from the group consisting of ADAMTS1-ADAMTS19, preferably ADAMTS5, ADAMTS4, ADAMTS1, ADAMTS8, ADAMTS9 and ADAMTS15 and ADAMTS20, most preferably ADAMTS5. In an aspect, the invention relates to a polypeptide as described herein, wherein said ISVD binding ADAMTS, preferably ADAMTS5 does not bind ADAMTS4, MMP1 or MMP14.

In a further preferred aspect, the invention relates to a polypeptide as described herein, wherein said ISVD specifically binding ADAMTS5 essentially consists of 4 framework regions (FR1 to FR4, respectively) and 3 complementarity determining regions (CDR1 to CDR3 respectively), in which (i) CDR1 is chosen from the group consisting of SEQ ID NOs: 21, 35, 20, 22, 25, 33, 28, 24, 23, 26, 27, 29, 30, 31, 32 and 34; and amino acid sequences that have 1, 2 or 3 amino acid difference(s) with SEQ ID NOs: 21, 35, 20, 22, 25, 33, 28, 24, 23, 26, 27, 29, 30, 31, 32 and 34; (ii) CDR2 is chosen from the group consisting of SEQ ID NOs: 37, 53, 36, 40, 50, 51, 44, 45, 43, 39, 38, 41, 119, 42, 46, 47, 48, 49 and 52; and amino acid sequences that have 1, 2 or 3 amino acid difference(s) with SEQ ID NOs: 37, 53, 36, 40, 50, 51, 44, 45, 43, 39, 38, 41, 119, 42, 46, 47, 48, 49 and 52; and (iii) CDR3 is chosen from the group consisting of SEQ ID NO: SEQ ID NOs: 55, 118, 71, 54, 58, 68, 69, 62, 63, 61, 57, 56, 59, 60, 64, 65, 66, 67 and 70; and amino acid sequences that have 1, 2, 3 or 4 amino acid difference(s) with SEQ ID NOs: 55, 118, 71, 54, 58, 68, 69, 62, 63, 61, 57, 56, 59, 60, 64, 65, 66, 67 and 70.

In a further preferred aspect, the invention relates to a polypeptide as described herein, wherein said ISVD specifically binding ADAMTS5 essentially consists of 4 framework regions (FR1 to FR4, respectively) and 3 complementarity determining regions (CDR1 to CDR3 respectively), in which (i) CDR1 is chosen from the group consisting of (a) SEQ ID NO: 22; and (b) amino acid sequence that has 1, 2, 3, 4, 5 or 6 amino acid difference(s) with SEQ ID NO: 22, wherein at position 2 the S has been changed into R; at position 3 the A has been changed into T; at position 4 the V has been changed into F; at position 6 the V has been changed into 5; at position 7 the N has been changed into Y; and/or at position 10 the A has been changed into G; (ii) CDR2 is SEQ ID NO: 36; and (iii) CDR3 is SEQ ID NO: 54.

In a further preferred aspect, the invention relates to a polypeptide as described herein, wherein said ISVD specifically binding ADAMTS5 essentially consists of 4 framework regions (FR1 to FR4, respectively) and 3 complementarity determining regions (CDR1 to CDR3 respectively), in which (i) CDR1 is SEQ ID NO: 33; (ii) CDR2 is chosen from the group consisting of (c) SEQ ID NO: 50; and (d) amino acid sequence that has 1, 2, or 3 amino acid difference(s) with SEQ ID NO: 50, wherein at position 8 the M has been changed into I; at position 9 the P has been changed into T; and/or at position 10 the Y has been changed into F; and (iii) CDR3 is chosen from the group consisting of (e) SEQ ID NO: 68; and (f) amino acid sequence that has 1 or 2 amino acid difference(s) with SEQ ID NO: 68, wherein at position 5 the F has been changed into L; and/or at position 11 the D has been changed into E.

In a further preferred aspect, the invention relates to a polypeptide as described herein, wherein said ISVD specifically binding ADAMTS5 essentially consists of 4 framework regions (FR1 to FR4, respectively) and 3 complementarity determining regions (CDR1 to CDR3 respectively), in which (i) CDR1 is SEQ ID NO: 28; (ii) CDR2 is chosen from the group consisting of (c) SEQ ID NO: 44; and (d) amino acid sequence that has 1, 2, or 3 amino acid difference(s) with SEQ ID NO: 44, wherein at position 3 the S has been changed into T; at position 4 the R has been changed into W; at position 8 the T has been changed into I; and/or at position 9 the T has been changed into L; and (iii) CDR3 is chosen from the group consisting of (e) SEQ ID NO: 62; and (f) amino acid sequence that has 1 or 2 amino acid difference(s) with SEQ ID NO: 62, wherein at position 1 the G has been changed into 5; and/or at position 14 the D has been changed into E.

In preferred embodiments of all aspects of the invention an immunoglobulin single variable domain (ISVD) according to the invention preferably consists of or essentially consists of 4 framework regions (FR1 to FR4, respectively) and 3 complementarity determining regions CDR1, CDR2 and CDR3 as outlined herein above and below. Preferred framework sequences are disclosed for example in the table A-2 below and can be used in an ISVD of the invention. Preferably, the CDRs depicted in Table A-2 are matched with the respective framework regions of the same ISVD construct.

In a further preferred aspect, the invention relates to a polypeptide as described herein, wherein said ISVD is chosen from the group of ISVDs, wherein: CDR1 is chosen from the group consisting of SEQ ID NOs: 21, 35, 20, 22, 25, 33, 28, 24, 23, 26, 27, 29, 30, 31, 32 and 34; CDR2 is chosen from the group consisting of SEQ ID NOs: 37, 53, 36, 40, 50, 51, 44, 45, 43, 39, 38, 41, 119, 42, 46, 47, 48, 49 and 52; and CDR3 is chosen from the group consisting of SEQ ID NOs: 55, 118, 71, 54, 58, 68, 69, 62, 63, 61, 57, 56, 59, 60, 64, 65, 66, 67 and 70.

In a further preferred aspect, the invention relates to a polypeptide as described herein, wherein said ISVD is chosen from the group of ISVDs, wherein:
- CDR1 is SEQ ID NO: 21, CDR2 is SEQ ID NO: 37 and CDR3 is SEQ ID NO: 55;
- CDR1 is SEQ ID NO: 35, CDR2 is SEQ ID NO: 53 and CDR3 is SEQ ID NO: 118;
- CDR1 is SEQ ID NO: 35, CDR2 is SEQ ID NO: 53 and CDR3 is SEQ ID NO: 71;
- CDR1 is SEQ ID NO: 20, CDR2 is SEQ ID NO: 36 and CDR3 is SEQ ID NO: 54;
- CDR1 is SEQ ID NO: 22, CDR2 is SEQ ID NO: 36 and CDR3 is SEQ ID NO: 54;
- CDR1 is SEQ ID NO: 25, CDR2 is SEQ ID NO: 40 and CDR3 is SEQ ID NO: 58;
- CDR1 is SEQ ID NO: 33, CDR2 is SEQ ID NO: 50 and CDR3 is SEQ ID NO: 68;
- CDR1 is SEQ ID NO: 33, CDR2 is SEQ ID NO: 51 and CDR3 is SEQ ID NO: 69;
- CDR1 is SEQ ID NO: 28, CDR2 is SEQ ID NO: 44 and CDR3 is SEQ ID NO: 62;
- CDR1 is SEQ ID NO: 28, CDR2 is SEQ ID NO: 45 and CDR3 is SEQ ID NO: 63;
- CDR1 is SEQ ID NO: 28, CDR2 is SEQ ID NO: 43 and CDR3 is SEQ ID NO: 61;
- CDR1 is SEQ ID NO: 24, CDR2 is SEQ ID NO: 39 and CDR3 is SEQ ID NO: 57;
- CDR1 is SEQ ID NO: 23, CDR2 is SEQ ID NO: 38 and CDR3 is SEQ ID NO: 56;
- CDR1 is SEQ ID NO: 26, CDR2 is SEQ ID NO: 41 and CDR3 is SEQ ID NO: 59;
- CDR1 is SEQ ID NO: 27, CDR2 is SEQ ID NO: 119 and CDR3 is SEQ ID NO: 60;
- CDR1 is SEQ ID NO: 27, CDR2 is SEQ ID NO: 42 and CDR3 is SEQ ID NO: 60;
- CDR1 is SEQ ID NO: 29, CDR2 is SEQ ID NO: 46 and CDR3 is SEQ ID NO: 64;
- CDR1 is SEQ ID NO: 30, CDR2 is SEQ ID NO: 47 and CDR3 is SEQ ID NO: 65;
- CDR1 is SEQ ID NO: 31, CDR2 is SEQ ID NO: 48 and CDR3 is SEQ ID NO: 66;
- CDR1 is SEQ ID NO: 32, CDR2 is SEQ ID NO: 49 and CDR3 is SEQ ID NO: 67; and
- CDR1 is SEQ ID NO: 34, CDR2 is SEQ ID NO: 52 and CDR3 is SEQ ID NO: 70.

In a further preferred aspect, the invention relates to a polypeptide as described herein, in which CDR1 is SEQ ID NO: 21, CDR2 is SEQ ID NO: 37 and CDR3 is SEQ ID NO: 55.

In a further preferred aspect, the invention relates to a polypeptide as described herein, in which said ISVD is chosen from the group consisting of SEQ ID NO:s 2, 116, 19, 1, 3, 6, 16, 17, 10, 11, 9, 5, 4, 7, 8, 117, 12, 13, 14, 15 and 18.

In a further preferred aspect, the invention relates to a polypeptide as described herein, wherein said polypeptide binds to ADAMTS5 with a $K_D$ between $1E^{-07}$ M and $1E^{-13}$ M, such as between $1E^{-08}$ M and $1E^{-12}$ M, preferably at most $1E^{-07}$ M, preferably lower than $1E^{-08}$ M or $1E^{-09}$ M, or even lower than $1E^{-10}$ M, such as $5E^{-11}$ M, $4E^{-11}$ M, $3E^{-11}$ M, $2E^{-11}$ M, $1.7E^{-11}$ M, $1E^{-11}$ M, or even $5E^{-12}$ M, $4E^{-12}$ M, $3E^{-12}$ M, $1E^{-12}$ M, for instance as determined by KinExA, or alternatively by Gyrolab.

In a further preferred aspect, the invention relates to a polypeptide as described herein, wherein said polypeptide inhibits an activity of ADAMTS5 with an $IC_{50}$ between $1E^{-07}$ M and $1E^{-12}$ M, such as between $1E^{-08}$ M and $1E^{-11}$ M, for instance as determined by human FRET assay or human AlphaLISA.

In a further preferred aspect, the invention relates to a polypeptide as described herein, wherein said polypeptide inhibits an (enzymatic) activity of ADAMTS5 with an $IC_{50}$ of at most $1E^{-07}$ M, preferably $1E^{-08}$ M, $5E^{-09}$ M, or $4E^{-9}$ M, $3E^{-9}$ M, $2E^{-9}$ M, such as $1E^{-9}$ M.

In a further preferred aspect, the invention relates to a polypeptide as described herein, wherein said polypeptide modulates ADAMTS5 with an $EC_{50}$ between $1E^{-07}$ M and $1E^{-12}$ M, such as between $1E^{-08}$ M and $1E^{-11}$ M, for instance as determined by binding ELISA.

In a further preferred aspect, the invention relates to a polypeptide as described herein, wherein said polypeptide binds to ADAMTS5 with an off-rate of less than $1E^{-04}$ $s^{-1}$, for instance as determined by SPR.

In a further preferred aspect, the invention relates to a polypeptide as described herein, wherein said ADAMTS5 is human ADAMTS5 (SEQ ID NO: 149), bovine ADAMTS5 (SEQ ID NO: 150), rat ADAMTS5 (SEQ ID NO: 151), guinea pig ADAMTS5 (SEQ ID NO: 152), mouse ADAMTS5, (SEQ ID NO: 153) or cynomolgus ADAMTS5, (SEQ ID NO: 154), preferably human ADAMTS5, most preferably SEQ ID NO: 149.

In a further preferred aspect, the invention relates to a polypeptide as described herein, wherein said polypeptide antagonizes an activity of ADAMTS5, such as a protease activity, such as cleavage of Aggrecan, versican, brevican, neurocan, decorin, and/or biglycan, preferably cleavage of Aggrecan; preferably antagonizes aggrecanase activity of ADAMTS5.

In a further preferred aspect, the invention relates to a polypeptide as described herein, wherein said polypeptide blocks the binding of ADAMTS5 to Aggrecan of at least 20%, such as at least 30%, 40%, 50%, 60%, 70%, 80%, 90%, 95% or even more, for instance as determined by FRET, AlplaLISA or ELISA.

In a further preferred aspect, the invention relates to a polypeptide as described herein, wherein said polypeptide inhibits the protease activity of ADAMTS5, such as inhibits the proteolysis of a substrate, such as Aggrecan, versican, brevican, neurocan, decorin, and/or biglycan, preferably Aggrecan.

In a further preferred aspect, the invention relates to a polypeptide as described herein, comprising at least 2 ISVDs, wherein at least 1 ISVD specifically binds ADAMTS, preferably ADAMTS5, preferably chosen from the group consisting of SEQ ID NO:s 2, 116, 19, 1, 3, 6, 16, 17, 10, 11, 9, 5, 4, 7, 117, 8, 12, 13, 14, 15 and 18, preferably wherein said at least 2 ISVDs specifically bind ADAMTS, preferably ADAMTS5.

In a further preferred aspect, the invention relates to a polypeptide comprising two or more ISVDs which specifically bind ADAMTS5, wherein (a) at least a "first" ISVD specifically binds a first antigenic determinant, epitope, part, domain, subunit or conformation of ADAMTS5; and wherein (b) at least a "second" ISVD specifically binds a second antigenic determinant, epitope, part, domain, subunit or conformation of ADAMTS5, different from the first antigenic determinant epitope, part, domain, subunit or conformation, respectively, preferably wherein said "first" ISVD specifically binding ADAMTS5 is chosen from the group consisting of SEQ ID NO:s 2, 1, 3, 6, 16, 17, 10, 11, 9, 5, 4, 7, 8, 117, 12, 13, 14, 15 and 18, preferably wherein said "second" ISVD specifically binding ADAMTS5 is SEQ ID NO: 118 or 19, even more preferably said polypeptide is chosen from the group consisting of SEQ ID NO: 127 (clone 130 049-093-Alb), SEQ ID NO: 126 (clone 129 2F3-093-Alb), SEQ ID NO: 127 (clone 130 049-093-Alb) and SEQ ID NO: 128 (clone 131 9D3-093-Alb).

In a further preferred aspect, the invention relates to a polypeptide as described herein, further comprising an ISVD binding serum albumin, preferably wherein said ISVD binding serum albumin essentially consists of 4 framework regions (FR1 to FR4, respectively) and 3 complementarity determining regions (CDR1 to CDR3 respectively), in which CDR1 is SEQ ID NO: 146, CDR2 is SEQ ID NO: 147, and CDR3 is SEQ ID NO: 148, even more preferably wherein said ISVD binding serum albumin is chosen from the group consisting of ALB8 (SEQ ID NO: 131), ALB23 (SEQ ID NO: 132), ALB129 (SEQ ID NO: 133), ALB132 (SEQ ID NO: 134), ALB11 (SEQ ID NO: 135), ALB11 (S112K)-A (SEQ ID NO: 136), ALB82 (SEQ ID NO: 137), ALB82-A (SEQ ID NO: 138), ALB82-AA (SEQ ID NO: 139), ALB82-AAA (SEQ ID NO: 140), ALB82-G (SEQ ID NO: 141), ALB82-GG (SEQ ID NO: 142), ALB82-GGG (SEQ ID NO: 143), ALB92 (SEQ ID NO: 144), and ALB223 (SEQ ID NO: 145), even more preferably wherein said polypeptide is chosen from the group consisting of SEQ ID NO: 129 (clone 577 2F3$^{SO}$-Alb), SEQ ID NO: 130 (clone 579 2F3$^{SO}$-093-Alb), SEQ ID NO: 120 (clone 4 2A12-Alb), SEQ ID NO: 121 (clone 5 2D7-Alb), SEQ ID NO: 122 (clone 6 2F3-Alb), SEQ ID NO: 123 (clone 69 049-Alb), SEQ ID NO: 124 (clone 70 9D3-Alb), SEQ ID NO: 125 (clone 71 3B2-Alb), SEQ ID NO: 126 (clone 129 2F3-093-Alb), SEQ ID NO: 127 (clone 130 049-093-Alb), and SEQ ID NO: 128 (clone 131 9D3-093-Alb).

In a further preferred aspect, the invention relates to a polypeptide as described herein, further comprising at least one ISVD specifically binding Aggrecan, preferably chosen from the group consisting of SEQ ID NO: 156 (Nanobody 00745 PEA114F08) and SEQ ID NO: 157 (Nanobody 00747 PEA604F02).

In a further preferred aspect, the invention relates to a polypeptide as described herein, comprising at least 2 ISVDs specifically binding Aggrecan, wherein said at least 2 ISVDs specifically binding Aggrecan can be the same or different, preferably wherein said at least 2 ISVDs specifically binding Aggrecan are independently chosen from the group consisting of SEQ ID NOs: 156 and 157, even more preferably wherein said ISVD specifically binding Aggrecan, specifically binds to human Aggrecan [SEQ ID NO: 155]. Preferably, said ISVD specifically binding Aggrecan, specifically binds dog Aggrecan (see also table 2), bovine Aggrecan, rat Aggrecan; pig Aggrecan; mouse Aggrecan, rabbit Aggrecan; cynomolgus Aggrecan and/or rhesus Aggrecan. Preferably, said ISVD specifically binding Aggrecan preferably binds to cartilaginous tissue such as cartilage and/or meniscus.

In a further preferred aspect, the invention relates to a polypeptide as described herein, wherein said polypeptide has a stability of at least 7 days, such as 14 days, 21 days, 1 month, 2 months or even 3 months in synovial fluid (SF) at 37° C.

In a further preferred aspect, the invention relates to a polypeptide as described herein, wherein said at least two ISVDs are directly linked to each other or are linked via a linker, preferably said linker is chosen from the group consisting of SEQ ID NOs: 158 to 174 (i.e. SEQ ID NO: 158, 159, 160, 161, 162, 163, 164, 165, 166, 167, 168, 169, 170, 171, 172, 173 and 174), preferably SEQ ID NO: 169.

In a further preferred aspect, the invention relates to a polypeptide as described herein, further comprising a C-terminal extension, preferably wherein said C-terminal extension is a C-terminal extension (X)n, in which n is 1 to 10, preferably 1 to 5, such as 1, 2, 3, 4 or 5 (and preferably 1 or 2, such as 1); and each X is an (preferably naturally occurring) amino acid residue that is independently chosen, and preferably independently chosen from the group consisting of alanine (A), glycine (G), valine (V), leucine (L) or isoleucine (I).

In a further preferred aspect, the invention relates to a polypeptide as described herein, wherein said polypeptide has at least 80%, 90%, 95% or 100% sequence identity with any of SEQ ID NOs: 1-19 (i.e. SEQ ID NO: 1, 2, 3, 4, 5, 6, 7, 8, 9, 10, 11, 12, 13, 14, 15, 16, 17, 18 and 19), 116-117 or 120-130 (i.e. SEQ ID NOs: 120, 121, 122, 123, 124, 125, 126, 127, 128, 129 and 130).

In a further preferred aspect, the invention relates to a method of treating and/or preventing diseases or disorders in an individual, for instance in which ADAMTS5 activity is involved, the method comprising administering the polypeptide to said individual in an amount effective to treat or prevent a symptom of said disease or disorder, preferably wherein said diseases or disorders is chosen from the group consisting of arthropathies and chondrodystrophies, arthritic disease, such as osteoarthritis, rheumatoid arthritis, gouty arthritis, psoriatic arthritis, traumatic rupture or detachment, achondroplasia, costochondritis, Spondyloepimetaphyseal dysplasia, spinal disc herniation, lumbar disk degeneration disease, degenerative joint disease, and relapsing polychondritis, osteochondritis dissecans and aggrecanopathies. More preferably, said disease or disorder is an arthritic disease and most preferably osteoarthritis.

In a further preferred aspect, the invention relates to a polypeptide as described herein, for use as a medicament.

In a further preferred aspect, the invention relates to a polypeptide as described herein, for use in treating or preventing a symptom of an ADAMTS5 associated disease, such as e.g. arthropathies and chondrodystrophies, arthritic disease, such as osteoarthritis, rheumatoid arthritis, gouty arthritis, psoriatic arthritis, traumatic rupture or detachment, achondroplasia, costochondritis, Spondyloepimetaphyseal dysplasia, spinal disc herniation, lumbar disk degeneration disease, degenerative joint disease, and relapsing polychondritis, osteochondritis dissecans and aggrecanopathies. More preferably, said disease is an arthritic disease and most preferably osteoarthritis.

In a further preferred aspect, the invention relates to a polypeptide as described herein, wherein said polypeptide cross-blocks the binding to ADAMTS5 of at least one of the polypeptides represented by any one of SEQ ID NO:s 2, 116, 19, 1, 3, 6, 16, 17, 10, 11, 9, 5, 4, 7, 117, 8, 12, 13, 14, 15 and 18, and/or is cross-blocked from binding to ADAMTS5 by at least a polypeptide represented by any one of SEQ ID NO:s 2, 116, 19, 1, 3, 6, 16, 17, 10, 11, 9, 5, 4, 7, 117, 8, 12, 13, 14, 15 and 18.

In a further preferred aspect, the invention relates to a polypeptide cross-blocking binding to ADAMTS5 by a polypeptide represented by any one of SEQ ID NO:s 2, 116, 19, 1, 3, 6, 16, 17, 10, 11, 9, 5, 4, 7, 117, 8, 12, 13, 14, 15 and 18, and/or is cross-blocked from binding to ADAMTS5 by at least a polypeptide represented by any one of SEQ ID NO:s 2, 116, 19, 1, 3, 6, 16, 17, 10, 11, 9, 5, 4, 7, 117, 8, 12, 13, 14, 15 and 18, wherein said polypeptide comprises at least one VH, VL, dAb, immunoglobulin single variable domain (ISVD) specifically binding to ADAMTS5, wherein binding to ADAMTS5 modulates an activity of ADAMTS5.

Other aspects, advantages, applications and uses of the polypeptides and compositions will become clear from the further disclosure herein. Several documents are cited throughout the text of this specification. Each of the documents cited herein (including all patents, patent applications, scientific publications, manufacturer's specifications, instructions, etc.), whether supra or infra, are hereby incorporated by reference in their entirety. Nothing herein is to be construed as an admission that the invention is not entitled to antedate such disclosure by virtue of prior invention.

6 FIGURE LEGENDS

Figure 1B:
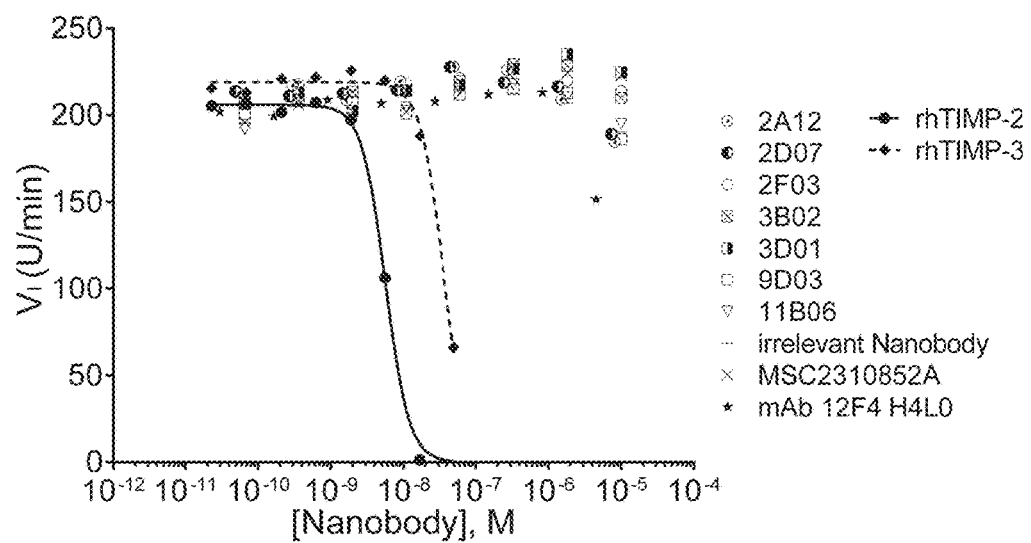

FIG. 1A-1B: ISVDs binding ADAMTS5 do not inhibit MMP1 (FIG. 1A) or MMP14 (FIG. 1B) activity.

Figure 2:
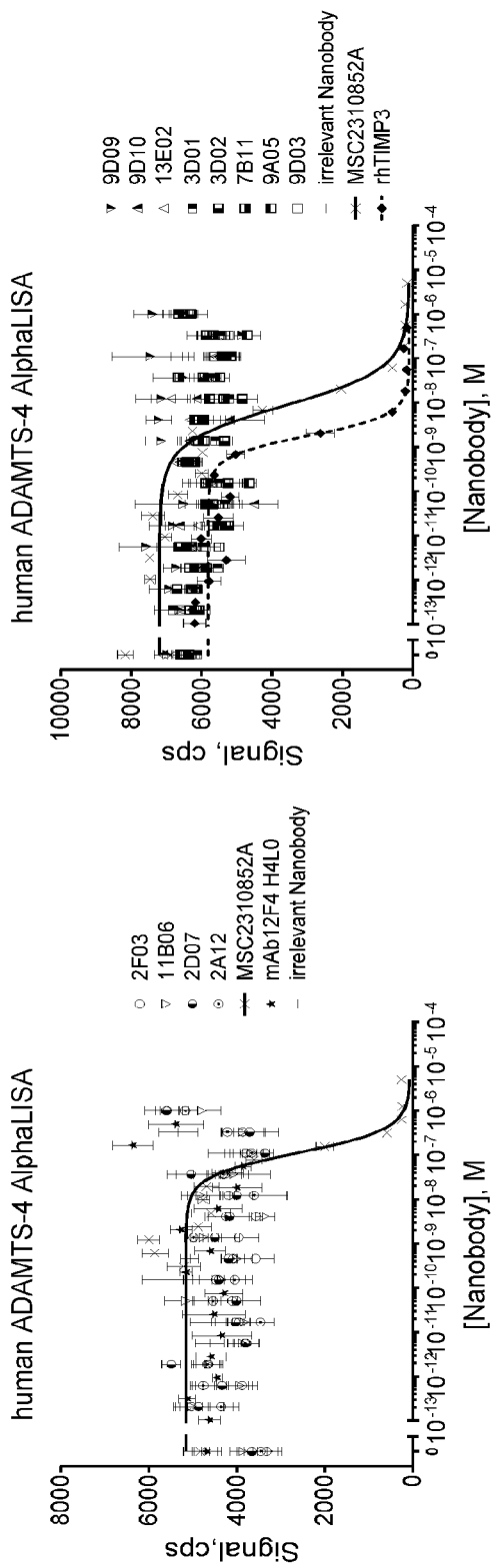

FIG. 2: ISVDs binding ADAMTS5 do not inhibit ADAMTS4 activity

Figure 3A:
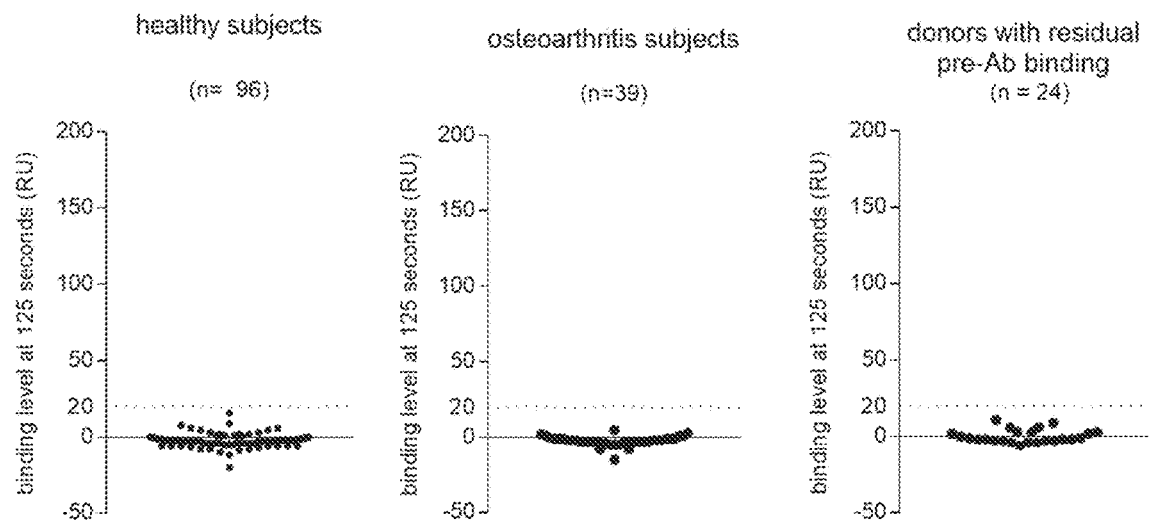
Figure 3B:
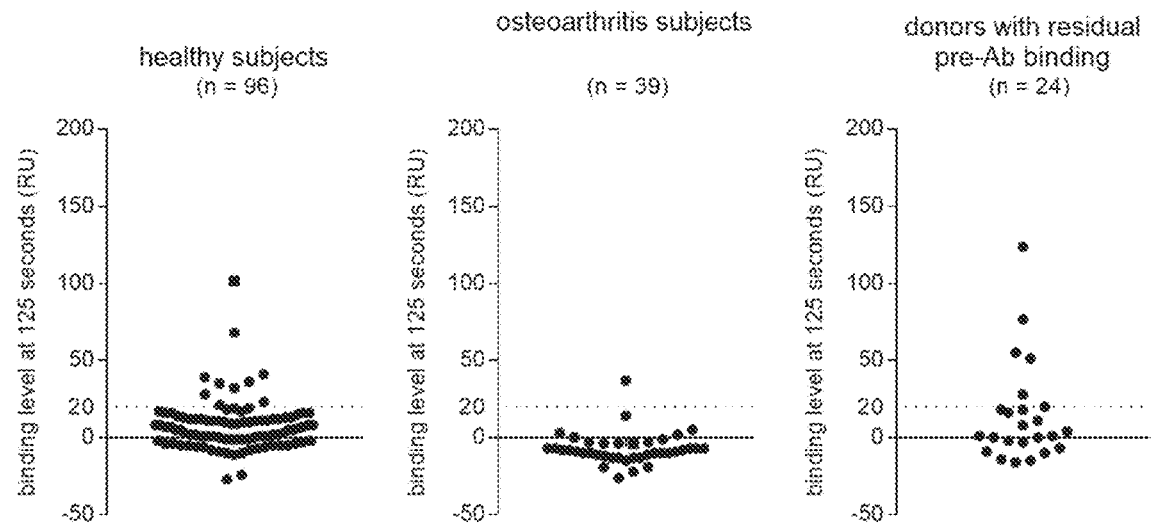

FIG. 3A-3B: pre-existing Antibody (preAb) binding levels to Nanobody construct 581 (FIG. 3A) and Nanobody construct 579 (FIG. 3B) from 3 donor sample sets derived from: healthy subjects, osteoarthritis subjects and donors with residual preAb binding.

Figure 4A:
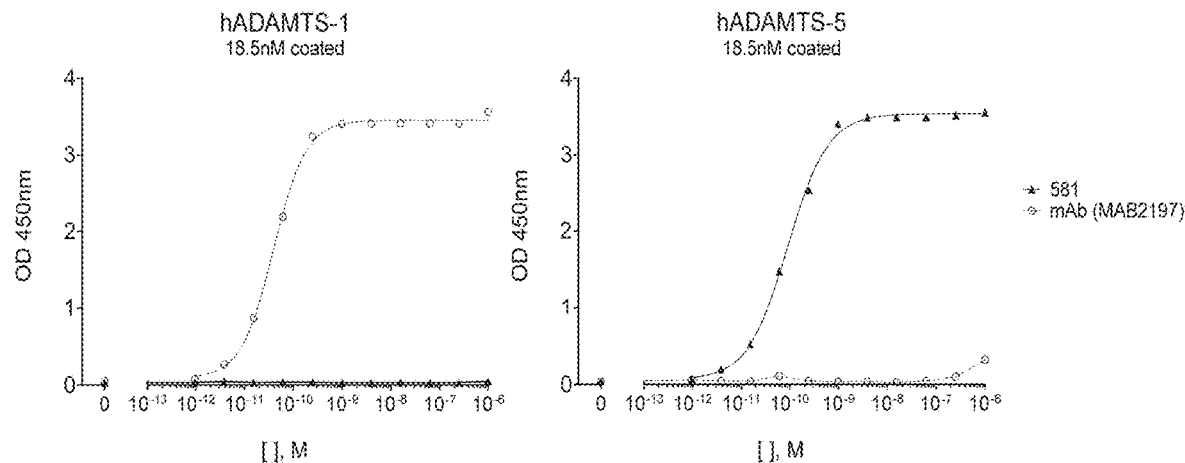
Figure 4B:
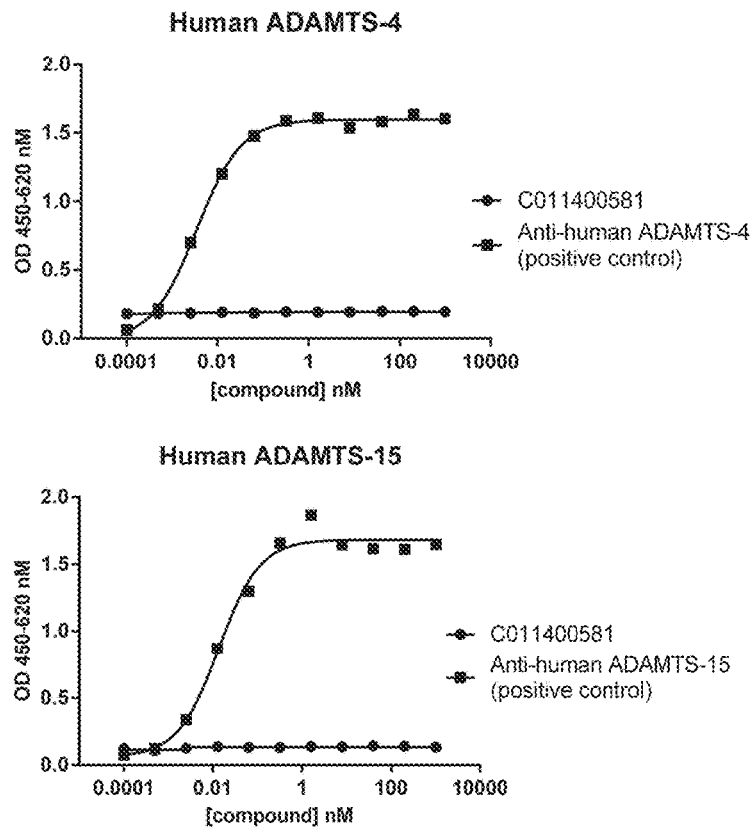

FIG. 4A-4B: Nanobody construct 581 ("C011400581") does not bind to human ADAMTS1 (FIG. 4A), and does not bind to human ADAMTS4 or human ADAMTS15 (FIG. 4B).

Figure 5:
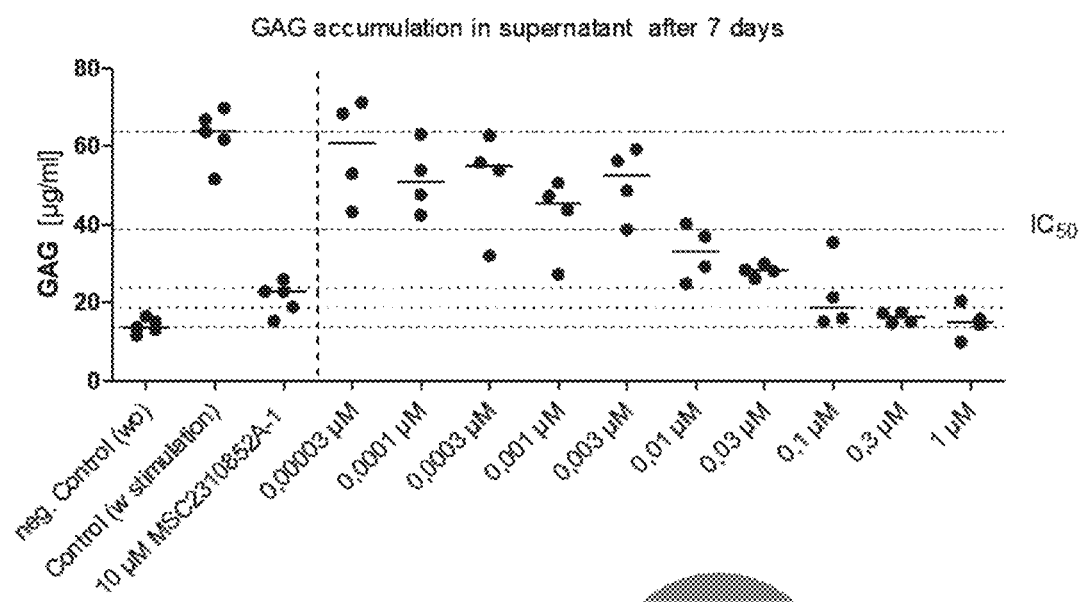

FIG. 5: Potency in human explant system. GAG accumulation in supernatant after 7 days is shown.

Figure 6A:
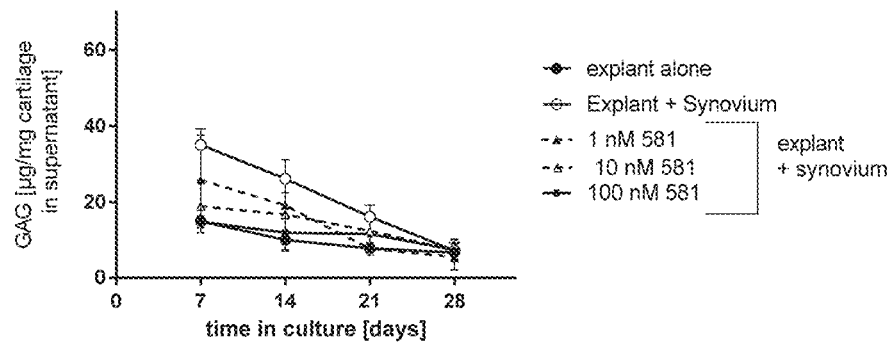
Figure 6B:
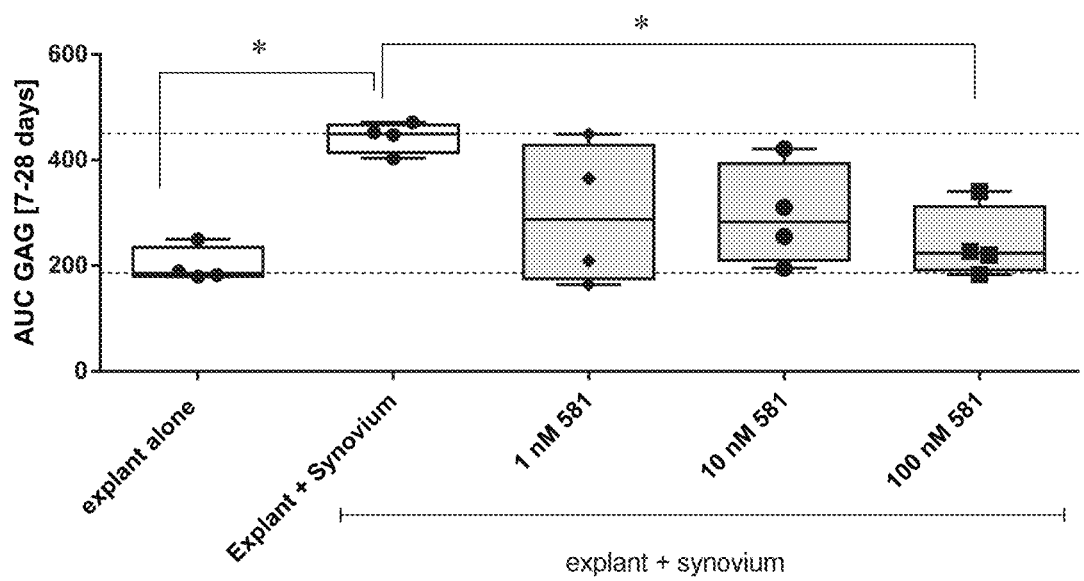
Figure 6C:
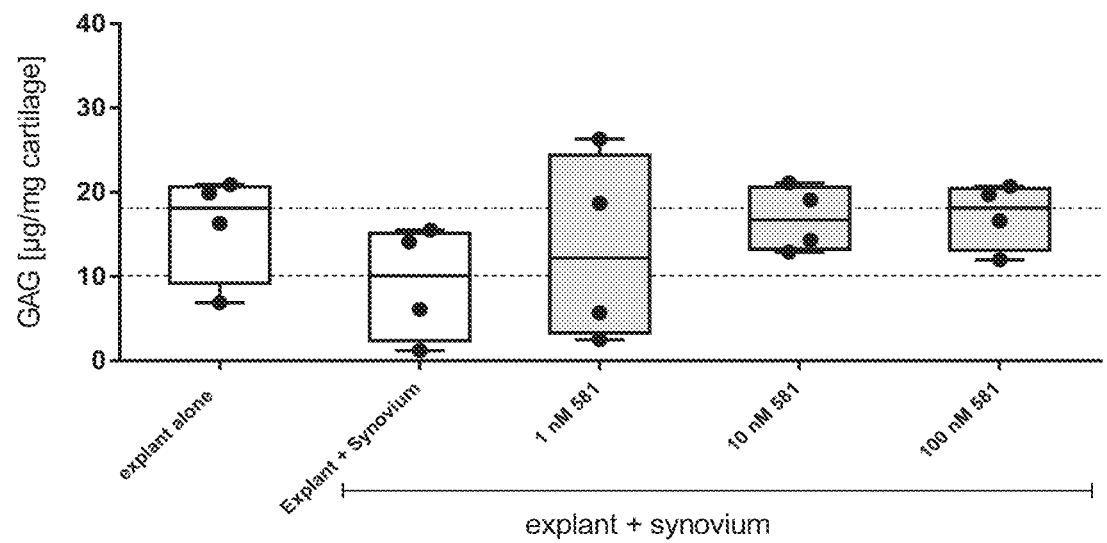

FIG. 6A-6C: FIG. 6A) Time course of GAG release into the supernatant in the bovine co-culture system.

FIG. 6B) Area under curve (AUC) calculation of GAG release over time (7-28 days). The number of replicates n=4. Data are shown in Box & Whiskers format with min to max.

FIG. 6C) The data show the GAG content [ng/mg cartilage] after papain digestion. The number of replicates n=4. Data are shown in Box & Whiskers format with min to max.

Figure 7:
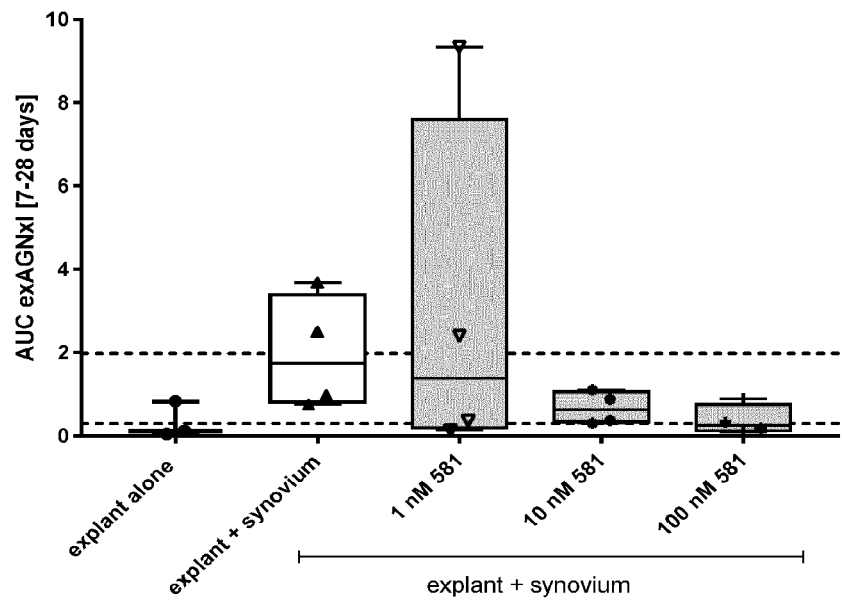

FIG. 7: Area under curve (AUC) calculation of exAGNx1 release over time (7-28 days). The number of replicates n=4. Data are shown in Box & Whiskers format with min to max.

Figure 8:
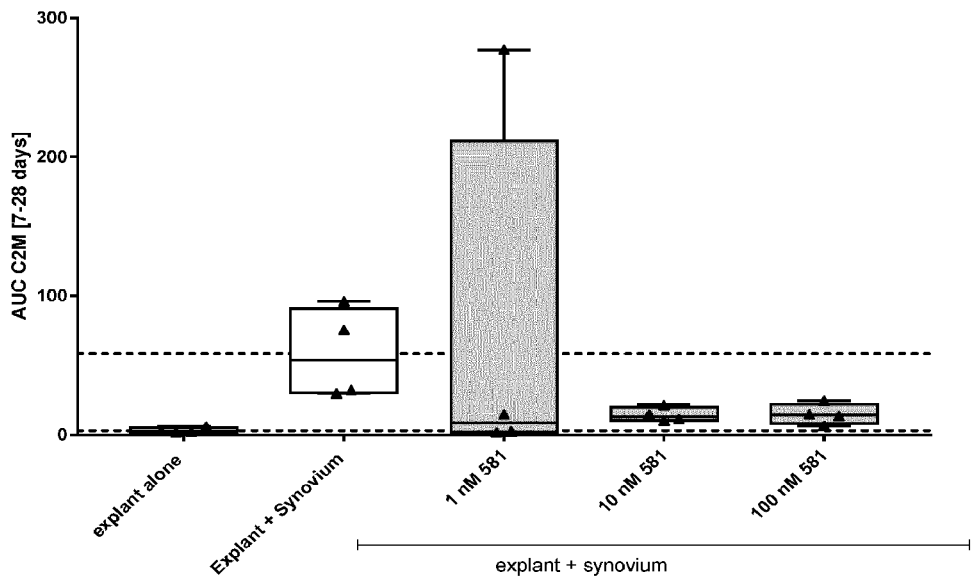

FIG. 8: Area under curve (AUC) calculation of C2M release over time (7-28 days). The number of replicates n=4. Data are shown in Box & Whiskers format with min to max.

Figure 9:
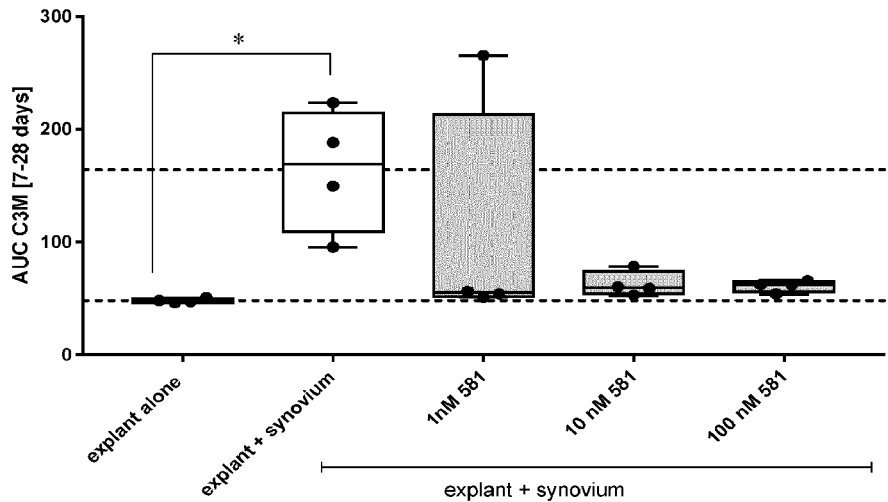

FIG. 9: Area under curve (AUC) calculation of C3M release over time (7-28 days). The number of replicates n=4. Data are shown in Box & Whiskers format with min to max.

Figure 10:
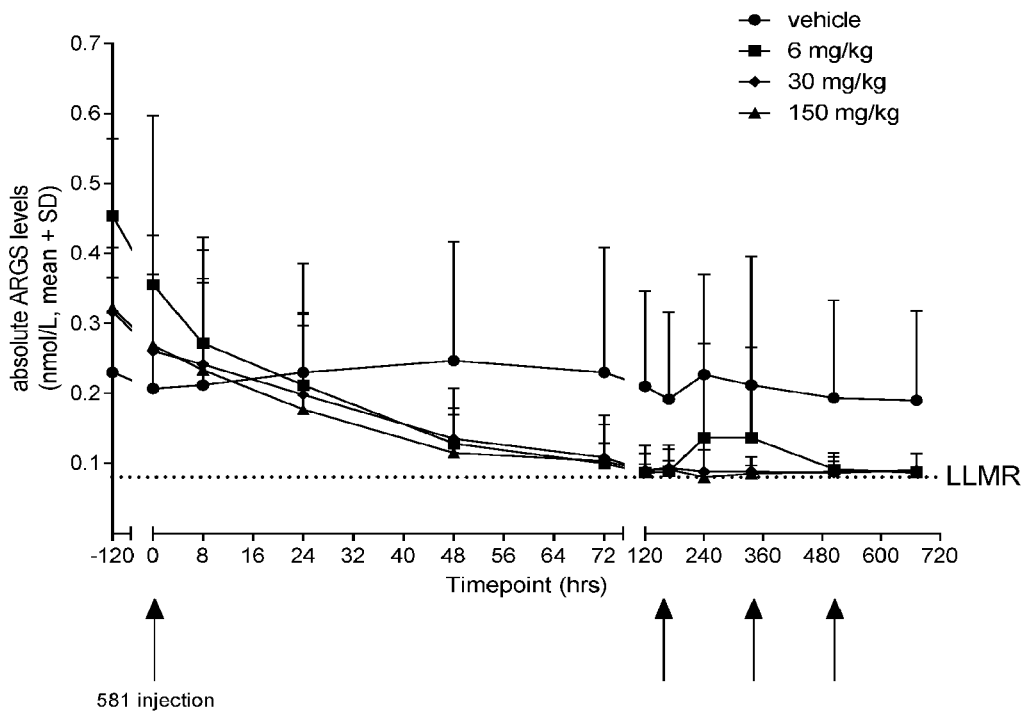

FIG. 10: Inhibition of aggrecanase activity in NHP. FIG. 10 discloses SEQ ID NO: 187

Figure 11:
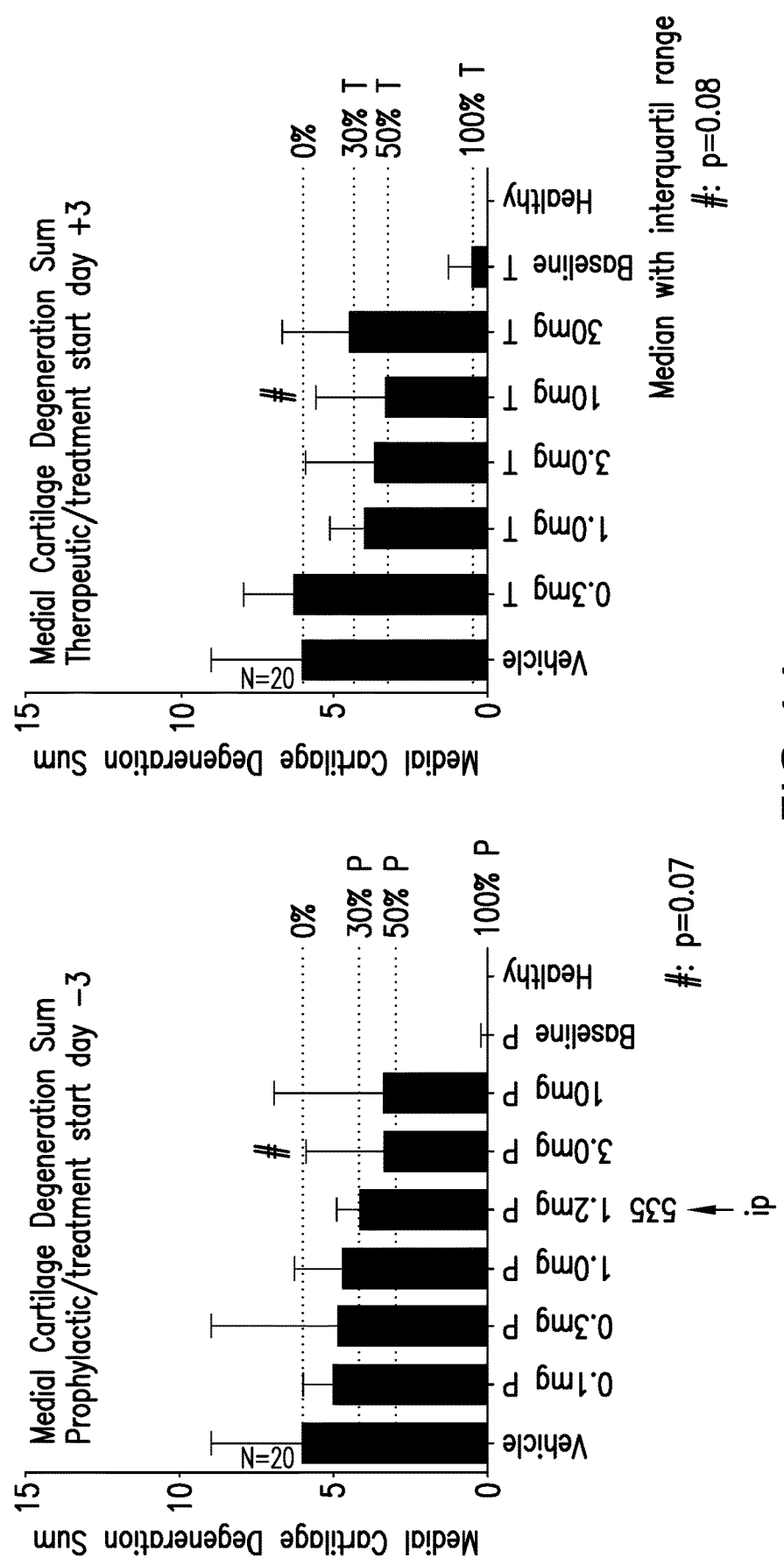

FIG. 11: Inhibition of cartilage degeneration. Median cartilage degeneration sum is shown in prophylactic (A) and therapeutic (B) treatment in a DMM mouse model.

Figure 12:
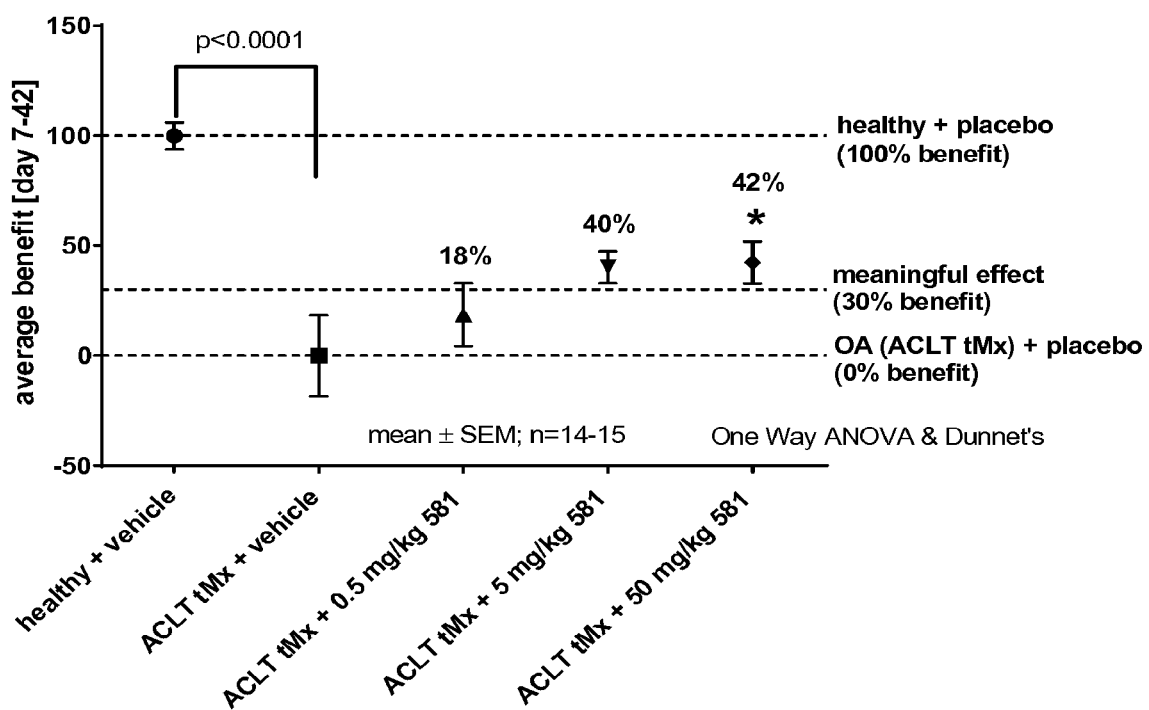

FIG. 12: Symptomatic behavior in a rat surgical OA model.

Figure 13:
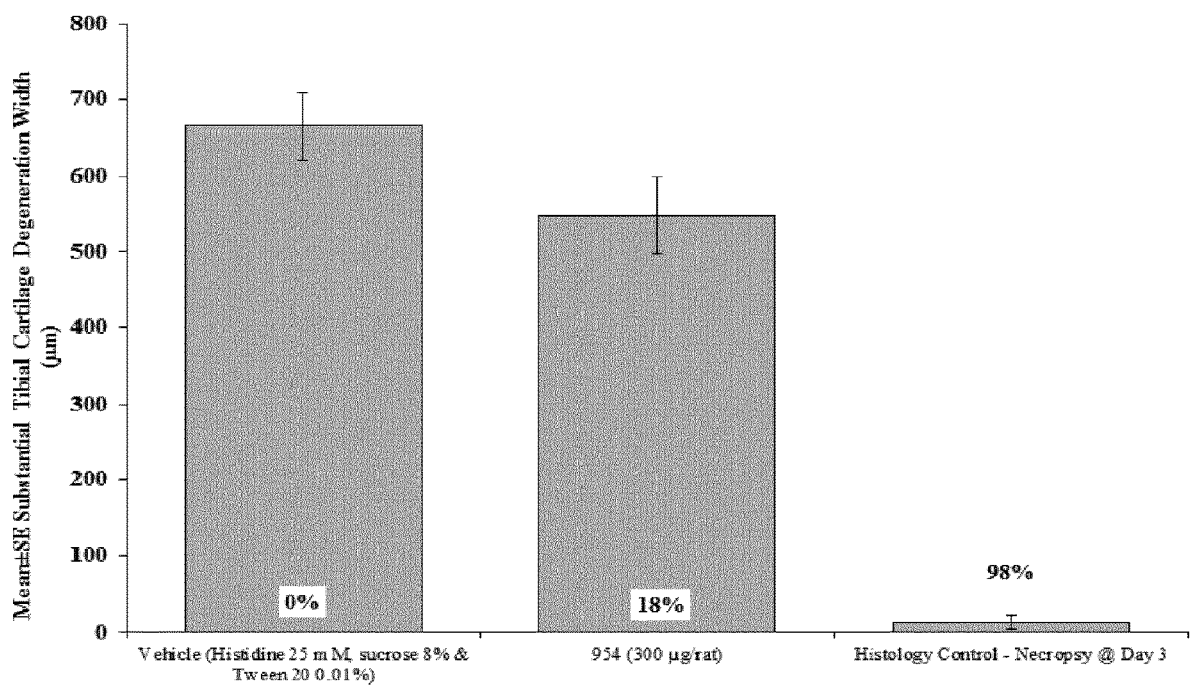

FIG. 13: Medial tibial cartilage degeneration width.

Figure 14A:
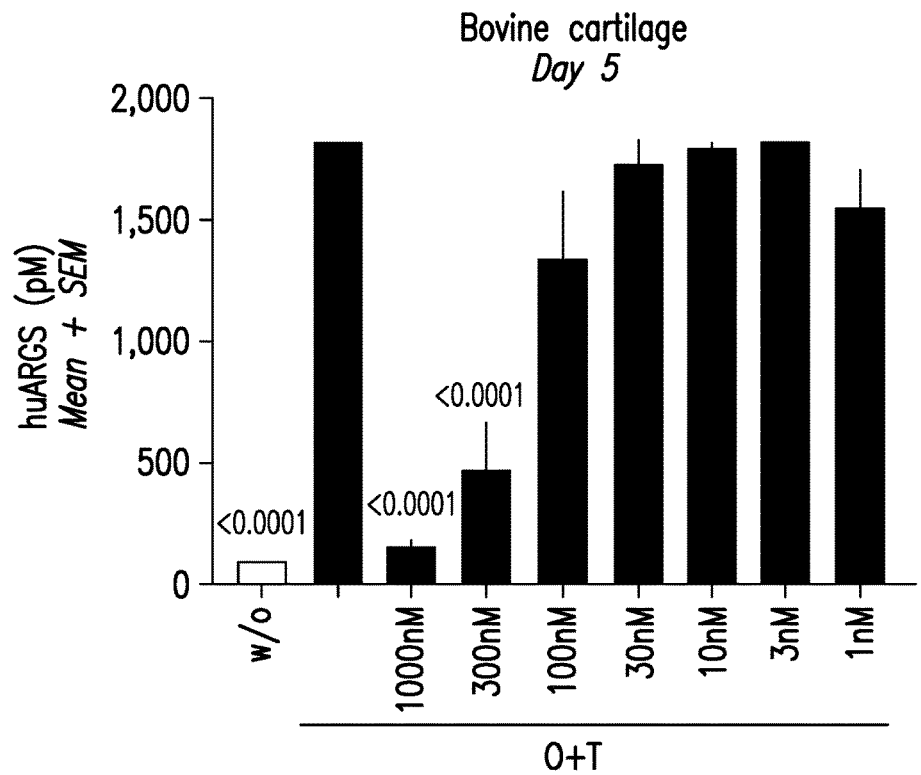
Figure 14B:
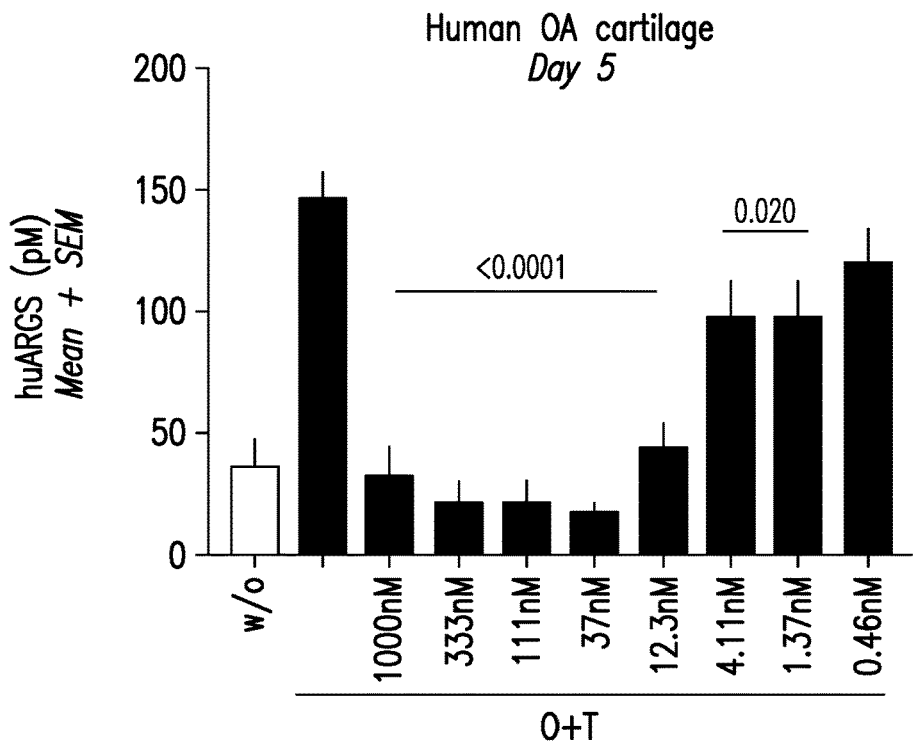
Figure 14C:
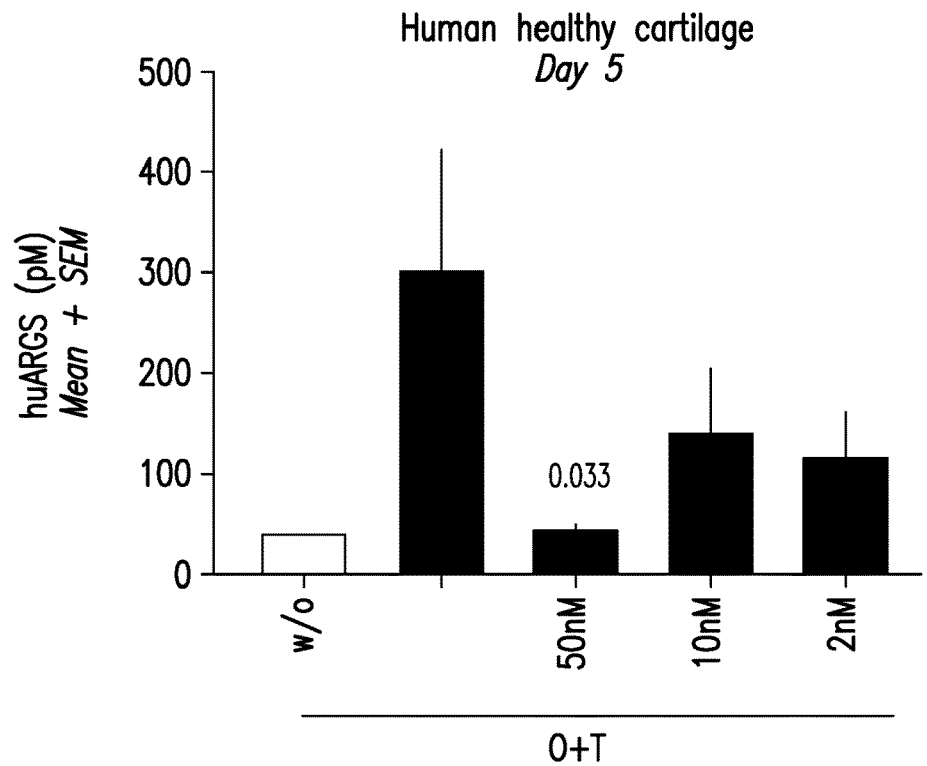
Figure 14D:
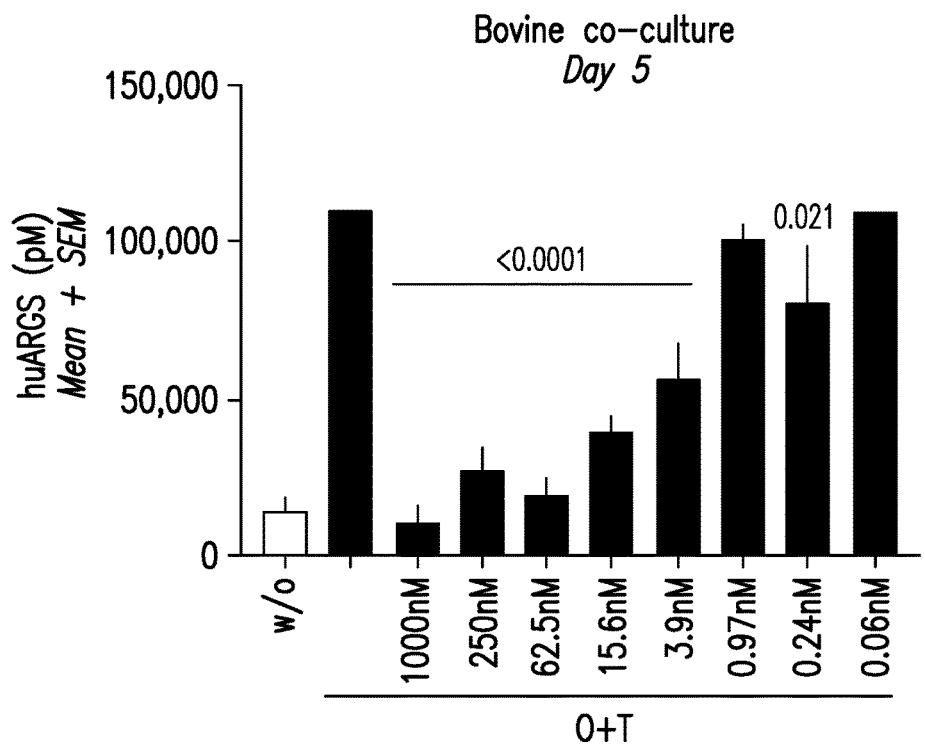
Figure 14E:
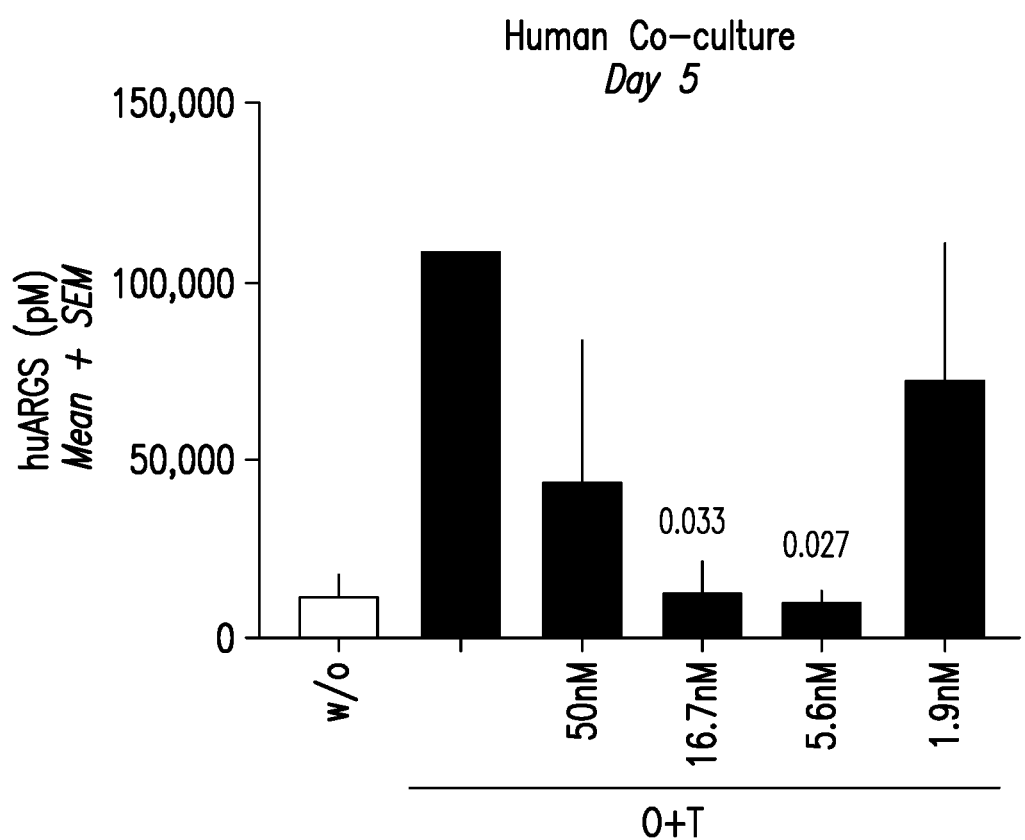

FIG. 14A-14E: The effect of the anti-ADAMTS-5 nanobody on aggrecanase derived aggrecan degradation in ex vivo cultures of cartilage (FIG. 14A, 14B, 14C) and co-cultures of cartilage and synovial membrane (FIG. 14D, 14E). The concentrations listed are the concentration of the nanobody. Statistical analysis was performed with ordinary one-way ANOVA or two-way ANOVA. Statistical significance was considered, when $p<0.05$.

7 DETAILED DESCRIPTION

There remains a need for safe and efficacious OA medicaments, in particular DMOADs. These medicaments should comply with various and frequently opposing requirements, especially when a broadly applicable format is intended. As such, the format should preferably be useful in a broad range of patients. The format should preferably be safe and not induce infections due to frequent administration. In addition, the format should preferably be patient friendly, such as a, the format should allowing for a convenient dosing regimen and route of administration, e.g. systemic administration. For instance, it is preferred that the format is not removed instantaneously from circulation upon administration. However, extending the half-life should preferably not introduce off-target activity and side effects or limit efficacy.

The present invention realizes at least one of these requirements.

Based on unconventional screening, characterization and combinatory strategies, the present inventors surprisingly observed that immunoglobulin single variable domains (ISVDs) performed exceptionally well in in vitro and in vivo experiments.

Moreover, the present inventors were able to re-engineer the ISVDs further outperforming comparator drugs in ameliorating OA. In addition, the ISVDs of the invention were also demonstrated to be significantly safer than the prior art compounds.

The present invention intends providing polypeptides antagonizing ADAMTSs in particular ADAMTS5 with improved prophylactic, therapeutic and/or pharmacological properties, including a safer profile, compared to the prior art amino acid sequences and antibodies.

Accordingly, the present invention relates to ISVDs and polypeptides that are directed against/and or that may specifically bind (as defined herein) to ADAMTS5.

Accordingly, the present invention relates to ISVDs and polypeptides that are directed against/and or that may specifically bind (as defined herein) to ADAMTSs and modulate the activity thereof, in particular a polypeptide comprising at least one ISVD specifically binding ADAMTS5, wherein binding to ADAMTS5 modulates an activity of ADAMTS5.

Unless indicated or defined otherwise, all terms used have their usual meaning in the art, which will be clear to the skilled person. Reference is for example made to the standard handbooks, such as Sambrook et al. (Molecular Cloning: A Laboratory Manual ($2^{nd}$ Ed.) Vols. 1-3, Cold Spring Harbor Laboratory Press, 1989), F. Ausubel et al. (Current protocols in molecular biology, Green Publishing and Wiley Interscience, New York, 1987), Lewin (Genes II, John Wiley & Sons, New York, N.Y., 1985), Old et al. (Principles of Gene Manipulation: An Introduction to Genetic Engineering (2nd edition) University of California Press, Berkeley, CA, 1981); Roitt et al. (Immunology ($6^{th}$ Ed.) Mosby/Elsevier, Edinburgh, 2001), Roitt et al. (Roitt's Essential Immunology ($10^{th}$ Ed.) Blackwell Publishing, UK, 2001), and Janeway et al. (Immunobiology ($6^{th}$ Ed.) Garland Science Publishing/Churchill Livingstone, New York, 2005), as well as to the general background art cited herein.

Unless indicated otherwise, all methods, steps, techniques and manipulations that are not specifically described in detail can be performed and have been performed in a manner known per se, as will be clear to the skilled person. Reference is for example again made to the standard handbooks and the general background art mentioned herein and to the further references cited therein; as well as to for example the following reviews Presta (Adv. Drug Deliv. Rev. 58 (5-6): 640-56, 2006), Levin and Weiss (Mol. Biosyst. 2(1): 49-57, 2006), Irving et al. (J. Immunol. Methods 248(1-2): 31-45, 2001), Schmitz et al. (Placenta 21 Suppl. A: S106-12, 2000), Gonzales et al. (Tumour Biol. 26(1): 31-43, 2005), which describe techniques for protein engineering, such as affinity maturation and other techniques for improving the specificity and other desired properties of proteins such as immunoglobulins.

It must be noted that as used herein, the singular forms "a", "an", and "the", include plural references unless the context clearly indicates otherwise. Thus, for example, reference to "a reagent" includes one or more of such different reagents and reference to "the method" includes reference to equivalent steps and methods known to those of ordinary skill in the art that could be modified or substituted for the methods described herein.

Unless otherwise indicated, the term "at least" preceding a series of elements is to be understood to refer to every element in the series. Those skilled in the art will recognize, or be able to ascertain using no more than routine experimentation, many equivalents to the specific embodiments of the invention described herein. Such equivalents are intended to be encompassed by the present invention.

The term "and/or" wherever used herein includes the meaning of "and", "or" and "all or any other combination of the elements connected by said term".

The term "about" or "approximately" as used herein means within 20%, preferably within 15%, more preferably within 10%, and most preferably within 5% of a given value or range.

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integer or step. When used herein the term "comprising" can be substituted with the term "containing" or "including" or sometimes when used herein with the term "having".

The term "sequence" as used herein (for example in terms like "immunoglobulin sequence", "antibody sequence", "variable domain sequence", "$V_{HH}$ sequence" or "protein sequence"), should generally be understood to include both the relevant amino acid sequence as well as nucleic acids or nucleotide sequences encoding the same, unless the context requires a more limited interpretation.

Amino acid sequences are interpreted to mean a single amino acid or an unbranched sequence of two or more amino acids, depending of the context. Nucleotide sequences are interpreted to mean an unbranched sequence of 3 or more nucleotides.

Amino acids are those L-amino acids commonly found in naturally occurring proteins. Amino acid residues will be indicated according to the standard three-letter or one-letter amino acid code. Reference is for instance made to Table A-2 on page 48 of WO 08/020079. Those amino acid sequences containing D-amino acids are not intended to be embraced by this definition. Any amino acid sequence that contains post-translationally modified amino acids may be described as the amino acid sequence that is initially translated using the symbols shown in this Table A-2 with the modified positions; e.g., hydroxylations or glycosylations, but these modifications shall not be shown explicitly in the amino acid sequence. Any peptide or protein that can be expressed as a sequence modified linkages, cross links and end caps, non-peptidyl bonds, etc., is embraced by this definition, all as known in the art.

The terms "protein", "peptide", "protein/peptide", and "polypeptide" are used interchangeably throughout the disclosure and each has the same meaning for purposes of this disclosure. Each term refers to an organic compound made of a linear chain of two or more amino acids. The compound may have ten or more amino acids; twenty-five or more amino acids; fifty or more amino acids; one hundred or more amino acids, two hundred or more amino acids, and even three hundred or more amino acids. The skilled artisan will appreciate that polypeptides generally comprise fewer amino acids than proteins, although there is no art-recognized cut-off point of the number of amino acids that distinguish a polypeptides and a protein; that polypeptides may be made by chemical synthesis or recombinant methods; and that proteins are generally made in vitro or in vivo by recombinant methods as known in the art. By convention, the amide bond in the primary structure of polypeptides is in the order that the amino acids are written, in which the amine end (N-terminus) of a polypeptide is always on the left, while the acid end (C-terminus) is on the right.

A nucleic acid or amino acid sequence is considered to be "(in) (essentially) isolated (form)"—for example, compared to the reaction medium or cultivation medium from which it has been obtained—when it has been separated from at least one other component with which it is usually associated in said source or medium, such as another nucleic acid, another protein/polypeptide, another biological component or macromolecule or at least one contaminant, impurity or minor component. In particular, a nucleic acid or amino acid sequence is considered "(essentially) isolated" when it has been purified at least 2-fold, in particular at least 10-fold, more in particular at least 100-fold, and up to 1000-fold or more. A nucleic acid or amino acid that is "in (essentially) isolated form" is preferably essentially homogeneous, as determined using a suitable technique, such as a suitable chromatographical technique, such as polyacrylamide-gel electrophoresis.

When a nucleotide sequence or amino acid sequence is said to "comprise" another nucleotide sequence or amino acid sequence, respectively, or to "essentially consist of" another nucleotide sequence or amino acid sequence, this may mean that the latter nucleotide sequence or amino acid sequence has been incorporated into the first mentioned nucleotide sequence or amino acid sequence, respectively, but more usually this generally means that the first mentioned nucleotide sequence or amino acid sequence comprises within its sequence a stretch of nucleotides or amino acid residues, respectively, that has the same nucleotide sequence or amino acid sequence, respectively, as the latter sequence, irrespective of how the first mentioned sequence has actually been generated or obtained (which may for example be by any suitable method described herein). By means of a non-limiting example, when a polypeptide of the invention is said to comprise an immunoglobulin single variable domain ("ISVD"), this may mean that said immunoglobulin single variable domain sequence has been incorporated into the sequence of the polypeptide of the invention, but more usually this generally means that the polypeptide of the invention contains within its sequence the sequence of the immunoglobulin single variable domains irrespective of how said polypeptide of the invention has been generated or obtained. Also, when a nucleic acid or nucleotide sequence is said to comprise another nucleotide sequence, the first mentioned nucleic acid or nucleotide sequence is preferably such that, when it is expressed into an expression product (e.g. a polypeptide), the amino acid sequence encoded by the latter nucleotide sequence forms part of said expression product (in other words, that the latter nucleotide sequence is in the same reading frame as the first mentioned, larger nucleic acid or nucleotide sequence). Also, when a construct of the invention is said to comprise a polypeptide or ISVD, this may mean that said construct at least encompasses said polypeptide or ISVD, respectively, but more usually this means that said construct encompasses groups, residues (e.g. amino acid residues), moieties and/or binding units in addition to said polypeptide or ISVD, irrespective of how said polypeptide or ISVD is connected to said groups, residues (e.g. amino acid residues), moieties and/or binding units and irrespective of how sad construct has been generated or obtained.

By "essentially consist of" is meant that the ISVD used in the invention either is exactly the same as the ISVD of the invention or corresponds to an ISVD of the invention, having a limited number of amino acid residues, such as 1-20 amino acid residues, for example 1-10 amino acid residues and preferably 1-6 amino acid residues, such as 1, 2, 3, 4, 5 or 6 amino acid residues, added at the amino terminal end, at the carboxy terminal end, or at both the amino terminal end and the carboxy terminal end of the ISVD.

For the purposes of comparing two or more nucleotide sequences, the percentage of "sequence identity" between a first nucleotide sequence and a second nucleotide sequence may be calculated by dividing [the number of nucleotides in the first nucleotide sequence that are identical to the nucleotides at the corresponding positions in the second nucleotide sequence] by [the total number of nucleotides in the first nucleotide sequence] and multiplying by [100%], in which each deletion, insertion, substitution or addition of a nucleotide in the second nucleotide sequence—compared to the first nucleotide sequence—is considered as a difference at a single nucleotide (position). Alternatively, the degree of sequence identity between two or more nucleotide sequences may be calculated using a known computer algorithm for sequence alignment such as NCBI Blast v2.0, using standard settings. Some other techniques, computer algorithms and settings for determining the degree of sequence identity are for example described in WO 04/037999, EP 0967284, EP 1085089, WO 00/55318, WO 00/78972, WO 98/49185 and GB 2357768. Usually, for the purpose of determining the percentage of "sequence identity" between two nucleotide sequences in accordance with the calculation method outlined hereinabove, the nucleotide sequence with the greatest number of nucleotides will be taken as the "first" nucleotide sequence, and the other nucleotide sequence will be taken as the "second" nucleotide sequence.

For the purposes of comparing two or more amino acid sequences, the percentage of "sequence identity" between a first amino acid sequence and a second amino acid sequence (also referred to herein as "amino acid identity") may be calculated by dividing [the number of amino acid residues in the first amino acid sequence that are identical to the amino acid residues at the corresponding positions in the second amino acid sequence] by [the total number of amino acid residues in the first amino acid sequence] and multiplying by [100%], in which each deletion, insertion, substitution or addition of an amino acid residue in the second amino acid sequence—compared to the first amino acid sequence—is considered as a difference at a single amino acid residue (position), i.e., as an "amino acid difference" as defined herein. Alternatively, the degree of sequence identity between two amino acid sequences may be calculated using a known computer algorithm, such as those mentioned above for determining the degree of sequence identity for nucleotide sequences, again using standard settings. Usually, for the purpose of determining the percentage of "sequence identity" between two amino acid sequences in accordance with the calculation method outlined hereinabove, the amino acid sequence with the greatest number of amino acid residues will be taken as the "first" amino acid sequence, and the other amino acid sequence will be taken as the "second" amino acid sequence.

Also, in determining the degree of sequence identity between two amino acid sequences, the skilled person may take into account so-called "conservative" amino acid substitutions, which can generally be described as amino acid substitutions in which an amino acid residue is replaced with another amino acid residue of similar chemical structure and which has little or essentially no influence on the function, activity or other biological properties of the polypeptide. Such conservative amino acid substitutions are well known in the art, for example from WO 04/037999, GB 335768, WO 98/49185, WO 00/46383 and WO 01/09300; and (preferred) types and/or combinations of such substitutions may be selected on the basis of the pertinent teachings from WO 04/037999 as well as WO 98/49185 and from the further references cited therein.

Such conservative substitutions preferably are substitutions in which one amino acid within the following groups (a)-(e) is substituted by another amino acid residue within the same group: (a) small aliphatic, nonpolar or slightly polar residues: Ala, Ser, Thr, Pro and Gly; (b) polar, negatively charged residues and their (uncharged) amides: Asp, Asn, Glu and Gln; (c) polar, positively charged residues: His, Arg and Lys; (d) large aliphatic, nonpolar residues: Met, Leu, Ile, Val and Cys; and (e) aromatic residues: Phe, Tyr and Trp. Particularly preferred conservative substitutions are as follows: Ala into Gly or into Ser; Arg into Lys; Asn into Gln or into His; Asp into Glu; Cys into Ser; Gln into Asn; Glu into Asp; Gly into Ala or into Pro; His into Asn or into Gln; Ile into Leu or into Val; Leu into Ile or into Val; Lys into Arg, into Gln or into Glu; Met into Leu, into Tyr or into Ile; Phe into Met, into Leu or into Tyr; Ser into Thr; Thr into Ser; Trp into Tyr; Tyr into Trp; and/or Phe into Val, into Ile or into Leu.

Any amino acid substitutions applied to the polypeptides described herein may also be based on the analysis of the frequencies of amino acid variations between homologous proteins of different species developed by Schulz et al. ("Principles of Protein Structure", Springer-Verlag, 1978), on the analyses of structure forming potentials developed by Chou and Fasman (Biochemistry 13: 211, 1974; Adv. Enzymol., 47: 45-149, 1978), and on the analysis of hydrophobicity patterns in proteins developed by Eisenberg et al. (Proc. Natl. Acad Sci. USA 81: 140-144, 1984), Kyte and Doolittle (J. Molec. Biol. 157: 105-132, 1981), and Goldman et al. (Ann. Rev. Biophys. Chem. 15: 321-353, 1986), all incorporated herein in their entirety by reference. Information on the primary, secondary and tertiary structure of Nanobodies is given in the description herein and in the general background art cited above. Also, for this purpose, the crystal structure of a $V_{HH}$ domain from a llama is for example given by Desmyter et al. (Nature Structural Biology, 3: 803, 1996), Spinelli et al. (Natural Structural Biology, 3: 752-757, 1996) and Decanniere et al. (Structure, 7 (4): 361, 1999). Further information about some of the amino acid residues that in conventional $V_H$ domains form the $V_H/V_L$ interface and potential camelizing substitutions on these positions can be found in the prior art cited above.

Amino acid sequences and nucleic acid sequences are said to be "exactly the same" if they have 100% sequence identity (as defined herein) over their entire length.

When comparing two amino acid sequences, the term "amino acid(s) difference" refers to an insertion, deletion or substitution of a single amino acid residue on a position of the first sequence, compared to the second sequence; it being understood that two amino acid sequences can contain one, two or more such amino acid differences. More particularly, in the ISVDs and/or polypeptides of the present invention, the term "amino acid(s) difference" refers to an insertion, deletion or substitution of a single amino acid residue on a position of the CDR sequence specified in b), d) or f), compared to the CDR sequence of respectively a), c) or e); it being understood that the CDR sequence of b), d) and f) can contain one, two, three, four or maximal five such amino acid differences compared to the CDR sequence of respectively a), c) or e).

The "amino acid(s) difference" can be any one, two, three, four or maximal five substitutions, deletions or insertions, or any combination thereof, that either improve the properties of the ADAMTS5 binder of the invention, such as the polypeptide of the invention or that at least do not detract too much from the desired properties or from the balance or combination of desired properties of the ADAMTS5 binder of the invention, such as the polypeptide of the invention. In this respect, the resulting ADAMTS5 binder of the invention, such as the polypeptide of the invention should at least bind ADAMTS5 with the same, about the same, or a higher affinity compared to the polypeptide comprising the one or more CDR sequences without the one, two, three, four or maximal five substitutions, deletions or insertions. The affinity can be measured by any suitable method known in the art, but is preferably measured by a method as described in the examples section.

In this respect, the amino acid sequence of the CDRs according to b), d) and/or f) as indicated below, may be an amino acid sequence that is derived from an amino acid sequence according to a), c) and/or e) respectively by means of affinity maturation using one or more techniques of affinity maturation known per se or as described in the Examples. For example, and depending on the host organism used to express the polypeptide of the invention, such deletions and/or substitutions may be designed in such a way that one or more sites for post-translational modification (such as one or more glycosylation sites) are removed, as will be within the ability of the person skilled in the art (cf. Examples).

A "Nanobody family", "$V_{HH}$ family" or "family" as used in the present specification refers to a group of Nanobodies and/or $V_{HH}$ sequences that have identical lengths (i.e. they have the same number of amino acids within their sequence) and of which the amino acid sequence between position 8 and position 106 (according to Kabat numbering) has an amino acid sequence identity of 89% or more.

The terms "epitope" and "antigenic determinant", which can be used interchangeably, refer to the part of a macromolecule, such as a polypeptide or protein that is recognized by antigen-binding molecules, such as immunoglobulins, conventional antibodies, immunoglobulin single variable domains and/or polypeptides of the invention, and more particularly by the antigen-binding site of said molecules. Epitopes define the minimum binding site for an immunoglobulin, and thus represent the target of specificity of an immunoglobulin.

The part of an antigen-binding molecule (such as an immunoglobulin, a conventional antibody, an immunoglobulin single variable domain and/or a polypeptide of the invention) that recognizes the epitope is called a "paratope".

An amino acid sequence (such as an immunoglobulin single variable domain, an antibody, a polypeptide of the invention, or generally an antigen binding protein or polypeptide or a fragment thereof) that can "bind to" or "specifically bind to", that "has affinity for" and/or that "has specificity for" a certain epitope, antigen or protein (or for at least one part, fragment or epitope thereof) is said to be "against" or "directed against" said epitope, antigen or protein or is a "binding" molecule with respect to such epitope, antigen or protein, or is said to be "anti"-epitope, "anti"-antigen or "anti"-protein (e.g., "anti"-ADAMTS5).

The affinity denotes the strength or stability of a molecular interaction. The affinity is commonly given as the $K_D$, or dissociation constant, which has units of mol/liter (or M). The affinity can also be expressed as an association constant, $K_A$, which equals $1/K_D$ and has units of (mol/liter)$^{-1}$ (or M$^{-1}$). In the present specification, the stability of the interaction between two molecules will mainly be expressed in terms of the $K_D$ value of their interaction; it being clear to the skilled person that in view of the relation $K_A=1/K_D$, specifying the strength of molecular interaction by its $K_D$ value can also be used to calculate the corresponding $K_A$ value. The $K_D$-value characterizes the strength of a molecular interaction also in a thermodynamic sense as it is related to the change of free energy (DG) of binding by the well-known relation DG=RT·ln($K_D$) (equivalently DG=−RT·ln($K_A$)), where R equals the gas constant, T equals the absolute temperature and ln denotes the natural logarithm.

The $K_D$ for biological interactions which are considered meaningful (e.g. specific) are typically in the range of 10$^{-12}$ M (0.001 nM) to 10$^{-5}$ M (10000 nM). The stronger an interaction is, the lower is its $K_D$.

The $K_D$ can also be expressed as the ratio of the dissociation rate constant of a complex, denoted as $k_{off}$, to the rate of its association, denoted $k_{on}$ (so that $K_D=k_{off}/k_{on}$ and $K_A=k_{on}/k_{off}$). The off-rate $k_{off}$ has units s$^{-1}$ (where s is the SI unit notation of second). The on-rate $k_{on}$ has units M$^{-1}$s$^{-1}$. The on-rate may vary between 10$^2$ M$^{-1}$s$^{-1}$ to about 10$^7$ M$^{-1}$s$^{-1}$, approaching the diffusion-limited association rate constant for bimolecular interactions. The off-rate is related to the half-life of a given molecular interaction by the relation $t_{1/2}=\ln(2)/k_{off}$. The off-rate may vary between 10$^{-6}$ s$^{-1}$ (near irreversible complex with a $t_{1/2}$ of multiple days) to 1 s$^{-1}$ ($t_{1/2}$=0.69 s).

Specific binding of an antigen-binding protein, such as an ISVD, to an antigen or antigenic determinant can be determined in any suitable manner known per se, including, for example, saturation binding assays and/or competitive binding assays, such as radio-immunoassays (RIA), enzyme immunoassays (EIA) and sandwich competition assays, and the different variants thereof known per se in the art; as well as the other techniques mentioned herein.

The affinity of a molecular interaction between two molecules can be measured via different techniques known per se, such as the well-known surface plasmon resonance (SPR) biosensor technique (see for example Ober et al. 2001, Intern. Immunology 13: 1551-1559) where one molecule is immobilized on the biosensor chip and the other molecule is passed over the immobilized molecule under flow conditions yielding $k_{on}$, $k_{off}$ measurements and hence $K_D$ (or $K_A$) values. This can for example be performed using the well-known BIACORE® instruments (Pharmacia Biosensor AB, Uppsala, Sweden). Kinetic Exclusion Assay (KINEXA®) (Drake et al. 2004, Analytical Biochemistry 328: 35-43) measures binding events in solution without labeling of the binding partners and is based upon kinetically excluding the dissociation of a complex. In-solution affinity analysis can also be performed using the GYROLAB® immunoassay system, which provides a platform for automated bioanalysis and rapid sample turnaround (Fraley et al. 2013, Bioanalysis 5: 1765-74), or ELISA.

It will also be clear to the skilled person that the measured $K_D$ may correspond to the apparent $K_D$ if the measuring process somehow influences the intrinsic binding affinity of the implied molecules for example by artifacts related to the coating on the biosensor of one molecule. Also, an apparent $K_D$ may be measured if one molecule contains more than one recognition site for the other molecule. In such situation the measured affinity may be affected by the avidity of the interaction by the two molecules. In particular, the accurate measurement of $K_D$ may be quite labor-intensive and as a consequence, often apparent $K_D$ values are determined to assess the binding strength of two molecules. It should be noted that as long as all measurements are made in a consistent way (e.g. keeping the assay conditions unchanged) apparent $K_D$ measurements can be used as an approximation of the true $K_D$ and hence in the present document $K_D$ and apparent $K_D$ should be treated with equal importance or relevance.

The term "specificity" refers to the number of different types of antigens or antigenic determinants to which a particular antigen-binding molecule or antigen-binding protein (such as an ISVD or polypeptide of the invention) molecule can bind. The specificity of an antigen-binding protein can be determined based on affinity and/or avidity, for instance as described on pages 53-56 of WO 08/020079 (incorporated herein by reference), which also describes some preferred techniques for measuring binding between an antigen-binding molecule (such as a polypeptide or ISVD of the invention) and the pertinent antigen. Typically, antigen-binding proteins (such as the ISVDs and/or polypeptides of the invention) will bind to their antigen with a dissociation constant ($K_D$) of $10^{-5}$ to $10^{-12}$ moles/liter or less, and preferably $10^{-7}$ to $10^{-12}$ moles/liter or less and more preferably $10^{-8}$ to $10^{-12}$ moles/liter (i.e., with an association constant ($K_A$) of $10^5$ to $10^{12}$ liter/moles or more, and preferably $10^7$ to $10^{12}$ liter/moles or more and more preferably $10^8$ to $10^{12}$ liter/moles). Any $K_D$ value greater than $10^{-4}$ mol/liter (or any $K_A$ value lower than $10^4$ liter/mol) is generally considered to indicate non-specific binding. Preferably, a monovalent ISVD of the invention will bind to the desired antigen with an affinity less than 500 nM, preferably less than 200 nM, more preferably less than 10 nM, such as less than 500 pM, such as e.g., between 10 and 5 pM or less. Reference is also made to paragraph n) on pages 53-56 of WO 08/020079.

An ISVD and/or polypeptide is said to be "specific for" a (first) target or antigen compared to another (second) target or antigen when it binds to the first antigen with an affinity (as described above, and suitably expressed as a $K_D$ value, $K_A$ value, $K_{off}$ rate and/or $K_{on}$ rate) that is at least 10 times, such as at least 100 times, and preferably at least 1000 times or more better than the affinity with which the ISVD and/or polypeptide binds to the second target or antigen. For example, the ISVD and/or polypeptide may bind to the first target or antigen with a $K_D$ value that is at least 10 times less, such as at least 100 times less, and preferably at least 1000 times less or even less than that, than the $K_D$ with which said ISVD and/or polypeptide binds to the second target or antigen. Preferably, when an ISVD and/or polypeptide is "specific for" a first target or antigen compared to a second target or antigen, it is directed against (as defined herein) said first target or antigen, but not directed against said second target or antigen.

Specific binding of an antigen-binding protein to an antigen or antigenic determinant can be determined in any suitable manner known per se, including, for example, saturation binding assays and/or competitive binding assays, such as radioimmunoassays (RIA), enzyme immunoassays (EIA) and the different variants thereof known in the art; as well as the other techniques mentioned herein.

A preferred approach that may be used to assess affinity is the 2-step ELISA (Enzyme-Linked Immunosorbent Assay) procedure of Friguet et al. 1985 (J. Immunol. Methods 77: 305-19). This method establishes a solution phase binding equilibrium measurement and avoids possible artifacts relating to adsorption of one of the molecules on a support such as plastic. As will be clear to the skilled person, the dissociation constant may be the actual or apparent dissociation constant. Methods for determining the dissociation constant will be clear to the skilled person, and for example include the techniques mentioned on pages 53-56 of WO 08/020079.

Finally, it should be noted that in many situations the experienced scientist may judge it to be convenient to determine the binding affinity relative to some reference molecule. For example, to assess the binding strength between molecules A and B, one may e.g. use a reference molecule C that is known to bind to B and that is suitably labelled with a fluorophore or chromophore group or other chemical moiety, such as biotin for easy detection in an ELISA or FACS (Fluorescent activated cell sorting) or other format (the fluorophore for fluorescence detection, the chromophore for light absorption detection, the biotin for streptavidin-mediated ELISA detection). Typically, the reference molecule C is kept at a fixed concentration and the concentration of A is varied for a given concentration or amount of B. As a result an $IC_{50}$ value is obtained corresponding to the concentration of A at which the signal measured for C in absence of A is halved. Provided $K_{D\ ref}$, the $K_D$ of the reference molecule, is known, as well as the total concentration $c_{ref}$ of the reference molecule, the apparent $K_D$ for the interaction A-B can be obtained from following formula: $K_D = IC_{50}/(1+C_{ref}/K_{Dref})$. Note that if $c_{ref} \ll K_{D\ ref}$, $K_D \approx IC_{50}$. Provided the measurement of the $IC_{50}$ is performed in a consistent way (e.g. keeping $c_{ref}$ fixed) for the binders that are compared, the difference in strength or stability of a molecular interaction can be assessed by comparing the $IC_{50}$ and this measurement is judged as equivalent to $K_D$ or to apparent $K_D$ throughout this text.

The half maximal inhibitory concentration ($IC_{50}$) can also be a measure of the effectiveness of a compound in inhibiting a biological or biochemical function, e.g. a pharmacological effect. This quantitative measure indicates how much of the polypeptide or ISVD (e.g. a Nanobody) is needed to inhibit a given biological process (or component of a process, i.e. an enzyme, cell, cell receptor, chemotaxis, anaplasia, metastasis, invasiveness, etc.) by half. In other words, it is the half maximal (50%) inhibitory concentration (IC) of a substance (50% IC, or $IC_{50}$). $IC_{50}$ values can be calculated for a given antagonist such as the polypeptide or ISVD (e.g. a Nanobody) of the invention by determining the concentration needed to inhibit half of the maximum biological response of the agonist. The $K_D$ of a drug can be determined by constructing a dose-response curve and examining the effect of different concentrations of antagonist such as the polypeptide or ISVD (e.g. a Nanobody) of the invention on reversing agonist activity.

The term half maximal effective concentration ($EC_{50}$) refers to the concentration of a compound which induces a response halfway between the baseline and maximum after a specified exposure time. In the present context it is used as a measure of a polypeptide, ISVD (e.g. a Nanobody) its potency. The $EC_{50}$ of a graded dose response curve represents the concentration of a compound where 50% of its maximal effect is observed. Concentration is preferably expressed in molar units.

In biological systems, small changes in ligand concentration typically result in rapid changes in response, following a sigmoidal function. The inflection point at which the increase in response with increasing ligand concentration begins to slow is the $EC_{50}$. This can be determined mathematically by derivation of the best-fit line. Relying on a graph for estimation is convenient in most cases. In case the $EC_{50}$ is provided in the examples section, the experiments were designed to reflect the $K_D$ as accurate as possible. In other words, the $EC_{50}$ values may then be considered as $K_D$ values. The term "average $K_D$" relates to the average $K_D$ value obtained in at least 1, but preferably more than 1, such as at least 2 experiments. The term "average" refers to the mathematical term "average" (sums of data divided by the number of items in the data).

It is also related to $IC_{50}$ which is a measure of a compound its inhibition (50% inhibition). For competition binding assays and functional antagonist assays $IC_{50}$ is the most common summary measure of the dose-response curve. For agonist/stimulator assays the most common summary measure is the $EC_{50}$.

The inhibition constant (Ki) is an indication of how potent an inhibitor is; it is the concentration required to produce half maximum inhibition. Unlike $IC_{50}$, which can change depending on the experimental conditions, Ki is an absolute value and is often referred to as the inhibition constant of a drug. The inhibition constant $K_i$ can be calculated by using the Cheng-Prusoff equation:

$$K_i = \frac{IC50}{\frac{[L]}{K_D} + 1}$$

in which [L] is the fixed concentration of the ligand.

The term "potency" of a polypeptide and/or ISVD of the invention, as used herein, is a function of the amount of polypeptide and/or ISVD of the invention required for its specific effect to occur. It refers to the capacity of said polypeptide and/or ISVD of the invention to modulate and/or partially or fully inhibit an activity of ADAMTS5. More particularly, it may refer to the capacity of said polypeptide and/or ISVD to reduce or even totally inhibit an ADAMTS5 activity as defined herein. As such, it may refer to the capacity of said polypeptide and/or ISVD to inhibit an activity of ADAMTS5, such as an enzymatic activity, such as proteolysis, e.g. the protease activity and/or endopeptidase activities, as well as binding of a substrate, including but not limited to Aggrecan, versican, brevican, neurocan, decorin, and/or biglycan, preferably cleavage of Aggrecan. Said polypeptide and/or ISVD preferably antagonizes aggrecanase activity of ADAMTS5. The potency may be measured by any suitable assay known in the art or described herein. As used herein, "aggrecanase activity" is defined as the proteolytic cleavage of Aggrecan.

The "efficacy" of the polypeptide of the invention measures the maximum strength of the effect itself, at saturating polypeptide concentrations. Efficacy indicates the maximum response achievable from the polypeptide of the invention. It refers to the ability of a polypeptide to produce the desired (therapeutic) effect.

In an aspect the invention relates to a polypeptide as described herein, wherein said polypeptide binds to ADAMTS5 with a $K_D$ between $1E^{-07}$ M and $1E^{-13}$ M, such as between $1E^{-08}$ and $1E^{-12}$ M, preferably at most $1E^{-07}$ M, preferably lower than $1E^{-08}$ M or $1E^{-09}$ M, or even lower than $1E^{-10}$ M, such as $5E^{-11}$ M, $4E^{-11}$ M, $3E^{-11}$ M, $2E^{-11}$ M, $1.7E^{-11}$ M, $1E^{-11}$ M, or even $5E^{-12}$ M, $4E^{-12}$ M, $3E^{-12}$ M, $1E^{-12}$ M, for instance as determined by Gyrolab or KinExA.

In an aspect the invention relates to a polypeptide as described herein, wherein said polypeptide modulates ADAMTS5 with an $EC_{50}$ between $1E^{-07}$ M and $1E^{-12}$ M, such as between $1E^{-08}$ M and $1E^{-11}$ M, for instance as determined by binding ELISA.

In an aspect the invention relates to a polypeptide as described herein, wherein said polypeptide binds to ADAMTS5 with an off-rate of less than $5E^{-04}$ $s^{-1}$, such as less than $1E^{-04}$ $s^{-1}$ or $5E^{-05}$ $s^{-1}$, or even less than $1E^{-05}$ $s^{-1}$, for instance as determined by SPR.

In an aspect the invention relates to a polypeptide as described herein, wherein said polypeptide inhibits an activity of ADAMTS5 with an $IC_{50}$ between $1E^{-07}$ M and $1E^{-12}$ M, such as between $1E^{-08}$ M and $1E^{-11}$ M, for instance as determined by human FRET assay or human AlphaLISA.

In an aspect the invention relates to a polypeptide as described herein, wherein said polypeptide inhibits an enzymatic activity of ADAMTS5 with an $IC_{50}$ of at most $1E^{-07}$ M, preferably $1E^{-08}$ M, $5E^{-09}$ M, or $4E^{-9}$ M, $3E^{-9}$ M, $2E^{-9}$ M, such as $1E^{-9}$ M.

An amino acid sequence, such as an ISVD or polypeptide, is said to be "cross-reactive" for two different antigens or antigenic determinants (such as e.g., ADAMTS5 from different species of mammal, such as e.g., human ADAMTS5, bovine ADAMTS5, rat ADAMTS5, guinea pig ADAMTS5, mouse ADAMTS5 or cynomolgus ADAMTS5) if it is specific for (as defined herein) these different antigens or antigenic determinants. It will be appreciated that an ISVD or polypeptide may be considered to be cross-reactive although the binding affinity for the two different antigens can differ, such as by a factor, 2, 5, 10, 50, 100 or even more provided it is specific for (as defined herein) these different antigens or antigenic determinants.

ADAMTS5 is also known as ADAMTS11, ADMP-2 or Aggrecanase-2.

Relevant structural information for ADAMTS5 may be found, for example, at UniProt Accession Numbers as depicted in the Table 1 below (cf. Table B).

TABLE 1

| Protein Acc. | Gene | Organism | SEQ ID NO: |
|---|---|---|---|
| Q9UNA0 | ADAMTS5 | H. sapiens | 149 |
| Q9TT92 | ADAMTS5 | B. taurus | 150 |
| Q6TY19 | ADAMTS5 | R. norvegicus | 151 |
| H0VFP0 | ADAMTS5 | Cavia Porcellus | 152 |
| Q9R001 | ADAMTS5 | M. musculus | 153 |
| F6Z3S6 | ADAMTS5 | M. mulatto | 154 |

"Human ADAMTS5" refers to the ADAMTS5 comprising the amino acid sequence of SEQ ID NO: 149. In an aspect the polypeptide of the invention specifically binds ADAMTS5 from *Homo sapiens, Mus musculus, Cavia porcellus, Bos taurus, Macaca mulatta* and/or *Rattus norvegicus*, preferably human ADAMTS5, preferably SEQ ID NO: 149.

The terms "(cross)-block", "(cross)-blocked", "(cross)-blocking", "competitive binding", "(cross)-compete", "(cross)-competing" and "(cross)-competition" are used interchangeably herein to mean the ability of an immunoglobulin, antibody, ISVD, polypeptide or other binding agent to interfere with the binding of other immunoglobulins, antibodies, ISVDs, polypeptides or binding agents to a given target. The extent to which an immunoglobulin, antibody, ISVD, polypeptide or other binding agent is able to interfere with the binding of another to the target, and therefore whether it may be said to cross-block according to the invention, may be determined using competition binding assays, which are common in the art, such as, for instance, by screening purified ISVDs against ISVDs displayed on phage in a competition ELISA. Particularly suitable quantitative cross-blocking assays include ELISA.

Other methods for determining whether an immunoglobulin, antibody, ISVD, polypeptide or other binding agent directed against a target (cross)-blocks, is capable of (cross)-blocking, competitively binds or is (cross)-competitive as defined herein, can be evaluated by an SPR-based "sandwich assay", such as for instance described in the Examples section. Other suitable methods are described e.g. in Xiao-Chi Jia et al. (Journal of Immunological Methods 288: 91-98, 2004), Miller et al. (Journal of Immunological Methods 365: 118-125, 2011).

Accordingly, the present invention relates to a polypeptide as described herein, such as represented by SEQ ID NO:s 2, 116, 19, 1, 3, 6, 16, 17, 10, 11, 9, 5, 4, 7, 117, 8, 12, 13, 14, 15 or 18 (cf. Table A-1), wherein said polypeptide competes with a cross-blocking polypeptide, for instance as determined by competition ELISA.

The present invention relates to a method for determining competitors, such as polypeptides, competing with a polypeptide as described herein, such as represented by any one of SEQ ID NO:s 2, 116, 19, 1, 3, 6, 16, 17, 10, 11, 9, 5, 4, 7, 117, 8, 12, 13, 14, 15 or 18, wherein the polypeptide as described herein competes with or cross blocks the competitor, such as a polypeptide, for binding to ADAMTS5, such as, for instance human ADAMTS5 (SEQ ID NO: 149), wherein the binding to ADAMTS5 of the competitor is reduced by at least 5%, such as 10%, 20%, 30%, 40%, 50% or even more, such as 80%, 90% or even 100% (i.e. virtually undetectable in a given assay) in the presence of a polypeptide of the invention, compared to the binding to ADAMTS5 of the competitor in the absence of the polypeptide of the invention. Competition and cross blocking may be determined by any means known in the art, such as, for instance, competition ELISA or FACS assay. In an aspect the present invention relates to a polypeptide of the invention, wherein said polypeptide cross-blocks the binding to ADAMTS5 of at least one of the polypeptides represented by SEQ ID NO:s 2, 116, 19, 1, 3, 6, 16, 17, 10, 11, 9, 5, 4, 7, 117, 8, 12, 13, 14, 15 or 18 and/or is cross-blocked from binding to ADAMTS5 by at least one of the polypeptides represented by SEQ ID NO:s 2, 116, 19, 1, 3, 6, 16, 17, 10, 11, 9, 5, 4, 7, 117, 8, 12, 13, 14, 15 or 18.

The present invention also relates to competitors competing with a polypeptide as described herein, such as SEQ ID NO:s 2, 116, 19, 1, 3, 6, 16, 17, 10, 11, 9, 5, 4, 7, 117, 8, 12, 13, 14, 15 or 18, wherein the competitor competes with or cross blocks the polypeptide as described herein for binding to ADAMTS5, wherein the binding to ADAMTS5 of the polypeptide of the invention is reduced by at least 5%, such as 10%, 20%, 30%, 40%, 50% or even more, such as 80%, or even more such as at least 90% or even 100% (i.e. virtually undetectable in a given assay) in the presence of said competitor, compared to the binding to ADAMTS5 by the polypeptide of the invention in the absence of said competitor. In an aspect the present invention relates to a polypeptide cross-blocking binding to ADAMTS5 by a polypeptide of the invention such as one of SEQ ID NO:s 2, 116, 19, 1, 3, 6, 16, 17, 10, 11, 9, 5, 4, 7, 117, 8, 12, 13, 14, 15 or 18 and/or is cross-blocked from binding to ADAMTS5 by at least one of SEQ ID NO:s 2, 116, 19, 1, 3, 6, 16, 17, 10, 11, 9, 5, 4, 7, 117, 8, 12, 13, 14, 15 or 18, preferably wherein said polypeptide comprises at least one VH, VL, dAb, or ISVD specifically binding to ADAMTS5, wherein binding to ADAMTS5 modulates an activity of ADAMTS5.

"ADAMTS5 activities" and "activities of ADAMTS5" (these terms are used interchangeably herein) include, but are not limited to enzymatic activities, such as proteolysis, e.g. protease activity (also called proteinase or peptidase activity), and endopeptidase activities, on the one hand, and the activities by the exosites, such as for instance recognizing and/or binding the substrate, e.g. by disintegrin-like domain, central thrombospondin type I-like (TS) repeat, cysteine-rich domain, spacer region and/or additional TS motifs. ADAMTS5 activities include binding and/or proteolysis of substrates such as hyaluronan-binding chondroitin sulfate proteoglycan (CSPG) extracellular proteins, such as Aggrecan, versican, brevican, neurocan, decorin and biglycan. As used herein, proteolysis is the breakdown of proteins into smaller polypeptides or amino acids by hydrolysis of the peptide bonds that link amino acids together in a polypeptide chain.

In the context of the present invention, "modulating" or "to modulate" generally means altering an activity by ADAMTS5, as measured using a suitable in vitro, cellular or in vivo assay (such as those mentioned herein). In particular, "modulating" or "to modulate" may mean either reducing or inhibiting an activity of, or alternatively increasing an activity of ADAMTS5, as measured using a suitable in vitro, cellular or in vivo assay (for instance, such as those mentioned herein), by at least 1%, preferably at least 5%, such as at least 10% or at least 25%, for example by at least 50%, at least 60%, at least 70%, at least 80%, or 90% or more, compared to activity of ADAMTS5 in the same assay under the same conditions but without the presence of the ISVD or polypeptide of the invention.

Accordingly, the present invention relates to a polypeptide as described herein, wherein said polypeptide modulates an activity of ADAMTS5, preferably inhibiting an activity of ADAMTS5.

Accordingly, the present invention relates to a polypeptide as described herein, wherein said polypeptide inhibits protease activity of ADAMTS5, such as inhibits the proteolysis of a substrate, such as Aggrecan, versican, brevican, neurocan, decorin, and/or biglycan.

Accordingly, the present invention relates to a polypeptide as described herein, wherein said polypeptide blocks the binding of ADAMTS5 to a substrate, such as Aggrecan, versican, brevican, neurocan, decorin, and/or biglycan, wherein said substrate is preferably Aggrecan.

In an aspect the invention relates to a polypeptide as described herein, wherein said polypeptide blocks the binding of ADAMTS5 to Aggrecan of at least 20%, such as at least 30%, 40%, 50%, 60%, 70%, 80%, 90%, 95% or even more, for instance as determined by ELISA.

In an aspect the invention relates to a polypeptide as described herein, wherein said polypeptide antagonizes or inhibits an activity of ADAMTS5, such as (i) a protease activity, preferably cleavage of Aggrecan, versican, brevican, neurocan, decorin, and/or biglycan, preferably cleavage of Aggrecan; preferably antagonizes aggrecanase activity of ADAMTS5; (ii) binding of a substrate to ADAMTS5, such as an exosite of ADAMTS5, for instance the disintegrin-like domain, the central thrombospondin type !-like (TS) repeat, the cysteine-rich domain, the spacer region or the additional TS motif.

Accordingly, the present invention relates to a polypeptide as described herein, wherein said polypeptide inhibits protease activity of ADAMTS5, preferably by at least 5%, such as 10%, 20%, 30%, 40%, 50% or even more, such as at least 60%, 70%, 80%, 90%, 95% or even more, as determined by any suitable method known in the art, such as for instance by enzyme inhibition assays or as described in the Examples section.

Although the ADAMs, ADAMTSs and MMPs share a binding site to Aggrecan that is very similar both in sequence and in overall shape, e.g., the catalytic domains of ADAMTS4 and ADAMTS5 share a high degree of sequence similarity, the inventors were able to identify ISVDs which were target specific, as demonstrated in the examples. The target specificity also would avoid or at least limit musculoskeletal syndrome, which is a side-effect caused by broad-spectrum inhibitors.

In an aspect the invention relates to an ADAMTS5 binder such as an ISVD and polypeptide of the invention, wherein said ADAMTS5 binder does not bind ADAMTS4, ADAMTS1, ADAMTS15, MMP1 and/or MMP14 (membrane type). Preferably, the present invention relates to a polypeptide as defined herein, wherein said ISVD binding ADAMTS5 does not bind ADAMTS4, MMP1 or MMP14.

Unless indicated otherwise, the terms "immunoglobulin" and "immunoglobulin sequence"—whether used herein to refer to a heavy chain antibody or to a conventional 4-chain antibody—is used as a general term to include both the full-size antibody, the individual chains thereof, as well as all parts, domains or fragments thereof (including but not limited to antigen-binding domains or fragments such as $V_{HH}$ domains or $V_H/V_L$ domains, respectively).

The term "domain" (of a polypeptide or protein) as used herein refers to a folded protein structure which has the ability to retain its tertiary structure independently of the rest of the protein. Generally, domains are responsible for discrete functional properties of proteins, and in many cases may be added, removed or transferred to other proteins without loss of function of the remainder of the protein and/or of the domain.

The term "immunoglobulin domain" as used herein refers to a globular region of an antibody chain (such as e.g., a chain of a conventional 4-chain antibody or of a heavy chain antibody), or to a polypeptide that essentially consists of such a globular region. Immunoglobulin domains are characterized in that they retain the immunoglobulin fold characteristic of antibody molecules, which consists of a two-layer sandwich of about seven antiparallel beta-strands arranged in two beta-sheets, optionally stabilized by a conserved disulphide bond.

The term "immunoglobulin variable domain" as used herein means an immunoglobulin domain essentially consisting of four "framework regions" which are referred to in the art and herein below as "framework region 1" or "FR1"; as "framework region 2" or "FR2"; as "framework region 3" or "FR3"; and as "framework region 4" or "FR4", respectively; which framework regions are interrupted by three "complementarity determining regions" or "CDRs", which are referred to in the art and herein below as "complementarity determining region 1" or "CDR1"; as "complementarity determining region 2" or "CDR2"; and as "complementarity determining region 3" or "CDR3", respectively. Thus, the general structure or sequence of an immunoglobulin variable domain may be indicated as follows: FR1-CDR1-FR2-CDR2-FR3-CDR3-FR4. It is the immunoglobulin variable domain(s) that confer specificity to an antibody for the antigen by carrying the antigen-binding site.

The term "immunoglobulin single variable domain" (abbreviated herein as "ISVD" or "ISV"), and interchangeably used with "single variable domain", defines molecules wherein the antigen binding site is present on, and formed by, a single immunoglobulin domain. This sets immunoglobulin single variable domains apart from "conventional" immunoglobulins or their fragments, wherein two immunoglobulin domains, in particular two variable domains, interact to form an antigen binding site. Typically, in conventional immunoglobulins, a heavy chain variable domain ($V_H$) and a light chain variable domain ($V_L$) interact to form an antigen binding site. In the latter case, the complementarity determining regions (CDRs) of both $V_H$ and $V_L$ will contribute to the antigen binding site, i.e. a total of 6 CDRs will be involved in antigen binding site formation.

In view of the above definition, the antigen-binding domain of a conventional 4-chain antibody (such as an IgG, IgM, IgA, IgD or IgE molecule; known in the art) or of a Fab fragment, a F(ab')2 fragment, an Fv fragment such as a disulphide linked Fv or a scFv fragment, or a diabody (all known in the art) derived from such conventional 4-chain antibody, would normally not be regarded as an immunoglobulin single variable domain, as, in these cases, binding to the respective epitope of an antigen would normally not occur by one (single) immunoglobulin domain but by a pair of (associating) immunoglobulin domains such as light and heavy chain variable domains, i.e., by a $V_H$-$V_L$ pair of immunoglobulin domains, which jointly bind to an epitope of the respective antigen.

In contrast, ISVDs are capable of specifically binding to an epitope of the antigen without pairing with an additional immunoglobulin variable domain. The binding site of an ISVD is formed by a single $V_{HH}$, $V_H$ or $V_L$ domain. Hence, the antigen binding site of an ISVD is formed by no more than three CDRs.

As such, the single variable domain may be a light chain variable domain sequence (e.g., a $V_L$-sequence) or a suitable fragment thereof; or a heavy chain variable domain sequence (e.g., a $V_H$-sequence or $V_{HH}$ sequence) or a suitable fragment thereof; as long as it is capable of forming a single antigen binding unit (i.e., a functional antigen binding unit that essentially consists of the single variable domain, such that the single antigen binding domain does not need to interact with another variable domain to form a functional antigen binding unit).

In one embodiment of the invention, the ISVDs are heavy chain variable domain sequences (e.g., a $V_H$-sequence); more specifically, the ISVDs may be heavy chain variable domain sequences that are derived from a conventional four-chain antibody or heavy chain variable domain sequences that are derived from a heavy chain antibody.

For example, the ISVD may be a (single) domain antibody (or an amino acid that is suitable for use as a (single) domain antibody), a "dAb" or dAb (or an amino acid that is suitable for use as a dAb) or a Nanobody (as defined herein, and including but not limited to a VHH); other single variable domains, or any suitable fragment of any one thereof.

In particular, the ISVD may be a Nanobody® (as defined herein) or a suitable fragment thereof. [Note: Nanobody®, Nanobodies® and Nanoclone® are registered trademarks of Ablynx N.V.] For a general description of Nanobodies, reference is made to the further description below, as well as to the prior art cited herein, such as e.g. described in WO 08/020079 (page 16).

"$V_{HH}$ domains", also known as VHHs, $V_HH$ domains, VHH antibody fragments, and VHH antibodies, have originally been described as the antigen binding immunoglobulin (variable) domain of "heavy chain antibodies" (i.e., of "antibodies devoid of light chains"; Hamers-Casterman et al. 1993 Nature 363: 446-448). The term "$V_{HH}$ domain" has been chosen in order to distinguish these variable domains from the heavy chain variable domains that are present in conventional 4-chain antibodies (which are referred to herein as "$V_H$ domains" or "VH domains") and from the light chain variable domains that are present in conventional 4-chain antibodies (which are referred to herein as "$V_L$ domains" or "VL domains"). For a further description of VHH's and Nanobodies, reference is made to the review article by Muyldermans (Reviews in Molecular Biotechnology 74: 277-302, 2001), as well as to the following patent applications, which are mentioned as general background art: WO 94/04678, WO 95/04079 and WO 96/34103 of the Vrije Universiteit Brussel; WO 94/25591, WO 99/37681, WO 00/40968, WO 00/43507, WO 00/65057, WO 01/40310, WO 01/44301, EP 1134231 and WO 02/48193 of Unilever; WO 97/49805, WO 01/21817, WO 03/035694, WO 03/054016 and WO 03/055527 of the Vlaams Instituut voor Biotechnologie (VIB); WO 03/050531 of Algonomics N.V. and Ablynx N.V.; WO 01/90190 by the National Research Council of Canada; WO 03/025020 (=EP 1433793) by the Institute of Antibodies; as well as WO 04/041867, WO 04/041862, WO 04/041865, WO 04/041863, WO 04/062551, WO 05/044858, WO 06/40153, WO 06/079372, WO 06/122786, WO 06/122787 and WO 06/122825, by Ablynx N.V. and the further published patent applications by Ablynx N.V. Reference is also made to the further prior art mentioned in these applications, and in particular to the list of references mentioned on pages 41-43 of the International application WO 06/040153, which list and references are incorporated herein by reference. As described in these references, Nanobodies (in particular VHH sequences and partially humanized Nanobodies) can in particular be characterized by the presence of one or more "Hallmark residues" in one or more of the framework sequences. A further description of the Nanobodies, including humanization and/or camelization of Nanobodies, as well as other modifications, parts or fragments, derivatives or "Nanobody fusions", multivalent constructs (including some non-limiting examples of linker sequences) and different modifications to increase the half-life of the Nanobodies and their preparations may be found e.g. in WO 08/101985 and WO 08/142164. For a further general description of Nanobodies, reference is made to the prior art cited herein, such as e.g. described in WO 08/020079 (page 16).

In particular, the framework sequences present in the ADAMTS5 binders of the invention, such as the ISVDs and/or polypeptides of the invention, may contain one or more of Hallmark residues (for instance as described in WO 08/020079 (Tables A-3 to A-8)), such that the ADAMTS5 binder of the invention is a Nanobody. Some preferred, but non-limiting examples of (suitable combinations of) such framework sequences will become clear from the further disclosure herein (see e.g., Table A-2). Generally, Nanobodies (in particular $V_{HH}$ sequences and partially humanized Nanobodies) can in particular be characterized by the presence of one or more "Hallmark residues" in one or more of the framework sequences (as e.g., further described in WO 08/020079, page 61, line 24 to page 98, line 3).

More in particular, the invention provides ADAMTS5 binders comprising at least one immunoglobulin single variable domain that is an amino acid sequence with the (general) structure

FR1-CDR1-FR2-CDR2-FR3-CDR3-FR4 in which FR1 to FR4 refer to framework regions 1 to 4, respectively, and in which CDR1 to CDR3 refer to the complementarity determining regions 1 to 3, respectively, and which:

i) have at least 80%, more preferably 90%, even more preferably 95% amino acid identity with at least one of the amino acid sequences of SEQ ID NO:s 2, 116, 19, 1, 3, 6, 16, 17, 10, 11, 9, 5, 4, 7, 117, 8, 12, 13, 14, 15 or 18 (see Table A-1), in which for the purposes of determining the degree of amino acid identity, the amino acid residues that form the CDR sequences are disregarded. In this respect, reference is also made to Table A-2, which lists the framework 1 sequences (SEQ ID NOs: 72-84), framework 2 sequences (SEQ ID NOs: 85-94), framework 3 sequences (SEQ ID NOs: 95-113) and framework 4 sequences (SEQ ID NOs: 114-115) of the immunoglobulin single variable domains of SEQ ID NOs: 2, 116, 19, 1, 3, 6, 16, 17, 10, 11, 9, 5, 4, 7, 117, 8, 12, 13, 14, 15 and 18; or ii) combinations of framework sequences as depicted in Table A-2;

and in which:

iii) preferably one or more of the amino acid residues at positions 11, 37, 44, 45, 47, 83, 84, 103, 104 and 108 according to the Kabat numbering are chosen from the Hallmark residues such as mentioned in Table A-3 to Table A-8 of WO 08/020079.

The ADAMTS5 binders of the invention, such as the ISVDs and/or polypeptides of the invention, may also contain the specific mutations/amino acid residues described in the following co-pending US provisional applications, all entitled "Improved immunoglobulin variable domains": U.S. 61/994,552 filed May 16, 2014; U.S. 61/014,015 filed Jun. 18, 2014; U.S. 62/040,167 filed Aug. 21, 2014; and U.S. 62/047,560, filed Sep. 8, 2014 (all assigned to Ablynx N.V.).

In particular, the ADAMTS5 binders of the invention, such as the ISVDs and/or polypeptides of the invention, may suitably contain (i) a K or Q at position 112; or (ii) a K or Q at position 110 in combination with a V at position 11; or (iii) a T at position 89; or (iv) an L on position 89 with a K or Q at position 110; or (v) a V at position 11 and an L at position 89; or any suitable combination of (i) to (v).

As also described in said co-pending US provisional applications, when the ADAMTS5 binder of the invention, such as the ISVD and/or polypeptide of the invention, contain the mutations according to one of (i) to (v) above (or a suitable combination thereof):

the amino acid residue at position 11 is preferably chosen from L, V or K (and is most preferably V); and/or the amino acid residue at position 14 is preferably suitably chosen from A or P; and/or the amino acid residue at position 41 is preferably suitably chosen from A or P; and/or the amino acid residue at position 89 is preferably suitably chosen from T, V or L; and/or the amino acid residue at position 108 is preferably suitably chosen from Q or L; and/or the amino acid residue at position 110 is preferably suitably chosen from T, K or Q; and/or the amino acid residue at position 112 is preferably suitably chosen from S, K or Q.

As mentioned in said co-pending US provisional applications, said mutations are effective in preventing or reducing binding of so-called "pre-existing antibodies" to the immunoglobulins and compounds of the invention. For this purpose, the ADAMTS5 binders of the invention, such as the ISVDs and/or polypeptides of the invention, may also contain (optionally in combination with said mutations) a C-terminal extension (X)n (in which n is 1 to 10, preferably 1 to 5, such as 1, 2, 3, 4 or 5 (and preferably 1 or 2, such as 1); and each X is an (preferably naturally occurring) amino acid residue that is independently chosen, and preferably independently chosen from the group consisting of alanine (A), glycine (G), valine (V), leucine (L) or isoleucine (I)), see e.g. US provisional applications as well as WO 12/175741. In particular, an ADAMTS5 binder of the invention, such as an ISVD and/or polypeptide of the invention, may contain such a C-terminal extension when it forms the C-terminal end of a protein, polypeptide or other compound or construct comprising the same (see e.g. said US provisional applications as well as WO 12/175741).

An ADAMTS5 binder of the invention may be an immunoglobulin, such as an immunoglobulin single variable domain, derived in any suitable manner and from any suitable source, and may for example be naturally occurring $V_{HH}$ sequences (i.e., from a suitable species of Camelid) or synthetic or semi-synthetic amino acid sequences, including but not limited to "humanized" (as defined herein) Nanobodies or VHH sequences, "camelized" (as defined herein) immunoglobulin sequences (and in particular camelized heavy chain variable domain sequences), as well as Nanobodies that have been obtained by techniques such as affinity maturation (for example, starting from synthetic, random or naturally occurring immunoglobulin sequences), CDR grafting, veneering, combining fragments derived from different immunoglobulin sequences, PCR assembly using overlapping primers, and similar techniques for engineering immunoglobulin sequences well known to the skilled person; or any suitable combination of any of the foregoing as further described herein. Also, when an immunoglobulin comprises a $V_{HH}$ sequence, said immunoglobulin may be suitably humanized, as further described herein, so as to provide one or more further (partially or fully) humanized immunoglobulins of the invention. Similarly, when an immunoglobulin comprises a synthetic or semi-synthetic sequence (such as a partially humanized sequence), said immunoglobulin may optionally be further suitably humanized, again as described herein, again so as to provide one or more further (partially or fully) humanized immunoglobulins of the invention.

"Domain antibodies", also known as "Dab"s, "Domain Antibodies", and "dAbs" (the terms "Domain Antibodies" and "dAbs" being used as trademarks by the GlaxoSmithKline group of companies) have been described in e.g., EP 0368684, Ward et al. (Nature 341: 544-546, 1989), Holt et al. (Tends in Biotechnology 21: 484-490, 2003) and WO 03/002609 as well as for example WO 04/068820, WO 06/030220, WO 06/003388 and other published patent applications of Domantis Ltd. Domain antibodies essentially correspond to the VH or VL domains of non-camelid mammalians, in particular human 4-chain antibodies. In order to bind an epitope as a single antigen binding domain, i.e., without being paired with a VL or VH domain, respectively, specific selection for such antigen binding properties is required, e.g. by using libraries of human single VH or VL domain sequences. Domain antibodies have, like VHHs, a molecular weight of approximately 13 to approximately 16 kDa and, if derived from fully human sequences, do not require humanization for e.g. therapeutical use in humans.

It should also be noted that, although less preferred in the context of the present invention because they are not of mammalian origin, single variable domains can be derived from certain species of shark (for example, the so-called "IgNAR domains", see for example WO 05/18629).

The present invention relates particularly to ISVDs, wherein said ISVDs are chosen from the group consisting of VHHs, humanized VHHs and camelized VHs.

The amino acid residues of a VHH domain are numbered according to the general numbering for $V_H$ domains given by Kabat et al. ("Sequence of proteins of immunological interest", US Public Health Services, NIH Bethesda, MD, Publication No. 91), as applied to VHH domains from Camelids, as shown e.g., in FIG. 2 of Riechmann and Muyldermans (J. Immunol. Methods 231: 25-38, 1999), all as known in the art. Alternative methods for numbering the amino acid residues of $V_H$ domains, which methods can also be applied in an analogous manner to VHH domains, are known in the art. However, in the present description, claims and figures, the numbering according to Kabat applied to VHH domains as described above will be followed, unless indicated otherwise.

It should be noted that—as is well known in the art for $V_H$ domains and for VHH domains—the total number of amino acid residues in each of the CDRs may vary and may not correspond to the total number of amino acid residues indicated by the Kabat numbering (that is, one or more positions according to the Kabat numbering may not be occupied in the actual sequence, or the actual sequence may contain more amino acid residues than the number allowed for by the Kabat numbering). This means that, generally, the numbering according to Kabat may or may not correspond to the actual numbering of the amino acid residues in the actual sequence. The total number of amino acid residues in a VH domain and a VHH domain will usually be in the range of from 110 to 120, often between 112 and 115. It should however be noted that smaller and longer sequences may also be suitable for the purposes described herein.

With regard to the CDRs, as is well-known in the art, there are multiple conventions to define and describe the CDRs of a VH or VHH fragment, such as the Kabat definition (which is based on sequence variability and is the most commonly used) and the Chothia definition (which is based on the location of the structural loop regions). Reference is for example made to the website www.bioinf.org.uk/abs/. For the purposes of the present specification and claims the CDRs are most preferably defined on the basis of the Abm definition (which is based on Oxford Molecular's AbM antibody modelling software), as this is considered to be an optimal compromise between the Kabat and Chothia definitions (cf. www.bioinf.org.uk/abs/). As used herein, FR1 comprises the amino acid residues at positions 1-25, CDR1 comprises the amino acid residues at positions 26-35, FR2 comprises the amino acids at positions 36-49, CDR2 comprises the amino acid residues at positions 50-58, FR3 comprises the amino acid residues at positions 59-94, CDR3 comprises the amino acid residues at positions 95-102, and FR4 comprises the amino acid residues at positions 103-113.

In the meaning of the present invention, the term "immunoglobulin single variable domain" or "single variable domain" comprises polypeptides which are derived from a non-human source, preferably a camelid, preferably a camelid heavy chain antibody. They may be humanized, as described herein. Moreover, the term comprises polypeptides derived from non-camelid sources, e.g. mouse or human, which have been "camelized", as described herein.

Hence, ISVDs such as Domain antibodies and Nanobodies (including VHH domains) may be subjected to humanization. In particular, humanized ISVDs, such as Nanobodies (including VHH domains) may be ISVDs that are as generally defined herein, but in which at least one amino acid residue is present (and in particular, in at least one of the framework residues) that is and/or that corresponds to a humanizing substitution (as defined herein). Potentially useful humanizing substitutions may be ascertained by comparing the sequence of the framework regions of a naturally occurring $V_{HH}$ sequence with the corresponding framework sequence of one or more closely related human $V_H$ sequences, after which one or more of the potentially useful humanizing substitutions (or combinations thereof) thus determined may be introduced into said $V_{HH}$ sequence (in any manner known per se, as further described herein) and the resulting humanized $V_{HH}$ sequences may be tested for affinity for the target, for stability, for ease and level of expression, and/or for other desired properties. In this way, by means of a limited degree of trial and error, other suitable humanizing substitutions (or suitable combinations thereof) may be determined by the skilled person based on the disclosure herein. Also, based on the foregoing, (the framework regions of) an ISVD, such as a Nanobody (including VHH domains) may be partially humanized or fully humanized.

Another particularly preferred class of ISVDs of the invention comprises ISVDs with an amino acid sequence that corresponds to the amino acid sequence of a naturally occurring $V_H$ domain, but that has been "camelized", i.e. by replacing one or more amino acid residues in the amino acid sequence of a naturally occurring $V_H$ domain from a conventional 4-chain antibody by one or more of the amino acid residues that occur at the corresponding position(s) in a $V_{HH}$ domain of a heavy chain antibody. This can be performed in a manner known per se, which will be clear to the skilled person, for example on the basis of the description herein. Such "camelizing" substitutions are preferably inserted at amino acid positions that form and/or are present at the $V_H$-$V_L$ interface, and/or at the so-called Camelidae hallmark residues, as defined herein (see also for example WO 94/04678 and Davies and Riechmann (1994 and 1996)). Preferably, the $V_H$ sequence that is used as a starting material or starting point for generating or designing the camelized immunoglobulin single variable domains is preferably a $V_H$ sequence from a mammal, more preferably the $V_H$ sequence of a human being, such as a $V_H3$ sequence. However, it should be noted that such camelized immunoglobulin single variable domains of the invention can be obtained in any suitable manner known per se and thus are not strictly limited to polypeptides that have been obtained using a polypeptide that comprises a naturally occurring $V_H$ domain as a starting material. Reference is made to Davies and Riechmann (FEBS 339: 285-290, 1994; Biotechnol. 13: 475-479, 1995; Prot. Eng. 9: 531-537, 1996) and Riechmann and Muyldermans (J. Immunol. Methods 231: 25-38, 1999)

For example, again as further described herein, both "humanization" and "camelization" can be performed by providing a nucleotide sequence that encodes a naturally occurring $V_{HH}$ domain or $V_H$ domain, respectively, and then changing, in a manner known per se, one or more codons in said nucleotide sequence in such a way that the new nucleotide sequence encodes a "humanized" or "camelized" ISVD of the invention, respectively. This nucleic acid can then be expressed in a manner known per se, so as to provide the desired ISVDs of the invention. Alternatively, based on the amino acid sequence of a naturally occurring $V_{HH}$ domain or $V_H$ domain, respectively, the amino acid sequence of the desired humanized or camelized ISVDs of the invention, respectively, can be designed and then synthesized de novo using techniques for peptide synthesis known per se. Also, based on the amino acid sequence or nucleotide sequence of a naturally occurring $V_{HH}$ domain or $V_H$ domain, respectively, a nucleotide sequence encoding the desired humanized or camelized ISVDs of the invention, respectively, can be designed and then synthesized de novo using techniques for nucleic acid synthesis known per se, after which the nucleic acid thus obtained can be expressed in a manner known per se, so as to provide the desired ISVDs of the invention.

ISVDs such as Domain antibodies and Nanobodies (including VHH domains and humanized VHH domains), can also be subjected to affinity maturation by introducing one or more alterations in the amino acid sequence of one or more CDRs, which alterations result in an improved affinity of the resulting ISVD for its respective antigen, as compared to the respective parent molecule. Affinity-matured ISVD molecules of the invention may be prepared by methods known in the art, for example, as described by Marks et al. (Biotechnology 10:779-783, 1992), Barbas, et al. (Proc. Nat. Acad. Sci, USA 91: 3809-3813, 1994), Shier et al. (Gene 169: 147-155, 1995), Yelton et al. (Immunol. 155: 1994-2004, 1995), Jackson et al. (J. Immunol. 154: 3310-9, 1995), Hawkins et al. (J. Mol. Biol. 226: 889 896, 1992), Johnson and Hawkins (Affinity maturation of antibodies using phage display, Oxford University Press, 1996).

The process of designing/selecting and/or preparing a polypeptide, starting from an ISVD such as an, $V_H$, $V_L$, $V_{HH}$, Domain antibody or a Nanobody, is also referred to herein as "formatting" said ISVD; and an ISVD that is made part of a polypeptide is said to be "formatted" or to be "in the format of" said polypeptide. Examples of ways in which an ISVD may be formatted and examples of such formats will be clear to the skilled person based on the disclosure herein; and such formatted immunoglobulin single variable domain form a further aspect of the invention.

Preferred CDRs are depicted in Table A-2.

In particular, the present invention relates to an ISVD as described herein, wherein said ISVD specifically binding ADAMTS5 essentially consists of 4 framework regions (FR1 to FR4, respectively) and 3 complementarity determining regions (CDR1 to CDR3 respectively), in which
    (i) CDR1 is chosen from the group consisting of SEQ ID NOs: 21, 35, 20, 22, 25, 33, 28, 24, 23, 26, 27, 29, 30, 31, 32 and 34; and
    amino acid sequences that have 1, 2 or 3 amino acid difference(s) with SEQ ID NOs: 21, 35, 20, 22, 25, 33, 33, 28, 24, 23, 26, 27, 29, 30, 31, 32 and 34;
    (ii) CDR2 is chosen from the group consisting of SEQ ID NOs: 37, 53, 36, 40, 50, 51, 44, 45, 43, 39, 38, 41, 119, 42, 46, 47, 48, 49 and 52; and amino acid sequences that have 1, 2 or 3 amino acid difference(s) with SEQ ID NOs: 37, 53, 36, 40, 50, 51, 44, 45, 43, 39, 38, 41, 119, 42, 46, 47, 48, 49 and 52; and (iii) CDR3 is chosen from the group consisting of SEQ ID NO: SEQ ID NOs: 55, 118, 71, 54, 58, 68, 69, 62, 63, 61, 57, 56, 59, 60, 64, 65, 66, 67 and 70; and amino acid sequences that have 1, 2, 3 or 4 amino acid difference(s) with SEQ ID NOs: 55, 118, 71, 54, 58, 68, 69, 62, 63, 61, 57, 56, 59, 60, 64, 65, 66, 67 and 70.

In particular, the present invention relates to an ISVD as described herein, wherein said ISVD specifically binding ADAMTS5 essentially consists of 4 framework regions (FR1 to FR4, respectively) and 3 complementarity determining regions (CDR1 to CDR3 respectively), in which (i) CDR1 is chosen from the group consisting of
  (a) SEQ ID NO: 22; and
  (b) amino acid sequence that has 1, 2, 3, 4, 5 or 6 amino acid difference(s) with SEQ ID NO: 22, wherein
    at position 2 the S has been changed into R;
    at position 3 the A has been changed into T;
    at position 4 the V has been changed into F;
    at position 6 the V has been changed into 5;
    at position 7 the N has been changed into Y; and/or
    at position 10 the A has been changed into G;
(ii) CDR2 is SEQ ID NO: 36; and
(iii) CDR3 is SEQ ID NO: 54.

In particular, the present invention relates to an ISVD as described herein, wherein said ISVD specifically binding ADAMTS5 essentially consists of 4 framework regions (FR1 to FR4, respectively) and 3 complementarity determining regions (CDR1 to CDR3 respectively), in which (i) CDR1 is SEQ ID NO: 33;
(ii) CDR2 is chosen from the group consisting of
  (c) SEQ ID NO: 50; and
  (d) amino acid sequence that has 1, 2, or 3 amino acid difference(s) with SEQ ID NO: 50, wherein
    at position 8 the M has been changed into I;
    at position 9 the P has been changed into T; and/or
    at position 10 the Y has been changed into F; and
(iii) CDR3 is chosen from the group consisting of
  (e) SEQ ID NO: 68; and
  (f) amino acid sequence that has 1 or 2 amino acid difference(s) with SEQ ID NO: 68, wherein
    at position 5 the F has been changed into L; and/or
    at position 11 the D has been changed into E.

In particular, the present invention relates to an ISVD as described herein, wherein said ISVD specifically binding ADAMTS5 essentially consists of 4 framework regions (FR1 to FR4, respectively) and 3 complementarity determining regions (CDR1 to CDR3 respectively), in which (i) CDR1 is SEQ ID NO: 28;
(ii) CDR2 is chosen from the group consisting of
  (c) SEQ ID NO: 44; and
  (d) amino acid sequence that has 1, 2, or 3 amino acid difference(s) with SEQ ID NO: 44, wherein
    at position 3 the S has been changed into T;
    at position 4 the R has been changed into W;
    at position 8 the T has been changed into I; and/or
    at position 9 the T has been changed into L; and
(iii) CDR3 is chosen from the group consisting of
  (e) SEQ ID NO: 62; and
  (f) amino acid sequence that has 1 or 2 amino acid difference(s) with SEQ ID NO: 62, wherein
    at position 1 the G has been changed into 5; and/or
    at position 14 the D has been changed into E.

In particular, the present invention relates to an ISVD as described herein, wherein said ISVD specifically binds ADAMTS5 and essentially consists of 4 framework regions (FR1 to FR4, respectively) and 3 complementarity determining regions (CDR1 to CDR3 respectively), in which CDR1 is chosen from the group consisting of SEQ ID NOs: 21, 35, 20, 22, 25, 33, 28, 24, 23, 26, 27, 29, 30, 31, 32 and 34;

CDR2 is chosen from the group consisting of SEQ ID NOs: 37, 53, 36, 40, 50, 51, 44, 45, 43, 39, 38, 41, 119, 42, 46, 47, 48, 49 and 52; and CDR3 is chosen from the group consisting of SEQ ID NOs: 55, 118, 71, 54, 58, 68, 69, 62, 63, 61, 57, 56, 59, 60, 64, 65, 66, 67 and 70.

In particular, the present invention relates to an ISVD as described herein, wherein said ISVD specifically binds ADAMTS5 and essentially consists of 4 framework regions (FR1 to FR4, respectively) and 3 complementarity determining regions (CDR1 to CDR3 respectively), in which said ISVD is chosen from the group of ISVDs, wherein:

CDR1 is SEQ ID NO: 21, CDR2 is SEQ ID NO: 37 and CDR3 is SEQ ID NO: 55;
CDR1 is SEQ ID NO: 35, CDR2 is SEQ ID NO: 53 and CDR3 is SEQ ID NO: 118;
CDR1 is SEQ ID NO: 35, CDR2 is SEQ ID NO: 53 and CDR3 is SEQ ID NO: 71;
CDR1 is SEQ ID NO: 20, CDR2 is SEQ ID NO: 36 and CDR3 is SEQ ID NO: 54;
CDR1 is SEQ ID NO: 22, CDR2 is SEQ ID NO: 36 and CDR3 is SEQ ID NO: 54;
CDR1 is SEQ ID NO: 25, CDR2 is SEQ ID NO: 40 and CDR3 is SEQ ID NO: 58;
CDR1 is SEQ ID NO: 33, CDR2 is SEQ ID NO: 50 and CDR3 is SEQ ID NO: 68;
CDR1 is SEQ ID NO: 33, CDR2 is SEQ ID NO: 51 and CDR3 is SEQ ID NO: 69;
CDR1 is SEQ ID NO: 28, CDR2 is SEQ ID NO: 44 and CDR3 is SEQ ID NO: 62;
CDR1 is SEQ ID NO: 28, CDR2 is SEQ ID NO: 45 and CDR3 is SEQ ID NO: 63;
CDR1 is SEQ ID NO: 28, CDR2 is SEQ ID NO: 43 and CDR3 is SEQ ID NO: 61;
CDR1 is SEQ ID NO: 24, CDR2 is SEQ ID NO: 39 and CDR3 is SEQ ID NO: 57;
CDR1 is SEQ ID NO: 23, CDR2 is SEQ ID NO: 38 and CDR3 is SEQ ID NO: 56;
CDR1 is SEQ ID NO: 26, CDR2 is SEQ ID NO: 41 and CDR3 is SEQ ID NO: 59;
CDR1 is SEQ ID NO: 27, CDR2 is SEQ ID NO: 119 and CDR3 is SEQ ID NO: 60;
CDR1 is SEQ ID NO: 27, CDR2 is SEQ ID NO: 42 and CDR3 is SEQ ID NO: 60;
CDR1 is SEQ ID NO: 29, CDR2 is SEQ ID NO: 46 and CDR3 is SEQ ID NO: 64;
CDR1 is SEQ ID NO: 30, CDR2 is SEQ ID NO: 47 and CDR3 is SEQ ID NO: 65;
CDR1 is SEQ ID NO: 31, CDR2 is SEQ ID NO: 48 and CDR3 is SEQ ID NO: 66;
CDR1 is SEQ ID NO: 32, CDR2 is SEQ ID NO: 49 and CDR3 is SEQ ID NO: 67; and
CDR1 is SEQ ID NO: 34, CDR2 is SEQ ID NO: 52 and CDR3 is SEQ ID NO: 70.

In a particular preferred aspect, the present invention relates to an ISVD as described herein, wherein said ISVD specifically binds ADAMTS5 and essentially consists of 4 framework regions (FR1 to FR4, respectively) and 3 complementarity determining regions (CDR1 to CDR3 respectively), in which CDR1 is or comprises SEQ ID NO: 21, CDR2 is SEQ ID NO: 37 and CDR3 is SEQ ID NO: 55.

In particular, the present invention relates to an ISVD as described herein, wherein said ISVD specifically binds ADAMTS5 and essentially consists of 4 framework regions (FR1 to FR4, respectively) and 3 complementarity determining regions (CDR1 to CDR3 respectively), in which said ISVD is chosen from the group consisting of SEQ ID NO:s 2, 116, 19, 1, 3, 6, 16, 17, 10, 11, 9, 5, 4, 7, 8, 117, 12, 13, 14, 15 and 18.

It will be appreciated that, without limitation, the immunoglobulin single variable domains of the present invention may be used as a "building block" for the preparation of a polypeptide, which may optionally contain one or more further immunoglobulin single variable domains that can serve as a building block (i.e., against the same or another epitope on ADAMTS5 and/or against one or more other antigens, proteins or targets than ADAMTS5).

The polypeptide of the invention (also indicated herein as "Nanobody construct") comprises at least one ISVD binding an ADAMTS, preferably ADAMTS5, such as two ISVDs binding ADAMTS5, and preferably also an ISVD binding Albumin. In a polypeptide of the invention, the ISVDs may be directly linked or linked via a linker. Even more preferably, the polypeptide of the invention comprises a C-terminal extension. As will be detailed herein, the C-terminal extension essentially prevents/removes binding of pre-existing antibodies/factors in most samples of human subjects/patients. The C-terminal extension is present C-terminally of the last amino acid residue (usually a serine residue) of the last (most C-terminally located) ISVD.

As further elaborated infra, the ISVDs may be derived from a $V_{HH}$, $V_H$ or a $V_L$ domain, however, the ISVDs are chosen such that they do not form complementary pairs of $V_H$ and $V_L$ domains in the polypeptides of the invention. The Nanobody, $V_{HH}$, and humanized $V_{HH}$ are unusual in that they are derived from natural camelid antibodies which have no light chains, and indeed these domains are unable to associate with camelid light chains to form complementary $V_{HH}$ and $V_L$ pairs. Thus, the polypeptides of the present invention do not comprise complementary ISVDs and/or form complementary ISVD pairs, such as, for instance, complementary $V_H/V_L$ pairs.

Generally, polypeptides or constructs that comprise or essentially consist of a single building block, single ISVD or single Nanobody will be referred to herein as "monovalent" polypeptides and "monovalent constructs", respectively. Polypeptides or constructs that comprise two or more building blocks (such as e.g., ISVDs) will also be referred to herein as "multivalent" polypeptides or constructs, and the building blocks/ISVDs present in such polypeptides or constructs will also be referred to herein as being in a "multivalent format". For example, a "bivalent" polypeptide may comprise two ISVDs, optionally linked via a linker sequence, whereas a "trivalent" polypeptide may comprise three ISVDs, optionally linked via two linker sequences; whereas a "tetravalent" polypeptide may comprise four ISVDs, optionally linked via three linker sequences, etc.

In a multivalent polypeptide, the two or more ISVDs may be the same or different, and may be directed against the same antigen or antigenic determinant (for example against the same part(s) or epitope(s) or against different parts or epitopes) or may alternatively be directed against different antigens or antigenic determinants; or any suitable combination thereof. Polypeptides and constructs that contain at least two building blocks (such as e.g., ISVDs) in which at least one building block is directed against a first antigen (i.e., ADAMTS5) and at least one building block is directed against a second antigen (i.e., different from ADAMTS5) will also be referred to as "multispecific" polypeptides and constructs, and the building blocks (such as e.g., ISVDs) present in such polypeptides and constructs will also be referred to herein as being in a "multispecific format". Thus, for example, a "bispecific" polypeptide of the invention is a polypeptide that comprises at least one ISVD directed against a first antigen (i.e., ADAMTS5) and at least one further ISVD directed against a second antigen (i.e., different from ADAMTS5), whereas a "trispecific" polypeptide of the invention is a polypeptide that comprises at least one ISVD directed against a first antigen (i.e., ADAMTS5), at least one further ISVD directed against a second antigen (i.e., different from ADAMTS5) and at least one further ISVD directed against a third antigen (i.e., different from both ADAMTS5 and the second antigen); etc.

In an aspect, the present invention relates to a polypeptide, comprising at least 2 ISVDs, wherein at least 1 ISVD specifically binds ADAMTS, preferably ADAMTS5, more preferably chosen from the group consisting of SEQ ID NO:s 2, 116, 19, 1, 3, 6, 16, 17, 10, 11, 9, 5, 4, 7, 117, 8, 12, 13, 14, 15 and 18.

In an aspect, the present invention relates to a polypeptide comprising at least 2 ISVDs, wherein said at least 2 ISVDs specifically bind ADAMTS, preferably ADAMTS5, more preferably each ISVD of said 2 ISVDs is chosen independently from the group consisting of SEQ ID NO:s 2, 116, 19, 1, 3, 6, 16, 17, 10, 11, 9, 5, 4, 7, 117, 8, 12, 13, 14, 15 and 18.

"Multiparatopic" polypeptides and "multiparatopic" constructs, such as e.g., "biparatopic" polypeptides or constructs and "triparatopic" polypeptides or constructs, comprise or essentially consist of two or more building blocks that each have a different paratope.

Accordingly, the ISVDs of the invention that bind ADAMTS5 can be in essentially isolated form (as defined herein), or they may form part of a construct or polypeptide, which may comprise or essentially consist of one or more ISVD(s) that bind ADAMTS5 and which may optionally further comprise one or more further amino acid sequences (all optionally linked via one or more suitable linkers). The present invention relates to a polypeptide or construct that comprises or essentially consists of at least one ISVD according to the invention, such as one or more ISVDs of the invention (or suitable fragments thereof), binding ADAMTS5.

The one or more ISVDs of the invention can be used as a building block in such a polypeptide or construct, so as to provide a monovalent, multivalent or multiparatopic polypeptide or construct of the invention, respectively, all as described herein. The present invention thus also relates to a polypeptide which is a monovalent construct comprising or essentially consisting of one monovalent polypeptide or ISVD of the invention.

The present invention thus also relates to a polypeptide or construct which is a multivalent polypeptide or multivalent construct, respectively, such as e.g., a bivalent or trivalent polypeptide or construct comprising or essentially consisting of two or more ISVDs of the invention (for multivalent and multispecific polypeptides containing one or more VHH domains and their preparation, reference is also made to Conrath et al. (J. Biol. Chem. 276: 7346-7350, 2001), as well as to for example WO 96/34103, WO 99/23221 and WO 2010/115998).

In an aspect, in its simplest form, the multivalent polypeptide or construct of the invention is a bivalent polypeptide or construct of the invention comprising a first ISVD, such as a Nanobody, directed against ADAMTS5, and an identical second ISVD, such as a Nanobody, directed against ADAMTS5, wherein said first and said second ISVDs, such as Nanobodies, may optionally be linked via a linker sequence (as defined herein). In another form, a multivalent polypeptide or construct of the invention may be a trivalent polypeptide or construct of the invention, comprising a first ISVD, such as Nanobody, directed against ADAMTS5, an identical second ISVD, such as Nanobody, directed against ADAMTS5 and an identical third ISVD, such as a Nanobody, directed against ADAMTS5, in which said first, second and third ISVDs, such as Nanobodies, may optionally be linked via one or more, and in particular two, linker sequences. In an aspect, the invention relates to a polypeptide or construct that comprises or essentially consists of at least two ISVDs according to the invention, such as 2, 3 or 4 ISVDs (or suitable fragments thereof), binding ADAMTS5. The two or more ISVDs may optionally be linked via one or more peptidic linkers.

In another aspect, the multivalent polypeptide or construct of the invention may be a bispecific polypeptide or construct of the invention, comprising a first ISVD, such as a Nanobody, directed against ADAMTS5, and a second ISVD, such as a Nanobody, directed against a second antigen, such as, for instance, Aggrecan, in which said first and second ISVDs, such as Nanobodies, may optionally be linked via a linker sequence (as defined herein); whereas a multivalent polypeptide or construct of the invention may also be a trispecific polypeptide or construct of the invention, comprising a first ISVD, such as a Nanobody, directed against ADAMTS5, a second ISVD, such as a Nanobody, directed against a second antigen, such as for instance Aggrecan, and a third ISVD, such as a Nanobody, directed against a third antigen, in which said first, second and third ISVDs, such as Nanobodies, may optionally be linked via one or more, and in particular two, linker sequences.

The invention further relates to a multivalent polypeptide that comprises or (essentially) consists of at least one ISVD (or suitable fragments thereof) binding ADAMTS5, preferably human ADAMTS5, and one additional ISVD, such as an ISVD binding Aggrecan.

Particularly preferred bivalent, bispecific polypeptides or constructs in accordance with the invention are those shown in the Examples described herein and in Table A-1 (cf. SEQ ID NO:s 120-130 (i.e. SEQ ID NO: 120, 121, 122, 123, 124, 125, 126, 127, 128, 129 and 130), most preferably SEQ ID NO:s 129 and 130).

In a preferred aspect, the polypeptide or construct of the invention comprises or essentially consists of at least two ISVDs, wherein said at least two ISVDs can be the same or different, but of which at least one ISVD is directed against ADAMTS5, preferably said ISVD binding ADAMTS5 is chosen from the group consisting of SEQ ID NO:s 2, 116, 19, 1, 3, 6, 16, 17, 10, 11, 9, 5, 4, 7, 117, 8, 12, 13, 14, 15 and 18.

The two or more ISVDs present in the multivalent polypeptide or construct of the invention may consist of a light chain variable domain sequence (e.g., a $V_L$-sequence) or of a heavy chain variable domain sequence (e.g., a $V_H$-sequence); they may consist of a heavy chain variable domain sequence that is derived from a conventional four-chain antibody or of a heavy chain variable domain sequence that is derived from heavy chain antibody. In a preferred aspect, they consist of a Domain antibody (or an amino acid that is suitable for use as a domain antibody), of a single domain antibody (or an amino acid that is suitable for use as a single domain antibody), of a "dAb" (or an amino acid that is suitable for use as a dAb), of a Nanobody® (including but not limited to $V_{HH}$), of a humanized $V_{HH}$ sequence, of a camelized $V_H$ sequence; or of a $V_{HH}$ sequence that has been obtained by affinity maturation. The two or more immunoglobulin single variable domains may consist of a partially or fully humanized Nanobody or a partially or fully humanized VHH.

In an aspect of the invention, the first ISVD and the second ISVD present in the multiparatopic (preferably biparatopic or triparatopic) polypeptide or construct of the invention do not (cross)-compete with each other for binding to ADAMTS5 and, as such, belong to different families. Accordingly, the present invention relates to a multiparatopic (preferably biparatopic) polypeptide or construct comprising two or more ISVDs wherein each ISVD belongs to a different family. In an aspect, the first ISVD of this multiparatopic (preferably biparatopic) polypeptide or construct of the invention does not cross-block the binding to ADAMTS5 of the second ISVD of this multiparatopic (preferably biparatopic) polypeptide or construct of the invention and/or the first ISVD is not cross-blocked from binding to ADAMTS5 by the second ISVD. In another aspect, the first ISVD of a multiparatopic (preferably biparatopic) polypeptide or construct of the invention cross-blocks the binding to ADAMTS5 of the second ISVD of this multiparatopic (preferably biparatopic) polypeptide or construct of the invention and/or the first ISVD is cross-blocked from binding to ADAMTS5 by the second ISVD.

In a particularly preferred aspect, the polypeptide or construct of the invention comprises or essentially consists of three or more ISVDs, of which at least two ISVDs are directed against ADAMTS5. It will be appreciated that said at least two ISVDs directed against ADAMTS5 can be the same or different, can be directed against the same epitope or different epitopes of ADAMTS5, can belong to the same epitope bin or to different epitope bins, and/or can bind to the same or different domains of ADAMTS5.

The relative affinities may depend on the location of the ISVDs in the polypeptide. It will be appreciated that the order of the ISVDs in a polypeptide of the invention (orientation) may be chosen according to the needs of the person skilled in the art. The order of the individual ISVDs as well as whether the polypeptide comprises a linker is a matter of design choice. Some orientations, with or without linkers, may provide preferred binding characteristics in comparison to other orientations. For instance, the order of a first ISVD (e.g. ISVD 1) and a second ISVD (e.g. ISVD 2) in the polypeptide of the invention may be (from N-terminus to C-terminus): (i) ISVD 1 (e.g. Nanobody 1)-[linker]-ISVD 2 (e.g. Nanobody 2)-[C-terminal extension]; or (ii) ISVD 2 (e.g. Nanobody 2)-[linker]-ISVD 1 (e.g. Nanobody 1)-[C-terminal extension]; (wherein the moieties between the square brackets, i.e. linker and C-terminal extension, are optional). All orientations are encompassed by the invention. Polypeptides that contain an orientation of ISVDs that provides desired binding characteristics may be easily identified by routine screening, for instance as exemplified in the examples section. A preferred order is from N-terminus to C-terminus: ISVD binding ADAMTS5-[linker]-ISVD binding Albumin or Aggrecan-[C-terminal extension], wherein the moieties between the square brackets are optional.

In an aspect, the present invention relates to a polypeptide comprising two or more ISVDs which specifically bind ADAMTS5, wherein a) at least a "first" ISVD specifically binds a first antigenic determinant, epitope, part, domain, subunit or conformation of ADAMTS5, preferably said "first" ISVD specifically binding ADAMTS5 is chosen from the group consisting of SEQ ID NO:s 2, 1, 3, 6, 16, 17, 10, 11, 9, 5, 4, 7, 8, 117, 12, 13, 14, 15 and 18; and
b) at least a "second" ISVD specifically binds a second antigenic determinant, epitope, part, domain, subunit or conformation of ADAMTS5, different from the first antigenic determinant epitope, part, domain, subunit or conformation, respectively, preferably said "second" ISVD specifically binding ADAMTS5 is SEQ ID NO: 116 or 19.

In a preferred aspect, the polypeptide or construct of the invention comprises or essentially consists of at least two ISVDs binding ADAMTS5, wherein said at least two ISVDs can be the same or different, which are independently chosen from the group consisting of SEQ ID NO:s 2, 116, 19, 1, 3, 6, 16, 17, 10, 11, 9, 5, 4, 7, 117, 8, 12, 13, 14, 15 and 18.

In a further aspect, the invention relates to a multi-paratopic (preferably biparatopic) polypeptide or construct comprising two or more ISVDs directed against ADAMTS5 that bind the same epitope(s) as is bound by any one of SEQ ID NO:s 2, 116, 19, 1, 3, 6, 16, 17, 10, 11, 9, 5, 4, 7, 117, 8, 12, 13, 14, 15 and 18.

In a further aspect, the invention relates to a polypeptide as described herein, wherein said polypeptide has at least 80%, 90%, 95% or 100% sequence identity with any of SEQ ID NO:s 1-19 (i.e. SEQ ID NO: 1, 2, 3, 4, 5, 6, 7, 8, 9, 10, 11, 12, 13, 14, 15, 16, 17, 18 and 19), 116-117 or 120-130 (i.e. SEQ ID NOs: 120, 121, 122, 123, 124, 125, 126, 127, 128, 129 and 130).

In an aspect, the present invention relates to a polypeptide as described herein, which is chosen from the group consisting of SEQ ID NO: 127 (clone 130 049-093-Alb), SEQ ID NO: 126 (clone 129 2F3-093-Alb), SEQ ID NO: 127 (clone 130 049-093-Alb) and SEQ ID NO: 128 (clone 131 9D3-093-Alb).

The art is in need of more effective therapies for disorders affecting cartilage in joints, such as osteoarthritis. Especially when administered systematically, the residence time of most drugs is insufficient. The present inventors hypothesized that the efficacy of a therapeutic drug, such as a construct, polypeptide and ISVD of the invention, could be increased significantly by coupling the therapeutic drug to a moiety which extends the half-life of the drug and consequently increase retention of the drug, but which should not disrupt the efficacy of said therapeutic drug.

In a specific aspect of the invention, a construct or polypeptide of the invention may have a moiety conferring an increased half-life, compared to the corresponding construct or polypeptide of the invention without said moiety. Some preferred, but non-limiting examples of such constructs and polypeptides of the invention will become clear to the skilled person based on the further disclosure herein, and for example comprise ISVDs or polypeptides of the invention that have been chemically modified to increase the half-life thereof (for example, by means of pegylation); ADAMTS5 binders of the invention, such as ISVDs and/or polypeptides of the invention that comprise at least one additional binding site for binding to a serum protein (such as serum albumin); or polypeptides of the invention which comprise at least one ISVD of the invention that is linked to at least one moiety (and in particular at least one amino acid sequence) which increases the half-life of the amino acid sequence of the invention. Examples of constructs of the invention, such as polypeptides of the invention, which comprise such half-life extending moieties or ISVDs will become clear to the skilled person based on the further disclosure herein; and for example include, without limitation, polypeptides in which the one or more ISVDs of the invention are suitably linked to one or more serum proteins or fragments thereof (such as (human) serum albumin or suitable fragments thereof) or to one or more binding units that can bind to serum proteins (such as, for example, domain antibodies, immunoglobulin single variable domains that are suitable for use as a domain antibody, single domain antibodies, immunoglobulin single variable domains that are suitable for use as a single domain antibody, dAbs, immunoglobulin single variable domains that are suitable for use as a dAb, or Nanobodies that can bind to serum proteins such as serum albumin (such as human serum albumin), serum immunoglobulins such as IgG, or transferrin; reference is made to the further description and references mentioned herein); polypeptides in which an amino acid sequence of the invention is linked to an Fc portion (such as a human Fc) or a suitable part or fragment thereof; or polypeptides in which the one or more immunoglobulin single variable domains of the invention are suitable linked to one or more small proteins or peptides that can bind to serum proteins, such as, without limitation, the proteins and peptides described in WO 91/01743, WO 01/45746, WO 02/076489, WO2008/068280, WO2009/127691 and PCT/EP2011/051559.

In an aspect the present invention provides a construct of the invention or a polypeptide, wherein said construct or said polypeptide further comprises a serum protein binding moiety or a serum protein. Preferably, said serum protein binding moiety binds serum albumin, such as human serum albumin.

In an aspect, the present invention relates to a polypeptide as described herein, comprising an ISVD binding serum albumin.

Generally, the constructs or polypeptides of the invention with increased half-life preferably have a half-life that is at least 1.5 times, preferably at least 2 times, such as at least 5 times, for example at least 10 times or more than 20 times, greater than the half-life of the corresponding constructs or polypeptides of the invention per se, i.e. without the moiety conferring the increased half-life. For example, the constructs or polypeptides of the invention with increased half-life may have a half-life e.g., in humans that is increased with more than 1 hours, preferably more than 2 hours, more preferably more than 6 hours, such as more than 12 hours, or even more than 24, 48 or 72 hours, compared to the corresponding constructs or polypeptides of the invention per se, i.e. without the moiety conferring the increased half-life.

In a preferred, but non-limiting aspect of the invention, the constructs of the invention and polypeptides of the invention, have a serum half-life e.g. in humans that is increased with more than 1 hours, preferably more than 2 hours, more preferably more than 6 hours, such as more than 12 hours, or even more than 24, 48 or 72 hours, compared to the corresponding constructs or polypeptides of the invention per se, i.e. without the moiety conferring the increased half-life.

In another preferred, but non-limiting aspect of the invention, such constructs of the invention, such as polypeptides of the invention, exhibit a serum half-life in human of at least about 12 hours, preferably at least 24 hours, more preferably at least 48 hours, even more preferably at least 72 hours or more. For example, constructs or polypeptides of the invention may have a half-life of at least 5 days (such as about 5 to 10 days), preferably at least 9 days (such as about 9 to 14 days), more preferably at least about 10 days (such as about 10 to 15 days), or at least about 11 days (such as about 11 to 16 days), more preferably at least about 12 days (such as about 12 to 18 days or more), or more than 14 days (such as about 14 to 19 days).

In a particularly preferred but non-limiting aspect of the invention, the invention provides a construct of the invention and a polypeptide of the invention, comprising besides the one or more building blocks binding ADAMTS5 at least one building block binding serum albumin, such as an ISVD binding serum albumin, such as human serum albumin as described herein. Preferably, said ISVD binding serum albumin comprises or essentially consists of 4 framework regions (FR1 to FR4, respectively) and 3 complementarity determining regions (CDR1 to CDR3 respectively), in which CDR1 is SFGMS (SEQ ID NO: 146), CDR2 is SISGSGSDTLYADSVKG (SEQ ID NO: 147) and CDR3 is GGSLSR (SEQ ID NO: 148). Preferably, said ISVD binding human serum albumin is chosen from the group consisting of Alb8, Alb23, Alb129, Alb132, Alb11, Alb11 (S112K)-A, Alb82, Alb82-A, Alb82-AA, Alb82-AAA, Alb82-G, Alb82-GG, Alb82-GGG, Alb92 or Alb223 (cf. Table D).

In an aspect, the present invention relates to a polypeptide as described herein, comprising at least one ISVD binding ADAMTS5 and an ISVD binding serum albumin, preferably chosen from the group consisting of SEQ ID NO: 129 (clone 577 2F3*-Alb), SEQ ID NO: 130 (clone 579 2F3*-093-Alb), SEQ ID NO: 120 (clone 4 2A12-Alb), SEQ ID NO: 121 (clone 5 2D7-Alb), SEQ ID NO: 122 (clone 6 2F3-Alb), SEQ ID NO: 123 (clone 69 049-Alb), SEQ ID NO: 124 (clone 70 9D3-Alb), SEQ ID NO: 125 (clone 71 3B2-Alb), SEQ ID NO: 126 (clone 129 2F3-093-Alb), SEQ ID NO: 127 (clone 130 049-093-Alb), and SEQ ID NO: 128 (clone 131 9D3-093-Alb)(cf. Table A-1).

In an embodiment, the present invention relates to construct of the invention, such as a polypeptide comprising a serum protein binding moiety, wherein said serum protein binding moiety is a non-antibody based polypeptide.

The art is in need of more effective therapies for disorders affecting cartilage in joints, such as osteoarthritis. Even when administered intra-articularly, the residence time of most drugs for treating affected cartilage is insufficient. The present inventors hypothesized that the efficacy of a therapeutic drug, such as a construct, polypeptide and ISVD of the invention, may be modulated by coupling the therapeutic drug to a moiety which would "anchor" the drug in the joint and consequently increase retention of the drug, but which should not disrupt the efficacy of said therapeutic drug (this moiety is herein also indicated as "cartilage anchoring protein" or "CAP"). This anchoring concept could not only modulate the efficacy of a drug, but also the operational specificity for a diseased joint by decreasing toxicity and side-effects, thus widening the number of possible useful drugs.

It was anticipated that a format of a molecule for clinical use comprises one or two building blocks, such as ISVDs, binding ADAMTS5 and one or more building blocks, e.g. ISVDs, with such a retention mode of action, and possibly further moieties. In the co-pending application it is demonstrated that such formats retain both ADAMTS5 binding and a therapeutic effect, e.g. inhibitory activity, as well as retention properties. The one or more building blocks, such as ISVDs, with a retention mode of action can be any building block having a retention effect ("CAP building block") in diseases in which ADAMTS5 is involved, such as arthritic disease, osteoarthritis, spondyloepimetaphyseal dysplasia, lumbar disk degeneration disease, Degenerative joint disease, rheumatoid arthritis, osteochondritis dissecans, aggrecanopathies.

A "CAP building block" is used for directing, anchoring and/or retaining other, e.g. therapeutic, building blocks, such as ISVDs binding ADAMTS5 at a desired site, such as e.g. in a joint, in which said other, e.g. therapeutic, building block is to exert its effect, e.g. binding and/or inhibiting ADAMTS5.

The present inventors further hypothesized that Aggrecan binders, such as ISVD(s) binding Aggrecan might potentially function as such an anchor, although Aggrecan is heavily glycosylated and degraded in various disorders affecting cartilage in joints. Moreover, in view of the costs and extensive testing in various animal models required before a drug can enter the clinic, such Aggrecan binders should preferentially have a broad cross-reactivity, e.g. the Aggrecan binders should bind to Aggrecan of various species.

Using various ingenious immunization, screening and characterization methods, the present inventors were able to identify various Aggrecan binders with superior selectivity, stability and specificity features, which enabled prolonged retention and activity in the joint (cf. co-pending application).

In an aspect, the present invention relates to a method for reducing and/or inhibiting the efflux of a composition, a polypeptide or a construct from a joint, wherein said method comprises administering a pharmaceutically active amount of at least one polypeptide according to the invention, a construct according to the invention, or a composition according to the invention to a person in need thereof.

In the present invention the term "reducing and/or inhibiting the efflux" means reducing and/or inhibiting the outward flow of the composition, polypeptide or construct from within a joint to the outside. Preferably, the efflux is reduced and/or inhibited by at least 10% such as at least 20%, 30%, 40% or 50% or even more such as at least 60%, 70%, 80%, 90% or even 100%, compared to the efflux of the aforementioned composition, polypeptide or construct in a joint under the same conditions but without the presence of the Aggrecan binder of the invention, e.g. ISVD(s) binding Aggrecan.

Next to the diseases in which ADAMTS5 is involved, such as arthritic disease, osteoarthritis, spondyloepimetaphyseal dysplasia, lumbar disk degeneration disease, Degenerative joint disease, rheumatoid arthritis, osteochondritis dissecans and aggrecanopathies it is anticipated that the Aggrecan binders of the invention can also be used in various other diseases affecting cartilage, such as arthropathies and chondrodystrophies, arthritic disease (such as osteoarthritis, rheumatoid arthritis, gouty arthritis, psoriatic arthritis, traumatic rupture or detachment), achondroplasia, costochondritis, Spondyloepimetaphyseal dysplasia, spinal disc herniation, lumbar disk degeneration disease, degenerative joint disease, and relapsing polychondritis (commonly indicated herein as "Aggrecan associated diseases").

Said CAP building block, e.g. ISVD(s) binding Aggrecan, preferably binds to cartilaginous tissue such as cartilage and/or meniscus. In a preferred aspect, the CAP building block is cross-reactive for other species and specifically binds one or more of human Aggrecan (SEQ ID NO: 155), dog Aggrecan, bovine Aggrecan, rat Aggrecan; pig Aggrecan; mouse Aggrecan, rabbit Aggrecan; cynomolgus Aggrecan and/or rhesus Aggrecan. Relevant structural information for Aggrecan may be found, for example, at (UniProt) Accession Numbers as depicted in the Table 2 below.

A preferred CAP building block is an ISVD binding Aggrecan, preferably human Aggrecan, preferably represented by SEQ ID NO: 155 as depicted in Table B.

TABLE 2

| name | accession number |
|---|---|
| human Aggrecan (SEQ ID NO: 155) | P16112 |
| dog Aggrecan | Q28343 |
| bovine Aggrecan | P13608 |
| rat Aggrecan | P07897 |
| pig Aggrecan (core) | Q29011 |
| mouse Aggrecan | Q61282 |
| rabbit Aggrecan | G1U677-1 |
| cynomolgus Aggrecan | XP_002804990.1 |
| rhesus Aggrecan | XP_002804990.1 |

The present invention thus pertains to a polypeptide or construct according to the invention, further comprising at least one CAP building block.

The present invention thus pertains to a polypeptide or construct according to the invention, further comprising at least one ISVD specifically binding Aggrecan, preferably chosen from the ISVDs represented by SEQ ID NO:s 156 and 157.

In an aspect the present invention relates to a polypeptide as described herein, comprising at least 2 ISVDs specifically binding Aggrecan.

In an aspect the present invention relates to a polypeptide as described herein, comprising at least 2 ISVDs specifically binding Aggrecan, wherein said at least 2 ISVDs specifically binding Aggrecan can be the same or different.

In an aspect the present invention relates to a polypeptide as described herein, comprising at least 2 ISVDs specifically binding Aggrecan, wherein said at least 2 ISVDs specifically binding Aggrecan are independently chosen from the group consisting of SEQ ID NOs: 156-157.

In an aspect the present invention relates to a polypeptide as described herein, comprising at least 2 ISVDs specifically binding Aggrecan, wherein said at least 2 ISVDs specifically binding Aggrecan are represented by SEQ ID NO:s 156-157.

In an aspect the present invention relates to a polypeptide as described herein, comprising an ISVD specifically binding Aggrecan, wherein said ISVD specifically binding Aggrecan, specifically binds to human Aggrecan [SEQ ID NO: 155].

In an aspect the present invention relates to a polypeptide as described herein, wherein said ISVD specifically binding Aggrecan, specifically binds human Aggrecan (SEQ ID NO: 155), dog Aggrecan, bovine Aggrecan, rat Aggrecan; pig Aggrecan; mouse Aggrecan, rabbit Aggrecan; cynomolgus Aggrecan and/or rhesus Aggrecan.

In an aspect the present invention relates to a polypeptide as described herein, wherein said ISVD specifically binding Aggrecan preferably binds to cartilaginous tissue such as cartilage and/or meniscus.

It will be appreciated that the ISVD, polypeptide and construct of the invention is preferably stable. The stability of a polypeptide, construct or ISVD of the invention can be measured by routine assays known to the person skilled in the art. Typical assays include (without being limiting) assays in which the activity of said polypeptide, construct or ISVD is determined, followed by incubating in Synovial Fluid for a desired period of time, after which the activity is determined again.

In an aspect the present invention relates to an ISVD, polypeptide or construct of the invention having a stability of at least 7 days, such as at least 14 days, 21 days, 1 month, 2 months or even 3 months in synovial fluid (SF) at 37° C.

The desired activity of the therapeutic building block, e.g. ISVD binding ADAMTS5 in the multivalent polypeptide or construct of the invention can be measured by routine assays known to the person skilled in the art.

In an aspect, the present invention relates to a construct as described herein comprising at least one ISVD or polypeptide and one or more other groups, residues, moieties or binding units. The one or more other groups, residues, moieties or binding units are preferably chosen from the group consisting of a polyethylene glycol molecule, serum proteins or fragments thereof, binding units that can bind to serum proteins, an Fc portion, and small proteins or peptides that can bind to serum proteins, further amino acid residues, tags or other functional moieties, e.g., toxins, labels, radiochemicals, etc.

In an embodiment, as mentioned infra, the present invention relates to a construct of the invention, such as a polypeptide comprising a moiety conferring half-life extension, wherein said moiety is a PEG. Hence, the present invention relates also to a construct or polypeptide of the invention comprising PEG.

The further amino acid residues may or may not change, alter or otherwise influence other (biological) properties of the polypeptide of the invention and may or may not add further functionality to the polypeptide of the invention. For example, such amino acid residues:

a) can comprise an N-terminal Met residue, for example as result of expression in a heterologous host cell or host organism.

b) may form a signal sequence or leader sequence that directs secretion of the polypeptide from a host cell upon synthesis (for example to provide a pre-, pro- or prepro-form of the polypeptide of the invention, depending on the host cell used to express the polypeptide of the invention). Suitable secretory leader peptides will be clear to the skilled person, and may be as further described herein. Usually, such a leader sequence will be linked to the N-terminus of the polypeptide, although the invention in its broadest sense is not limited thereto;

c) may form a "tag", for example an amino acid sequence or residue that allows or facilitates the purification of the polypeptide, for example using affinity techniques directed against said sequence or residue. Thereafter, said sequence or residue may be removed (e.g. by chemical or enzymatical cleavage) to provide the polypeptide (for this purpose, the tag may optionally be linked to the amino acid sequence or polypeptide sequence via a cleavable linker sequence or contain a cleavable motif). Some preferred, but non-limiting examples of such residues are multiple histidine residues, glutathione residues and a myc-tag such as AAAEQKLISEEDLNGAA (SEQ ID NO: 182);

d) may be one or more amino acid residues that have been functionalized and/or that can serve as a site for attachment of functional groups. Suitable amino acid residues and functional groups will be clear to the skilled person and include, but are not limited to, the amino acid residues and functional groups mentioned herein for the derivatives of the polypeptides of the invention.

Also encompassed in the present invention are constructs comprising a polypeptide and/or ISVD of the invention, which further comprise other functional moieties, e.g., toxins, labels, radiochemicals, etc.

The other groups, residues, moieties or binding units may for example be chemical groups, residues, moieties, which may or may not by themselves be biologically and/or pharmacologically active. For example, and without limitation, such groups may be linked to the one or more ISVDs or polypeptides of the invention so as to provide a "derivative" of the polypeptide or construct of the invention.

Accordingly, the invention in its broadest sense also comprises constructs and/or polypeptides that are derivatives of the constructs and/or polypeptides of the invention. Such derivatives can generally be obtained by modification, and in particular by chemical and/or biological (e.g., enzymatic) modification, of the constructs and/or polypeptides of the invention and/or of one or more of the amino acid residues that form a polypeptide of the invention.

Examples of such modifications, as well as examples of amino acid residues within the polypeptide sequences that can be modified in such a manner (i.e. either on the protein backbone but preferably on a side chain), methods and techniques that can be used to introduce such modifications and the potential uses and advantages of such modifications will be clear to the skilled person (see also Zangi et al., Nat Biotechnol 31(10):898-907, 2013).

For example, such a modification may involve the introduction (e.g., by covalent linking or in any other suitable manner) of one or more (functional) groups, residues or moieties into or onto the polypeptide of the invention, and in particular of one or more functional groups, residues or moieties that confer one or more desired properties or functionalities to the construct and/or polypeptide of the invention. Examples of such functional groups will be clear to the skilled person.

For example, such modification may comprise the introduction (e.g., by covalent binding or in any other suitable manner) of one or more functional moieties that increase the half-life, the solubility and/or the absorption of the construct or polypeptide of the invention, that reduce the immunogenicity and/or the toxicity of the construct or polypeptide of the invention, that eliminate or attenuate any undesirable side effects of the construct or polypeptide of the invention, and/or that confer other advantageous properties to and/or reduce the undesired properties of the construct or polypeptide of the invention; or any combination of two or more of the foregoing. Examples of such functional moieties and of techniques for introducing them will be clear to the skilled person, and can generally comprise all functional moieties and techniques mentioned in the general background art cited hereinabove as well as the functional moieties and techniques known per se for the modification of pharmaceutical proteins, and in particular for the modification of antibodies or antibody fragments (including ScFv's and single domain antibodies), for which reference is for example made to Remington (Pharmaceutical Sciences, 16th ed., Mack Publishing Co., Easton, PA, 1980). Such functional moieties may for example be linked directly (for example covalently) to a polypeptide of the invention, or optionally via a suitable linker or spacer, as will again be clear to the skilled person.

One specific example is a derivative polypeptide or construct of the invention wherein the polypeptide or construct of the invention has been chemically modified to increase the half-life thereof (for example, by means of pegylation). This is one of the most widely used techniques for increasing the half-life and/or reducing the immunogenicity of pharmaceutical proteins and comprises attachment of a suitable pharmacologically acceptable polymer, such as poly(ethyleneglycol) (PEG) or derivatives thereof (such as methoxypoly(ethyleneglycol) or mPEG). Generally, any suitable form of pegylation can be used, such as the pegylation used in the art for antibodies and antibody fragments (including but not limited to (single) domain antibodies and ScFv's); reference is made to, for example, Chapman (Nat. Biotechnol. 54: 531-545, 2002), Veronese and Harris (Adv. Drug Deliv. Rev. 54: 453-456, 2003), Harris and Chess (Nat. Rev. Drug. Discov. 2: 214-221, 2003) and WO 04/060965. Various reagents for pegylation of proteins are also commercially available, for example from Nektar Therapeutics, USA.

Preferably, site-directed pegylation is used, in particular via a cysteine-residue (see for example Yang et al. (Protein Engineering 16: 761-770, 2003). For example, for this purpose, PEG may be attached to a cysteine residue that naturally occurs in a polypeptide of the invention, a construct or polypeptide of the invention may be modified so as to suitably introduce one or more cysteine residues for attachment of PEG, or an amino acid sequence comprising one or more cysteine residues for attachment of PEG may be fused to the N- and/or C-terminus of a construct or polypeptide of the invention, all using techniques of protein engineering known per se to the skilled person.

Preferably, for the constructs or polypeptides of the invention, a PEG is used with a molecular weight of more than 5000, such as more than 10,000 and less than 200,000, such as less than 100,000; for example in the range of 20,000-80,000.

Another, usually less preferred modification comprises N-linked or O-linked glycosylation, usually as part of co-translational and/or post-translational modification, depending on the host cell used for expressing the polypeptide of the invention.

Yet another modification may comprise the introduction of one or more detectable labels or other signal-generating groups or moieties, depending on the intended use of the polypeptide or construct of the invention. Suitable labels and techniques for attaching, using and detecting them will be clear to the skilled person, and for example include, but are not limited to, fluorescent labels (such as fluorescein, isothiocyanate, rhodamine, phycoerythrin, phycocyanin, allophycocyanin, o-phthaldehyde, and fluorescamine and fluorescent metals such as $^{152}Eu$ or others metals from the lanthanide series), phosphorescent labels, chemiluminescent labels or bioluminescent labels (such as luminal, isoluminol, theromatic acridinium ester, imidazole, acridinium salts, oxalate ester, dioxetane or GFP and its analogs), radio-isotopes (such as $^3H$, $^{125}I$, $^{32}P$, $^{35}S$, $^{14}C$, $^{51}Cr$, $^{36}Cl$, $^{57}Co$, $^{58}Co$, $^{59}Fe$, and $^{75}Se$), metals, metals chelates or metallic cations (for example metallic cations such as $^{99m}Tc$, $^{123}I$, $^{111}In$, $^{131}I$, $^{97}Ru$, $^{67}Cu$, $^{67}Ga$, and $^{68}Ga$ or other metals or metallic cations that are particularly suited for use in in vivo, in vitro or in situ diagnosis and imaging, such as ($^{157}Gd$, $^{55}Mn$, $^{162}Dy$, $^{52}Cr$, and $^{56}Fe$)), as well as chromophores and enzymes (such as malate dehydrogenase, staphylococcal nuclease, delta-V-steroid isomerase, yeast alcohol dehydrogenase, alpha-glycerophosphate dehydrogenase, triose phosphate isomerase, biotinavidin peroxidase, horseradish peroxidase, alkaline phosphatase, asparaginase, glucose oxidase, β-galactosidase, ribonuclease, urease, catalase, glucose-VI-phosphate dehydrogenase, glucoamylase and acetylcholine esterase). Other suitable labels will be clear to the skilled person, and for example include moieties that can be detected using NMR or ESR spectroscopy.

Such labelled polypeptides and constructs of the invention may, for example, be used for in vitro, in vivo or in situ assays (including immunoassays known per se such as ELISA, RIA, EIA and other "sandwich assays", etc.) as well as in vivo diagnostic and imaging purposes, depending on the choice of the specific label.

As will be clear to the skilled person, another modification may involve the introduction of a chelating group, for example to chelate one of the metals or metallic cations referred to above. Suitable chelating groups for example include, without limitation, diethyl-enetriaminepentaacetic acid (DTPA) or ethylene-diaminetetraacetic acid (EDTA).

Yet another modification may comprise the introduction of a functional moiety that is one part of a specific binding pair, such as the biotin-(strept)avidin binding pair. Such a functional moiety may be used to link the polypeptide of the invention to another protein, polypeptide or chemical compound that is bound to the other half of the binding pair, i.e. through formation of the binding pair. For example, a construct or polypeptide of the invention may be conjugated to biotin, and linked to another protein, polypeptide, compound or carrier conjugated to avidin or streptavidin. For example, such a conjugated construct or polypeptide of the invention may be used as a reporter, for example in a diagnostic system where a detectable signal-producing agent is conjugated to avidin or streptavidin. Such binding pairs may for example also be used to bind the construct or polypeptide of the invention to a carrier, including carriers suitable for pharmaceutical purposes. One non-limiting example is the liposomal formulations described by Cao and Suresh (Journal of Drug Targeting 8: 257, 2000). Such binding pairs may also be used to link a therapeutically active agent to the polypeptide of the invention.

Other potential chemical and enzymatical modifications will be clear to the skilled person. Such modifications may also be introduced for research purposes (e.g. to study function-activity relationships). Reference is for example made to Lundblad and Bradshaw (Biotechnol. Appl. Biochem. 26: 143-151, 1997).

Preferably, the constructs, polypeptides and/or derivatives are such that they bind to ADAMTS5, with an affinity (suitably measured and/or expressed as a $K_D$-value (actual or apparent), a $K_A$-value (actual or apparent), a $k_{on}$-rate or on-rate and/or $k_{off}$ or off-rate, or alternatively as an $IC_{50}$ value, as further described herein) that is as defined herein (e.g. as defined for the polypeptides of the invention).

Such constructs and/or polypeptides of the invention and derivatives thereof may also be in essentially isolated form (as defined herein).

In an aspect, the present invention relates to a construct of the invention, that comprises or essentially consists of an ISVD according to the invention or a polypeptide according to the invention, and which further comprises one or more other groups, residues, moieties or binding units, which are optionally linked via one or more peptidic linkers.

In an aspect, the present invention relates to a construct of the invention, in which one or more other groups, residues, moieties or binding units are chosen from the group consisting of a polyethylene glycol molecule, serum proteins or fragments thereof, binding units that can bind to serum proteins, an Fc portion, and small proteins or peptides that can bind to serum proteins.

In the constructs of the invention, such as the polypeptides of the invention, the two or more building blocks, such as e.g. ISVDs, and the optionally one or more other groups, drugs, agents, residues, moieties or binding units may be directly linked to each other (as for example described in WO 99/23221) and/or may be linked to each other via one or more suitable spacers or linkers, or any combination thereof. Suitable spacers or linkers for use in multivalent and multispecific polypeptides will be clear to the skilled person, and may generally be any linker or spacer used in the art to link amino acid sequences. Preferably, said linker or spacer is suitable for use in constructing constructs, proteins or polypeptides that are intended for pharmaceutical use.

For instance, the polypeptide of the invention may, for example, be a trivalent, trispecific polypeptide, comprising one building block, such as an ISVD binding ADAMTS5, an ISVD binding albumin, and potentially another building block, such as a third ISVD, in which said first, second and third building blocks, such as ISVDs, may optionally be linked via one or more, and in particular 2, linker sequences. Also, the present invention provides a construct or polypeptide of the invention comprising a first ISVD binding ADAMTS5 and possibly a second ISVD binding albumin and/or possibly a third ISVD and/or possibly a fourth ISVD, wherein said first ISVD and/or said second ISVD and/or possibly said third ISVD and/or possibly said fourth ISVD are linked via linkers, in particular 3 linkers.

Some particularly preferred linkers include the linkers that are used in the art to link antibody fragments or antibody domains. These include the linkers mentioned in the general background art cited above, as well as for example linkers that are used in the art to construct diabodies or ScFv fragments (in this respect, however, it should be noted that, whereas in diabodies and in ScFv fragments, the linker sequence used should have a length, a degree of flexibility and other properties that allow the pertinent $V_H$ and $V_L$ domains to come together to form the complete antigen-binding site, there is no particular limitation on the length or the flexibility of the linker used in the polypeptide of the invention, since each ISVD, such as Nanobodies, by itself forms a complete antigen-binding site).

For example, a linker may be a suitable amino acid sequence, and in particular amino acid sequences of between 1 and 50, preferably between 1 and 30, such as between 1 and 10 amino acid residues. Some preferred examples of such amino acid sequences include gly-ser linkers, for example of the type (glyxsery)2 (SEQ ID NO: 188), such as (for example (gly4ser)3 (SEQ ID NO: 164) or (gly3ser2)3 (SEQ ID NO: 183), as described in WO 99/42077 and the GS30, GS15, GS9 and GS7 linkers described in the applications by Ablynx mentioned herein (see for example WO 06/040153 and WO 06/122825), as well as hinge-like regions, such as the hinge regions of naturally occurring heavy chain antibodies or similar sequences (such as described in WO 94/04678). Preferred linkers are depicted in Table C.

Some other particularly preferred linkers are poly-alanine (such as AAA (SEQ ID NO: 158)), as well as the linkers GS30 (see also SEQ ID NO: 85 in WO 06/122825) and GS9 (see also SEQ ID NO: 84 in WO 06/122825).

Other suitable linkers generally comprise organic compounds or polymers, in particular those suitable for use in proteins for pharmaceutical use. For instance, poly(ethyleneglycol) moieties have been used to link antibody domains, see for example WO 04/081026.

It is encompassed within the scope of the invention that the length, the degree of flexibility and/or other properties of the linker(s) used (although not critical, as it usually is for linkers used in ScFv fragments) may have some influence on the properties of the final the construct of the invention, such as the polypeptide of the invention, including but not limited to the affinity, specificity or avidity for a chemokine, or for one or more of the other antigens. Based on the disclosure herein, the skilled person will be able to determine the optimal linker(s) for use in a specific construct of the invention, such as the polypeptide of the invention, optionally after some limited routine experiments.

For example, in multivalent polypeptides of the invention that comprise building blocks, ISVDs or Nanobodies directed against ADAMTS5 and another target, the length and flexibility of the linker are preferably such that it allows each building block, such as an ISVD, of the invention present in the polypeptide to bind to its cognate target, e.g. the antigenic determinant on each of the targets. Again, based on the disclosure herein, the skilled person will be able to determine the optimal linker(s) for use in a specific construct of the invention, such as a polypeptide of the invention, optionally after some limited routine experiments.

It is also within the scope of the invention that the linker(s) used confer one or more other favourable properties or functionality to the constructs of the invention, such as the polypeptides of the invention, and/or provide one or more sites for the formation of derivatives and/or for the attachment of functional groups (e.g. as described herein for the derivatives of the ISVDs of the invention). For example, linkers containing one or more charged amino acid residues can provide improved hydrophilic properties, whereas linkers that form or contain small epitopes or tags can be used for the purposes of detection, identification and/or purification. Again, based on the disclosure herein, the skilled person will be able to determine the optimal linkers for use in a specific polypeptide of the invention, optionally after some limited routine experiments.

Finally, when two or more linkers are used in the constructs such as polypeptides of the invention, these linkers may be the same or different. Again, based on the disclosure herein, the skilled person will be able to determine the optimal linkers for use in a specific construct or polypeptide of the invention, optionally after some limited routine experiments.

Usually, for easy of expression and production, a construct of the invention, such as a polypeptide of the invention, will be a linear polypeptide. However, the invention in its broadest sense is not limited thereto. For example, when a construct of the invention, such as a polypeptide of the invention, comprises three of more building blocks, ISVDs or Nanobodies, it is possible to link them by use of a linker with three or more "arms", which each "arm" being linked to a building block, ISVD or Nanobody, so as to provide a "star-shaped" construct. It is also possible, although usually less preferred, to use circular constructs.

Accordingly, the present invention relates to a construct of the invention, such as a polypeptide of the invention, wherein said ISVDs are directly linked to each other or are linked via a linker.

Accordingly, the present invention relates to a construct of the invention, such as a polypeptide of the invention, wherein a first ISVD and/or a second ISVD and/or possibly an ISVD binding serum albumin are linked via a linker.

Accordingly, the present invention relates to a construct of the invention, such as a polypeptide of the invention, wherein said linker is chosen from the group consisting of linkers of 3A, 5GS, 7GS, 9GS, 10GS, 15GS, 18GS, 20GS, 25GS, 30GS, 35GS, poly-A, 8GS, 40GS, G1 hinge, 9GS-G1 hinge, llama upper long hinge region, and G3 hinge, such as e.g. presented in Table C (SEQ ID NO:s 158-174).

Accordingly, the present invention relates to a construct of the invention, such as a polypeptide of the invention, wherein said polypeptide is chosen from the group consisting of SEQ ID NOs: 120-130.

The invention further relates to methods for preparing the constructs, polypeptides, ISVDs, nucleic acids, host cells, and compositions described herein.

The multivalent polypeptides of the invention can generally be prepared by a method which comprises at least the step of suitably linking the ISVD and/or monovalent polypeptide of the invention to one or more further ISVDs, optionally via the one or more suitable linkers, so as to provide the multivalent polypeptide of the invention. Polypeptides of the invention can also be prepared by a method which generally comprises at least the steps of providing a nucleic acid that encodes a polypeptide of the invention, expressing said nucleic acid in a suitable manner, and recovering the expressed polypeptide of the invention. Such methods can be performed in a manner known per se, which will be clear to the skilled person, for example on the basis of the methods and techniques further described herein.

A method for preparing multivalent polypeptides of the invention may comprise at least the steps of linking two or more ISVDs of the invention and for example one or more linkers together in a suitable manner. The ISVDs of the invention (and linkers) can be coupled by any method known in the art and as further described herein. Preferred techniques include the linking of the nucleic acid sequences that encode the ISVDs of the invention (and linkers) to prepare a genetic construct that expresses the multivalent polypeptide. Techniques for linking amino acids or nucleic acids will be clear to the skilled person, and reference is again made to the standard handbooks, such as Sambrook et al. and Ausubel et al., mentioned above, as well as the Examples below.

Accordingly, the present invention also relates to the use of an ISVD of the invention in preparing a multivalent polypeptide of the invention. The method for preparing a multivalent polypeptide will comprise the linking of an ISVD of the invention to at least one further ISVD of the invention, optionally via one or more linkers. The ISVD of the invention is then used as a binding domain or building block in providing and/or preparing the multivalent polypeptide comprising 2 (e.g., in a bivalent polypeptide), 3 (e.g., in a trivalent polypeptide), 4 (e.g., in a tetravalent) or more (e.g., in a multivalent polypeptide) building blocks. In this respect, the ISVD of the invention may be used as a binding domain or binding unit in providing and/or preparing a multivalent, such as bivalent, trivalent or tetravalent polypeptide of the invention comprising 2, 3, 4 or more building blocks.

Accordingly, the present invention also relates to the use of an ISVD polypeptide of the invention (as described herein) in preparing a multivalent polypeptide. The method for the preparation of the multivalent polypeptide will comprise the linking of the ISVD of the invention to at least one further ISVD of the invention, optionally via one or more linkers.

The polypeptides and nucleic acids of the invention can be prepared in a manner known per se, as will be clear to the skilled person from the further description herein. For example, the polypeptides of the invention can be prepared in any manner known per se for the preparation of antibodies and in particular for the preparation of antibody fragments (including but not limited to (single) domain antibodies and ScFv fragments). Some preferred, but non-limiting methods for preparing the polypeptides and nucleic acids include the methods and techniques described herein.

The method for producing a polypeptide of the invention may comprise the following steps: the expression, in a suitable host cell or host organism (also referred to herein as a "host of the invention") or in another suitable expression system of a nucleic acid that encodes said polypeptide of the invention (also referred to herein as a "nucleic acid of the invention"); optionally followed by isolating and/or purifying the polypeptide of the invention thus obtained.

In particular, such a method may comprise the steps of: cultivating and/or maintaining a host of the invention under conditions that are such that said host of the invention expresses and/or produces at least one polypeptide of the invention; optionally followed by isolating and/or purifying the polypeptide of the invention thus obtained.

Accordingly, the present invention also relates to a nucleic acid or nucleotide sequence that encodes a polypeptide, ISVD or construct of the invention (also referred to as "nucleic acid of the invention").

A nucleic acid of the invention can be in the form of single or double stranded DNA or RNA. According to one embodiment of the invention, the nucleic acid of the invention is in essentially isolated from, as defined herein. The nucleic acid of the invention may also be in the form of, be present in and/or be part of a vector, e.g. expression vector, such as for example a plasmid, cosmid or YAC, which again may be in essentially isolated form. Accordingly, the present invention also relates to an expression vector comprising a nucleic acid or nucleotide sequence of the invention.

The nucleic acids of the invention can be prepared or obtained in a manner known per se, based on the information on the polypeptides of the invention given herein, and/or can be isolated from a suitable natural source. Also, as will be clear to the skilled person, to prepare a nucleic acid of the invention, also several nucleotide sequences, such as at least two nucleic acids encoding ISVDs of the invention and for example nucleic acids encoding one or more linkers can be linked together in a suitable manner. Techniques for generating the nucleic acids of the invention will be clear to the skilled person and may for instance include, but are not limited to, automated DNA synthesis; site-directed mutagenesis; combining two or more naturally occurring and/or synthetic sequences (or two or more parts thereof), introduction of mutations that lead to the expression of a truncated expression product; introduction of one or more restriction sites (e.g. to create cassettes and/or regions that may easily be digested and/or ligated using suitable restriction enzymes), and/or the introduction of mutations by means of a PCR reaction using one or more "mismatched" primers. These and other techniques will be clear to the skilled person, and reference is again made to the standard handbooks, such as Sambrook et al. and Ausubel et al., mentioned above, as well as to the Examples below.

In a preferred but non-limiting embodiment, a genetic construct of the invention comprises
a) at least one nucleic acid of the invention;
b) operably connected to one or more regulatory elements, such as a promoter and optionally a suitable terminator; and optionally also
c) one or more further elements of genetic constructs known per se;
in which the terms "regulatory element", "promoter", "terminator" and "operably connected" have their usual meaning in the art.

The genetic constructs of the invention may generally be provided by suitably linking the nucleotide sequence(s) of the invention to the one or more further elements described above, for example using the techniques described in the general handbooks such as Sambrook et al. and Ausubel et al., mentioned above.

The nucleic acids of the invention and/or the genetic constructs of the invention may be used to transform a host cell or host organism, i.e., for expression and/or production of the polypeptide of the invention. Suitable hosts or host cells will be clear to the skilled person, and may for example be any suitable fungal, prokaryotic or eukaryotic cell or cell line or any suitable fungal, prokaryotic or (non-human) eukaryotic organism as well as all other host cells or (non-human) hosts known per se for the expression and production of antibodies and antibody fragments (including but not limited to (single) domain antibodies and ScFv fragments), which will be clear to the skilled person. Reference is also made to the general background art cited hereinabove, as well as to for example WO 94/29457; WO 96/34103; WO 99/42077; Frenken et al. (Res Immunol. 149: 589-99, 1998); Riechmann and Muyldermans (1999), supra; van der Linden (J. Biotechnol. 80: 261-70, 2000); Joosten et al. (Microb. Cell Fact. 2: 1, 2003); Joosten et al. (Appl. Microbiol. Biotechnol. 66: 384-92, 2005); and the further references cited herein. Furthermore, the polypeptides of the invention can also be expressed and/or produced in cell-free expression systems, and suitable examples of such systems will be clear to the skilled person. Suitable techniques for transforming a host or host cell of the invention will be clear to the skilled person and may depend on the intended host cell/host organism and the genetic construct to be used. Reference is again made to the handbooks and patent applications mentioned above. The transformed host cell (which may be in the form or a stable cell line) or host organisms (which may be in the form of a stable mutant line or strain) form further aspects of the present invention. Accordingly, the present invention relates to a host or host cell comprising a nucleic acid according to the invention, or an expression vector according to the invention. Preferably, these host cells or host organisms are such that they express, or are (at least) capable of expressing (e.g., under suitable conditions), a polypeptide of the invention (and in case of a host organism: in at least one cell, part, tissue or organ thereof). The invention also includes further generations, progeny and/or offspring of the host cell or host organism of the invention, that may for instance be obtained by cell division or by sexual or asexual reproduction.

To produce/obtain expression of the polypeptides of the invention, the transformed host cell or transformed host organism may generally be kept, maintained and/or cultured under conditions such that the (desired) polypeptide of the invention is expressed/produced. Suitable conditions will be clear to the skilled person and will usually depend upon the host cell/host organism used, as well as on the regulatory elements that control the expression of the (relevant) nucleotide sequence of the invention. Again, reference is made to the handbooks and patent applications mentioned above in the paragraphs on the genetic constructs of the invention.

The polypeptide of the invention may then be isolated from the host cell/host organism and/or from the medium in which said host cell or host organism was cultivated, using protein isolation and/or purification techniques known per se, such as (preparative) chromatography and/or electrophoresis techniques, differential precipitation techniques, affinity techniques (e.g., using a specific, cleavable amino acid sequence fused with the polypeptide of the invention) and/or preparative immunological techniques (i.e. using antibodies against the polypeptide to be isolated).

In an aspect the invention relates to method for producing a construct, polypeptide or ISVD according to the invention comprising at least the steps of: (a) expressing, in a suitable host cell or host organism or in another suitable expression system, a nucleic acid sequence according to the invention; optionally followed by (b) isolating and/or purifying the construct, polypeptide ISVD according to the invention.

In an aspect the invention relates to a composition comprising a construct, polypeptide, ISVD or nucleic acid according to the invention.

As mentioned supra, there remains a need for safe and efficacious OA medicaments. Based on unconventional screening, characterization and combinatory strategies, the present inventors identified ISVDs binding and inhibiting ADAMTS5. These ADAMTS5 binders performed exceptionally well in in vitro and in vivo experiments. Moreover, the ISVDs of the invention were also demonstrated to be significantly more efficacious than the prior art compounds. The present invention thus provides ISVDs and polypeptides antagonizing ADAMTSs, in particular ADAMTS5, with improved prophylactic, therapeutic and/or pharmacological properties, including a safer profile, compared to the prior art amino acid sequences and antibodies. In addition, these ADAMTS5 binders when linked to ISVDs binding albumin had an increased retention in a subject, could be administered systematically while retaining activity.

In an aspect the present invention relates to a method of treating or prevention of diseases or disorders in an individual, for instance in which ADAMTS5 activity is involved, the method comprising administering an ISVD or polypeptide according to the invention to said individual in an amount effective to treat or prevent a symptom of said disease or disorder.

In an aspect the present invention relates to a composition according to the invention, an ISVD according to the invention, a polypeptide according to the invention, and/or a construct according to the invention for use as a medicament.

In another aspect, the invention relates to the use of an ISVD, polypeptide and/or construct of the invention in the preparation of a pharmaceutical composition for prevention and/or treatment of at least an ADAMTS5 associated disease; and/or for use in one or more of the methods of treatment mentioned herein.

The invention also relates to the use of an ISVD, polypeptide and/or construct of the invention in the preparation of a pharmaceutical composition for the prevention and/or treatment of at least one disease or disorder that can be prevented and/or treated by modulating the activity of an ADAMTS, preferably ADAMTS5 e.g. inhibiting Aggrecan degradation.

The invention also relates to the use of an ISVD, polypeptide, compound and/or construct of the invention in the preparation of a pharmaceutical composition for the prevention and/or treatment of at least one disease, disorder or condition that can be prevented and/or treated by administering an ISVD, polypeptide, compound and/or construct of the invention to a patient.

The invention further relates to an ISVD, polypeptide, compound and/or construct of the invention or a pharmaceutical composition comprising the same for use in the prevention and/or treatment of at least one ADAMTS5 associated disease.

It is anticipated that the ADAMTS5 binders of the invention can be used in various diseases affecting cartilage, such as arthropathies and chondrodystrophies, arthritic disease, such as osteoarthritis, rheumatoid arthritis, gouty arthritis, psoriatic arthritis, traumatic rupture or detachment, achondroplasia, costochondritis, Spondyloepimetaphyseal dysplasia, spinal disc herniation, lumbar disk degeneration disease, degenerative joint disease, and relapsing polychondritis, osteochondritis dissecans and aggrecanopathies and non-alcoholic steatohepatitis (NASH) (commonly indicated herein as "ADAMTS5 associated diseases")

In an aspect the present invention relates to a composition, an ISVD, a polypeptide and/or a construct according to the invention for use in treating or preventing a symptom of an ADAMTS5 associated disease, such as e.g. arthropathies and chondrodystrophies, arthritic disease, such as osteoarthritis, rheumatoid arthritis, gouty arthritis, psoriatic arthritis, traumatic rupture or detachment, achondroplasia, costochondritis, Spondyloepimetaphyseal dysplasia, spinal disc herniation, lumbar disk degeneration disease, degenerative joint disease, and relapsing polychondritis, osteochondritis dissecans and aggrecanopathies and NASH.

In an aspect the present invention relates to a method for preventing or treating arthropathies and chondrodystrophies, arthritic disease, such as osteoarthritis, rheumatoid arthritis, gouty arthritis, psoriatic arthritis, traumatic rupture or detachment, achondroplasia, costo-chondritis, Spondyloepimetaphyseal dysplasia, spinal disc herniation, lumbar disk degeneration disease, degenerative joint disease, and relapsing polychondritis and NASH wherein said method comprises administering, to a subject in need thereof, a pharmaceutically active amount of at least a composition, immunoglobulin, polypeptide, or construct according to the invention to a person in need thereof.

In an aspect the present invention relates to the use of an ISVD, polypeptide, composition or construct according to the invention, in the preparation of a pharmaceutical composition for treating or preventing such as arthropathies and chondrodystrophies, arthritic disease, such as osteoarthritis, rheumatoid arthritis, gouty arthritis, psoriatic arthritis, traumatic rupture or detachment, achondroplasia, costochondritis, Spondyloepimetaphyseal dysplasia, spinal disc herniation, lumbar disk degeneration disease, degenerative joint disease, and relapsing polychondritis, osteochondritis dissecans and aggrecanopathies and NASH.

It is also expected that by binding to Aggrecan, the constructs and/or polypeptides of the invention may reduce or inhibit an activity of a member of the serine protease family, cathepsins, matrix metalloproteinases (MMPs), such as e.g. MMP20, but also ADAMTS4 (Aggrecanase-1) and/or ADAMTS11 in degrading Aggrecan.

In the context of the present invention, the term "prevention and/or treatment" not only comprises preventing and/or treating the disease, but also generally comprises preventing the onset of the disease, slowing or reversing the progress of disease, preventing or slowing the onset of one or more symptoms associated with the disease, reducing and/or alleviating one or more symptoms associated with the disease, reducing the severity and/or the duration of the disease and/or of any symptoms associated therewith and/or preventing a further increase in the severity of the disease and/or of any symptoms associated therewith, preventing, reducing or reversing any physiological damage caused by the disease, and generally any pharmacological action that is beneficial to the patient being treated.

The dosage regimen will be determined by the attending physician and clinical factors. As is well known in the medical arts, dosage for any one patient depends upon many factors, including the patient's size, weight, body surface area, age, the particular compound to be administered, the activity of the employed polypeptide (including antibodies), time and route of administration, general health, and combination with other therapies or treatments. Proteinaceous pharmaceutically active matter may be present in amounts between 1 g and 100 mg/kg body weight per dose; however, doses below or above this exemplary range are also envisioned. If the regimen is a continuous infusion, it may be in the range of 1 pg to 100 mg per kilogram of body weight per minute.

An ISVD, polypeptide or construct of the invention may be employed at a concentration of, e.g., 0.01, 0.1, 0.5, 1, 2, 5, 10, 20 or 50 pg/ml in order to inhibit and/or neutralize a biological function of ADAMTS5 by at least about 50%, preferably 75%, more preferably 90%, 95% or up to 99%, and most preferably approximately 100% (essentially completely) as assayed by methods well known in the art.

Generally, the treatment regimen will comprise the administration of one or more ISVDs, polypeptides and/or constructs of the invention, or of one or more compositions comprising the same, in one or more pharmaceutically effective amounts or doses. The specific amount(s) or doses to be administered can be determined by the clinician, again based on the factors cited above. Useful dosages of the constructs, polypeptides, and/or ISVDs of the invention can be determined by comparing their in vitro activity, and in vivo activity in animal models. Methods for the extrapolation of effective dosages in mice, and other animals, to humans are known to the art; for example, see U.S. Pat. No. 4,938,949.

Generally, depending on the specific disease, disorder or condition to be treated, the potency of the specific ISVD, polypeptide and/or construct of the invention to be used, the specific route of administration and the specific pharmaceutical formulation or composition used, the clinician will be able to determine a suitable dosing regimen.

The amount of the constructs, polypeptides, and/or ISVDs of the invention required for use in treatment will vary not only with the particular immunoglobulin, polypeptide, compound and/or construct selected but also with the route of administration, the nature of the condition being treated and the age and condition of the patient and will be ultimately at the discretion of the attendant physician or clinician. Also the dosage of the constructs, polypeptides, and/or ISVDs of the invention varies depending on the target cell, tumor, tissue, graft, or organ.

The desired dose may conveniently be presented in a single dose or as divided doses administered at appropriate intervals, for example, as two, three, four or more sub-doses per day. The sub-dose itself may be further divided, e.g., into a number of discrete loosely spaced administrations.

An administration regimen could include long-term, daily treatment. By "long-term" is meant at least two weeks and preferably, several weeks, months, or years of duration. Necessary modifications in this dosage range may be determined by one of ordinary skill in the art using only routine experimentation given the teachings herein. See Remington's Pharmaceutical Sciences (Martin, E. W., ed. 4), Mack Publishing Co., Easton, PA The dosage can also be adjusted by the individual physician in the event of any complication.

Usually, in the above method, an ISVD, polypeptide and/or construct of the invention will be used. It is however within the scope of the invention to use two or more ISVDs, polypeptides and/or constructs of the invention in combination.

The ISVDs, polypeptides and/or constructs of the invention may be used in combination with one or more further pharmaceutically active compounds or principles, i.e., as a combined treatment regimen, which may or may not lead to a synergistic effect.

The pharmaceutical composition may also comprise at least one further active agent, e.g. one or more further antibodies or antigen-binding fragments thereof, peptides, proteins, nucleic acids, organic and inorganic molecules.

Again, the clinician will be able to select such further compounds or principles, as well as a suitable combined treatment regimen, based on the factors cited above and his expert judgment.

In particular, the ISVDs, polypeptides and/or constructs of the invention may be used in combination with other pharmaceutically active compounds or principles that are or can be used for the prevention and/or treatment of the diseases, disorders and conditions cited herein, as a result of which a synergistic effect may or may not be obtained. Examples of such compounds and principles, as well as routes, methods and pharmaceutical formulations or compositions for administering them will be clear to the clinician.

When two or more substances or principles are to be used as part of a combined treatment regimen, they can be administered via the same route of administration or via different routes of administration, at essentially the same time or at different times (e.g. essentially simultaneously, consecutively, or according to an alternating regime). When the substances or principles are to be administered simultaneously via the same route of administration, they may be administered as different pharmaceutical formulations or compositions or part of a combined pharmaceutical formulation or composition, as will be clear to the skilled person.

Also, when two or more active substances or principles are to be used as part of a combined treatment regimen, each of the substances or principles may be administered in the same amount and according to the same regimen as used when the compound or principle is used on its own, and such combined use may or may not lead to a synergistic effect. However, when the combined use of the two or more active substances or principles leads to a synergistic effect, it may also be possible to reduce the amount of one, more or all of the substances or principles to be administered, while still achieving the desired therapeutic action. This may for example be useful for avoiding, limiting or reducing any unwanted side-effects that are associated with the use of one or more of the substances or principles when they are used in their usual amounts, while still obtaining the desired pharmaceutical or therapeutic effect.

The effectiveness of the treatment regimen used according to the invention may be determined and/or followed in any manner known per se for the disease, disorder or condition involved, as will be clear to the clinician. The clinician will also be able, where appropriate and on a case-by-case basis, to change or modify a particular treatment regimen, so as to achieve the desired therapeutic effect, to avoid, limit or reduce unwanted side-effects, and/or to achieve an appropriate balance between achieving the desired therapeutic effect on the one hand and avoiding, limiting or reducing undesired side effects on the other hand.

Generally, the treatment regimen will be followed until the desired therapeutic effect is achieved and/or for as long as the desired therapeutic effect is to be maintained. Again, this can be determined by the clinician.

Thus, in a further aspect, the invention relates to a pharmaceutical composition that contains at least one construct of the invention, at least one polypeptide of the invention, at least one ISVD of the invention, or at least one nucleic acid of the invention and at least one suitable carrier, diluent or excipient (i.e., suitable for pharmaceutical use), and optionally one or more further active substances. In a particular aspect, the invention relates to a pharmaceutical composition that comprises a construct, polypeptide, ISVD or nucleic acid according to the invention, preferably at least one of SEQ ID NOs: 000 and at least one suitable carrier, diluent or excipient (i.e., suitable for pharmaceutical use), and optionally one or more further active substances.

The subject to be treated may be any warm-blooded animal, but is in particular a mammal, and more in particular a human being. In veterinary applications, the subject to be treated includes any animal raised for commercial purposes or kept as a pet. As will be clear to the skilled person, the subject to be treated will in particular be a person suffering from, or at risk of, the diseases, disorders and conditions mentioned herein. Hence, in a preferred embodiment of the invention, the pharmaceutical compositions comprising a polypeptide of the invention are for use in medicine or diagnostics. Preferably, the pharmaceutical compositions are for use in human medicine, but they may also be used for veterinary purposes.

Again, in such a pharmaceutical composition, the one or more immunoglobulins, polypeptides, compounds and/or constructs of the invention, or nucleotide encoding the same, and/or a pharmaceutical composition comprising the same, may also be suitably combined with one or more other active principles, such as those mentioned herein.

The invention also relates to a composition (such as, without limitation, a pharmaceutical composition or preparation as further described herein) for use, either in vitro (e.g. in an in vitro or cellular assay) or in vivo (e.g. in an a single cell or multi-cellular organism, and in particular in a mammal, and more in particular in a human being, such as in a human being that is at risk of or suffers from a disease, disorder or condition of the invention).

It is to be understood that reference to treatment includes both treatment of established symptoms and prophylactic treatment, unless explicitly stated otherwise.

Generally, for pharmaceutical use, the constructs, polypeptides and/or ISVDs of the invention may be formulated as a pharmaceutical preparation or composition comprising at least one construct, polypeptide and/or ISVD of the invention and at least one pharmaceutically acceptable carrier, diluent or excipient and/or adjuvant, and optionally one or more pharmaceutically active polypeptides and/or compounds. By means of non-limiting examples, such a formulation may be in a form suitable for oral administration, for parenteral administration (such as by intravenous, intramuscular or subcutaneous injection or intravenous infusion), for topical administration, for administration by inhalation, by a skin patch, by an implant, by a suppository, etc., wherein the parenteral administration is preferred. Such suitable administration forms—which may be solid, semi-solid or liquid, depending on the manner of administration—as well as methods and carriers for use in the preparation thereof, will be clear to the skilled person, and are further described herein. Such a pharmaceutical preparation or composition will generally be referred to herein as a "pharmaceutical composition".

As exemplary excipients, disintegrators, binders, fillers, and lubricants may be mentioned. Examples of disintegrators include agar-agar, algins, calcium carbonate, cellulose, colloid silicon dioxide, gums, magnesium aluminium silicate, methylcellulose, and starch. Examples of binders include micro-crystalline cellulose, hydroxymethyl cellulose, hydroxypropylcellulose, and polyvinylpyrrolidone. Examples of fillers include calcium carbonate, calcium phosphate, tribasic calcium sulfate, calcium carboxymethylcellulose, cellulose, dextrin, dextrose, fructose, lactitol, lactose, magnesium carbonate, magnesium oxide, maltitol, maltodextrins, maltose, sorbitol, starch, sucrose, sugar, and xylitol. Examples of lubricants include agar, ethyl oleate, ethyl laureate, glycerin, glyceryl palmitostearate, hydrogenated vegetable oil, magnesium oxide, stearates, mannitol, poloxamer, glycols, sodium benzoate, sodium lauryl sulfate, sodium stearyl, sorbitol, and talc. Usual stabilizers, preservatives, wetting and emulsifying agents, consistency-improving agents, flavour-improving agents, salts for varying the osmotic pressure, buffer substances, solubilizers, diluents, emollients, colorants and masking agents and antioxidants come into consideration as pharmaceutical adjuvants.

Suitable carriers include but are not limited to magnesium carbonate, magnesium stearate, talc, sugar, lactose, pectin, dextrin, starch, gelatine, tragacanth, methylcellulose, sodium carboxymethyl-cellulose, a low melting-point wax, cocoa butter, water, alcohols, polyols, glycerol, vegetable oils and the like.

Generally, the constructs, polypeptides, and/or ISVDs of the invention can be formulated and administered in any suitable manner known per se. Reference is for example made to the general background art cited above (and in particular to WO 04/041862, WO 04/041863, WO 04/041865, WO 04/041867 and WO 08/020079) as well as to the standard handbooks, such as Remington's Pharmaceutical Sciences, 18$^{th}$ Mack Publishing Company, USA (1990), Remington, the Science and Practice of Pharmacy, 21st Edition, Lippincott Williams and Wilkins (2005); or the Handbook of Therapeutic Antibodies (S. Dubel, Ed.), Wiley, Weinheim, 2007 (see for example pages 252-255).

In a particular aspect, the invention relates to a pharmaceutical composition that comprises a construct, polypeptide, ISVD or nucleic acid according to the invention, and which further comprises at least one pharmaceutically acceptable carrier, diluent or excipient and/or adjuvant, and optionally comprises one or more further pharmaceutically active polypeptides and/or compounds.

The constructs, polypeptides, and/or ISVDs of the invention may be formulated and administered in any manner known per se for conventional antibodies and antibody fragments (including ScFv's and diabodies) and other pharmaceutically active proteins. Such formulations and methods for preparing the same will be clear to the skilled person, and for example include preparations preferable for suitable for parenteral administration (e.g. intravenous, intraperitoneal, subcutaneous, intramuscular, intraluminal, intra-arterial, intrathecal intranasal or intrabronchial administration) but also for topical (i.e., transdermal or intradermal) administration.

Preparations for parenteral administration may for example be sterile solutions, suspensions, dispersions or emulsions that are suitable for infusion or injection. Suitable carriers or diluents for such preparations for example include, without limitation, those mentioned on page 143 of WO 08/020079. Usually, aqueous solutions or suspensions will be preferred.

The constructs, polypeptides, and/or ISVDs of the invention can also be administered using methods of delivery known from gene therapy, see, e.g., U.S. Pat. No. 5,399,346, which is incorporated by reference for its gene therapy delivery methods. Using a gene therapy method of delivery, primary cells transfected with the gene encoding a construct, polypeptide, and/or ISVD of the invention can additionally be transfected with tissue specific promoters to target specific organs, tissue, grafts, tumors, or cells and can additionally be transfected with signal and stabilization sequences for subcellularly localized expression.

According to further aspects of the invention, the polypeptide of the invention may be used in additional applications in vivo and in vitro. For example, polypeptides of the invention may be employed for diagnostic purposes, e.g. in assays designed to detect and/or quantify the presence of ADAMTS5 and/or to purify ADAMTS5. Polypeptides may also be tested in animal models of particular diseases and for conducting toxicology, safety and dosage studies.

Finally, the invention relates to a kit comprising at least one polypeptide according to the invention, at least one nucleic acid sequence encoding said components, the vector or vector system of the invention, and/or a host cell according to the invention. It is contemplated that the kit may be offered in different forms, e.g. as a diagnostic kit.

The invention will now be further described by means of the following non-limiting preferred aspects, examples and figures.

The entire contents of all of the references (including literature references, issued patents, published patent applications, and co-pending patent applications) cited throughout this application are hereby expressly incorporated by reference, in particular for the teaching that is referenced hereinabove.

Sequences are disclosed in the main body of the description and in a separate sequence listing according to WIPO standard ST.25. A SEQ ID specified with a specific number should be the same in the main body of the description and in the separate sequence listing. By way of example SEQ ID no.: 1 should define the same sequence in both, the main body of the description and in the separate sequence listing. Should there be a discrepancy between a sequence definition in the main body of the description and the separate sequence listing (if e.g. SEQ ID no.: 1 in the main body of the description erroneously corresponds to SEQ ID no.: 2 in the separate sequence listing) then a reference to a specific sequence in the application, in particular of specific embodiments, is to be understood as a reference to the sequence in the main body of the application and not to the separate sequence listing. In other words a discrepancy between a sequence definition/designation in the main body of the description and the separate sequence listing is to be resolved by correcting the separate sequence listing to the sequences and their designation disclosed in the main body of the application which includes the description, examples, figures and claims.

EXAMPLES

Example 1 Generation of Recombinant ADAMTS5 Protein from Different Species

Various formats of bovine, rat, guinea pig, mouse and cynomolgus monkey recombinant ADAMTS5 protein were generated in house via the HEK293 Flp-In™ expression system using FuGENE® HD transfection reagent (Promega). Two days post-transfection, selection medium containing 100 μg/ml HygromycinB was added to the cells to select for stably expressing cells.

Stably expressing cells were expanded. Conditioned medium containing secreted ADAMTS5 were harvested every day from the cells, purified by HisTrap chromatography and followed by a buffer exchange in 50 mM Hepes buffer pH 7.5. The purity of the protein was confirmed by SDS-PAGE.

Example 2 Immunization of Llamas with ADAMTS5 Protein, Cloning of the Heavy Chain-Only Antibody Fragment Repertoires and Preparation of Phage 2.1 Immunizations After approval of the Ethical Committee of the faculty of Veterinary Medicine (University Ghent, Belgium), 3 llamas were immunized with recombinant human ADAMTS5 Protein (R&D Systems, Minneapolis, US; cat #2198-AD).

2.2 Cloning of Heavy Chain-Only Antibody Fragment Repertoires and Preparation of Phage Following the final immunogen injection, blood samples were collected. From these blood samples, peripheral blood mononuclear cells (PBMCs) were prepared using Ficoll-Hypaque according to the manufacturer's instructions (Amersham Biosciences, Piscataway, NJ, US). From the PBMCs, total RNA was extracted and used as starting material for RT-PCR to amplify the VHH/Nanobody-encoding DNA segments, essentially as described in WO 05/044858. Subsequently, phages were prepared according to standard protocols (see for example the prior art and applications filed by Ablynx N.V. cited herein.) and stored after filter sterilization at 4° C. for further use.

Example 3 Selection of Human ADAMTS5 Specific VHHs Via Phage Display

VHH repertoires obtained from all llamas and cloned in phage libraries were used to select for human ADAMTS5 binding Nanobodies. Recombinant human ADAMTS5 protein (R&D Systems, Minneapolis, US; cat #2198-AD) was immobilized at 5 μg/ml on a Maxisorp plate (Nunc, Wiesbaden, Germany), next to a negative control of 0 μg/ml antigen. Following incubation with the phage libraries and extensive washing, bound phages are eluted with trypsin (1 mg/mL), and used to infect $E.\ coli$ cells. Infected $E.\ coli$ cells were either used to prepare phage for the next selection round or plated on agar plates for analysis. In addition, synthetic libraries were used in three consecutive selection rounds.

Outputs of all selection rounds were analyzed for enrichment factor, which is the number of phages present in eluate relative to controls. The best selection conditions were chosen for further analysis.

In order to screen a selection output for specific binders, single colonies were picked from the agar plates and grown in 1 mL 96-deep-well plates. LacZ-controlled VHH expression was induced by addition of IPTG. Periplasmic extracts were prepared according to standard protocols (see for example the prior art and applications filed by Ablynx N.V. cited herein.)

Example 4 Screening of Periplasmic Extracts for Functional Blocking Nanobodies

In a first step, periplasmic extracts were tested for binding to recombinant human ADAMTS5 by binding ELISA. In brief, recombinant human ADAMTS5 (R&D Systems, Minneapolis, US; cat #2198-AD) at a concentration of 1 μg/ml was coated on 384-well MaxiSorp plates (Nunc, Wiesbaden, Germany). Wells were blocked with a casein solution (1%). After addition of a 10-fold dilution of the periplasmic extracts, Nanobody binding was detected using a mouse anti-Flag-HRP conjugate (Sigma, St. Louis, US) and a subsequent enzymatic reaction in the presence of the substrate esTMB (3,3',5,5'-tetramentylbenzidine) (SDT, Brussels, Belgium). Clones showing ELISA signals higher than the sum of the average signal of the irrelevant Nanobody controls and 3 times the standard deviation of the irrelevant Nanobody controls were considered to encode positive human ADAMTS5 binding Nanobodies.

To identify Nanobodies which are able to prevent ADAMTS5 mediated cleavage of Aggrecan, clones were tested in a FRET-based human ADAMTS5 enzymatic assay, using 50 mM HEPES (pH 7.5), 100 mM NaCl, 5 mM CaCl2*2H2O, 0.1% CHAPS, 5% glycerol as assay buffer. In brief, periplasmic extracts containing ADAMTS5 binding Nanobodies were incubated in a 384-well OptiPlate (PerkinElmer, Waltham, MA, US) with 10 μl of 25 μM quenched fluorogenic human peptide substrate (Abz-TEGEARGSVI-Dap(Dnp)-KK-NH2 (SEQ ID NO: 184), Anaspec, Serain Belgium, cat #60431-1) and 10 μl of 25 nM of human ADAMTS5 (R&D Systems, Minneapolis, US; cat #2198-AD). The ability of the Nanobodies to prevent ADAMTS5 mediated cleavage was monitored every minute for 2 hours on a Tecan Infinite M1000 plate reader. Data were analysed with Graphpad Prism software. From the enzyme progression curve, the initial velocity for the negative control (v0) was determined, as well as the velocity for every Nanobody clone in the plate (vi) and the background signal (Sb). Using the formula 100*(1−(vi−Sb)/(v0−Sb)), the percentage inhibition was calculated.

Periplasmic extract containing irrelevant Nanobody was used as negative control. Periplasmic extracts containing ADAMTS5 Nanobodies which were able to decrease the fluorescence signal with more than 50% relative to the signal of the negative control were considered as inhibitory Nanobodies. The DNA sequence of the positive clones was subsequently determined.

A summary of the periplasmic extract screening data is given in Table 4.1. The amino acid sequences of the anti-ADAMTS5 Nanobodies are shown in Table A-1.

TABLE 4.1

Screening results of periplasmic extracts containing anti-ADAMTS5 Nanobodies

| sequence ID | binding ELISA (OD 450 nm) | FRET assay vi (U/min) | % inh |
|---|---|---|---|
| 2A02 | 1.646 | 2 | 91 |
| 2A12 | 1.745 | −1 | 104 |
| 2C10 | 1.627 | 2 | 90 |
| 2D07 | 1.551 | −1 | 104 |
| 2D12 | 1.354 | 2 | 90 |
| 2F03 | 1.842 | −1 | 103 |
| 2G01 | 1.710 | 10 | 55 |
| 3B02 | 2.570 | −1 | 105 |
| 3B03 | 2.295 | 2 | 93 |
| 3D01 | 2.573 | −2 | 111 |
| 3D02 | 2.581 | −2 | 111 |
| 7B11 | 0.368 | 2 | 90 |
| 9A05 | ND | −3 | 113 |

TABLE 4.1-continued

Screening results of periplasmic extracts containing anti-ADAMTS5 Nanobodies

| sequence ID | binding ELISA (OD 450 nm) | FRET assay vi (U/min) | % inh |
|---|---|---|---|
| 9D03 | ND | −2 | 110 |
| 9D09 | ND | 0 | 102 |
| 9D10 | ND | −2 | 111 |
| 11B06 | ND | −1 | 106 |
| 13E02 | ND | 0 | 99 |
| 3F04 | 2.555 | 19 | 8 |

After cloning and sequencing, various families were identified, which consisted of clones with differences in CDRs, but which displayed similar binding and inhibition characteristics.

After cloning and sequencing, Nanobody 02A12 was identified as a family member of clone 09D03 (cf. Tables A-1 and A-2). The sequence variability of CDR regions is depicted in the Tables 4.1A, 4.1B and 4.1C below. The amino acid sequences of the CDRs of clone 09D03 were used as reference against which the CDRs of the family members were compared (CDR1 starts at Kabat position 26, CDR1 starts at Kabat position 50, and CDR3 starts at Kabat position 95).

TABLE 4.1A (09D03 CDR1)

| 09D03 | CDR1* | | | | | | | | | |
|---|---|---|---|---|---|---|---|---|---|---|
| Kabat numbering | 26 | 27 | 28 | 29 | 30 | 31 | 32 | 33 | 34 | 35 |
| absolute numbering | 1 | 2 | 3 | 4 | 5 | 6 | 7 | 8 | 9 | 10 |
| wildtype sequence | G | S | A | V | S | V | N | A | M | A |
| mutations | | R | T | F | | | S | Y | | G |

*Up to 6 CDR1 mutations in one clone (SEQ. ID NO: 22)

TABLE 4.1B (09D03 CDR21)

| 09D03 | CDR2* | | | | | | | | | |
|---|---|---|---|---|---|---|---|---|---|---|
| Kabat numbering | 50 | 51 | 52 | 53 | 54 | 55 | 56 | 57 | 58 | 59 |
| absolute numbering | 1 | 2 | 3 | 4 | 5 | 6 | 7 | 8 | 9 | 10 |
| wildtype sequence | G | I | S | R | S | A | G | R | T | Y |
| mutations | | | | | | | | | | |

*Up to 0 CDR2 mutations in one clone (SEQ. ID NO: 36)

TABLE 4.1C (09D03 CDR3)

| 09D03 | CDR3* | | | | | | | | | | | | | | |
|---|---|---|---|---|---|---|---|---|---|---|---|---|---|---|---|
| Kabat numbering | 95 | 96 | 97 | 98 | 99 | 100 | 100a | | | | | | | | |
| absolute numbering | 1 | 2 | 3 | 4 | 5 | 6 | 7 | 8 | 9 | 10 | 11 | 12 | 13 | 14 | 15 |
| wildtype sequence mutations | D | L | D | P | N | R | I | F | S | R | D | E | A | A | Y |
| | . | . | . | | . | | | | | | | | | | |

*Up to 0 CDR mutations in one clone (HQ ID NO: 54)

After cloning and sequencing Clone 09A05 was identified as a family member of clone 03B02 (cf. Tables A-1 and A-2). The sequence variability of CDR regions is depicted in the Tables 4.1D, 4.1E and 4.1F below. The amino acid sequences of the CDRs of clone 03602 were used as reference against which the CDRs of the family members were compared (CDR1 starts at Kabat position 26, CDR1 starts at Kabat position 50, and CDR3 starts at Kabat position 95).

TABLE 4.1D (03B02 CDR1)

| 03B02 | | | | | CDR1* | | | | | |
|---|---|---|---|---|---|---|---|---|---|---|
| Kabat numbering | 26 | 27 | 28 | 29 | 30 | 31 | 32 | 33 | 34 | 35 |
| absolute numbering | 1 | 2 | 3 | 4 | 5 | 6 | 7 | 8 | 9 | 10 |
| wildtype sequence | R | R | T | I | S | S | G | T | M | G |
| mutations | | | | | | | | | | |

*Up to 0 CDR1 mutations in one clone (SEQ. ID NO: 33)

TABLE 4.1E (03B02 CDR2)

| 03B02 | | | | | CDR2* | | | | | |
|---|---|---|---|---|---|---|---|---|---|---|
| Kabat numbering | 50 | 51 | 52 | 53 | 54 | 55 | 56 | 57 | 58 | 59 |
| absolute numbering | 1 | 2 | 3 | 4 | 5 | 6 | 7 | 8 | 9 | 10 |
| wildtype sequence | A | I | R | W | S | S | G | M | P | Y |
| mutations | | | | | | | | I | T | F |

*Up to 3 CDR2 mutations in one clone (SEQ ID NO: 50)

TABLE 4.1F (03B02 CDR3)

| 03B02 | | | | | | | CDR3* | | | | | | | | | |
|---|---|---|---|---|---|---|---|---|---|---|---|---|---|---|---|---|
| Kabat numbering | 95 | 96 | 97 | 98 | 99 | 100 | 100a | | | | | | | | | |
| absolute numbering | 1 | 2 | 3 | 4 | 5 | 6 | 7 | 8 | 9 | 10 | 11 | 12 | 13 | 14 | 15 | 16 |
| wildtype sequence | D | R | S | A | F | R | D | P | S | F | D | V | N | Y | E | Y |
| mutations | . | . | . | | L | E | | | | | | | | | | |

*Up to 2 CDR mutations in one clone (SEQ ID NO: 68)

After cloning and sequencing clones 03D02 and 02C10 were identified as family members of clone 03D01 (cf. Tables A-1 and A-2). The sequence variability of CDR regions is depicted in the Tables 4.1G, 4.1H and 4.1I below. The amino acid sequences of the CDRs of clone 03D01 were used as reference against which the CDRs of the family members were compared (CDR1 starts at Kabat position 26, CDR1 starts at Kabat position 50, and CDR3 starts at Kabat position 95).

TABLE 4.1G (03D01 CDR1)

03D01 CDR1*

| | | | | | | | | | | |
|---|---|---|---|---|---|---|---|---|---|---|
| Kabat numbering | 26 | 27 | 28 | 29 | 30 | 31 | 32 | 33 | 34 | 35 |
| absolute numbering | 1 | 2 | 3 | 4 | 5 | 6 | 7 | 8 | 9 | 10 |
| wildtype sequence | G | F | T | F | S | P | Y | Y | M | G |
| mutations | | | | | | | | | | |

*Up to 0 CDR1 mutations in one clone (SEQ ID NO: 28)

TABLE 4.1H (03D01 CDR2)

03D01 CDR2*

| | | | | | | | | | | |
|---|---|---|---|---|---|---|---|---|---|---|
| Kabat numbering | 50 | 51 | 52 | 53 | 54 | 55 | 56 | 57 | 58 | 59 |
| absolute numbering | 1 | 2 | 3 | 4 | 5 | 6 | 7 | 8 | 9 | 10 |
| wildtype sequence | A | I | S | R | S | R | G | T | T | Y |
| mutations | | | T | W | | | | I | L | |

*Up to 3 CDR2 mutations in one clone (SEQ. ID NO: 44)

TABLE 4.1I (03D01 CDR3)

03D01 CDR3*

| | | | | | | | | | | | | | | | |
|---|---|---|---|---|---|---|---|---|---|---|---|---|---|---|---|
| Kabat numbering | 95 | 96 | 97 | 98 | 99 | 100 | 100a | | | | | | | | |
| absolute numbering | 1 | 2 | 3 | 4 | 5 | 6 | 7 | 8 | 9 | 10 | 11 | 12 | 13 | 14 | 15 |
| wildtype sequence | G | R | S | P | G | D | P | S | R | T | Y | L | Y | D | Y |
| mutations | S | . | . | . | | | | | | | | | | E | |

*Up to 1 CDR mutation in one clone (SEQ. ID NO: 62)

The above results demonstrate that some amino acid variation is permissible, while retaining binding and inhibition characteristics. Notably, binding to ADAMTS5 is not a predictor for inhibition of ADAMTS5 activity. For instance, clone 3F04 is a potent binder but a weak inhibitor.

Example 5 Characterization of Purified Monovalent ADAMTS5 Nanobodies

Clones selected from the screening described in Example 4 were further characterized. Upon transformation in E. coli (TG-1) of selected Nanobodies, expression was induced by addition of 1 mM IPTG and allowed to continue for 4 hours at 37° C. After spinning the cell cultures, periplasmic extracts were prepared by freeze-thawing the pellets followed by centrifugation. These extracts were then used as starting material for purification via IMAC on HisTrap FF crude 1 ml columns (GE healthcare, Buckinghamshire, United Kingdom) followed by desalting via Zeba spin columns (Pierce, Rockford, IL, USA) resulting in at least 95% purity as assessed via SDS-PAGE.

5.1 Evaluation of ADAMTS5 Blocking Nanobodies in Enzymatic ADAMTS5 Assays

The ability of Nanobodies to prevent ADAMTS5 mediated cleavage of Aggrecan was confirmed in a FRET-based enzymatic assay, essentially as described in Example 4. Data were analysed with Graphpad Prism software. From the enzyme progression curve, the initial velocity was determined ($v_i$) and these values were plotted as a function of inhibitor concentrations and $IC_{50}$ values were calculated. In essence, the human FRET assay with purified Nanobodies confirmed the results described in Example 4 with the periplasmic extracts. The $IC_{50}$s ranged between 1.8E-09 M to 3.7E-08 M. Notably, although the conventional mAb 12F4 had a somewhat better $IC_{50}$ of 1.0E-09 M than the monovalent Nanobodies, all Nanobodies showed better efficacy (data not shown).

Next to the FRET-based assay, an AlphaLISA (Perkin Elmer, Waltham, MA, US) based human ADAMTS5 assay with a biotinylated 43-mer Aggrecan oligopeptide as substrate was performed. Upon ADAMTS5 cleavage of this substrate, a biotinylated ARGSV neo epitope product (SEQ ID NO: 185) is released, which can be detected by streptavidin-AlphaScreen donor beads and an anti-neo epitope ("ARGSV" (SEQ ID NO: 185)) antibody captured on anti-mouse IgG-coated AlphaLISA acceptor beads, resulting in the generation of a luminescence AlphaScreen signal upon laser excitation.

To determine the inhibitory potential of the Nanobodies, serial dilutions of purified Nanobodies (together with a positive control and a negative irrelevant Nanobody control) were incubated with human ADAMTS5 (R&D Systems, Minneapolis, US; cat #2198-AD) for 15 minutes at room temperature in a 384-well Optiplate (Perkin Elmer, Waltham, MA, US). Following addition of a biotinylated 43-mer Aggrecan oligopeptide substrate (Biosyntan, Berlin, Germany) and incubation of 3 hours at 37° C. the reaction was stopped. The first detection step was performed by the addition of 5 µl detection solution 1 comprising Aggrecan antibody against the neo-epitope "ARGSV" (SEQ ID NO: 185), mouse BC3 mAb (MDBioproducts, Egg, Switzerland) and Streptavidin AlphaScreen donor beads (Perkin Elmer). After 1 h incubation at room temperature, 5 µl of a second detection solution was added, comprising the anti-mouse AlphaLISA acceptor beads (Perkin Elmer). The plates were incubated for 2 hours at room temperature in the dark. Measurement was performed by reading the plates on the Envision Multi label Plate reader (Perkin Elmer, Waltham, MA, US).

To determine the ability of the Nanobodies to prevent ADAMTS5 mediated cleavage of the substrate, the decrease in signal was analysed in function of Nanobody concentration and $IC_{50}$ values were calculated.

The results are summarized in Table 5.1.

TABLE 5.1

Potency ($IC_{50}$) and % inhibition of ADAMTS5 for Nanobodies and reference compounds in human AlphaLISA enzymatic assay.

| Compound ID | Human AlphaLISA | |
|---|---|---|
| | IC50 [M] | % inhibition |
| mAb 12F4 H4L0 | 6.5E−11 | 100 |
| 2F03 | 7.5E−11 | 100 |
| 11B06 | 1.0E−10 | 100 |
| 9D03 | 1.1E−10 | 100 |
| 2A12 | 1.5E−10 | 100 |
| 2D07 | 1.9E−10 | 100 |
| 3D02 | 2.2E−10 | 100 |
| 3B02 | 3.0E−10 | 100 |
| 9A05 | 3.2E−10 | 100 |
| 3D01 | 3.9E−10 | 96 |
| 2C10 | 4.5E−10 | 100 |
| rhTIMP3 | 6.1E−10 | 100 |
| 2D12 | 6.9E−10 | 100 |
| 9D10 | 9.7E−10 | 100 |
| 13E02 | 2.2E−09 | 100 |
| 9D09 | 2.6E−09 | 100 |
| 7B11 | 3.6E−09 | 100 |
| 2A02 | 4.3E−09 | 99 |
| 3B03 | 1.2E−08 | 100 |
| MSC2310852A | 1.4E−07 | 99 |

In the AlphaLISA assay, at least three monovalent Nanobodies (2F03, 11606 and 9D03) show similar $IC_{50}$ values than the conventional mAb 12F4, while the remainder has higher values. However, all Nanobodies show a near 100% inhibition. Remarkably, Nanobody 3603, which has an $IC_{50}$ value at least a factor 100 higher than mAb 12F04 still has 100% inhibition.

5.2 Evaluation of ADAMTS5 Blocking Nanobodies in Bovine Explant Assay

Evaluation of the ability of the Nanobodies to block cartilage degradation in an ex vivo assay, in which the substrate is presented in a condition closer to the physiological condition compared to biochemical assays, a bovine explant assay was performed. In brief, bovine cartilage explant chips (diameter 4 mm) were prepared freshly from cow knee joints and incubated in 96-well plates in presence of IL-1α to induce cartilage degradation. As a measure of cartilage/Aggrecan degradation, the release of GAG was detected in the supernatant after 5 days of incubation (37° C., 7.5% $CO_2$) via the metachromatic dye 1,9 dimethylmethylene blue (emission at 633 nm). Chondroitin sulphate was included as assay standard. Efficacy was defined by means of the IL-1α-induced controls without compound (0%) and in presence of MSC2310852A (100% effect).

Results are summarized in Table 5.2.

TABLE 5.2

$IC_{50}$ values from monovalent Nanobodies in the bovine explant assay.

| ID | IC50 [M] | Experiment ID* |
|---|---|---|
| mAb 12F4 H4L0 | 3.2E−06 | exp A |
| 2F03 | 1.4E−08 | exp A |
| 11B06 | 4.80E−08 | exp C |
| 9D03 | 5.9E−08/2.7E−07 | exp G/exp F |

TABLE 5.2-continued $IC_{50}$ values from monovalent Nanobodies in the bovine explant assay.

| ID | IC50 [M] | Experiment ID* |
|---|---|---|
| 2A12 | 2.40E−08 | exp C |
| 02D07 | 3.30E−08 | exp C |
| 3D02 | 8.80E−07 | exp F |
| 3B02 | 1.40E−07 | exp D |
| 9A05 | 5.10E−07 | exp F |
| 3D01 | 2.2E−08/1.3E−07 | exp D/exp G |
| 2D12 | 8.00E−07 | exp D |
| 2A02 | 2.40E−06 | exp D |

*results can only be compared within 1 assay using the same explant, with identical experiment ID 5.3 Epitope Binning An SPR-based "sandwich assay" on a Biacore TWO instrument was performed to group the ADAMTS5 Nanobodies into different epitope bins. To this end, each anti-ADAMTS5 Nanobody was immobilized on a CM5 sensor chip via amine coupling using EDC and NHS chemistry. After a capturing step of 100 nM ADAMTS5, purified Nanobodies at a concentration of 1 μM were injected, each in a single cycle and without regeneration, with a surface contact time of 120 seconds and a flow rate of 45 μL/minute. Curves were processed with Biacore T100 Evaluation software and evaluated for additional binding to the captured ADAMTS5 (different bin) or not (same bin).

Nanobodies could be divided in two groups: one large bin ("bin 1"), which comprises all inhibitory Nanobodies having similar or overlapping epitopes, and a second group comprising the binding, non-functional Nanobody 3F04 which recognizes a different epitope on ADAMTS5 ("bin 2").

Table 5.3 summarizes the binding epitopes of the tested Nanobodies.

TABLE 5.3 epitope bins of the anti-ADAMTS5 Nanobodies

| bin 1 | 2A02 | 2A12 | 2C10 | 2D07 | 2D12 | 2F03 | 2G01 | 3B02 | 3B03 |
| | 3D01 | 3D02 | 7611 | 9A05 | 9D03 | 9D09 | 9D10 | 11B06 | 13E02 |
| bin 2 | 3F04 | | | | | | | | |

5.4 Species Cross Reactivity

Species cross-reactivity was initially evaluated via SPR-based off-rate analysis on a Biacore T100 instrument. Nanobodies were tested for binding to human, cynomolgus monkey ("cyno"), guinea pig, mouse, and bovine ADAMTS5. To this end, recombinant ADAMTS5 was immobilized onto a CM5 chip via amine coupling using EDC and NHS. Purified Nanobodies were injected for 2 minutes at a concentration of 100 nM and allowed to dissociate for 15 min at a flow rate of 45 ul/min. Off-rate for each individual Nanobody was determined by fitting a 1:1 interaction model (Langmuir model) onto the individual dissociation curves using the BIA Evaluation software. As a reference, off-rates on human ADAMTS5 were determined in each experiment.

The results are summarized in Table 5.4A.

TABLE 5.4A

Overview of species cross reactivity data of monovalent anti-ADAMTS5 Nanobodies

| | SPR based off-rate, kd (1/s) on ADAMTS5 | | | | | | |
|---|---|---|---|---|---|---|---|
| | Experiment 1 | | | Experiment 2 | | Experiment 3 | |
| Nanobody ID | Human | Cyno | Guinea pig | Human | Mouse | Human | Bovine |
| 2F03 | 3.3E-05 | 2.2E-05 | 3.4E-05 | 6.5E-05 | 2.9E-04 | 9.7E-05 | 4.3E-05 |
| 11B06 | 1.7E-04 | 1.4E-04 | 1.7E-04 | 2.7E-04 | 5.3E-04 | 3.8E-04 | 2.4E-04 |
| 9D03 | 9.8E-04 | 9.2E-04 | 1.0E-03 | 1.2E-03 | 3.7E-03 | 1.4E-03 | 9.9E-04 |
| 2A12 | 1.4E-04 | 1.0E-04 | 1.2E-04 | 2.3E-04 | 4.4E-04 | 3.1E-04 | 1.7E-04 |
| 2D07 | 1.1E-03 | 9.8E-04 | 1.1E-03 | 9.4E-04 | 1.8E-03 | 1.0E-03 | 6.2E-04 |
| 3B02 | 7.3E-04 | 7.4E-04 | 1.0E-03 | 8.5E-04 | 2.0E-03 | 1.2E-03 | 1.1E-03 |
| 3D01 | 2.3E-04 | 2.0E-04 | 2.7E-04 | 3.2E-04 | 6.4E-04 | 4.6E-04 | 3.5E-04 |

For each Nanobody tested, similar off-rates were observed for all tested species.

In addition, cross-reactivity for cynomolgus monkey and guinea pig ADAMTS5 was also addressed by potency determination using AlphaLISA, essentially as described in Example 5.1, but using a biotinylated cynomolgus 43-Aggrecan oligopeptide substrate and a biotinylated guinea pig 43-Aggrecan oligopeptide substrate. To determine the ability of the Nanobodies to prevent ADAMTS5 mediated cleavage of the substrate, the decrease in signal was analysed in function of Nanobody concentration and $IC_{50}$ values were calculated.

The resulting potencies are summarised in Table 5.4B.

TABLE 5.4B

Overview of species cross reactivity data of monovalent anti-ADAMTS5 Nanobodies

| | Potency (IC50, M) Alpha LISA | | |
|---|---|---|---|
| Nanobody ID | Human | Cyno | Guinea pig |
| 2F03 | 7.5E-11 | 8.1E-11 | 3.0E-10 |
| 11B06 | 1.0E-10 | 1.2E-10 | 3.5E-10 |
| 9D03 | 1.1E-10 | 1.2E-10 | 1.3E-10 |
| 2A12 | 1.5E-10 | 1.9E-10 | 5.3E-10 |
| 2D07 | 1.9E-10 | 1.5E-10 | 3.6E-10 |
| 3B02 | 3.0E-10 | 1.9E-10 | 4.6E-10 |
| 3D01 | 3.9E-10 | 2.2E-10 | 3.5E-10 |

All Nanobodies and the control compounds blocked human and cyno ADAMTS5 with similar potencies. In the guinea pig AlphaLISA, the most potent Nanobodies showed slightly lower potencies than in the human AlphaLISA, but this is most likely the result of lower assay sensitivity due to increased enzyme concentration.

Rat cross-reactivity of Nanobodies 2A12, 2F03, 093 and 049 was evaluated by means of an SPR-based affinity determination using Biacore T100. For referencing, affinity for human ADAMTS5 was also determined. Thereto, rat and human ADAMTS5 were immobilized onto a CM5 chip via amine coupling, using EDC and NHS chemistry. Purified Nanobodies were injected for 2 minutes at different concentrations (between 1 and 1000 nM) and allowed to dissociate for 25 min at a flow rate of 45 µl/min. The kinetic constants were calculated from the sensorgrams using the BIAEvaluation software (1:1 interaction).

As presented in Table 5.4C, similar affinities on human ADAMTS5 and rat ADAMTS5 were obtained for all tested Nanobodies. The affinity of the half-life extended Nanobody 069 (cf. infra) was similar to the affinity of its monovalent counterpart (which is Nanobody 049), indicating that the addition of ALB11 at the C-terminus has no effect on the affinity. The affinity of half-life extended biparatopic Nanobody 130 was on both species higher (15-fold on human ADAMTS5 and 10-fold on rat ADAMTS5) compared to the affinity of half-life extended Nanobody 069 (Table 5.4C).

TABLE 5.4C overview of affinities on human ADAMTS5 and rat ADAMTS5

| ID | Description | KD (nM) human ADAMTS5 | KD (nM) rat ADAMTS5 |
|---|---|---|---|
| 2A12 | | 1.9 | 1 |
| 2F03 | | 1.6 | 0.7 |
| 093 | 3F04 (N100,0) | 4.9 | 5.3 |
| 049 | 11B06 (N52S) | 3.5 | 1.7 |
| 069 | 049-35GS-ALB11 | 2.7 | 1.3 |
| 130 | 049-35GS-093-35GS-ALB11 | 0.18 | 0.13 |

5.5 Inhibition of MMP-1 and MMP-14 Activity

To confirm the selectivity of the Nanobodies for ADAMTS5, inhibition of the enzyme activity of MMP-1 and MMP-14 was evaluated with FRET-based assays with the respective enzymes. In brief, activated human MMP-1 or MMP-14 was incubated for 30 minutes at room temperature with 10 µl of dilution series of Nanobody. After incubation, 20 µl of respectively 5 µM or 2.5 µM fluorogenic peptide substrate (Mca-PLGL-Dpa-AR-NH2 (SEQ ID NO: 189) Fluorogenic MMP Substrate (R&D Systems cat #ES001)) was added. The ability of the Nanobodies to prevent MMP-1 and MMP-14 mediated cleavage was monitored every minute for 2 hours at 37° C. on a Tecan Infinite M1000 plate reader.

The resulting titration curves are shown in FIGS. 1A and 1B.

Whereas the natural inhibitors TIMP2 and TIMP3 inhibited MMP-1 and MMP-14 activity, none of the tested Nanobodies showed inhibition.

5.6 Inhibition of Human ADAMTS4 Activity

To evaluate inhibition of human ADAMTS4, an assay similar to the human ADAMTS5 AlphaLISA was carried out, essentially as described in Example 5.1, but using human ADAMTS4 (R&D Systems, Minneapolis, US; cat #4307-AD). To determine the ability of the Nanobodies to prevent human ADAMTS4 mediated cleavage of the substrate, the decrease in signal was analysed in function of Nanobody concentration and $IC_{50}$ values were calculated.

The results are shown in FIG. 2.

Whereas the small molecule MSC2310852A inhibited human ADAMTS4 activity, none of the tested Nanobodies or mAb 12F4 showed inhibitory activity (see FIG. 2). The monoclonal antibody 12F4 (H4L0) was described to be selective over ADAMTS4 in WO 2011/002968.

Example 6 Formatting of Nanobodies 6.1 Knock Out of N-Glycosylation Motifs

N-glycosylation motifs present in Nanobody 11606 (position N52) and Nanobody 3F04 (position N110f) were knocked out prior to formatting. The sites were randomized by means of an NNK codon library. Since these positions are located in the CDRs, mutation of the motif may potentially influence binding characteristics. Accordingly, the libraries were screened for possible substitutions which did not affect the binding property by SPR based off-rate analysis on human ADAMTS5 using a Biacore T100 instrument, essentially as described in Example 5.4.

Surprisingly, substituting amino acid N52 by Serine in Nanobody 11B06 and amino acid $N100_F$ by Glutamine in Nanobody 3F04 did not affect binding (data not shown).

Hence, as building blocks for further formatting, Nanobodies 049 (=11B06 (N52S)) and 093 (3F04 ($N100_FQ$)) were used to represent Nanobodies 11B06 and 3F04, respectively (see Table A-1).

6.2 Generation of Formatted Nanobodies

For the generation of half-life extended Nanobody constructs which block human ADAMTS5 aggrecanase activity, Nanobodies 2A12, 2D07, 2F03, 049, 9D03 and 3602 were fused to an anti-Human serum albumin (HSA)-Nanobody ALB11 (see Table 6.3). In addition, ALB11 half-life extended constructs were also generated from a combination of two Nanobodies from different binding epitopes (a combination of a bin 1 member and a bin 2 member). The formatted Nanobody constructs were expressed in *Pichia pastoris*, secreted into the cultivation medium and affinity purified on Poros MabCaptureA Protein A beads (Applied Biosystems, Bleiswijk, Netherlands cat #4374729). The integrity of the Nanobody constructs was confirmed.

6.3 Potency in AlphaLISA in Absence and Presence of HSA

The formatted Nanobody constructs were tested in the AlphaLISA, as described in Example 5.1. Additionally, the influence of HSA binding on Nanobody potency was addressed by performing the experiment in presence of an excess of HSA (4.2 µM final concentration).

The $IC_{50}$ values of all half-life extended Nanobody constructs are listed in Table 6.3.

TABLE 6.3

Potencies of formatted Nanobody constructs (+/− HSA) as determined in AlphaLISA

| Nanobody ID | Description | IC50 (M) −HSA | +HSA | Nanobody ID | IC50(M) −HSA |
|---|---|---|---|---|---|
| 004 | 2A12-35GS-ALB11 | 1.3E−10 | 1.1E−10 | 2A12 | 1.5E−10 |
| 005 | 2D07-35GS-ALB11 | 2.9E−10 | 3.4E−10 | 2D07 | 1.9E−10 |
| 006 | 2F03-35GS-ALB11 | 7.0E−11 | 9.2E−11 | 2F03 | 7.5E−11 |
| 069 | 049-35GS-ALB11 | 6.9E−11 | 9.8E−11 | 049 | 1.0E−10 |
| 070 | 9D03-35GS-ALB11 | 4.1E−10 | 6.0E−10 | 9D03 | 1.1E−10 |
| 071 | 3B02-35GS-ALB11 | 2.8E−10 | 4.1E−10 | 3B02 | 3.0E−10 |
| 129 | 2F03-35GS-093*-35GS-ALB11 | 1.1E−10 | ND | | |
| 130 | 049$^{2*}$-35GS-093-35GS-ALB11 | 9.7E−11 | ND | | |
| 131 | 9D03-35GS-093-35GS-ALB11 | 8.1E−11 | ND | | |

ND = not determined ;

093* = 3F04 ($NI00_FQ$);

049$^{2*}$ = 11B06 (N52S)

The results indicate that neither ALB11 formatting nor HSA binding affects the potency of the Nanobody constructs.

6.4 Binding to HSA

The affinity of the ALB11 Nanobody to HSA was determined via SPR on a Biacore TWO. To this end, HSA was immobilized onto a CM5 chip via amine coupling and processed essentially as described in Example 5.3 As a reference, the affinity of monovalent ALB11 was also determined, which was 3.2 nM.

The results are summarized in Table 6.4.

TABLE 6.4

Affinity of HLE Nanobody constructs for HSA

| ID | KD (nM) | | |
|---|---|---|---|
| from FNb* | FNb-ALB11 | FNb-093³*-ALB11 | FNb-ALB11-093 |
| 2F03 | 46 | 66 | 52 |
| 049²* | 40 | 55 | 40 |
| 2A12 | 27 | ND | ND |

ND = not determined;
*FNb = functional Nanobody;
049²* = 11B06 (N52S);
093³* = 3F04 (NI00<sub>i</sub>Q)

All half-life extended ADAMTS5 Nanobody constructs had similar affinities (see Table 6.4), which was lower than the affinity of monovalent ALB11 for HSA.

6.5 Affinity Determination for Human ADAMTS5 with KinExA

The affinity of the formatted Nanobody construct 069 (049-35GS-ALB11) and Nanobody construct 130 (049-35GS-093-ALB11)(see also Table 6.5) were determined in solution with a kinetic exclusion assay on a KinExA3000 instrument (Sapidyne, Boise, USA). To this end, human ADAMTS5 was coupled to PMMA beads according to the manufacturer's instructions, described in detail by Darling and Brault (2004 Assay Drug Dev Technol. 2:647-57). A fixed concentration of Nanobody construct (50 μM Nanobody construct 069 or 5 μM Nanobody construct 130) was added to a dilution series of human ADAMTS5 ranging from 2 nM-0.2 μM and incubated at room temperature for 16 hours till equilibrium was reached. Subsequently, mixtures were injected via KinExA's autosampler over a column packed with human ADAMTS5-conjugated PMMA beads to capture free Nanobody construct on the beads and detect with Alexa647-labeled HSA. Percent free Nanobody construct was plotted as a function of titrated human ADAMTS5 and fitted using the KinExA Pro Software v3.2.6.

The results are shown in Table 6.5.

TABLE 6.5

Affinities of 2 Nanobody constructs for binding to human ADAMTS5 as determined via KinExA

| Nanobody | Description | KD (pM) |
|---|---|---|
| 069 | 049*-35GS-ALB11 | 20.4 |
| 130 | 049-35GS-093*-ALB11 | 1.2 |

049* = 11B06 (N52S);
093²* = 3F04 (N100<sub>i</sub>Q)

A circa 20 times higher affinity is observed for Nanobody construct 130 compared to Nanobody construct 069. These data confirm the avid binding on human ADAMTS5 of Nanobody construct 130.

Example 7 Sequence Optimization (SO) of Nanobodies

Exemplary Nanobody 2F03, Nanobody 049 (11606 (N52S)) and Nanobody 093 (3F04 (N100<sub>i</sub>Q)) were subjected to a sequence optimisation process. Sequence optimisation is a process in which a parental Nanobody sequence is mutated and this process covers the humanisation (i) of the Nanobody and knocks-out post-translational modifications (ii) as well as epitopes for potential pre-existing antibodies (iii). Nanobody ALB11 was also mutated to knock out epitopes for potential pre-existing antibodies.

(i) for humanisation purposes the parental Nanobody sequence is mutated to yield a Nanobody sequence which is more identical to the human IGHV3-IGHJ germline consensus sequence. Specific amino acids in the framework regions (with the exception of the so-called hallmark residues) that differ between the Nanobody and the human IGHV3-IGHJ germline consensus are altered to the human counterpart in such a way that the protein structure, activity and stability are kept intact. A handful of hallmark residues are known to be critical for the stability, activity and affinity of the Nanobody and are therefore not mutated.

(ii) the amino acids present in the CDRs and for which there is experimental evidence that they are sensitive to post-translational modifications (PTM) are altered in such a way that the PTM site is inactivated while the protein structure, activity and stability are kept intact.

(iii) the sequence of the Nanobody is optimised, without affecting protein structure, activity and stability, to minimise binding of any naturally occurring pre-existing antibodies and reduce the potential to evoke a treatment-emergent immunogenicity response.

For the generation of sequence optimised formatted Nanobody construct 581 and Nanobody construct 579, respective building blocks were connected via 35GS linkers. The resulted in Nanobody construct 581 (2F3$^{SO}$-35GS linker-Alb11) and Nanobody construct 579 (2F3$^{SO}$-35GS linker-093$^{SO}$-35GS linker-Alb11), respectively (cf. Table A-1). The constructs were produced in *Pichia pastoris* as tagless proteins and purified via Protein A affinity chromatography, followed by desalting. The integrity of the Nanobody constructs was confirmed.

7.1 Affinity for Human ADAMTS5

Affinity of Nanobody construct 581 (2F3$^{SO}$-35GS linker-Alb11) was determined using KinExA, as described in Example 6.5 with a few minor adaptations to the described protocol. A fixed concentration of 20 μM of Nanobody construct 581 was incubated together with a dilution series of human ADAMTS5 (2.2-fold serial dilutions ranging between 20 nM and 0.32 μM and a blank without ADAMTS5). To test for interference of albumin, HSA was added to this pre-incubation in selected experiments with human ADAMTS5, at a concentration of 100-fold its KD for Nanobody construct 581. Mixtures were incubated and allowed to reach equilibrium for 24 hours prior to injection via KinExA's autosampler over a column packed with human ADAMTS5-conjugated PMMA beads. Captured Nanobody construct 581 was detected using an AF647-labelled anti-Nanobody tool recognizing Nanobody construct 581 (generated by Ablynx).

Results are presented in Table 7.1.

TABLE 7.1

Affinity of Nanobody construct 581 for
human ADAMTS5 with and without HSA

| + or − HSA | $K_D$ (pM) | 95%CI on $K_D$ (pM) |
|---|---|---|
| − HSA (n = 3) | 3.65 (CV 20%) | 2.27-5.86 |
| + HSA (n = 3) | 4.84 (CV 22%) | 3.45-6.80 |

The results show that the affinity of Nanobody construct 581 for human ADAMTS5 is 3.65 µM without HSA and 4.84 µM with HSA.

7.2 Affinity for Serum Albumin

Affinity of the ALB11 building block in Nanobody construct 581 (2F3$^{SO}$-35GS linker-Alb11) for binding to human, cynomolgus monkey, guinea pig, mouse and rat serum albumin (SA) was determined using SPR as described in Example 5.3.

Results are shown in Table 7.2.

TABLE 7.2

Affinity ($K_D$, nM) of Nanobody construct
581 for binding to human, cynomolgus monkey,
guinea pig, mouse and rat serum albumin

| Nanobody ID | human SA | cyno SA | guinea Pig SA | mouse SA | rat SA |
|---|---|---|---|---|---|
| 581 | 48 | 51 | 420 | 790 | >7500* |

*off-rate is outside detection limit: >5.0E−01 (1/s)

7.3 Pre-Ab Binding

Nanobody construct 581 (2F3$^{SO}$-35GS linker-Alb11) and Nanobody construct 579 (2F3$^{SO}$-35GS linker-093$^{SO}$-35GS linker-Alb11) were screened for pre-existing antibody (pre-Ab) binding from 3 relevant donor serum sample sets (samples from healthy subjects, OA samples and a biased set of samples with known residual pre-Ab binding to other Nanobodies) via SPR technology on a ProteOn XPR36 instrument. Blood samples were analysed for binding to anti-ADAMTS5 Nanobody constructs, which were captured on HSA. Pre-existing antibody binding levels were determined after double referencing of the sensorgrams by setting report points at 125 seconds (5 seconds after end of association). Analysis was performed with ProteOn manager 3.1 (Bio-Rad Laboratories, Inc.).

The results are shown in FIG. 3A-3B.

Both Nanobody constructs had low residual pre-Ab binding levels with Nanobody construct 581 clearly showing the least residual pre-Ab binding (cf. FIG. 3A-3B).

7.4 Functionality in Human AlphaLISA

An AlphaLISA was performed with Nanobody construct 581 (2F3$^{SO}$-35GS linker-Alb11) using human ADAMTS5 essentially as described in Example 5.1.

The results are shown in Table 7.4.

TABLE 7.4

Potency (pM) of Nanobody construct 581 as determined by AlphaLISA.

| Sample | IC50(pM) | 95% CI (pM) |
|---|---|---|
| mAb 12F4H4L0 | 120 | 102-140 |
| 581 | 188 | 157-226 |

The results show that the potency of Nanobody construct 581 is 188 µM.

7.5 Immunogenicity Profiling in Dendritic Cell-T Cell Assay

The relative immunogenicity was determined in a Dendritic Cell-T cell proliferation assay. In essence, Nanobodies were tested against a set of 50 healthy donor cell samples containing the most abundant HLA class II alleles, as such representing the majority of the global population. The immune response was assessed using T cell proliferation as a surrogate marker for anti-drug antibody formation. Keyhole Limpet Hemocyanin (KLH) was used as a positive control. The positive control KLH led to a positive response in all of the 50 donors. None of the donors tested positive for Nanobody construct 581 (2F3$^{SO}$-35GS linker-Alb11). Nanobody construct 579 (2F3$^{SO}$-35GS linker-093$^{SO}$-35GS linker-Alb11) led to a positive response in three donors, or 6%. In the blank condition (medium only), 2 out of 50 donors, or 4%, were found to respond positive. These results were used to set an overall response threshold of more than 3 out of 50 donors corresponding to an overall response threshold of >6%. The overall immunogenic potential for the tested Nanobodies was considered low as the percentage of significant, positive responses was 6% (see Table 7.5).

TABLE 7.5

Result immunogenicity profiling as determined in a DC-T Cell Assay

| Test product | # Positive responses | Immunogenic potential |
|---|---|---|
| Blank | 2 (4%) | / |
| KLH | 50 (100%) | / |
| 581 | 0 (0%) | Low |
| 579 | 3 (6%) | Low |
| Control Nb | 1 (2%) | Low |

7.6 Binding to human ADAMTS1

Binding to human ADAMTS1 was tested in a binding ELISA (FIG. 4A). In brief, 18.5 nM of human ADAMTS1 (R&D Systems, Minneapolis, US; cat #2197-AD) and human ADAMTS5 (R&D Systems, Minneapolis, US; cat #2198-AD) were coated on 384-well MaxiSorp plates (Nunc, Wiesbaden, Germany). Wells were blocked with a casein solution (1%) and dilution series of Nanobody construct 581 (2F3SO-35GS linker-Alb11) and anti-human ADAMTS1 mAb (R&D Systems, Minneapolis, US; cat #MAB2197) were tested for binding on both coated proteins. After detection with an HRP conjugated anti-Nanobody tool recognizing Nanobody construct 581 (generated by Ablynx) and an HRP conjugated anti-mouse antibody (Abcam, Cambridge, UK) respectively, and a subsequent enzymatic reaction in the presence of the substrate esTMB (3,3',5,5'-tetramentylbenzidine) (SDT, Brussels, Belgium), OD450 nm was measured.

A dose response curve was observed for Nanobody construct 581 on human ADAMTS5 and for anti-human ADAMTS1 mAb on human ADAMTS1, showing that Nanobody construct 581 does not bind to human ADAMTS1.

7.7 Binding to Human ADAMTS4 and ADAMTS15

Binding to human ADAMTS4 and ADAMTS15 was tested in a binding ELISA (see FIG. 4B). In brief, 1 µg/mL of human ADAMTS4 (R&D Systems, Minneapolis, US; cat #4307-AD) or human ADAMTS15 (R&D Systems, Minneapolis, US; cat #5149-AD) was coated overnight at 1 µg/mL onto 96-well Maxisorp ELISA plates (Nunc, Wiesbaden, Germany). After blocking of the plates with SuperBlock T20 (PBS) (Thermo Scientific Pierce; cat #37516) a dose response curve of Nanobody construct 581 ("C011400581") or the positive control anti-ADAMTS4 mAb (R&D Systems, Minneapolis, US; cat #MA64307) or the positive control anti-ADAMTS15 mAb (R&D Systems, Minneapolis, US; cat #MAB5149) was applied on the coated plate starting at 1 µM and incubated for 1 hour at room temperature. Bound C011400581 Nanobody was detected with a biotinylated anti-Nanobody tool recognizing Nanobody construct 581 (generated by Ablynx), while the positive control mAb's were detected with a biotinylated goat anti-mouse pAb (Jackson Immuno Research; cat #115-065-062). For both streptavidin-HRP was used as a secondary detection tool (Thermo Scientific Pierce; cat #21126). Plates were then visualized by adding sTMB) (SDT, Brussels, Belgium). All dilutions and detection tools were prepared in assay diluent (=PBS+10% Superblock+0.05% Tween20). The colouring reaction was stopped after 2.5 minutes by adding 1M HCl. Optical density was measured at 450 nm with 620 nm as reference wavelength.

7.8 Species Cross-Reactivity Via KinExA Affinity Determination

Affinity of Nanobody construct 581 (2F3$^{SO}$-35GS linker-Alb11) towards several species' ADAMTS5 was determined using KinExA, as described in Example 7.1 For all species, human ADAMTS5 conjugated PMMA beads were prepared and use for capture of free Nanobody construct 581 as described above. Captured Nanobody construct 581 was detected using an AF647-labelled anti-Nanobody tool recognizing Nanobody construct 581 (generated by Ablynx). The results are shown in Table 7.7

TABLE 7.7

Affinity of Nanobody construct 581 for ADAMTS5 of cynomolgus monkey, rat, mouse and bovine

| Species ADAMTS5 | $K_D$ (pM) | 95% CI on $K_D$ (pM)| |
| --- | --- | --- |
| 3 Cynomolgus Monkey (n = 1) | 2.22 | 0.88-4.76 |
| Rat (n = 1) | 2.77 | 1.48-5.07 |
| Mouse (n = 1) | 2.81 | 0.30-11.42 |
| Bovine (n = 1) | 7.66 | 3.33-19.88| |

Example 8 Potency in Human Explant Assay

Nanobody construct 581 (2F3$^{SO}$-35GS linker-Alb11) was evaluated on the ability to block cartilage degradation in an ex vivo assay, essentially as described in Example 5.2, but now in a human explant assay. In brief, human cartilage explant chips (diameter 4 mm) were prepared freshly from human knee joints and incubated in 96-well plates in presence of 10 ng/ml IL-1α to induce cartilage degradation). As a measure of cartilage/Aggrecan degradation, the release of GAG was detected in the supernatant after 7 days of incubation (37° C., 7.5% $CO_2$) via the metachromatic dye 1,9 dimethylmethylene blue (emission at 633 nm). Chondroitin sulphate was included as assay standard. Efficacy was defined by means of the IL-1β and OSM induced controls without compound and in presence of MSC2310852A. CRB0017 is an anti-ADAMTS5 mAb that is to be used in a Phase I clinical trial (Rottapharm).

Results are summarized in FIG. 5 and Table 8.

TABLE 8

| Compound | Assay | IC50 GAG [µM] |
| --- | --- | --- |
| 581 | Human | 0.0025-0.0079 |
| 581 | Bovine | 0.035 |
| CRB0017 | Bovine | 0.33 |

Nanobodies demonstrate high potency and 100% inhibition of cartilage degradation (GAG loss) in human explant assay. As shown in Table 8, the Nanobodies are at least 10-fold better than CRB0017 in the bovine explant assay.

Example 9 Modulation C2M, C3M and exAGNX1 in a Bovine Co-Culture Model

The effect of Nanobody construct 581 ("581" in the figures) on GAG release and content, C2M (marker of collagen II degradation), C3M (marker of collagen III degradation) and exAGNx1 (marker for aggrecan degradation characterized the neo-epitope TEGE (SEQ ID NO: 186)) in a bovine co-culture system was investigated. In this co-culture systems, cartilage explants from a bovine knee were incubated together with the synovial membrane from the same animal for 28 days. Highest GAG release was detected after 7 days in culture (FIG. 6A). The Nanobody construct 581 was tested in three concentrations: 1 nM, 10 nM, 100 nM. Incubation of cartilage explants with synovium resulted in increased GAG release. Nanobody construct 581 inhibited GAG release (FIG. 6B).

In line with the GAG release, the analysis of the remaining GAG content of the cartilage explant (after papain digestion) revealed a decreased GAG content after co-incubation of explants with synovium compared to explants alone (FIG. 6C).

Parallel to the analysis of the GAG release, the release of exAGNx1 as a specific marker for aggrecan degradation was measured. The area under the curve analysis (AUC) showed a robust induction of exAGNx1 release when cartilage explants and synovium were incubated together. In addition, Nanobody construct 581 inhibited exAGNx1 release in a concentration dependent manner with complete inhibition at 100 nM 581 (FIG. 7).

To determine the effect of Nanobody construct 581 on the collagen network of the cartilage in the co-culture system, C2M, as a marker for collagen II degradation was determined. In contrast to the markers for degradation of the aggrecan network (GAG and exAGNx1), C2M started to increase between day 14 and 21. Incubation of Nanobody construct 581 in the co-culture system inhibited release of C2M (FIG. 8).

As additional marker for synovial inflammation, C3M (i.e. a collagen type III degradation marker) was determined. A time course analysis of C3M release indicated that C3M started to increase after 14 days, peaking around day 21. Treatment with Nanobody construct 581 inhibited C3M in all three concentrations (FIG. 9).

Example 10 Inhibition of Aggrecanase Activity in NHP

The ability of Nanobody construct 581 (2F3$^{SO}$-35GS linker-Alb11; "C011400581") to inhibit the aggrecanase activity in vivo was evaluated in cynomolgus monkey, a non-human primate (NHP) model. In short, Nanobody construct 581 was given to groups of 3 male and 3 female cynomolgus monkeys once weekly by subcutaneous (s.c.)

administration at dose levels of 6, 30 or 150 mg/kg for 4 weeks. A concomitant control group was treated with the vehicle, i.e. 20 mM Histidine, 8% Sucrose, 0.01% Tween 20 pH 6.0.

Inhibition of the aggrecanase activity was measured on serum samples collected at several timepoints by determining the level of aggrecan degradation fragments characterized by the presence of the neo-epitope ARGS (SEQ ID NO: 187) in serum. All Nanobody construct 581-treated animals showed a similar profile, i.e. ARGS (SEQ ID NO: 187) levels decreased upon first dosing and reached very low levels around or below the lower limit of measuring range (LLMR) of the assay (0.08 nM) between 48 hours and 120 hours. Subsequently, the ARGS (SEQ ID NO: 187) levels showed a sustained maximal decrease around or below the LLMR and did not return to baseline by the end of the study at 4 weeks.

An overview of the results is shown in FIG. 10.

In conclusion, ADAMTS5 specific Nanobodies engage the target following systemic administration and potently modulate ARGS neo-epitope (SEQ ID NO: 187) levels in vivo at all tested dose levels. Moreover, in contrast to the prior art mAbs, no test-item related pathological arrhythmias were observed. In addition, there was no evidence for any test-related ST-elevation was noted in male and female monkeys treated with the Nanobodies at any of the tested dose levels.

Example 11 Inhibition of Cartilage Degeneration

In order to further evaluate the ability of Nanobodies and Nanobody constructs to the inhibit cartilage degeneration in vivo, a mouse DMM (destabilization of the medial meniscus) model was used. In short, the medial meniscus was surgically destabilized. Exemplary Nanobody construct 581 ($2F3^{SO}$-35GS linker-Alb11) was either administered subcutaneously 3 days before induction of the DMM (prophylactic) or administered 3 days after induction of the DMM (therapeutic) at various concentrations. Upon 8 weeks of treatment, the animals were sacrificed and knees were removed. The knees were embedded in paraffin blocks, sectioned and stained with toluidine blue. Subsequently, the sections were scored for several parameters, including the medial cartilage degeneration sum.

The results are shown in FIG. 11.

The results show that there is a structural benefit up to 50% for both prophylactic and therapeutic treatment (s.c.) with Nanobodies in the DMM mouse model.

Example 12 Symptomatic Benefit in Rat Surgical OA Model

In order to evaluate the ability of Nanobodies to establish a symptomatic benefit, a rat surgical OA model was used. In short, rats were treated with ACLt and tMx surgery to induce OA at day 0. In the ACLt and tMx surgical model (anterior cruciate ligament transection extended with a medial meniscectomy) Nanobody construct 581 was administered s.c. every other day from day 3 onwards. On a weekly basis, the symptomatic benefit via gait analysis (on a CatWalk) as well as decrease in joint diameter were determined.

The results are shown in FIG. 12.

Osteoarthritis was induced (at day 0) in adult male rats (Lister Hooded; average body weight of 346±20 g) by anterior cruciate ligament transection (ACLT)+resection of the medial meniscus (tMx) surgery at the right knee joint. Treatment with vehicle or test item (sc) started at day 3 after surgery and continued every second day until day 42. The healthy control group had no surgical intervention but received sc vehicle at the same time points as the dosing groups. (A) Gait disturbance over time calculated as "% benefit over vehicle". Mean of the "healthy+placebo" group=100% benefit. Mean of the "ACLT tMx+vehicle" group=0% benefit. (B) Average "benefit over vehicle" at all investigated time points after treatment start. Shown is the mean±SEM of 14-15 rats/group. *=p<0.05 calculated with OneWay ANOVA and Dunnett's.

Early treatment with Nanobodies caused a dose-dependent, significant and meaningful symptomatic benefit during ACLT+tMx induced OA.

Example 13 Toxicity Studies in Cynomolgus Monkeys

A 4-week subchronic toxicity study in cynomolgus monkeys was conducted to obtain information on the systemic toxicity, local tolerability and safety pharmacology of Nanobodies. Exemplary Nanobody construct 581 ($2F3^{SO}$-35GS linker-Alb11) was given s.c. to groups of 3 male and 3 female cynomolgus monkeys (*Macaca fascicularis*) (once weekly by subcutaneous administration into the dorsal region at doses of 6, 30 or 150 mg/kg for 4 weeks. A concomitant control group was treated with the vehicle, 20 mM Histidine, 8% Sucrose, 0.01% Tween 20 pH 6.0.

No test item-related signs of local intolerance were noted at any of the tested dose levels. No test item-related effects were noted on the behavior, the body weight, the food consumption, the hematological and biochemical parameters, the lymphocytes typing, the CRP levels, the urinalysis parameters, the ophthalmological and auditory functions and the organ weights of any of the animals at any dose level (data not shown). Neither the macroscopic inspection at necropsy nor the histopathological examination did reveal any local or systemic organ changes that were related to the treatment with test item in any of the animals examined at any tested dose level.

Since it has been reported that mAb 12F4 demonstrated focal endocardial hemorrhage, a dose-dependent increase in blood pressure with no evidence of reversibility as well as cardiac conductance abnormalities (ST elevation and ventricular arrhythmias) (Larkin, et al., *The highs and lows of translational drug development: Antibody-mediated inhibition of ADAMTS-5 for osteoarthritis disease modification*, OARSI conference 2014: Paris; Renninger et al., *Identification of Altered Cardiovascular Function Produced by a Novel Biologic Compound in a Stand Alone Safety Pharmacology Primate Study*, in *SPS meeting*, 2013), extensive non-invasive telemetry employing the EMKA system was performed on the animals.

No test item-related influence was noted in any of the telemetric parameters (employing the non-invasive EMKA system) of any of the animals at any dose level. In particular, no pathological arrhythmias were observed and there was no evidence for any test item-related ST-elevation in male and female monkeys treated with the Nanobodies at any of the tested dose levels (data not shown).

These studies confirm that ADAMTS5 specific Nanobodies can be considered safe.

Example 14 In Vivo Rat MMT Model DMOAD Study

In order to demonstrate the in vivo efficacy of the ADAMTS5 inhibitors fused to a CAP binder of the invention, a surgically induced Medial Meniscal Tear (MMT) model in rats was used. In short, an anti-ADAMTS5 Nanobody was coupled to a CAP binder (indicated as Nanobody construct C010100954 or Nanobody construct 954). Rats were operated in one knee to induce OA-like symptoms. Treatment started 3 days post-surgery by IA injection. Histopathology was performed at day 42 post surgery. Interim and terminal serum samples were taken for exploratory biomarker analysis. The medial and total substantial cartilage degeneration width were determined, as well as the percentage reduction of cartilage degeneration. 20 animals were used per group.

The sub-cartilage defect in the medial tibia is shown in FIG. 13.

The results demonstrate that the cartilage width was substantially reduced by the ADAMTS5-CAP construct after 42 days compared to the vehicle. These results further suggest that
 (a) the CAP-moiety has no negative impact on the activity of the anti-ADAMTS5 Na nobody;
 (b) the CAP-moiety enables the retention of the anti-ADAMTS5 Nanobody; and
 (c) the anti-ADAMTS5 Nanobody has a positive effect on the cartilage width, even when coupled to a CAP-moiety.

Example 15

Methods: Bovine cartilage explants from four animals (BEX), as well as human cartilage explants from eight surgically replaced knee joints (HEX) and from one healthy human knee joint (hHEX), were cultured for up to 21 days in medium alone (w/o), in the presence of pro-inflammatory cytokines (oncostatin M [10 ng/mL]+TNFα [20 ng/mL] (O+T)) or O+T with exemplary Nanobody construct 581 ($2F3^{SO}$-35GS linker-Alb11) [1 µM-1 nM]. Cartilage and synovium from cows (bCC) and from 4 replaced osteoarthritic human knee joints (hCC) were co-cultured ex vivo for up to 28 days in medium alone (w/o), with O+T or O+T plus exemplary Nanobody construct 581 ($2F3^{SO}$-35GS linker-Alb11) [1 µM-0.6 nM]. Cartilage was cut into equal size explants using a biopsy puncher. Synovial membranes were cut into explants of equally sized (30 mg [±3 mg]) by scalpel. Metabolic activity of explants was assessed by Alamar Blue. Cartilage tissue turnover was assessed using enzyme-linked immunosorbent assay (ELISA) to measure well-characterized biomarkers of degradation (huARGS, exAGNx1, C2M) and formation (ProC2) in the conditioned medium. ProC2 and C2M are type II collagen formation and degradation metabolites, respectively, while exAGNx1 and huARGS are metabolites of ADAMTS-5 degraded aggrecan. Mean values and standard error of mean (SEM) are reported. Statistical analysis was done using one-way analysis of variance (ANOVA) with Dunn's multiple comparisons test or two-way ANOVA with Dunnett's multiple comparisons test assuming normal distribution.

Results: Metabolic activity of BEX, HEX, and bCC was stable throughout the culture period, whereas the metabolic activity in hCC and hHEX dropped significantly from day 14 in O+T treated conditions compared to w/o. In cultures stimulated with O+T, metabolites of ADAMTS-5 degraded aggrecan peaked within the first week of the culture, except for hHEX in which huARGS and exAGNx1 increased slightly later. Type II collagen degradation, C2M, by O+T peaked after day 19. Type II collagen formation, Pro-C2, remained relatively stable throughout the cultures, compared to the w/o control.

Treatment with exemplary Nanobody construct 581 ($2F3^{SO}$-35GS linker-Alb11) in combination with O+T dose dependently decreased huARGS on day 5 in BEX (highest dose: 8% of O+T), HEX (highest dose: 40% of O+T), bCC (highest dose: 10% of O+T), hCC (highest dose: 40% of O+T), and hHEX (highest dose: 24% of O+T) (FIG. 14A-14E). The 1050 of exemplary Nanobody construct 581 ($2F3^{SO}$-35GS linker-Alb11) based on the reduction of huARGS ranged from 300 nM in BEX to <15 nM HEX, hHEX, bCC and hCC (FIG. 14A-14E). The effect of exemplary Nanobody construct 581 ($2F3^{SO}$-35GS linker-Alb11) on exAGNx1 was similar to huARGS in the cultures tested. Exemplary Nanobody construct 581 ($2F3^{SO}$-35GS linker-Alb11) also reduced C2M (marker for type II collagen degradation) significantly and dose dependently, albeit the effect was less than for aggrecan degradation markers. exemplary Nanobody construct 581 ($2F3^{SO}$-35GS linker-Alb11) showed no effect on type II collagen formation metabolite Pro-C2 in any of the tested conditions.

Conclusions: Here, we have shown that the exemplary Nanobody construct 581 ($2F3^{SO}$-35GS linker-Alb11) has cartilage protective effects due to its dose-dependent inhibition of ADAMTS-5-mediated aggrecan degradation and MMP-mediated type II collagen degradation in pro-inflammatory conditions of bovine and human cartilage ex vivo cultures and in co-cultures of cartilage and synovium. $2F3^{SO}$-35GS linker-Alb (SEQ ID NO: 129) is one of the preferred embodiments of the invention.

Example 16 Present Nanobody Constructs Outperform Prior Art Nanobodies

In WO2008/074840 various ADAMTS5 Nanobodies have been described. In the present experiment a comparison was made between the 26 Nanobodies described in WO2008/074840 versus the Nanobodies of the present invention represented by the exemplary Nanobody $2F3^{so}$ ($2F3^*$).

All constructs were tested in the AlphaLISA assay, as described in Example 5.1. Nanobody $2F3^{so}$ ($2F3^*$) is the ADAMTS5 binding monovalent building block of C011400581 (SEQ ID NO: 129). As a negative control, the irrelevant Nanobody IRR00028 was used.

First the activity of the prior art Nanobodies was determined in the AlphaLISA. The results are shown in Table 16.1.

TABLE 16.1

Activity of the prior art Nanobodies in AlphaLISA

| No | Name | Length | $CDR^3$ length | AlphaLisa Results |
|---|---|---|---|---|
| 1 | 36A01 | 149 | 17 | Blocking |
| 2 | 36A06 | 147 | 15 | enhancer |
| 3 | 36C06 | 150 | 17 | Enhancer |
| 4 | 36D06 | 146 | 14 | Blocking |
| 5 | 36E01 | 147 | 15 | Enhancer |
| 6 | 36F01 | 149 | 17 | Blocking |
| 7 | 37B01 | 146 | 15 | Enhacer |
| 8 | 37B06 | 145 | 13 | Blocking |
| 9 | 37B12 | 151 | 16 | Enhancer |
| 10 | 37C06 | 150 | 18 | Enhancer |
| 11 | 37C12 | 150 | 18 | Enhancer |
| 12 | 37D06 | 146 | 15 | Enhancer |
| 13 | 37E06 | 151 | 16 | No Activity |
| 14 | 37F01 | 146 | 15 | Enhancer |
| 15 | 37F12 | 150 | 18 | Enhancer |
| 16 | 37G01 | 150 | 18 | Blocking |

TABLE 16.1-continued

Activity of the prior art Nanobodies in AlphaLISA

| No | Name | Length | CDR3 length | AlphaLisa Results |
|---|---|---|---|---|
| 17 | 37G06 | 146 | 15 | Enhancer |
| 18 | 40A07 | 151 | 16 | No Activity |
| 19 | 40B08 | 146 | 15 | No Activity |
| 20 | 40D07 | 146 | 14 | No Activity |
| 21 | 40E08 | 147 | 15 | No Activity |
| 22 | 40F07 | 146 | 14 | Blocking |
| 23 | 40F08 | 151 | 19 | No Activity |
| 24 | 40G07 | 146 | 14 | Blocking |
| 25 | 40G08 | 151 | 16 | No Activity |
| 26 | 40H07 | 146 | 14 | No Activity |

The results demonstrate that only 7 prior art Nanobodies have a blocking activity. The remainder of the prior art Nanobodies had no activity or enhanced the activity.

In a second phase of this comparative experiment, the blocking Nanobodies were compared vis-à-vis the exemplary monovalent Nanobody 2F3$^{so}$ (2F3*).

The IC$_{50}$ values of the Nanobody constructs are listed in Table 16.2. The fold-difference with the exemplary monovalent Nanobody 2F3$^{so}$ (2F3*) is also indicated for ease of comparison.

TABLE 16.2

Potencies of prior art Nanobody constructs vis-a-vis Nanobody 2F3$^{SO}$ (2F3*) as determined in AlphaLISA

| Exp ID | Nb ID | IC50 [M] | Fold-difference vs 2F3$^{SO}$ (2F3*) |
|---|---|---|---|
| 1 | 2F3$^{SO}$ (2F3*) | 2.0E−10 [1.2E−10; 3.1E−10] | — |
|  | 36D06 | 1.4E−09 [8.5E−10; 3.6E−09] | 7× |
|  | 36F01 | 7.0E−09 [2.3E−09] | 35× |
|  | 36B06 | 2.2E−09 [1.4E−09; 3.7E−09] | 11× |
| 2 | 2F3$^{SO}$ (2F3*) | 2.7E−10 [2.2E−10; 3.4E−10] | — |
|  | 37G01 | 7.3E−09 [5.2E−09; 1.2E−08] | 27× |
| 3 | 2F3$^{SO}$ (2F3*) | 1.9E−10 [1.5E−10; 2.3E−10] | — |
|  | 40F07 | 1.9E−09 [1.4E−09; 2.8E−09] | 10× |
|  | 40G07 | 1.7E−09 [1.2E−09; 2.4E−09] | 9× |
| 4 | 2F3$^{SO}$ (2F3*) | 4.4E−10 [3.6E−10; 5.3E−10] | — |
|  | C011400581 | 3.5E−10 [2.8E−10; 4.4E−10] |  |
|  | 36A01 | Partial inhibition |  |

It can be concluded that the Nanobody constructs of the present invention outperformed the prior art ADAMTS5 Nanobodies.

TABLE A-1

Name and short description ("ID"), SEQ ID NO:s ("SEQ") and amino acid sequences of monovalent and multivalent anti-ADAMTS5 Nanobodies

| ID | SEQ | Sequence |
|---|---|---|
| 2A02 | 5 | EVQLVESGGGLVQPGGSLRLSCAASRRTFSSYVMAWFRQAPGKEREFVAAISRSGDSTYYYDSLEGRFTISRDNAKNTVHLQMNSLKPEDTAVYICAASRAPSFRTIDAINYYDYWGQGTLVTVSS |
| 2A12 | 1 | EVQLVESGGGLVQAGGSLRLSCAASGRTFSSYAMGWFRQAPGKERDFVAGISRSAGRTYYVDSVKGRFTISRDSAKNTVYLQMNRLKPEDTAVYYCAADLDPNRIFSRDEAAYWGQGTLVTVSS |
| 2C10 | 9 | EVQLVESGGGLVQAGGSLRLSCATSGFTFSPYYMGWFRQAPGKERDFVAAITRSRGTTYYLDSTEGRFTISRDNAKNTMYLQMNSLNPEDTAVYYCAAGRSPGDPSRTYLYEYWGQGTLVTVSS |
| 2D07 | 6 | EVQLVESGGGLVQAGGSLRLSCSFSGPGRTFARYAMGWFRQAPGKNRDFITGISGSGDSTYYVYPMKDRFTISRDNAKNMVYLQMNALKPEDTAVYYCAADREINRIANDKELDFWGQGTLVTVSS |
| 2D12 | 4 | EVQLVESGGGLVQAGDSLRLSCAASGRTFSTYFVGWFRQAPGKERDFVAAISRNGARTYYYDSVAGLFTISRDNAKNTVYLQMSSLKPEDTAVYYCAAARISPSDPSNEDGYDYWGQGTLVTVSS |
| 2F03 | 2 | EVQLVESGGGLVQAGGSLRLSCAASGRTVSSYAMGWFRLAPGKEREFVAGISRSAERTYYVDSLKGRFTISRDSAKNTVYLHMNRLKPEDTAVYYCAADLDPNRIFSREEYAYWGQGTLVTVSS |
| 2G01 | 7 | EVQLVESGGGLVQAGGSLRLSCAASGRTTFSSYAMGWFRQAPGKERAFVATIWSGGLTVYADSAKGRFTISRDNAKNTVYLQMNSLRPEDTAVYYCAAEAVGTYYTPDGWTYWGQGTLVTVSS |
| 3B02 | 16 | EVQLVESGGGFVQAGGSLRLSCVASRRTISSGTMGWFRQAPGKEREFVAAIRWSSGMPYYLDSVMDRFTISRDNAKNTVSLQMNSLQPEDTAVYYCAADRSAFRDPSFDVNYEYWGRGTLVTVSS |
| 3B03 | 13 | EVQLVESGGDLVQPGGSLRLSCAASGSDVVVNDMGWYRQAPGKQRELVADITTGGRTNYADSVKGRFTISRDNVKNTVYLQMNSLKPEDTAVYYCNAQVGDSDDDVWYAYWGQGTLVTVSS |
| 3D01 | 10 | EVQLVESGGGLVQAGGSLRLSCAPSGFTFSPYYMGWFRQAPGKERDFVAAISRSRGTTYYLDSTEGRFTISRDNANDTVYLQMNSLNPEDTAVYYCAAGRSPGDPSRTYLYDYWGQGTLVTVSS |
| 3D02 | 11 | EVQLVESGGGLVQAGASLRLSCATSGFTFSPYYMGWFRQAPGKERDFVAAISWSRGILYYTDSTEGRFTISRDNAKNTMYLQMDNLNPEDTAVYYCAASRSPGDPSRTYLYDYWGQGTLVTVSS |
| 7B11 | 14 | EVQLVESGGGLVQPGGSLRLSCAASGSIFSINVMGWYRQAPGKQRELVAAIISGGRTNYADSVKGRFTISRDNSKNTVYLQMNSLRPEDTAVYYCNAEVDAGIYAYGYWGQGTLVTVSS |
| 9A05 | 17 | EVQLVESGGGFVQAGGSLRLSCAASRRTISSGTMGWFRQAPGKEREFVAAIRWSSGITFYPDSVEGRFTISGDNAKNTVSLQMNSLKPEDTAVYYCAADRSALRDPSFEVNYEYWGRGTLVTVSS |
| 9D03 | 3 | EVQLVESGGGLVQSGGSLRLSCAASGSAVSVNAMAWYRQAPGKQRDFVAGISRSAGRTYYTDSVKDRFTIARDSAKNTVYLQMNRLKPEDTAVYYCAADLDPNRIFSRDEAAYWGQGTLVTVSS |

TABLE A-1-continued

Name and short description ("ID"), SEQ ID NO:s ("SEQ") and amino acid sequences of monovalent and multivalent anti-ADAMTS5 Nanobodies

| ID | SEQ | Sequence |
|---|---|---|
| 9D09 | 15 | EVQLVESGGGLVQAGGSLRLSCAASGLTFSSYTMGWFRQAPGQEREFVSAISWNTFTTYYVDSVKDRFTVS RDNAKNTLYLRMNSLKPEDTAVYYCAAAGGSPRQHEPYEYRVWGQGTLVTVSS |
| 9D10 | 12 | EVQLVESGGGLVQAGGSLRLSCAASGRALSSSIMGWFRQAPGKEREFVAAITWSGGRAYYADVSDFEKGRF TISRDNGKNTVNLQMKGLKPEDTAVYYCAAALAIPVTMSPHEYPYWGQGTLVTVSS |
| 11B06 | 8 | EVQLVESGGGLVQAGGSLRLSCAASGLTFRRNAMGWFRQAPGKERELLAGINWSGGTTYYVDSVKGRFTIS RDNAKNTVDLQMISPKPEDTAVYYCAADGDIGTLVNDENPRYWGQGTLVTVSS |
| 13E02 | 18 | EVQLVESGGGLVQAGGSLRLSCVASGSIFSIDAMGWYRQAPGKERELVASVTTGASPNYGDSVTGRFTASR DRAKNALYLQMNSLKPEDTAVYYCNLIMTIPGGSQIMYWGQGTLVTVSS |
| 3F04 | 19 | EVQLVESGGGSVQAGGSLRLSCVASGRYPMAWFRQAPGKEREFVAGVSWGGDRTYYADSVQGRFTVSRDYA KNTLYLQMNSLKPEDAAVYYCAGDPWGRLFRVKDNYSDWGQGTLVTVSS |
| construct 049 11B06: N52 | 117 | EVQLVESGGGLVQAGGSLRLSCAASGLTFRRNAMGWFRQAPGKERELLAGISWSGGTTYYVDSVKGRFTIS RDNAKNTVDLQMISPKPEDTAVYYCAADGDIGTLVNDENPRYWGQGTLVTVSS |
| construct 093 3F04: N100fQ | 116 | EVQLVESGGGSVQAGGSLRLSCVASGRYPMAWFRQAPGKEREFVAGVSWGGDRTYYADSVQGRFTVSRDYA KNTLYLQMNSLKPEDAAVYYCAGDPWGRLFRVKDQYSDWGQGTLVTVSS |
| construct 004 2A12-Alb | 120 | EVQLVESGGGLVQAGGSLRLSCAASGRTFSSYAMGWFRQAPGKERDFVAGISRSAGRTYYVDSVKGRFTIS RDSAKNTVYLQMNRLKPEDTAVYYCAADLDPNRIFSRDEAAYWGQGTLVTVSSGGGGSGGGGSGGGGSGGG GSGGGGSGGGGSGGGGSEVQLVESGGGLVQPGNSLRLSCAASGFTFSSFGMSWVRQAPGKGLEWVSSISGS GSDTLYADSVKGRFTISRDNAKTTLYLQMNSLRPEDTAVYYCTIGGSLSRSSQGTLVTVSS |
| construct 005 2D7-Alb | 121 | EVQLVESGGGLVQAGGSLRLSCSFSGPGRTFARYAMGWFRQAPGKNRDFITGISGSGDSTYYVYPMKDRFT ISRDNAKNMVYLQMNALKPEDTAVYYCAADREINRIANDKELDPWGQGTLVTVSSGGGGSGGGGSGGGGSG GGGSGGGGSGGGGSGGGGSEVQLVESGGGLVQPGNSLRLSCAASGFTFSSFGMSWVRQAPGKGLEWVSSIS GSGSDTLYADSVKGRFTISRDNAKTTLYLQMNSLRPEDTAVYYCTIGGSLSRSSQGTLVTVSS |
| construct 006 2F3-Alb | 122 | EVQLVESGGGLVQAGGSLRLSCAASGRTVSSYAMGWFRLAPGKEREFVAGISRSAERTYYVDSLKGRFTIS RDNAKNTVYLHMNRLKPEDTAVYYCAADLDPNRIFSREEYAYWGQGTLVTVSSGGGGSGGGGSGGGGSGGG GSGGGGSGGGGSGGGGSEVQLVESGGGLVQPGNSLRLSCAASGFTFSSFGMSWVRQAPGKGLEWVSSISGS GSDTLYADSVKGRFTISRDNAKTTLYLQMNSLRPEDTAVYYCTIGGSLSRSSQGTLVTVSS |
| construct 069 049-Alb | 123 | EVQLVESGGGLVQAGGSLRLSCAASGLTFRRNAMGWFRQAPGKERELLAGISWSGGTTYYVDSVKGRFTIS RDNAKNTVDLQMISPKPEDTAVYYCAADGDIGTLVNDENPRYWGQGTLVTVSSGGGGSGGGGSGGGGSGGG GSGGGGSGGGGSGGGGSEVQLVESGGGLVQPGNSLRLSCAASGFTFSSFGMSWVRQAPGKGLEWVSSISGS GSDTLYADSVKGRFTISRDNAKTTLYLQMNSLRPEDTAVYYCTIGGSLSRSSQGTLVTVSS |
| construct 070 9D3-Alb | 124 | EVQLVESGGGLVQSGGSLRLSCAASGSAVSVNAMAWYRQAPGKQRDFVAGISRSAGRTYYTDSVKDRFTIA RDSAKNTVYLQMNRLKPEDTAVYYCAADLDPNRIFSRDEAAYWGQGTLVTVSSGGGGSGGGGSGGGGSGGG GSGGGGSGGGGSGGGGSEVQLVESGGGLVQPGNSLRLSCAASGFTFSSFGMSWVRQAPGKGLEWVSSISGS GSDTLYADSVKGRFTISRDNAKTTLYLQMNSLRPEDTAVYYCTIGGSLSRSSQGTLVTVSS |
| construct 071 3B2-Alb | 125 | EVQLVESGGGFVQAGGSLRLSCVASRRTISSGTMGWFRQAPGKEREFVAAIRWSSGMPYYLDSVMDRFTIS RDNAKNTVSLQMNSLQPEDTAVYYCAADRSAFRDPSFDVNYEYWGRGTLVTVSSGGGGSGGGGSGGGGSGG GGSGGGGSGGGGSGGGGSEVQLVESGGGLVQPGNSLRLSCAASGFTFSSFGMSWVRQAPGKGLEWVSSISG SGSDTLYADSVKGRFTISRDNAKTTLYLQMNSLRPEDTAVYYCTIGGSLSRSSQGTLVTVSS |
| construct 129 2F3-093-Alb | 126 | EVQLVESGGGLVQAGGSLRLSCAASGRTVSSYAMGWFRLAPGKEREFVAGISRSAERTYYVDSLKGRFTIS RDNAKNTVYLHMNRLKPEDTAVYYCAADLDPNRIFSREEYAYWGQGTLVTVSSGGGGSGGGGSGGGGSGGG GSGGGGSEVQLVESGGGSVQAGGSLRLSCVASGRYPMAWFRQAPGKEREFVAGVSWGGDRT YYADSVQGRFTVSRDYAKNTLYLQMNSLKPEDAAVYYCAGDPWGRLFRVKDQYSDWGQGTLVTVSSGGGGS GGGGSGGGGSGGGGSGGGGSGGGGSEVQLVESGGGLVQPGNSLRLSCAASGFTFSSFGMSWVRQAP GKGLEWVSSISGSGSDTLYADSVKGRFTISRDNAKTTLYLQMNSLRPEDTAVYYCTIGGSLSRSSQGTLVT VSS |
| construct 130 049-093-Alb | 127 | EVQLVESGGGLVQAGGSLRLSCAASGLTFRRNAMGWFRQAPGKERELLAGISWSGGTTYYVDSVKGRFTIS RDNAKNTVDLQMISPKPEDTAVYYCAADGDIGTLVNDENPRYWGQGTLVTVSSGGGGSGGGGSGGGGSGGG GSGGGGSEVQLVESGGGSVQAGGSLRLSCVASGRYPMAWFRQAPGKEREFVAGVSWGGDRT YYADSVQGRFTVSRDYAKNTLYLQMNSLKPEDAAVYYCAGDPWGRLFRVKDQYSDWGQGTLVTVSSGGGGS GGGGSGGGGSGGGGSGGGGSGGGGSEVQLVESGGGLVQPGNSLRLSCAASGFTFSSFGMSWVRQAP GKGLEWVSSISGSGSDTLYADSVKGRFTISRDNAKTTLYLQMNSLRPEDTAVYYCTIGGSLSRSSQGTLVT VSS |
| construct 131 9D3-093-Alb | 128 | EVQLVESGGGLVQSGGSLRLSCAASGSAVSVNAMAWYRQAPGKQRDFVAGISRSAGRTYYTDSVKDRFTIA RDSAKNTVYLQMNRLKPEDTAVYYCAADLDPNRIFSRDEAAYWGQGTLVTVSSGGGGSGGGGSGGGGSGGG GSGGGGSEVQLVESGGGSVQAGGSLRLSCVASGRYPMAWFRQAPGKEREFVAGVSWGGDRT YYADSVQGRFTVSRDYAKNTLYLQMNSLKPEDAAVYYCAGDPWGRLFRVKDQYSDWGQGTLVTVSSGGGGS |

TABLE A-1-continued

Name and short description ("ID"), SEQ ID NO:s ("SEQ") and amino acid sequences of monovalent and multivalent anti-ADAMTS5 Nanobodies

| ID | SEQ | Sequence |
|---|---|---|
| | | GGGGSGGGGSGGGGSGGGGSGGGGSGGGGSEVQLVESGGGLVQPGNSLRLSCAASGFTFSSFGMSWVRQAPGKGLEWVSSISGSGSDTLYADSVKGRFTISRDNAKTTLYLQMNSLRPEDTAVYYCTIGGSLSRSSQGTLVTVSS |
| construct 577 = 581 2F3*-Alb | 129 | DVQLVESGGGVVPGGSLRLSCAASGRTVSSYAMGWFRQAPGKEREFVAGISRSAERTYYVDSLKGRFTISRDNSKNTVYLQMNSLRPEDTALYYCAADLDPNRIFSREEYAYWGQGTLVTVSSGGGGSGGGGSGGGGSGGGGSGGGGSGGGGSEVQLVESGGGVVPGNSLRLSCAASGFTFSSFGMSWVRQAPGKGLEWVSSISGSGSDTLYADSVKGRFTISRDNAKTTLYLQMNSLRPEDTALYYCTIGGSLSRSSQGTLVTVSSA |
| construct 579 2F3-093*-Alb | 130 | DVQLVESGGGVVPGGSLRLSCAASGRTVSSYAMGWFRQAPGKEREFVAGISRSAERTYYVDSLKGRFTISRDNSKNTVYLQMNSLRPEDTALYYCAADLDPNRIFSREEYAYWGQGTLVTVSSGGGGSGGGGSGGGGSGGGGSEVQLVESGGGVVPGGSLRLSCAASGRYPMAWFRQAPGKEREFVAGVSWGGDRTYYADSVKGRFTISRDYSKNTLYLQMNSLRPEDTALYYCAGDPFGRLFRVKDQYSDWGQGTLVTVSSGGGGSGGGGSGGGGSGGGGSGGGGSGGGGSEVQLVESGGGVVPGNSLRLSCAASGFTFSSFGMSWVRQAPGKGLEWVSSISGSGSDTLYADSVKGRFTISRDNAKTTLYLQMNSLRPEDTALYYCTIGGSLSRSSQGTLVTVSSA |

*SO (sequence optimized) version

TABLE A-2

Sequences for CDRs and frameworks, plus preferred combinations as provided in formula I, namely FR1-CDR1-FR2-CDR2-FR3-CDR3-FR4 (the following terms: "ID" refers to the given SEQ ID NO)

| ID | Nanobody | ID | FR1 | ID | CDR1 | ID | FR2 | ID | CDR2 |
|---|---|---|---|---|---|---|---|---|---|
| 1 | 02A12 | 72 | EVQLVESGGGLVQAGGSLRLSCAAS | 20 | GRTFSSYAMG | 85 | WFRQAPGKERDFVA | 36 | GISRSAGRTY |
| 2 | 02F03 | 72 | EVQLVESGGGLVQAGGSLRLSCAAS | 21 | GRTVSSYAMG | 86 | WFRLAPGKEREFVA | 37 | GISRSAERTY |
| 3 | 09D03 | 73 | EVQLVESGGGLVQSGGSLRLSCAAS | 22 | GSAVSVNAMA | 87 | WYRQAPGKQRDFVA | 36 | GISRSAGRTY |
| 4 | 02D12 | 74 | EVQLVESGGGLVQAGDSLRLSCAAS | 23 | GRTFSTYFVG | 85 | WFRQAPGKERDFVA | 38 | AISRNGARTYY |
| 5 | 02A02 | 75 | EVQLVESGGGLVQPGGSLRLSCAAS | 24 | RRTFSSYVMA | 88 | WFRQAPGKEREFVA | 39 | AISRSGDSTY |
| 6 | 02D07 | 76 | EVQLVESGGGLVQAGGSLRLSCSFS | 25 | GPGRTFARYAMG | 89 | WFRQAPGKNRDFIT | 40 | GISGSGDSTY |
| 7 | 02G01 | 72 | EVQLVESGGGLVQAGGSLRLSCAAS | 26 | GRTTFSSYAMG | 90 | WFRQAPGKERAFVA | 41 | TIWSGGLTV |
| 8 | 11B06 | 72 | EVQLVESGGGLVQAGGSLRLSCAAS | 27 | GLTFRRNAMG | 91 | WFRQAPGKERELLA | 42 | GINWSGGTTY |
| 117 | 49 11B06: N52S | 72 | EVQLVESGGGLVQAGGSLRLSCAAS | 27 | GLTFRRNAMG | 91 | WFRQAPGKERELLA | 119 | GISWSGGTTY |
| 9 | 02C10 | 77 | EVQLVESGGGLVQAGGSLRLSCATS | 28 | GFTFSPYYMG | 85 | WFRQAPGKERDFVA | 43 | AITRSRGTTY |
| 10 | 03D01 | 78 | EVQLVESGGGLVQAGGSLRLSCAPS | 28 | GFTFSPYYMG | 85 | WFRQAPGKERDFVA | 44 | AISRSRGTTY |
| 11 | 03D02 | 79 | EVQLVESGGGLVQAGASLRLSCATS | 28 | GFTFSPYYMG | 85 | WFRQAPGKERDFVA | 45 | AISWSRGILY |
| 12 | 09D10 | 72 | EVQLVESGGGLVQAGGSLRLSCAAS | 29 | GRALSSSIMG | 88 | WFRQAPGKEREFVA | 46 | AITWSGGRAYYAD |
| 13 | 03B03 | 80 | EVQLVESGGDLVQPGGSLRLSCAAS | 30 | GSDVVNDMG | 92 | WYRQAPGKQRELVA | 47 | DITTGGRTN |
| 14 | 07B11 | 75 | EVQLVESGGGLVQPGGSLRLSCAAS | 31 | GSIFSINVMG | 92 | WYRQAPGKQRELVA | 48 | AIISGGRTN |
| 15 | 09D09 | 72 | EVQLVESGGGLVQAGGSLRLSCAAS | 32 | GLTFSSYTMG | 93 | WFRQAPGQEREFVS | 49 | AISWNTFTTY |

TABLE A-2-continued

Sequences for CDRs and frameworks, plus preferred combinations as provided in formula I, namely FR1-CDR1-FR2-CDR2-FR3-CDR3-FR4 (the following terms: "ID" refers to the given SEQ ID NO)

| | | | | | | | | | |
|---|---|---|---|---|---|---|---|---|---|
| 16 | 03B02 | 81 | EVQLVESGGGFVQ AGGSLRLSCVAS | 33 | RRTISSGTMG | 88 | WFRQAPGK EREFVA | 50 | AIRWSSGMPY |
| 17 | 09A05 | 82 | EVQLVESGGGFVQ AGGSLRLSCAAS | 33 | RRTISSGTMG | 88 | WFRQAPGK EREFVA | 51 | AIRWSSGITF |
| 18 | 13E02 | 83 | EVQLVESGGGLVQ AGGSLRLSCVAS | 34 | GSIFSIDAMG | 94 | WYRQAPGK ERELVA | 52 | SVTTGASPN |
| 19 | 03F04 | 84 | EVQLVESGGGSVQ AGGSLRLSCVAS | 35 | GRYPMA | 88 | WFRQAPGK EREFVA | 53 | GVSWGGDRTY |
| 116 | 93 (3F04 N100fQ) | 84 | EVQLVESGGGSVQ AGGSLRLSCVAS | 35 | GRYPMA | 88 | WFRQAPGK EREFVA | 53 | GVSWGGDRTY |

| | | ID | Nanobody | ID | FR3 | ID | CDR3 | ID | FR4 |
|---|---|---|---|---|---|---|---|---|---|
| | | 1 | 02A12 | 95 | YVDSVKGRFTISRDSAKNTV YLQMNRLKPEDTAVYYCAA | 54 | DLDPNRIFSRDEAA Y | 114 | WGQGTL VTVSS |
| | | 2 | 02F03 | 96 | YVDSLKGRFTISRDSAKNTV YLHMNRLKPEDTAVYYCAA | 55 | DLDPNRIFSREEYA Y | 114 | WGQGTL VTVSS |
| | | 3 | 09D03 | 97 | YTDSVKDRFTIARDSAKNTV YLQMNRLKPEDTAVYYCAA | 54 | DLDPNRIFSRDEAA Y | 114 | WGQGTL VTVSS |
| | | 4 | 02D12 | 98 | YDSVAGLFTISRDNAKNTVY LQMSSLKPEDTAVYYCAA | 56 | ARISPSDPSNEDGY DY | 114 | WGQGTL VTVSS |
| | | 5 | 02A02 | 99 | YYDSLEGRFTISRDNAKNTV HLQMNSLKPEDTAVYICAA | 57 | SRAPSFRTIDAINY YDY | 114 | WGQGTL VTVSS |
| | | 6 | 02D07 | 100 | YVYPMKDRFTISRDNAKNMV YLQMNALKPEDTAVYYCAA | 58 | DREINRIANDKELD F | 114 | WGQGTL VTVSS |
| | | 7 | 02G01 | 101 | YADSAKGRFTISRDNAKNTV YLQMNSLRPEDTAVYYCAA | 59 | EAVGTYYTPDGWTY | 114 | WGQGTL VTVSS |
| | | 8 | 11B06 | 102 | YVDSVKGRFTISRDNAKNTV DLQMISPKPEDTAVYYCAA | 60 | DGDIGTLVNDENPR Y | 114 | WGQGTL VTVSS |
| | | 117 | 49 11B06: N52S | 102 | YVDSVKGRFTISRDNAKNTV DLQMISPKPEDTAVYYCAA | 60 | DGDIGTLVNDENPR Y | 114 | WGQGTL VTVSS |
| | | 9 | 02C10 | 103 | YLDSTEGRFTISRDNAKNTM YLQMNSLNPEDTAVYYCAA | 61 | GRSPGDPSRTYLYE Y | 114 | WGQGTL VTVSS |
| | | 10 | 03D01 | 104 | YLDSTEGRFTISRDNANDTV YLQMNSLNPEDTAVYYCAA | 62 | GRSPGDPSRTYLYD Y | 114 | WGQGTL VTVSS |
| | | 11 | 03D02 | 105 | YTDSTEGRFTISRDNAKNTM YLQMDNLNPEDTAVYYCAA | 63 | SRSPGDPSRTYLYD Y | 114 | WGQGTL VTVSS |
| | | 12 | 09D10 | 106 | VSDFEKGRFTISRDNGKNTV NLQMKGLKPEDTAVYYCAA | 64 | ALAIPVTMSPHEYP Y | 114 | WGQGTL VTVSS |
| | | 13 | 03B03 | 107 | YADSVKGRFTISRDNVKNTV YLQMNSLKPEDTAVYYCNA | 65 | QVGDSDDDVWYAY | 114 | WGQGTL VTVSS |
| | | 14 | 07B11 | 108 | YADSVKGRFTISRDNSKNTV YLQMNSLRPEDTAVYYCNA | 66 | EVDAGIYAYGY | 114 | WGQGTL VTVSS |
| | | 15 | 09D09 | 109 | YVDSVKDRFTVSRDNAKNTL YLRMNSLKPEDTAVYYCAA | 67 | AGGSPRQHEPYEYR V | 114 | WGQGTL VTVSS |
| | | 16 | 03B02 | 110 | YLDSVMDRFTISRDNAKNTV SLQMNSLQPEDTAVYYCAA | 68 | DRSAFRDPSFDVNY EY | 115 | WGRGTL VTVSS |
| | | 17 | 09A05 | 111 | YPDSVEGRFTISGDNAKNTV SLQMNSLKPEDTAVYYCAA | 69 | DRSALRDPSFEVNY EY | 115 | WGRGTL VTVSS |
| | | 18 | 13E02 | 112 | YGDSVTGRFTASRDRAKNAL YLQMNSLKPEDTAVYYCNL | 70 | IMTIPGGSQIMY | 114 | WGQGTL VTVSS |
| | | 19 | 03F04 | 113 | YADSVQGRFTVSRDYAKNTL YLQMNSLKPEDAAVYYCAG | 71 | DPWGRLFRVKDNYS D | 114 | WGQGTL VTVSS |

TABLE A-2-continued

Sequences for CDRs and frameworks, plus preferred combinations as provided in formula I, namely
FR1-CDR1-FR2-CDR2-FR3-CDR3-FR4 (the following terms: "ID" refers to the given SEQ ID NO)

| | | | | | | | | | |
|---|---|---|---|---|---|---|---|---|---|
| | 116 | 93 | (3F04 N100fQ) | 113 | YADSVQGRFTVSRDYAKNTL YLQMNSLKPEDAAVYYCAG | 118 | DPWGRLFRVKDQYS D | 114 | WGQGTL VTVSS |

TABLE B

Miscellaneous Amino acid sequences: Name and short description ("ID"), SEQ. ID NO:s ("SEQ") and amino acid sequences ("sequences")

| species | SEQ ID | Amino acid sequence |
|---|---|---|
| human ADAM-TS5 Q9UNA0-1 | 149 | MLLGWASLLLLCAFRLPLAAVGPAATPAQDKAGQPPTAAAAAQPRRRQGEEVQERAEPPGHPHPLAQRRRSKGLVQNI DQLYSGGGKVGYLVYAGGRRFLLDLERDGSVGIAGFVPAGGGTSAPWRHRSHCFYRGTVDGSPRSLAVFDLCGGLDG FFAVKHARYTLKPLLRGPWAEEEKGRVYGDGSARILHVYTREGFSFEALPPRASCETPASTPEAHEHAPAHSNPSGR AALASQLLDQSALSPAGGSGPQTWWRRRRRSISRARQVELLLVADASMARLYGRGLQHYLLTLASIANRLYSHASIE NHIRLAVVKVVVLGDKDKSLEVSKNAATTLKNFCKWQHQHNQLGDDHEEHYDAAILFTREDLCGHHSCDTLGMADVG TICSPERSCAVIEDDGLHAAFTVAHEIGHLLGLSHDDSKFCEETFGSTEDKRLMSSILTSIDASKPWSKCTSATITE FLDDGHGNCLLDLPRKQILGPEELPGQTYDATQQCNLTFGPEYSVCPGMDVCARLWCAVVRQGQMVCLTKKLPAVEG TPCGKGRICLQGKCVDKTKKKYYSTSSHGNWGSWGSWGQCSRSCGGGVQFAYRHCNNPAPRNNGRYCTGKRAIYRSC SLMPCPPNGKSFRHEQCEAKNGYQSDAKGVKTFVEWVPKYAGVLPADVCKLTCRAKGTGYYVVFSPKVTDGTECRLY SNSVCVRGKCVRTGCDGIIGSKLQYDKCGVCGGDNSSCTKIVGTFNKKSKGYTDVVRIPEGATHIKVRQFKAKDQTR FTAYLALKKKNGEYLINGKYMISTSETIIDINGTVMNYSGWSHRDDFLHGMGYSATKEILIVQILATDPTKPLDVRY SFFVPKKSTPKVNSVTSHGSNKVGSHTSQPQWVTGPWLACSRTCDTGWHTRTVQCQDGNRKLAKGCPLSQRPSAFKQ CLLKKC |
| bovine (AA residues 1-626) | 150 | MLLGWAALMLCALRLPPVAAGPTAAPAQDKAGQPPRAAAVAAAAQPRGRREEAQEPAEPPGHPHPLAPQRGSRGLVQ NIDQLYSGGGKVGYLVYAGGRRFLLDLERDDSVGAAGLVPAGGGPNATRRHRGHCFYRGTVDGSPRSLAVFDLCGGL DGFFAVKRARYTLQPLLRGPWAEAEGDARVYGDESARILHVYTREGFSFEALPPRTSCETHASPPGARERPPAPSRP DGRWALAPQQLPGQSAPSSDGSQGPRTWWRRRRRSISRARQVELLLVADASMARLYGRGLQHYLLTLASIANRLYSH ASIENHIRLVVVKVVVLGDKDKSLEVSKNAATTLKNFCKWQHQHNQLGDDHEEHYDAAILFTREDLCGHHSCDTLGM ADVGTICSPERSCAVIEDDGLHAAFTVAHEIGHLLGLSHDDSKFCEENFGSTEDKRLMSSILTSIDASKPWSKCTSA TITEFLDDGHGNCLLDLPRKQIPGPEELPGQTYDASQQCNLTFGPEYSVCPGMDVCARLWCAVVRQGQMVCLTKKLP AVEGTPCGKGRICLQGKCVDKTKKKYYSTSSHGNWGSWGSWGQCSRSCGGGVQFAYRHCNNPAPRNNGRYCTGKRAI YRSCSVTPCPHHHHHHHHH |
| rat (AA residues 1-619) | 151 | MRLEWASLLLLLLLLLCASCLALAADNPAAAPAQDKTRQPRAAAAAQPDQRQWEETQERGHPQPLARQRRSSGLVQN IDQLYSGGGKVGYLVYAGGRRFLLDLERDDTVGAAGGIVTAGGLSASSGHRGHCFYRGTVDGSPRSLAVFDLCGGLD GFFAVKHARYTLKPLLRGSWAESERVYGDGSSRILHVYTREGFSFEALPPRTSCETPASPSGAQESPSVHSSSRRRT ELAPQLLDHSAFSPAGNAGPQTWWRRRRRSISRARQVELLLVADSSMAKMYGRGLQHYLLTLASIANRLYSHASIEN HIRLAVVKVVVLTDKSLEVSKNAATTLKNFCKWQHQHNQLGDDHEEHYDAAILFTREDLCGHHSCDTLGMADVGTIC SPERSCAVIEDDGLHAAFTVAHEIGHLLGLSHDDSKFCEENFGSTEDKRLMSSILTSIDASKPWSKCTSATITEFLD DGHGNCLLDVPRKQILGPEELPGQTYDATQQCNLTFGPEYSVCPGMDVCARLWCAVVRQGQMVCLTKKLPAVEGTPC GKGRICLQGKCVDKTKKKYYSTSSHGNWGSWGPWGQCSRSCGGGVQFAYRHCNNPAPRNSGRYCTGKRAIYRSCSVI PCPHHHHHHHHHH |
| guinea pig (AA residues 1-622) | 152 | MLLGWASLLLCAFRLPQAAASAAAAPAQDKAGQPRAAAAAAPQPRRRQGEHAPLRVEPPGHPHALAPQRRGRGLLQSI DRLYSGGGKVGYLVYAGGRRFLLDLERDGSVGAAGLFPAGGGLSAPRRHRSHCFYRGTVDGSPRSLAVFDLCGGLRG FFAVKHARYTVKPLLRGPWAEADTPRVYGDESARIPHVYTREGFSFEALPPRASCETPASQPGPHERPPAHNSPGRH STVDPQLPELSALSPAGDPGQQIWWRRRRRSISRARQVELLLVADGSMAKMYGRGLQHYLLTLASIANRLYSHASIE NHIRLAVVKVVVLGDKDKSLEVSKNAATTLKNFCKWQHQHNQLGDDHEEHYDAAILFTREDLCGHHSCDTLGMADVG TICSPERSCAVIEDDGLHAAFTVAHEIGHLLGLSHDDSKFCEENFGLTEDKRLMSSILTSIDASKPWSKCTSATMTE FLDDGHGNCLLDVPRKQIPSPEELPGQTYDATQQCNLTFGPEYSVCPGMDVCARLWCAVVRQGQMVCLTKKLPAVEG TPCGKGRICLQGKCVDKTKKKYYSTSSHGNWGSWGPWGQCSRSCGGGVQFAYRHCNNPAPRNSGRYCTGKRAIYRSC SVTPCPHHHHHHHH |
| mouse (AA residues 1-622) | 153 | MRLEWAPLLLLLLLLLSASCLSLAADSPAAAPAQDKTRQPQAAAAAAEPDQPQGEETRERGHLQPLAGQRRSSGLVQN IDQLYSGGGKVGYLVYAGGRRFLLDLERDDTVGAAGSIVTAGGGLSASSGHRGHCFYRGTVDGSPRSLAVFDLCGGL DGFFAVKHARYTLKPLLRGSWAEYERIYGDGSSRILHVYTREGFSFEALPPRASCETPASPSGPQESPSVHSRSRRR SALAPQLLDHSAFSPSGNAGPQTWWRRRRRSISRARQVELLLVADSSMARMYGRGLQHYLLTLASIANRLYSHASIE NHIRLAVVKVVVLTDKDTSLEVSKNAATTLKNFCKWQHQHNQLGDDHEEHYDAAILFTREDLCGHHSCDTLGMADVG TICSPERSCAVIEDDGLHAAFTVAHEIGHLLGLSHDDSKFCEENFGTTEDKRLMSSILTSIDASKPWSKCTSATITE FLDDGHGNCLLDLPRKQILGPEELPGQTYDATQQCNLTFGPEYSVCPGMDVCARLWCAVVRQGQMVCLTKKLPAVEG TPCGKGKCVDKTKKKYYSTSSHGNWGSWGPWGQCSRSCGGGVQFAYRHCNNPAPRNSGRYCTGKRAIYRSC SVTPCPHHHHHHHHH |
| cynomolgus monkey (AA residues 1-622) | 154 | MLLGWASLLLLCAFRLPLAAAGPAAAPAQDKAGQPATAAAAAQPRRRQGEEVQERTEPPGHPHPLAQRRSSKGLVQNI DQLYSGGGKVGYLVYAGGRRFLLDLERDGSVGTAGFVPTEGGGSAPWRHRSHCFYRGTVDGSPRSLAVFDLCGGLDG FFAVKHARYTLKPLLRGPWAEEETRRVYGDGSARILHVYTREGFSFEALQPRASCETPASTPEPHERPPAHSNPGGR AALASQLLDQSAVSPAGGPGPQTWWRRRRRSISRARQVELLLVADASMARLYGRGLQHYLLTLASIANRLYSHASIE NHIRLAVVKVVVLGDKDKSLEVSKNAATTLKNFCKWQHQHNQLGDDHEEHYDAAILFTREDLCGHHSCDTLGMADVG TICSPERSCAVIEDDGLHAAFTVAHEIGHLLGLSHDDSKFCEENFGSTEDKRLMSSILTSIDASKPWSKCTSATITE |

TABLE B-continued

Miscellaneous Amino acid sequences: Name and short description ("ID"), SEQ. ID NO:s ("SEQ") and amino acid sequences ("sequences")

| species | SEQ ID | Amino acid sequence |
|---|---|---|
| | | FLDDGHGNCLLDQPRKQILGPEELPGQTYDATQQCNLTFGPEYSVCPGMDVCARLWCAVVRQGQMVCLTKKLPAVEG TPCGKGRICLQGKCVDKTKKKYYSTSSHGNWGSWGSWGQCSRSCGGGVQFAYRHCNNPAPRNNGRYCTGKRAIYRSC GLMPCPHHHHHHHHHH |
| human aggrecan | 155 | MTTLLWVFVTLRVITAAVTVETSDHDNSLSVSIPQPSPLRVLLGTSLTIPCYFIDPMHPVTTAPSTAPLAPRIKWSR VSKEKEVVLLVATEGRVRVNSAYQDKVSLPHYPAIPSDATLEVQSLRSNDSGVYRCEVMHGIEDSEATLEVVVKGIV FHYRAISTRYTLDFDRAQRACLQNSAIIATPEQLQAAYEDGFHQCDAGWLADQTVRYPIHTPREGCYGDKDEFPGVR TYGIRDTNETYDVYCFAEEMEGEVFYATSPEKFTFQEEAANECRRLGARLATTGHVYLAWQAGMDMCSAGWLADRSVR YPISKARPNCGGNLLGVRTVYVHANQTGYPDPSSRYDAICYTGEDFVDIPENFFGVGGEEDITVQTVTWPDMELPLP RNITEGEARGSVILTVKPIFEVSPSPLEPEEPFTFAPEIGATAFAEVENETGEATRPWGFPTPGLPATAFTSEDLV VQVTAVPGQPHLPGGVVFHYRPGPTRYSLTFEEAQQACPGTGAVIASPEQLQAAYEAGYEQCDAGWLRDQTVRYPIV SPRTPCVGDKDSSPGVRTYGVRPSTETYDVYCFVDRLEGEVFFATRLEQFTFQEALEFCESHNATATTGQLYAAWSR GLDKCYAGWLADGSLRYPIVTPRPACGGDKPGVRTVYLYPNQTGLPDDPLSRHHAFCFRGISAVPSPGEEEGGTPTSP SGVEEWIVTQVVPGVAAVPVEEETTAVPSGETTAILEFTTEPENQTEWEPAYTPVGTSPLPGILPTWPPTGAETEES TEGPSATEVPSASEEPSPSEVPPPSEEPPSEEPFPSVRPFPSVELFPSEEPFPSKEPSPSEEPSSEEPYTPSPPE PSWTELPSSGEESGAPDVSGDFTGSGDVSGHLDFSGQLSGDRASGLPSGDLDSSGLTSTVGSGLTVESGLPSGDEER IEWPSTPTVGELPSGAEILEGSASGVGDLSGLPSGEVLETSASGVGDLSGLPSGEVLETTAPGVEDISGLPSGEVLE TTAPGVEDISGLPSGEVLETTAPGVEDISGLPSGEVLETTAPGVEDISGLPSGEVLETTAPGVEDISGLPSGEVLET AAPGVEDISGLPSGEVLETAAPGVEDISGLPSGEVLETAAPGVEDISGLPSGEVLETAAPGVEDISGLPSGEVLETA APGVEDISGLPSGEVLETAAPGVEDISGLPSGEVLETAAPGVEDISGLPSGEVLETAAPGVEDISGLPSGEVLETAA PGVEDISGLPSGEVLETAAPGVEDISGLPSGEVLETAAPGVEDISGLPSGEVLETTAPGVEEISGLPSGEVLETTAP GVDEISGLPSGEVLETTAPGVEEISGLPSGEVLETSTSAVGDLSGLPSGGEVLEISVSGVEDISGLPSGEVVETSAS GIEDVSELPSGEGLETSASGVEDLSRLPSGEEVLEISASGFGDLSGVPSGEVLETSASEVGTDLSGLPSGREGLET SASGAEDLSGLPSGKEDLVGSASGDLDLGKLPSGTLGSGQAPETSGLPSGFSGEYSGVDLGSGPPSGLPDFSGLPSG FPTVSLVDSTLVEVVTASTASELEGRGTIGISGAGEISGLPSSELDISGRASGLPSGTELSGQASGSPDVSGEIPGL FGVSGQPSGFPDTSGETSGVTELSGLSSGQPGVSGEASGVLYGTSQPFGITDLSGETSGVPDLSGQPSGLPGFSGAT SGVPDLVSGTTSGSGESSGITFVDTSLVEVAPTTFKEEEGLGSVELSGLPSGEADLSGKSGMVDVSGQFSGTVDSSG FTSQTPEFSGLPSGIAEVSGESSRAEIGSSLPSGAYYGSGTPSSFPTVSLVDRTLVESVTQAPTAQEAGEGPSGILE LSGAHSGAPDMSGEHSGFLDLSGLQSGLIEPSGEPPGTPYFSGDFASTTNVSGESSVAMGTSGEASGLPEVTLITSE FVEGVTEPTISQELGQRPPVTHTPQLFESSGKVSTAGDISGATPVLPGSGVEVSSVPESSSETSAYPEAGFGASAAP EASREDSGSPDLSETTSAPHEANLERSSGLGVSGSTLTFQEGEASAAPEVSGESTTTSDVGTEAPGLPSATPTASGD RTEISGDLSGHTSQLGVVISTSIPESEWTQQTQRPAETHLEIESSSLLYSGEETHTVETATSPTDASIPASPEWKRE SESTAAAPARSCAEEPCGAGTCKETEGHVICLCPPGYTGEHCNIDQEVCEEGWNKYQGHCYRHFPDRETWVDAERRC REQQSHLSSIVTPEEQEFVNNNAQDYQWIGLNDRTIEGDFRWSDGHPMQFENWRPNQPDNEFAAGEDCVVMIWHEKG EWNDVPCNYHLPFTCKKGTVACGEPPVVEHARTFGQKKDRYEINSLVRYQCTEGFVQRHMPTIRCQPSGHWEEPRIT CTDATTYKRRLQKRSSRHPRRSRPSTAH |
| 00745 PEA114F08 | 156 | EVQLVESGGGVVQPGGSLRLSCAASGSTFIINVVRWYRRAPGKQRELVATISSGGNANYVDSVRGRFTISRDNSKNT VYLQMNSLRPEDTALYYCNVPTTHYGGVYYGPYWGQGTLVTVSSA |
| 00747 PEA604F02 | 157 | EVQLVESGGGVVQPGGSLRLSCAASGRTFSSYTMGWFRQAPGKEREEVAAISWSGGRTYYADSVKGRFTISRDNSKN TVYLQMNSLRPEDTALYYCAAYRRRRASSNRGLWDYWGQGTLVTVSSA |

TABLE C

Various Linker sequences ("ID" refers to the SEQ ID NO as used herein)

| Name | ID | Amino acid sequence |
|---|---|---|
| A3 | 158 | AAA |
| 5GS linker | 159 | GGGGS |
| 7GS linker | 160 | SGGSGGS |
| 8GS linker | 161 | GGGGGGGS |
| 9GS linker | 162 | GGGGSGGGS |
| 10GS linker | 163 | GGGGSGGGGS |
| 15GS linker | 164 | GGGGSGGGGSGGGGS |
| 18GS linker | 165 | GGGGSGGGGSGGGGGGGS |
| 20GS linker | 166 | GGGGSGGGGSGGGGSGGGGS |
| 25GS linker | 167 | GGGGSGGGGSGGGGSGGGGSGGGGS |
| 30GS linker | 168 | GGGGSGGGGSGGGGSGGGGSGGGGSGGGGS |
| 35GS linker | 169 | GGGGSGGGGSGGGGSGGGGSGGGGSGGGGSGGGGS |
| 40GS linker | 170 | GGGGSGGGGSGGGGSGGGGSGGGGSGGGGSGGGGSGGGGS |
| G1 hinge | 171 | EPKSCDKTHTCPPCP |
| 9GS-G1 hinge | 172 | GGGGSGGGSEPKSCDKTHTCPPCP |
| Llama upper long hinge region | 173 | EPKTPKPQPAAA |
| G3 hinge | 174 | ELKTPLGDTTHTCPRCPEPKSCDT PPPCPRCPEPKSCDTPPPCPRCPE PKSCDTPPPCPRCP |

TABLE D

Serum albumin binding ISVD sequences ("ID" refers to the SEQ ID NO as used herein), including the CDR sequences

| Name | ID | Amino acid sequence |
|---|---|---|
| Alb8 | 131 | EVQLVESGGGLVQPGNSLRLSCAASGFTFSSFGMSWVRQAPGKGLEWVSSISGSGSDTLYADS<br>VKGRFTISRDNAKTTLYLQMNSLRPEDTAVYYCTIGGSLSRSSQGTLVTVSS |
| Alb23 | 132 | EVQLLESGGGLVQPGGSLRLSCAASGFTFRSFGMSWVRQAPGKGPEWVSSISGSGSDTLYADS<br>VKGRFTISRDNSKNTLYLQMNSLRPEDTAVYYCTIGGSLSRSSQGTLVTVSS |
| Alb129 | 133 | EVQLVESGGGVVQPGNSLRLSCAASGFTFSSFGMSWVRQAPGKGLEWVSSISGSGSDTLYADS<br>VKGRFTISRDNAKTTLYLQMNSLRPEDTATYYCTIGGSLSRSSQGTLVTVSSA |
| Alb132 | 134 | EVQLVESGGGVVQPGGSLRLSCAASGFTFRSFGMSWVRQAPGKGPEWVSSISGSGSDTLYADS<br>VKGRFTISRDNSKNTLYLQMNSLRPEDTATYYCTIGGSLSRSSQGTLVTVSSA |
| Alb11 | 135 | EVQLVESGGGLVQPGNSLRLSCAASGFTFSSFGMSWVRQAPGKGLEWVSSISGSGSDTLYADS<br>VKGRFTISRDNAKTTLYLQMNSLRPEDTAVYYCTIGGSLSRSSQGTLVTVSS |
| Alb11<br>(S112K)-A | 136 | EVQLVESGGGLVQPGNSLRLSCAASGFTFSSFGMSWVRQAPGKGLEWVSSISGSGSDTLYADS<br>VKGRFTISRDNAKTTLYLQMNSLRPEDTAVYYCTIGGSLSRSSQGTLVKVSSA |
| Alb82 | 137 | EVQLVESGGGVVQPGNSLRLSCAASGFTFSSFGMSWVRQAPGKGLEWVSSISGSGSDTLYADS<br>VKGRFTISRDNAKTTLYLQMNSLRPEDTALYYCTIGGSLSRSSQGTLVTVSS |
| Alb82-A | 138 | EVQLVESGGGVVQPGNSLRLSCAASGFTFSSFGMSWVRQAPGKGLEWVSSISGSGSDTLYADS<br>VKGRFTISRDNAKTTLYLQMNSLRPEDTALYYCTIGGSLSRSSQGTLVTVSSA |
| Alb82-AA | 139 | EVQLVESGGGVVQPGNSLRLSCAASGFTFSSFGMSWVRQAPGKGLEWVSSISGSGSDTLYADS<br>VKGRFTISRDNAKTTLYLQMNSLRPEDTALYYCTIGGSLSRSSQGTLVTVSSAA |
| Alb82-AAA | 140 | EVQLVESGGGVVQPGNSLRLSCAASGFTFSSFGMSWVRQAPGKGLEWVSSISGSGSDTLYADS<br>VKGRFTISRDNAKTTLYLQMNSLRPEDTALYYCTIGGSLSRSSQGTLVTVSSAAA |
| Alb82-G | 141 | EVQLVESGGGVVQPGNSLRLSCAASGFTFSSFGMSWVRQAPGKGLEWVSSISGSGSDTLYADS<br>VKGRFTISRDNAKTTLYLQMNSLRPEDTALYYCTIGGSLSRSSQGTLVTVSSG |
| Alb82-GG | 142 | EVQLVESGGGVVQPGNSLRLSCAASGFTFSSFGMSWVRQAPGKGLEWVSSISGSGSDTLYADS<br>VKGRFTISRDNAKTTLYLQMNSLRPEDTALYYCTIGGSLSRSSQGTLVTVSSGG |
| Alb82-GGG | 143 | EVQLVESGGGVVQPGNSLRLSCAASGFTFSSFGMSWVRQAPGKGLEWVSSISGSGSDTLYADS<br>VKGRFTISRDNAKTTLYLQMNSLRPEDTALYYCTIGGSLSRSSQGTLVTVSSGGG |
| Alb92 | 144 | EVQLVESGGGVVQPGGSLRLSCAASGFTFRSFGMSWVRQAPGKGPEWVSSISGSGSDTLYADS<br>VKGRFTISRDNSKNTLYLQMNSLRPEDTALYYCTIGGSLSRSSQGTLVTVSS |
| Alb223 | 145 | EVQLVESGGGVVQPGGSLRLSCAASGFTFRSFGMSWVRQAPGKGPEWVSSISGSGSDTLYADS<br>VKGRFTISRDNSKNTLYLQMNSLRPEDTALYYCTIGGSLSRSSQGTLVTVSSA |
| ALB CDR1 | 146 | SFGMS |
| ALB CDR2 | 147 | SISGSGSDTLYADSVKG |
| ALB CDR3 | 148 | GGSLSR |

The invention claimed is:

1. A method of treating osteoarthritis in an individual comprising administering a bispecific polypeptide comprising at least 1 immunglobulin single variable domain (ISVD) binding a serum albumin and at least 1 ISVD binding A Disintegrin and Metalloproteinase with Thrombospondin 5 motifs (ADAMTS5) to said individual in an amount effective to treat said osteoarthritis, wherein said ISVD binding ADAMTS5 comprises three complementarity determining regions (CDR1, CDR2, CDR3) selected from the group consisting of:

i. CDR1 is SEQ ID NO: 21, CDR2 is SEQ ID NO: 37 and CDR3 is SEQ ID NO: 55;
ii. CDR1 is SEQ ID NO: 35, CDR2 is SEQ ID NO: 53 and CDR3 is SEQ ID NO: 118;
iii. CDR1 is SEQ ID NO: 35, CDR2 is SEQ ID NO: 53 and CDR3 is SEQ ID NO: 71;
iv. CDR1 is SEQ ID NO: 20, CDR2 is SEQ ID NO: 36 and CDR3 is SEQ ID NO: 54;
v. CDR1 is SEQ ID NO: 22, CDR2 is SEQ ID NO: 36 and CDR3 is SEQ ID NO: 54;
vi. CDR1 is SEQ ID NO: 25, CDR2 is SEQ ID NO: 40 and CDR3 is SEQ ID NO: 58;
vii. CDR1 is SEQ ID NO: 33, CDR2 is SEQ ID NO: 50 and CDR3 is SEQ ID NO: 68;
viii. CDR1 is SEQ ID NO: 33, CDR2 is SEQ ID NO: 51 and CDR3 is SEQ ID NO: 69;
ix. CDR1 is SEQ ID NO: 28, CDR2 is SEQ ID NO: 44 and CDR3 is SEQ ID NO: 62;
x. CDR1 is SEQ ID NO: 28, CDR2 is SEQ ID NO: 45 and CDR3 is SEQ ID NO: 63;
xi. CDR1 is SEQ ID NO: 28, CDR2 is SEQ ID NO: 43 and CDR3 is SEQ ID NO: 61;
xii. CDR1 is SEQ ID NO: 24, CDR2 is SEQ ID NO: 39 and CDR3 is SEQ ID NO: 57;
xiii. CDR1 is SEQ ID NO: 23, CDR2 is SEQ ID NO: 38 and CDR3 is SEQ ID NO: 56;
xiv. CDR1 is SEQ ID NO: 26, CDR2 is SEQ ID NO: 41 and CDR3 is SEQ ID NO: 59;
xv. CDR1 is SEQ ID NO: 27, CDR2 is SEQ ID NO: 119 and CDR3 is SEQ ID NO: 60;
xvi. CDR1 is SEQ ID NO: 27, CDR2 is SEQ ID NO: 42 and CDR3 is SEQ ID NO: 60;
xvii. CDR1 is SEQ ID NO: 29, CDR2 is SEQ ID NO: 46 and CDR3 is SEQ ID NO: 64;

xviii. CDR1 is SEQ ID NO: 30, CDR2 is SEQ ID NO: 47 and CDR3 is SEQ ID NO: 65;

xix. CDR1 is SEQ ID NO: 31, CDR2 is SEQ ID NO: 48 and CDR3 is SEQ ID NO: 66;

xx. CDR1 is SEQ ID NO: 32, CDR2 is SEQ ID NO: 49 and CDR3 is SEQ ID NO: 67; and xxi. CDR1 is SEQ ID NO: 34, CDR2 is SEQ ID NO: 52 and CDR3 is SEQ ID NO: 70.

2. The method of claim 1, wherein said CDR1 is SEQ ID NO: 21, CDR2 is SEQ ID NO: 37, and CDR3 is SEQ ID NO: 55.

3. The method of claim 1, wherein said ISVD binding ADAMTS5 is chosen from the group consisting of SEQ ID NO:s 2, 116, 19, 1, 3, 6, 16, 17, 10, 11, 9, 5, 4, 7, 8, 117, 12, 13, 14, 15 and 18, and amino acids 1-124 of SEQ ID NO: 129.

4. The method of claim 1, wherein said serum albumin is human serum albumin.

5. The method of claim 4, wherein said ISVD binding serum albumin is chosen from the group consisting of SEQ ID NOs: 131, 132, 133, 134, 135, 136, 137, 138, 139, 140, 141, 142, 143, 144, or 145.

6. The method of claim 1, wherein said polypeptide has at least 95% sequence identity with any of SEQ ID NO:s 120, 121, 122, 123, 124, 125, 126, 127, 128, 129, or 130.

7. The method of claim 6, wherein said polypeptide is selected from the group consisting of:

i. SEQ ID NO: 129 (clone 577 2F3so-Alb), ii. SEQ ID NO: 130 (clone 579 2F3so-093-Alb), iii. SEQ ID NO: 120 (clone 4 2A12-Alb), iv. SEQ ID NO: 121 (clone 5 2D7-Alb), v. SEQ ID NO: 122 (clone 6 2F3-Alb), vi. SEQ ID NO: 123 (clone 69 049-Alb), vii. SEQ ID NO: 124 (clone 70 9D3-Alb), viii. SEQ ID NO: 125 (clone 71 3B2-Alb)

ix. SEQ ID NO: 126 (clone 129 2F3-093-Alb), x. SEQ ID NO: 127 (clone 130 049-093-Alb), and xi. SEQ ID NO: 128 (clone 131 9D3-093-Alb).

8. The method of claim 1, wherein said polypeptide is SEQ ID NO: 129.

9. The method of claim 1, wherein said ISVD binding ADAMTS5 has at least 95% sequence identity with any of SEQ ID NO:s 1, 2, 3, 4, 5, 6, 7, 8, 9, 10, 11, 12, 13, 14, 15, 16, 17, 18, 19, 116, 117, or amino acids 1-124 of SEQ ID NO: 129.

10. The method of claim 1, wherein said polypeptide is administered by intravenous, intramuscular, or subcutaneous injection.

11. The method of claim 1, wherein said polypeptide is administered by intravenous infusion.

12. The method of claim 1, wherein said individual is a human.

13. The method of claim 1, comprising administering the polypeptide in a pharmaceutical composition.

14. The method of claim 13, wherein said pharmaceutical composition comprises at least one suitable carrier, diluent, buffer, or excipient.

* * * * *

UNITED STATES PATENT AND TRADEMARK OFFICE
CERTIFICATE OF CORRECTION

| | | |
|---|---|---|
| PATENT NO. | : 12,209,136 B2 | |
| APPLICATION NO. | : 17/579345 | |
| DATED | : January 28, 2025 | |
| INVENTOR(S) | : Buyse et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 383 days.

Signed and Sealed this
Sixteenth Day of December, 2025

John A. Squires
*Director of the United States Patent and Trademark Office*